United States Patent [19]

Garret et al.

[11] Patent Number: 4,985,419
[45] Date of Patent: Jan. 15, 1991

[54] PHENOTHIAZINE DERIVATIVES, THEIR PREPARATION AND PHARMACEUTICAL COMPOSITIONS CONTAINING THEM

[75] Inventors: Claude Garret, Fontenay sous Bois; Claude Guyon, Saint Maur Des Fosses; Bernard Plau, Fresnes; Gerard Taurand, Creteil, all of France

[73] Assignee: Rhone-Poulenc Sante, France

[21] Appl. No.: 364,465

[22] Filed: Jun. 12, 1989

[30] Foreign Application Priority Data

Jun. 10, 1988 [FR] France ................ 88 07771

[51] Int. Cl.$^5$ .............. A61K 31/54; A61K 31/55; C07D 279/24; C07D 417/06
[52] U.S. Cl. .................. 514/211; 514/224.8; 514/226.2; 544/41; 544/42; 544/44
[58] Field of Search .............. 544/41, 42, 44; 514/224.8, 226.2, 211; 540/599

[56] References Cited

U.S. PATENT DOCUMENTS 2,997,468  6/1961  Schwartz ............... 544/42
3,112,310  11/1963 Cusic et al.
3,134,773  5/1964  Horclois ............... 544/44

Primary Examiner—Mukund J. Shah
Assistant Examiner—Celia Chang
Attorney, Agent, or Firm—Morgan & Finnegan

[57] ABSTRACT

Phenothiazine derivatives of formula:

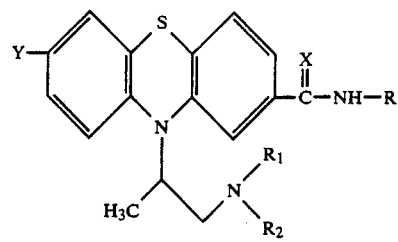

in which Y is hydrogen or halogen, $R_1$ and $R_2$, which may be identical or different, denote alkyl, cycloalkylalkyl, hydroxyalkyl or acetyloxyalkyl radicals or form, together with the nitrogen atom to which they are attached, an optionally substituted, saturated or partially unsaturated 4- to 7-membered heterocycle; and either X is oxygen, sulphur or: N-$R_4$, R is cycloalkyl, phenyl or —$CH_2R_3$, $R_3$ is H, alkyl (1 to 5 C), alkenyl or alkynyl (2 to 4 C), cycloalkyl (3 to 6 C), phenyl, substituted phenyl or a heterocyclic radical, $R_4$ is H or —CN, except that X is not oxygen if, simultaneously, $R_3$ is H or alkyl, $R_1$ and $R_2$ are alkyl or $NR_1R_2$ forms an unsubstituted heterocycle, and Y is H; or X is: N-$R_4$ and $R_4$ forms, with R and the neighbouring atoms, an optionally substituted imidazolyl or imidazolinyl radical or a hexahydrobenzimidazolyl radical, in their isomeric forms and mixtures thereof and their acid addition salts are useful as analgesics and diuretics.

9 Claims, No Drawings

PHENOTHIAZINE DERIVATIVES, THEIR PREPARATION AND PHARMACEUTICAL COMPOSITIONS CONTAINING THEM

THIS INVENTION relates to phenothiazine derivatives, their preparation and pharmaceutical compositions containing them.

In the analgesic field, recent progress in the study of receptors has enabled several types of opiate receptors to be demonstrated, in particular the Mu and Kappa type receptors.

Traditional compounds of the morphine type act at the level of the Mu receptors, but have the drawback of causing troublesome side effects (phenomena of physical and mental dependence, respiratory depression, etc.), in consequence of which it is hazardous to use such products in some subjects.

Products which are more specific for the Kappa receptors exhibit a potent analgesic activity without causing the side effects of traditional morphine type compounds.

It has now been found that phenothiazine derivatives of the formula (I) as defined below exhibit a potent analgesic activity associated with a preferential affinity for the Kappa receptors.

Phenothiazine amides of formula:

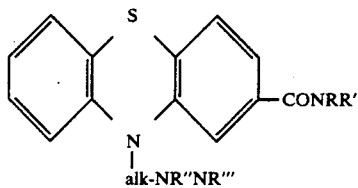

in which R is, in particular, a hydrogen atom, have been described in U.S. Pat. No. 3,112,310 and are stated to have activity on the central nervous system.

Phenothiazine thioamides of formula:

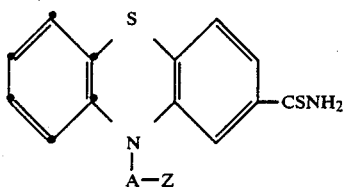

in which A is a carbon chain and Z is, in particular, a dialkylamino radical or a nitrogen-containing heterocycle, have been described in Belgian Pat. No. 612,885 as neuroleptic, anti-emetic, adrenolytic and anti-tuberculosis agents.

The phenothiazines of the invention have the formula:

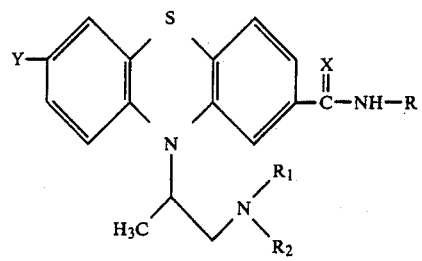

in which Y denotes hydrogen or halogen and $R_1$ and $R_2$, which may be identical or different, each denote alkyl, cycloalkylalkyl, hydroxyalkyl or acetyloxyalkyl or form, together with the nitrogen atom to which they are attached, a saturated or partially unsaturated 4- to 7-membered heterocyclic ring which is unsubstituted or substituted by 1 or 2 alkyl, hydroxyalkyl or acetyloxyalkyl radicals; and - either X denotes oxygen, sulphur or :N-$R_4$, in which $R_4$ is hydrogen or cyano, and R denotes 4- to 6-membered cycloalkyl or phenyl, or —CH$_2$R$_3$, in which $R_3$ is hydrogen, alkyl of 1 to 5 carbon atoms, alkenyl or alkynyl of 2 to 4 carbon atoms, 3- to 6-membered cycloalkyl, or phenyl which is unsubstituted or substituted(by 1 or 2 halogen atoms or by hydroxy, alkyl, alkyloxy, trifluoromethyl or nitro)or furyl, thienyl or pyridyl, provided that $R_3$ is hydrogen or alkyl, $R_1$ and $R_2$ are both alkyl or together form an unsubstituted nitrogen-containing heterocyclic ring and Y is hydrogen, X is not oxygen;

or X is :N-$R_4$ and R forms, with $R_4$ and the atoms to which they are attached, imidazolinyl or imidazolyl unsubstituted or substituted by 1 or 2 alkyl radicals, or hexahydrobenzimidazolyl; the aforesaid alkyl radicals being (except where otherwise stated) linear or branched and having 1 to 4 carbon atoms each.

When the symbol Y denotes halogen or when R bears a halogen substituent, the latter is advantageously chosen from chlorine, fluorine or bromine.

The products of formula (I) exist in isomeric forms; These isomeric forms and mixtures thereof fall within the scope of the present invention.

According to a feature of the invention, the phenothiazine derivatives of the formula (I), in which X is not :NR$_4$ in which R$_4$ forms imidazolyl with R and the neighbouring atoms, are obtained from a phenothiazine of formula:

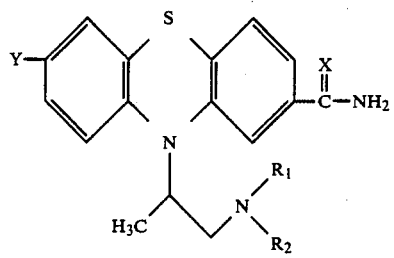

in which Y, $R_1$ and $R_2$ are as defined above and X denotes sulphur or :N-$R_4$ in which $R_4$ is hydrogen or cyano by the action of an amine of formula:

R - NH$_2$     (III)

in which R is as defined above, or by the action of a diamine chosen from 1,2-diaminoethane optionally substituted by 1 or 2 alkyl radicals, or 1,2-diaminocyclohexane if X denotes an $N_H$ radical and if it is desired to obtain phenothiazine in which R and $R_4$ are linked together with the neighbouring atoms to form optionally substituted imidazolinyl or hexahydrobenzimidazolyl, and then, when it is desired to obtain the amide, oxidizing a substituted thioamide of formula (I) in which X is sulphur to the corresponding amide.

The reaction is advantageously performed in an organic solvent such as an alcohol (e.g. ethanol, methanol or isopropanol) or without a solvent, at a temperature of between 100° and 250°C. When the reaction is performed starting with the thioamide of general formula (II), it is sometimes advantageous to work in the presence of hydrogen sulphide. When the reaction is performed starting with the amidine of general formula (II), it is also possible to employ the salt of this product.

In practice, to prepare the amide of general formula (I), it is not essential to isolate the intermediate substituted thioamide.

When it is desired to isolate the amide of general formula (I) directly, without prior isolation of the thioamide of general formula (I), chromatography or crystallization is employed directly.

When it is desired to isolate the substituted thioamide of general formula (I), it is preferable to work in the presence of hydrogen sulphide, and then, when it is desired to obtain the amide, the secondary thioamide obtained or its salt is oxidized by any known method for obtaining an amide from the corresponding thioamide without affecting the remainder of the molecule.

The oxidation is advantageously accomplished by means of a mercuric salt (e.g. mercuric acetate) or a cuprous salt, in an organic solvent such as a ketone (e.g. acetone), an alcohol, an ester or a carboxylic acid such as, e.g., acetic acid, at a temperature of between 0° and 100° C.

It is also possible to perform the oxidation using methods similar to those described by:

H. J. Kim et al., Synthesis, 11, 970 (1986),

M. T. M. El-Wassimy, Tetrahedron 39 (10), 1729 (1983),

K. A. Jørgensen et al., Tetrahedron 38, (9), 1163 (1982),

A. G. Samuelson et al., Tetrahedron Letters, 27 (33), 3911 (1986).

When it is desired to obtain a product of formula (I) in which X is a radical $N-R_4$ and R and $R_4$ are linked together in such a way as to form, with the neighbouring atoms, an optionally substituted imidazolinyl radical or a hexahydrobenzimidazolyl radical, the diamine may be used either on the thioamide of formula (II) or on an amidine in which $R_4$ is hydrogen.

When it is desired to obtain an amide of formula (I) in which the chain at the 10-position bears an acetyloxy substituent, this substituent can be placed in position from the beginning of the synthesis (i.e. in the preparation of the starting material of formula (V) below) o it can be advantageous to employ a phenothiazine derivative of formula (II) bearing a hydroxy substituent on the chain at the 10-position, isolating the secondary thioamide of formula (I) and then oxidizing this product with mercuric acetate, and separating the expected product by chromatography or crystallization.

According to a further feature of the invention, the amides of formula (I) in which X is oxygen may also be obtained from an acid of formula:

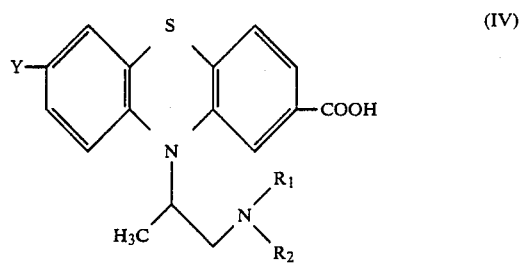

(IV)

in which Y, $R_1$ and $R_2$ are as defined above, by any known method for obtaining a substituted amide from an acid without affecting the remainder of the molecule.

The procedure used employs, in particular, the action of an amine of formula (III) on a reactive derivative of the acid (optionally prepared in situ), e.g. the acid chloride, an activated ester or a mixed anhydride, in an organic solvent such as an ether or a chlorinated solvent (e.g. methylene chloride, chloroform, dichloroethane) or in an amide (dimethylformamide), in the presence of an acid acceptor such as a nitrogenous organic base such as, e.g., a trialkylamine (triethylamine in particular), at a temperature of between $-40°$ and $+40°$ C.

It is also possible to react the amine of formula (III) directly with the acid, working in the presence of a condensing agent such as a carbodiimide (dicylohexylcarbodiimide), N,N'-carbonyldiimidazole or N-hydroxybenzotriazole in an organic solvent as mentioned above, at a temperature as defined above.

It is understood that, in the case where the radical R of the amine of formula (III) contains groups capable of interfering with the reaction, this radical must be protected beforehand. The protective radical introduced is removed after the reaction. In particular, when the radical R contains a hydroxy radical, it is preferable to protect this radical. The protection is accomplished, e.g., in the form of a methoxy or benzyloxy radical, which can be removed, respectively, by treatment with hydrobromic acid or boron tribromide, or by hydrogenolysis in the case of the benzyloxy radical.

According to another feature of the invention, the products of formula (I) in which X is oxygen may also be obtained from a nitrile of formula:

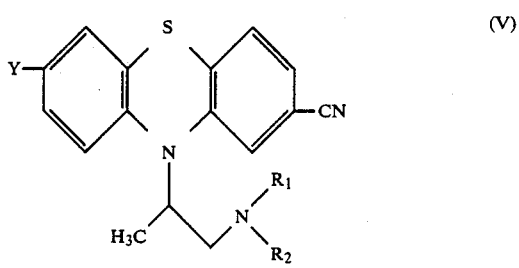

(V)

in which Y, $R_1$ and $R_2$ are as defined above, by any known method for obtaining a substituted amide from a nitrile without affecting the remainder of the molecule.

In particular, an intermediate imidate may be prepared in situ, which is then reacted with a halogenated derivative of general formula:

R - Hal      (VI)

in which R is as defined above and Hal denotes an iodine or bromine atom.

Preferably, the reaction is performed in an alcohol/alcoholate or alcohol/potassium hydroxide mixture, e.g. tert-butanol/potassium tert-butylate, tert-butanol/potassium hydroxide or isobutanol/potassium isobutylate at a temperature of between 50° and 150° C.

It is also possible to work in the presence of a large excess of an amine of formula (III), with or without a solvent, at a temperature of between 150° and 250° C.

Where appropriate, the solvents are advantageously chosen from alcohols (e.g. ethanol, methanol), ethers having a high boiling point, polyethers and aromatic hydrocarbons e.g. toluene, xylene or chlorobenzene).

It is also possible to work according to the method described by S. LINKE, Synthesis, 4, 303 (1978) or according to the method described by G. W. CANNON et al., J. Org. Chem., 18, 516 (1953).

According to another feature of the invention, the carboxamidines of formula (I) in which X is :N-R$_4$, in which R$_4$ is hydrogen and R is as defined above, or R$_4$ forms, with R and atoms to which they are attached, optionally substituted imidazolinyl or hexahydrobenzimidazolyl are also prepared from an imidate of formula:

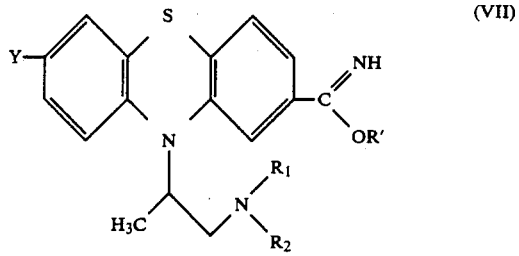

in which Y, R$_1$ and R$_2$ are as defined above and R' is alkyl of 1 to 10 carbon atoms, or from its salt, by the action of an amine of formula (III) or a diamine defined as above, such that R$_4$ and R are defined as above.

The reaction is generally performed in an organic solvent such as an alcohol (e.g. methanol, ethanol) at a temperature of between −10° and 60° C.

According to another feature of the invention, the phenothiazine derivatives of formula (I) in which X is :N-R$_4$ and R forms with R$_4$ an imidazolyl radical optionally substituted by alkyl may also be obtained from a phenothiazine derivative of formula (II) in which X is an NH radical and Y, R$_1$, R$_2$ are defined as above, or from its salt, by the action of an α-halo ketone or α-halo aldehyde, of formula:

in which Hal is halogen and R" and R''', which may be identical or different, each denote hydrogen or alkyl.

The reaction is advantageously performed in an organic solvent such as an alcohol (e.g. methanol, ethanol), an ether (e.g. tetrahydrofuran, diglyme or dioxane) or a halogenated solvent (e.g. methylene chloride, chloroform, 1,2-dichloroethane) at a temperature between 10° C. and the refluxing temperature of the reaction mixture.

Preferably, the halogen atom is chlorine or bromine.

The phenothiazine derivative of formula (II) in which X is sulphur may be obtained from a nitrile of formula (V) by any known method for obtaining a thioamide from a nitrile without affecting the remainder of the molecule.

The procedure is generally performed in an anhydrous basic medium, in the presence of hydrogen sulphide, at a temperature of between 0° and 100° C. The reaction is advantageously performed in the presence of a nitrogenous organic base such as triethylamine, in an organic solvent such as pyridine.

The phenothiazine derivatives of formula (II) in which X is NR$_4$ may be obtained from an imidate of formula (VII), by the action of ammonia when it is desired to obtain an amidine in which R$_4$ is hydrogen, or by the action of cyanamide when it is desired to obtain an amidine in which R$_4$ is cyano, respectively.

The reaction is generally performed in an organic solvent such as an alcohol (e.g. methanol, ethanol) or in an ether (e.g. dioxane, glyme, diglyme) at a temperature of between 0° and 50° C. when ammonia is reacted or at a temperature between 70° and the refluxing temperature of the reaction mixture when cyanamide is reacted.

The acid of formula (IV) may be obtained from a nitrile of formula (V) by any known method for obtaining an acid from a nitrile without affecting the remainder of the molecule. The procedure used employs in particular hydrolysis in an acid or basic medium in an organic solvent at a temperature between 50° C. and the refluxing temperature of the reaction mixture. The reaction is advantageously performed in glycol in the presence of potassium hydroxide.

The nitrile of general formula (V) may be obtained according to the following scheme:

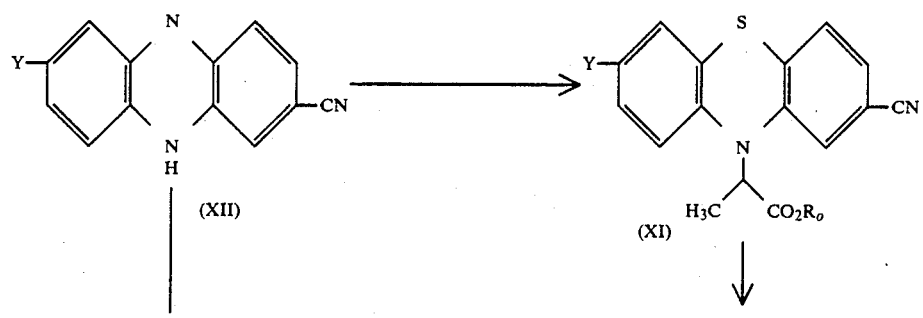

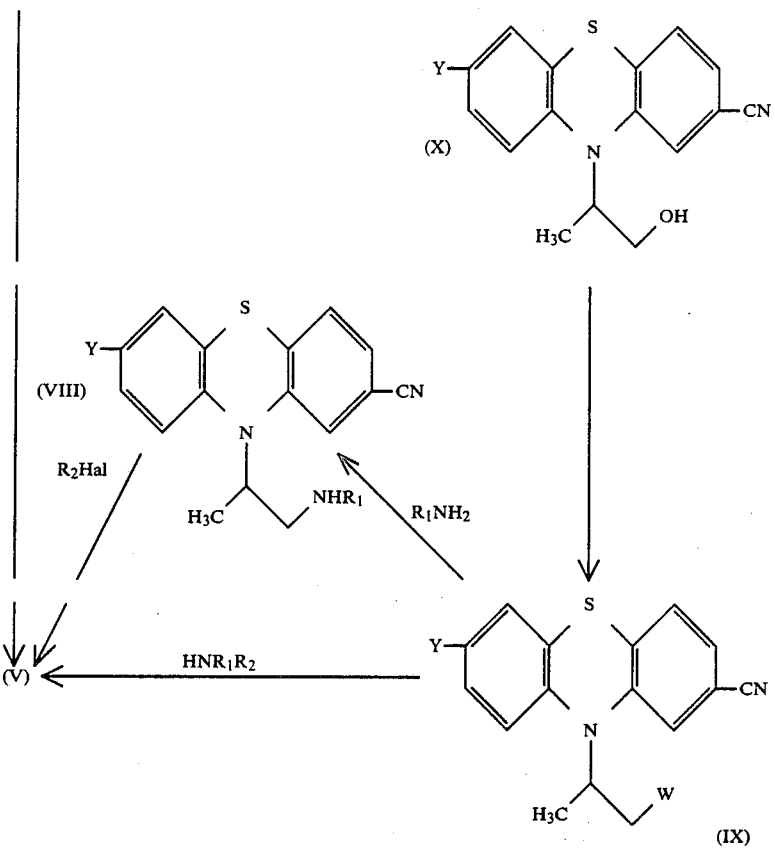

in which W is a p-toluenesulphonyloxy, methylsulphonyloxy or diaryloxyphosphoryloxy residue and $R_0$ is an alkyl radical containing 1 to 4 carbon atoms (e.g. ethyl), and the working conditions of which are defined in greater detail below in Examples 2, 8 to 12, 14, 16, 17, 18, 21, 34, 35, 37, 39, 47, 52, 58 and 88 to 90.

The nitrile of formula (XII) for which Y is a hydrogen atom may be obtained as described in U.S. Pat. No. 2,877,224.

The nitrile of formula (XII) for which Y is a chlorine or bromine atom may be obtained by the action of a halogenating agent on the phenothiazine derivative of formula (XII) for which Y is a hydrogen atom.

The halogenation is preferably performed by the action of the halogen (chlorine, bromine) or sulphuryl chloride, in the presence of aluminium trichloride, in an organic solvent such as a halogenated hydrocarbon (e.g. dichloroethane) or an ether, at a temperature of between −50° C. and the refluxing temperature of the reaction mixture.

When it is desired to obtain a product of formula (XII) for which Y is a fluorine atom, the procedure is performed according to the method described in GB Patent Application No. 2,132,194.

The imino ether of formula (VII) may be obtained by the treatment of a nitrile of formula (V) in an acid medium with an alcohol of formula: ps

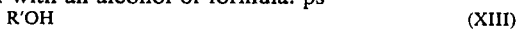

R'OH        (XIII)

in which R' is defined as above.

In general, the procedure is performed in the presence of hydrochloric acid, at a temperature of between −10° and 60° C.

The isomers of the products of general formula (I) may be obtained according to known methods.

The procedure used employs, in particular, the preparation of the isomer of the phenothiazine derivative of general formula (X), which is then converted to a phenothiazine derivative of formula (I) by the methods described above.

The optically active derivative of the product of formula (X) is obtained, in particular, by the preparation of a diacid ester, formation of an optically active salt, separation of the isomers by crystallization and saponification of the isomer obtained.

More especially, the ester is obtained by means of a diacid anhydride such as, e.g., phthalic anhydride or maleic or succinic anhydride. The salt is formed by the addition of an optically active amine, e.g., (+)-1-phenylethylamine or (−)-1-phenylethylamine.

In the Examples which follow, the phenothiazine derivatives prepared from the alcohol of formula (X) for which the optical rotation in chloroform solution is positive are referred to as the D series; the phenothiazine derivatives prepared from the alcohol of formula (X) for which the optical rotation in chloroform solution is negative are referred to as the L series.

The products of formula (I) may be purified by chromatography or crystallization.

The phenothiazine derivatives of formula (I) may be converted into addition salts with acids, by the action of an acid in an organic solvent such as an alcohol, a ketone, an ester, an ether or a chlorinated solvent. The salt precipitates, where appropriate after concentration of its solution; it is separated by filtration or decantation.

As pharmaceutically acceptable salts, there may be mentioned the addition salts with inorganic acids such as hydrochlorides, hydrobromides, sulphates, nitrates or phosphates, or organic acids such as acetates, propionates, succinates, maleates, fumarates, methanesulphonates, p-toluenesulphonates, isethionates or substitution derivatives of these compounds.

The phenothiazine derivatives of general formula (I) exhibit an especially advantageous analgesic and diuretic activity on account of their preferential affinity for the Kappa receptors and their low toxicity.

They have been shown, in effect, to be active at concentrations of between 1 and 500 nM in the method of tritiated ethylketocyclazocine binding in guinea pig cerebellum homogenates, based on the technique of L. E. Robson et al., Opioid binding sites of the Kappa type in guinea pig cerebellum, Neuroscience, 12, 621 (1984).

They have also been shown to be active in the technique of inhibition of the contractions induced by electrical stimulation on isolated guinea pig ileum (based on W. D. M. Paton, Brit. J. Pharmacol., 11, 119 (1957)) at concentrations of between 1 and 300 nM.

Products having an affinity for the Kappa receptors manifest a diuretic effect [J. D. Leander, The Journal of Pharmacology and Experimental Therapeutics, 224 (1), 89 (1983) and G. R. Slizgi et al., The Journal of Pharmacology and Experimental Therapeutics 230 (3), 641 (1984)]. It has also been demonstrated, by studying several products, that the products of general formula (I) manifest a significant diuretic effect in rats, at doses of between 1 and 20 mg/kg administered subcutaneously, in the technique described by J. D. Leander (reference above).

Moreover, the acute toxicity ($LD_{50}$) of the products of formula (I) in mice is low compared with the doses at which they are used. Their $LD_{50}$ is generally between 30 to 100 mg/kg p.o. or even much greater than 100 mg/kg p.o.

Of special importance are the products of general formula (I) in which:

Y is hydrogen or halogen, $R_1$ and $R_2$, which may be identical or different, each denote alkyl of 1 and 3 carbon atoms in a straight or branched chain, or alkyl of 1 or 2 carbon atoms substituted by cycloalkyl, hydroxy or acetyloxy, or $R_1$ and $R_2$ form, together with the nitrogen atom to which they are attached, a saturated or partially unsaturated 4- to 7-membered heterocycle optionally substituted by 1 or 2 methyl radicals or alkyl radicals of 1 or 2 carbon atoms substituted by hydroxy or acetyloxy, and either X denotes oxygen, sulphur, or :$NR_4$, and R denotes a 4- to 6-membered cycloalkyl or phenyl, or a radical -$CH_2R_3$, in which $R_3$ is hydrogen, a linear or branched alkyl radical of 1 to 5 carbon atoms, alkenyl or alkynyl of 2 to 4 carbon atoms, 3- to 6-membered cycloalkyl, phenyl which is unsubstituted or substituted (with 1 or 2 halogen atoms or with a hydroxy, methyl, methoxy, trifluoromethyl or nitro radical) or furyl, thienyl or pyridyl, and $R_4$ is hydrogen or cyano, provided that X cannot denote oxygen when, simultaneously, $R_3$ is hydrogen or alkyl, $R_1$ and $R_2$ are alkyl or together form an unsubstituted nitrogenous heterocycle, and Y is hydrogen, or X is :$N-R_4$ and R forms, with $R_4$ and the atoms to which they are attached, imidazolyl optionally substituted with 1 or 2 methyl or ethyl radicals or hexahydrobenzimidazolyl.

Among these products, more especial activity is to be found in the phenothiazine derivatives of formula (I) for which:

Y is hydrogen or halogen, $R_1$ and $R_2$, which may be identical or different, denote alkyl radicals 1 or 2 carbon atoms, but are not both methyl, or acetyloxyalkyl in which the alkyl has 1 or 2 carbon atoms, or form, together with the nitrogen atom to which they are attached, a saturated or partially unsaturated 4- to 7-membered heterocycle which is unsubstituted or substituted with 1 or 2 methyl, hydroxymethyl or acetyloxymethyl radicals, and - either the symbol X denotes oxygen, sulphur or :$N-R_4$ and R denotes 4- to 6-membered cycloakyl —$CH_2R_3$ in which $R_3$ is linear or branched alkyl of 1 to 5 carbon atoms, alkenyl or alkynyl of 2 to 4 carbon atoms, 3- to 6-membered cycloalkyl, or phenyl which is optionally substituted (with 1 or 2 halogen atoms or with a hydroxy, methyl, methoxy, trifluoromethyl or nitro radical), or furyl, thienyl or pyridyl, and $R_4$ is hydrogen or cyano, provided that X cannot denote oxygen when, simultaneously, $R_3$ is hydrogen or alkyl, $R_1$ and $R_2$ are alkyl or together form an unsubstituted nitrogenous heterocycle and Y is hydrogen, or X is a :$N-R_4$ and R forms, with $R_4$ and the atoms to which they are attached, imidazolyl optionally substituted with 1 alkyl radical containing 1 or 2 carbon atoms or hexahydrobenzimidazolyl, in the form of a mixture of isomers or in the form of their isomers of the L series. The following products are of particular interest:

cyclobutylmethyl-10-[1-(1-pyrrolidinyl)-2-propyl]-2-phenothiazinecarboxamide;

N-(3-chlorobenzyl)-10-[1-(1-pyrrolidinyl)-2-propyl]-2-phenothiazinecarboxamide;

N-(2-chlorobenzyl)-10-[1-(1-pyrrolidinyl)-2-propyl]-2-phenothiazinecarboxamide;

N-(2-fluorobenzyl)-10-[1-(1-pyrrolidinyl)-2-propyl]-2-phenothiazinecarboxamide;

N-benzyl-10-[1-(1-pyrrolidinyl)-2-propyl]-2-phenothiazinecarboxamide.

The examples which follow, given without implied limitation, illustrate the present invention.

EXAMPLE 1

A solution of 10-[(2RS)-1-(N-methyl-N-ethylamino)-2-propyl]-2-phenothiazinecarbothioamide (1.3 g) and a 33% strength solution (52 cc) of methylamine in ethanol in absolute ethanol (26 cc) is heated for 16 hours to a temperature in the region of 100° C. After cooling, the mixture is concentrated to dryness under reduced pressure (30 mm Hg; 4 kPa) at 40° C. The residue is dissolved in ethyl acetate (100 cc) and the solution is washed with distilled water (2×50 cc), dried over magnesium sulphate, filtered and concentrated to dryness under reduced pressure (30 mm Hg; 4 kPa) at 40° C. The gummy yellow residue (1.1 g) is purified by chromatography on a column (height: 20 cm; diameter: 3 cm) of silica gel (0.04–0.063 mm) with a slight excess pressure of nitrogen (40 kPa), eluting successively with a mixture (97.5:2.5 by volume) (500 cc) of methylene chloride and methanol and then a mixture (95:5 by volume) (500 cc) of methylene chloride and methanol and collecting 25-cc fractions. Fractions 13 to 28 are combined and concentrated to dryness under reduced pressure (30 mm Hg; 4 kPa) at 40° C. The residual yellow oil (0.55 g) is dissolved in isopropyl ether (100 cc) and ethyl acetate (10 cc) and the solution is treated with stirring with a 3 N solution (0.5 cc) of hydrochloric acid in ethyl ether. The solid formed is drained, washed with isopropyl ether (5 cc) and dried under reduced pressure (5 mm Hg; 0.68 kPa) at 40° C. N-Methyl-10-[(2RS)-1-(N-methyl-N-ethylamino)-2-propyl]-2-phenothiazinecarbothioamide hydrochloride (0.58 g) is thereby obtained in the form of yellow crystals, m.p. 140°-145° C. (melts forming a paste).

NM(250 MHz, DMSO, δ in ppm, J in Hz):

In solution in DMSO, two forms are observed, due to salification of the nitrogen.

1.07 and 1.21 (2T, J=7, 3H, —NCH$_2$CH$_3$); 1.85 (D, J=7, 3H, —CH$_3$); 2.8 (Cx, 3H, >N—CH$_3$); 3.1 g (D, J=5, 3H —CSNH—CH$_3$); approximately 3.20 (Mt, 2H, >N—CH$_2$—CH$_3$); 3.51 and 3.78 (2 Mt, 1H each, >N—CH$_2$—); 4.86 (Cx, 1H, >N—CH<); 7.05 to 7.4 (Mt, 5H, aromatic); 7.52 (broad D, J=8, 1H, —H at 3-position); 7.65 (broad S, 1H, —H at 1-position); 10.37 and 10.63 (2Cx, 1H each, —N$^+$ and —CSNH—).

Infrared spectrum (KBr), characteristic bands in cm$^{-1}$: 3200, 2970, 2650, 2480, 1590, 1535, 1460, 880, 820, 755.

EXAMPLE 2

A mixture of a 33% strength solution (10 cc) of methylamine in absolute ethanol and 10-[(2RS)-1-diethylamino-2-propyl]-2-phenothiazinecarbothioamide (2 g) in absolute ethanol (15 cc) is brought for 24 hours to a temperature in the region of 100° C. After cooling, the mixture is concentrated to dryness under reduced pressure (30 mm Hg; 4 kPa) at 40° C. The residue is taken up with ethyl acetate (100° C.), washed with distilled water (2×50 cc), dried over magnesium sulphate in the presence of charcoal 3S, filtered and concentrated to dryness under reduced pressure (30 mm Hg; 4 kPa) at 40° C. The residual orange oil (1.7 g) is purified by chromatography on a column (height: 25 cm; diameter: 2.5 cm) of silica gel (0.04-0.063 mm) with a slight excess pressure of nitrogen (40 kPa), eluting successively with ethyl acetate (750 cc) and with a mixture (90:10 by volume) (500 cc) of ethyl acetate and ethanol and collecting 50-cc fractions. Fractions 2 to 7 are combined and concentrated to dryness under reduced pressure (30 mm Hg; 4 kPa) at 40° C. The residual brown oil (1.3 g) is dissolved at 50° C. in ethanol (3 cc) and the solution obtained is poured into a solution of fumaric acid (0.39 g) in ethanol (3 cc), with stirring and at a temperature in the region of 60° C. After 1 hour with stirring at a temperature in the region of 5° C., the solid formed is drained, washed with ethanol (3×1 cc) and dried in the air. This solid is redissolved in ethanol (20 cc) under reflux and then stored for 1 hour at a temperature in the region of 5° C. The solid formed is drained, washed with ethanol (3×1 cc) and dried under reduced pressure (5 mm Hg; 0.68 kPa) at 40° C. 10-[(2RS)-1-diethylamino-2-propyl]-N-methyl-2-phenothiazinecarbothioamide acid fumarate (1.15 g) is thereby obtained in the form of a yellow solid, m.p. 224° C.;

Proton NM(250 MHz, DMSO, δ in ppm, J in Hz):

0.9 (T, J=7, 6H, —N(CH$_2$CH$_3$)$_2$); 1.65 (D, J=7, 3H, —CH$_3$); 2.6 (Mt, 4H, —N(CH$_2$CH$_3$)$_2$); 2.85 (DD, J=14 and 6, 1H of >N—CH$_2$); 3.14 (DD, J=14 and 7.5, 1H, 1H of >NCH$_2$—); 3.12 (D, J=4.5, 3H, >N—CH$_3$); 4.27 (Mt, J=7.5, 7 and 4.5, 1H, >N—CH<); 6.58 (S, 2H, fumarate —CH=CH—); 6.9 to 7.25 (Mt, 5H, aromatic); 7.3 (DD, J=8 and 1, 1H, —H at 3-position); 7.65 (D, J=1, 1H, —H at 1-position); 10.28 (Q, J=4.5, 1H, —CSNH—).

Infrared spectrum (KBr), characteristic bands in cm$^{-1}$: 3230, 2980, 2650, 2490, 1690, 1615, 1590, 1540, 1465, 980, 750, 645.

A solution of 10-[(2RS)-1-diethylamino-2-propyl]2-phenothiazinecarbonitrile (5.66 g) and triethylamine (2.35 cc) in pyridine (113 cc) is treated with hydrogen sulphide for 1 hour and then stirred for 3 days at a temperature in the region of 20° C. The greenish solution obtained is purged with nitrogen, poured into distilled water (500 cc) and extracted with ethyl acetate (2×500 cc). The combined organic phases are washed successively with distilled water (2×200 cc) and with saturated aqueous sodium chloride solution (200 cc), dried over magnesium sulphate, filtered and concentrated to dryness under reduced pressure (30 mm Hg, 4 kPa) at 40° C. The residual orange oil (9.1 g) is purified by chromatography on a column (height: 25 cm, diameter: 3 cm) of silica gel (0.04-0.063 mm) with a slight excess pressure of nitrogen (40 kPa), eluting with ethyl acetate (750 cc) and collecting 50-cc fractions. The combined fractions 4 to 10 are concentrated to dryness under reduced pressure (30 mm Hg; 4 kPa) at 40° C. 10-[2RS)-1-diethylamino-2-propyl]-2-phenothiazinecarbothioamide (6.2 g) is thereby obtained in the form of an orange oil.

10-[(2RS)-1-Diethylamino-2-propyl]-2-phenothiazinecarbonitrile may be prepared in the following manner:

A solution of 1-diethylamino-2-propanol (78.7 g) in N,N-dimethylformamide (60 cc) is added dropwise in the course of 55 minutes to a solution of p-toluenesulphonyl chloride (114.4 g) in N,N-dimethylformamide (600 cc). The mixture is stirred at 25° C. for 12 hours.

Sodium hydride (19.2 g; in 50% strength dispersion in vaseline) is added in the course of 20 minutes to a solution of 2-phenothiazinecarbonitrile (44.86 g) in N,N-dimethylformamide (600 cc). The mixture obtained is then heated to 110° C., after which the solution of 1-diethylamino-2-propyl p-toluenesulphonate hydrochloride prepared above is added in the course of 35 minutes. The reaction mixture is stirred at 110° C. for 7 hours and then diluted, after cooling, with ethyl acetate (2 liters). The mixture is washed with distilled water (5×1 liter). The organic phase is extracted with 4N hydrochloric acid (240 cc) and the acid aqueous phase is washed with ethyl acetate (750 cc) and then alkalinized with 5N caustic soda (250 cc). The alkaline medium is then extracted with ethyl acetate (1250 cc). The organic phase is washed with distilled water (3×300 cc), dried over magnesium sulphate, filtered and concentrated to dryness under reduced pressure (30 mm Hg; 4 kPa) at 40° C. The residue is stirred in the presence of ethyl ether (100 cc); a precipitate forms and this is filtered off, and the filtrate is purified by chromatography on a column of silica gel (0.2-0.063 mm) (height: 82 cm; diameter: 4.5 cm), eluting with an 80:20 (by volume) mixture (7 liters) of cyclohexane and ethyl acetate and collecting 100-cc fractions. After concentration to dryness under reduced pressure (30 mm Hg; 4 kPa) at 50° C., 10-[(2RS)-1-diethylamino-2-propyl]-2-phenothiazinecarbonitrile (6.76 g) is obtained from fractions 4 to 9, and a mixture (8.5 g) of 10-[(2RS)-1-diethylamino-2-propyl]-2-phenothiazinecarbonitrile and 10-[(1RS)-2-diethylamino-1-propyl]-2-phenothiazinecarbonitrile is obtained from fractions 10 to 22. The mixture is purified by chromatography on column of silica gel (0.2-0.063 mm) (height: 67 cm; diameter: 3.0 cm), eluting with an 85:15 (by volume) mixture (3 liters) of cyclohexane and ethyl acetate and collecting 50-cc fractions. Fractions 22 to 29 are combined and concentrated to dryness at 50° C. under reduced pressure (30 mm Hg; 4 kPa) to give 10-[(2RS)-1-diethylamino-2-propyl]-2-phenothiazinecarbonitrile (2.76 g).

The proton NMR spectrum (250 MHz, DMSO, δ in ppm, J in Hz):

0.85 (T, J=7.5, 6H, —N(CH$_2$CH$_3$)$_2$; 1.57 (D, J=7, 3H, —CH$_2$); 2.25 to 2.57 (Mt, approximately 4H, —N(CH$_2$CH$_3$)$_2$); 2.63 (DD, J=13.5 and 6, 1H, 1H of >NCH$_2$—); 2.98 (DD, J=13.5 and 6.5, 1H, 1H of <N—CH$_2$—); 4.08 (Mt, J=7, 6.5 and 6, 1H >N—CH>); 6.9 to 7.25 (Mt, 5H, aromatic); 7.31 (DD, J=8 and 1, 1H, —H at 3-position), 7.59 (D, J=1, 1H, —H at 1-position).

EXAMPLE 3

A solution of 10-[(2RS)-1-diethylamino-2-propyl]2-phenothiazinecarbothioamide (2.9 g) and ethylamine (7.8 cc) in absolute ethanol (40 cc) is saturated with hydrogen sulphide and then heated for 16 hours to a temperature in the region of 100° C. After cooling, the yellow solution obtained is concentrated to dryness under reduced pressure (30 mm Hg; 4 kPa) at 40° C. The oily orange residue is purified by chromatography on a column (height: 25 cm; diameter: 3 cm) of silica gel (0.04–0.063 mm) with a slight excess pressure of nitrogen (40 kPa), eluting with a mixture (90-10 by volume) (500 c ) of ethyl acetate and ethanol and collecting 60-cc fractions. Fractions 3 to 5 are combined and concentrated to dryness under reduced pressure (30 mm Hg; 4 kPa) at 40° C. The residual orange oil (2.38 g) is dissolved at 50° C. in ethanol (6 cc) and poured into a solution at 60° C. of fumaric acid (0.69 g) in ethanol (6 cc), with stirring. After 1 hour's stirring at a temperature in the region of 5° C., the solid formed is drained, washed successively with ethanol (3×2 cc) and with carbon disulphide (25 cc and then 5 cc) and dried under reduced pressure (5 mm Hg; 0.68 kPa).

10-[(2RS)-1-Diethylamino-2-propyl]-N-ethyl-2-phenothiazinecarbothioamide acid fumarate (2.2 g) is thereby obtained in the form of a yellow solid, m.p. 194° C.

Proton NMR(250 MHz, DMSO, δ in ppm, J in Hz):
0.90 (T, J=7, 6H, —N(CH$_2$C$_3$)$_2$); 1.23 (T, J=7, 3H, —NH—CH$_2$—CH—$_3$); 1.65 (D, J=7, 3H, —CH$_3$); 2.6 ( Mt, 4H, —N(CH$_2$CH$_3$)$_2$); 2.84 (DD, J=13.5 and 5.5, 1H, 1H of >N—CH$_2$—); 3.13 (DD, J=13.5 and 7.5, 1H, 1H of >N—CH$_2$—); 3.7 (Mt, —CSNH—CH$_2$—); 4.26 (Mt, J=7.5, 7 and 5.5, 1H, >N—CH<); 6.6 (S, 2H, fumarate —CH=CH—); 6.9 to 7.25 (Mt, 5H, aromatic); 7.28 (DD, J=8 and 1, 1H, —H at 3-position); 7.63 (D, J=1, 1H, —H at 1-position); 9.25 (T, J=5, 1H, —CSNH—).

Infrared spectrum (KBr), characteristic bands in cm$^{-1}$: 3240, 2980, 2940, 2500, 1690, 1590, 1535, 1465, 975, 870, 800, 750, 640.

EXAMPLE 4

A mixture 10-[(2RS)-1-dimethylamino-2-propyl]-2-phenothiazinecarbothioamide methanesulphonate (4.4 g) and propylamine (12.5 cc) in absolute ethanol (50 cc) is heated for 22 hours to a temperature in the region cf 100° C. After cooling, the mixture is concentrated to dryness under reduced pressure (30 mm Hg; 4 kPa) at 40° C. The residue is taken up with methylene chloride (200 cc) and the solution obtained is washed with distilled water (2×50 cc), dried over magnesium sulphate, filtered and concentrated to dryness under reduced pressure (30 mm Hg; 4 kPa) at 40° C. The residual orange gum is purified by chromatography on a column (height: 25 cm; diameter: 4 cm) of silica gel (0.04–0.063 mm) with a slight excess pressure of nitrogen (40 kPa), eluting with a mixture (75:25 by volume) (1 liter) of ethyl acetate and ethanol and collecting 60-cc fractions. Fractions 5 to 10 are combined and concentrated to dryness under reduced pressure (30 mm Hg; 4 kPa) at 40° C. The gummy orange residue (3.3 g) is dissolved in ethyl ether (100 cc) and treated, with stirring at a temperature in the region of 5° C., with a 3.3N solution (2.4 cc) of hydrochloric acid in ethyl ether. The precipitate formed is drained, washed with ethyl ether (3×10 cc) and dried under reduced pressure (5 mm Hg; 0.68 kPa) at 40° C. 10-[(2RS)-1-dimethylamino-2-propyl]-N-propyl-2-phenothiazinecarbothioamide hydrochloride (2.95 g) is thereby obtained in the form of a yellow solid, m.p. 130° C. (melts forming a paste).

Proton NMR(250 MHz, DMSO, δ in ppm, J in Hz):
0.94 (T, J=7.5, 3H, —(CH$_2$)$_2$CH$_3$); 1.71 (Mt, 2H, propyl —CH$_2$—CH$_3$); 1.76 (D, J=7, 3H, —CH$_3$); 2.8 (S, 6H, —N(CH$_3$)$_2$); 3.53 (DD, J=14 and 4.5, 1H, 1H of >N—CH$_2$—) 3.66 (Mt, 2H, —CSNH—CH$_2$—); 3.75 (DD, J=14 and 8, 1H, 1H of >N—CH$_2$); 4.78 (Mt, J=8, 7 and 4.5, 1H, >N—CH<); 7 to 7.35 (Mt, 5H, aromatic); 7.43 (DD, J=8 and 1, 1H, —H at 3-position); 7.55 (D, J=1, 1H, —H at 1-position); 10.5 (T, J=5, 1H, —CSNH—); 10.53 (Cx, 1H, —NH$^+$).

Infrared spectrum (KBr), characteristic bands in cm$^{-1}$:
3200, 2960, 2930, 2870, 2660, 2510, 2470, 1590, 1530, 1460, 880, 825, 750.

EXAMPLE 5

A mixture of 10-[(2RS)-1-(N-methyl-N-ethylamino)-2-propyl]-2-phenothiazinecarbothioamide (2.4 g) and propylamine (8.27 cc) in ethanol (48 cc) is heated for 16 hours to a temperature in the region of 100° C. After cooling, the mixture is concentrated to dryness under reduced pressure (30 mm Hg; 4 kPa) at 40° C. The residual brown oil (3 g) is purified by chromatography on a column (height: 25 cm; diameter: 4 cm) of silica gel (0.04–0.063 mm) with a slight excess pressure of nitrogen (40 kPa), eluting with a mixture (95:5 by volume) (2 liters) of methylene chloride and methanol and collecting 60-cc fractions. Fractions 8 to 20 are combined and concentrated to dryness under reduced pressure (30 mm Hg; 4 kPa) at 40° C. The residual oil (1.68 g) is dissolved in ethyl ether (50 cc) in the presence of charcoal 3S. The mixture is filtered and the yellow filtrate is treated, with stirring, with a 3.3N solution (1.3 cc) of hydrochloric acid in ethyl ether, and stirring is continued for 2 hours at a temperature in the region of 20° C. The precipitate formed is drained, washed with ethyl ether (5 cc) and dried under reduced pressure (5 mm Hg; 0.68 kPa) at 35° C. 10-[(2RS)-1-(N-methyl-N-ethylamino)-2-propyl]-N-propyl-2-phenothiazinecarbothioamide hydrochloride (1.35 g) is thereby obtained in the form of a yellow solid, m.p. 110°–115° C. (melts forming a paste).

Proton NMR(250 MHz, DMSO, δ in ppm, J in Hz):

In solution in DMSO, two forms are observed, due to salification of the nitrogen; this phenomenon disappears on adding CD$_3$COOD.

0.97 (T, J=7.5, 3H, —(CH$_2$)$_2$CH$_3$; 1.06 and 1.20 (2T, J=7.5, 3H, >NCH$_2$CH$_3$); 1.74 (Mt, 2H, —CH$_2$—CH$_2$—CH$_3$); 1.82 (Mt, 3H, —CH$_3$); 2.8 (Mt, 3H, >N—CH$_3$); 3.18 (Mt, 2H, >N—CH$_2$—CH$_3$); 3.54 and 3.80 (2Mt, 1H each, >N—CH₂—); 3.7 (Mt, 2H, —CSNH—CH₂—); 7.05 to 7.4 (Mt, 5H, aromatic); 7.45 (broad D, J=8, 1H, H at 3-position); 7.6 (broad S, 1H, —H at 1-position); 10.31 and 10.52 (2Mt, 1H each, —NH⁺ and —CSNH—).

Infrared spectrum (KBr), characteristic bands in cm⁻¹:

3210, 2970, 2940, 2880, 2650, 2480, 1590, 1535, 1465, 880, 820, 750.

EXAMPLE 6

A solution of 10-[(2RS)-1-diethylamino-2-propyl]2-phenothiazinecarbothioamide (2.1 g) and propylamine (7 cc) in absolute ethanol (30 cc) is saturated with hydrogen sulphide and then heated for 16 hours to a temperature in the region of 100° C. After cooling, the orange solution obtained is concentrated to dryness under reduced pressure (30 mm Hg; 4 kPa) at 40° C. The residue is taken up with distilled water (100 cc) and the mixture is extracted successively with ethyl acetate (200 cc and then 100 cc). The combined organic phases are washed with saturated aqueous sodium chloride solution (100 cc), dried over magnesium sulphate, filtered and concentrated to dryness under reduced pressure (30 mm Hg; 4 kPa) at 40° C. The oily orange residue (2.2 g) is purified by chromatography on a column (height: 25 cm; diameter: 3 cm) of silica gel (0.04–0.063 mm) with a slight excess pressure of nitrogen (40 kPa), eluting with ethyl acetate (500 cc) and collecting 50-cc fractions. Fractions 2 to 6 are combined and concentrated to dryness under reduced pressure (30 mm Hg; 4 kPa) at 40° C. The residual yellow oil (2 g) is dissolved in isopropyl ether (100 cc) and treated, with stirring, with a 3.3N solution (1.45 cc) of hydrochloric acid in isopropyl ether. After 15 minutes' stirring at a temperature in the region of 20° C., the solid formed is drained, washed with isopropyl ether (3×20 cc) and dried under reduced pressure (5 mm Hg; 0.68 kPa) at 40° C. 10-[(2RS)-1-diethylamino-2-propyl]-N-propyl-2-phenothiazinecarbothioamide hydrochloride (1.7 g) is thereby obtained in the form of a yellow solid, m.p. 120° C. (melts forming a paste).

Proton NMR(250 MHz, DMSO, δ in ppm, J in Hz):

0.95 (T, J=7, 3H, —(CH₂)₂CH₃); 1.02 and 1.15 (2T, J=7, 6H, —N(CH₂CH₃)₂); 1.71 (Mt, 2H, —CH₂CH₂CH₃); 1.83 (D, J=7, 3H, —CH₃); 3.17 (Mt, 4H, —N(CH₂CH₃)₂); 3.41 (broad D, J=14, 1H, 1H of N—CH₂—); 3.66 (Mt, 2H, —CSNH—CH₂—); 3.78 (DD, J=14 and 7.5, 1H 1H of >N—CH₂); 4.88 (Mt, 1H, >N—CH<); 7 to 7.35 (Mt, 5H, aromatic); 7.41 (D, J=8, 1H, —H at 3-position); 7.57 (S, 1H, —H at 1-position); 10.43 (Cx, 1H, —NH⁺); 10.52 (T, J=5, 1H, —CSNH—).

Infrared spectrum (KBr), characteristic bands in cm⁻¹:

3200, 2970, 2940, 2880, 2580, 2480, 1590, 1535, 1465, 885, 825, 750.

EXAMPLE 7

A solution of 10-(1-diethylamino-2-propyl)-2-phenothiazinecarbothioamide acid fumarate, L series (0.56 g) and propylamine (1.4 cc) in absolute ethanol (10 cc) is saturated with hydrogen sulphide and heated for 16 hours to a temperature in the region of 100° C. After cooling, the mixture is concentrated to dryness under reduced pressure (30 mm Hg; 4 kPa) at 40° C. The residual orange oil is purified by chromatography on a column (height: 25 cm; diameter: 1 cm) of silica gel (0.04–0.063 mm) with a slight excess pressure of nitrogen (40 kPa), eluting with a mixture (80:20 by volume) (150 cc) of ethyl acetate and cyclohexane and collecting 15-cc fractions. The combined fractions 4 to 7 are concentrated to dryness under reduced pressure (30 mm Hg; 4 kPa) at 40° C. 10-(1-Diethylamino-2-propyl)-N-propyl-2-phenothiazinecarbothioamide, L series (0.5 g) is thereby obtained in the form of a yellow oil. 0.25 g of this product is dissolved in isopropyl ether (25 cc) and a 0.3N solution (2.2 cc) of hydrochloric acid in isopropyl ether is added dropwise, with stirring and at a temperature in the region of 5° C. Stirring is maintained for 1 hour at a temperature in the region of 5° C. The precipitate is drained, washed with isopropyl ether (3×5 cc) and dried under reduced pressure (5 mm Hg; 4 kPa) at 40° C. 10-(1-Diethylamino-2-propyl)-N-propyl-2-phenothiazinecarbothioamide hydrochloride, L series (0.24 g) is thereby obtained in the form of a yellow solid, m.p. 95°–100 C. (melts forming a paste), the NMR characteristics of which are identical to those of the product described in Example 6.

Infrared spectrum (KBr), characteristic bands in cm⁻¹:

3180, 2960, 2930, 2870, 2620, 2580, 2480, 1590, 1530, 460, 1415, 880, 825, 750.

EXAMPLE 8

Propylamine (0.75 cc) is added to a solution of 7-chloro-10-[(2RS)-1-diethylamino-2-propyl]-2-phenothiazinecarbothioamide (0.6 g) in absolute ethanol (5 cc). The mixture is brought to 200° C. for 4 hours and then diluted with ethyl acetate (50 cc), washed with distilled water (2×100 cc), dried over magnesium sulphate and then concentrated to dryness under reduced pressure (30 mm Hg; 4 kPa) at 40° C. The residual solid is purified by chromatography on a column (height: 8.5 cm; diameter: 2 cm) of silica gel (0.6–0.02 mm), eluting with a 20:80 (by volume) mixture (1.5 liters) of ethyl acetate and cyclohexane, collecting 30-cc fractions. Fractions 25 to 36 are combined and concentrated under reduced pressure (30 mm Hg; 4 kPa) to give a brown oil, which is dissolved in ethyl ether (10 cc). 2.2N ethereal hydrochloric acid (2 cc) is added to this solution. The suspension obtained is filtered to give 7-chloro-10-[(2RS)-1-diethylamino-2-propyl]-N-propyl-2-phenothiazinecarbothioamide (0.06 g), m.p. 130° C.

NMR spectrum (250 MHz, DMSO, δ in ppm, J in Hz):

0.92 (T, J=7.5, 3H, propyl —CH₃); 0.97 and 1.16 (2T, J=7.5, 6H, —CH₃ of diethyl at 10-position); 1.7 (Mt, 2H, —CH₂—CH₂CH₃); 1.79 (D, J=7.5, 3H, —CH₃); 3.14 (Cx, 4H, —N(CH₂CH₃)₂); 3.35 (Cx, 1H, 1H of >N—CH₂—); 3.64 (Mt, J=7 and 5, 2H, —CSNH—CH₂—); 3.75 (Cx, 1H, 1H of >N—CH₂—); 4.77 (Cx, 1H, N—CH); 7.1 to 7.45 (Mt, 5H, aromatic); 7.56 (D, J=1, 1H, —H at 1-position); 9.97 (Cx, 1H, —N⁺); 10.44 (T, J=5, 1H, —CSNH—).

Infrared spectrum (KBr), characteristic bands in cm⁻¹:

3200, 2960, 2930, 2870, 2640, 2580, 2480, 1590, 1530, 1460, 1420, 870, 805.

7-Chloro-10-[(2RS)-1-diethylamino-2-propyl]-2-phenothiazinecarbothioamide may be prepared in the following manner:

A mixture of 7-chloro-10-[(2RS)-1-diethylamino-2-propyl]-2-phenothiazinecarbonitrile (55.1 g) and triethylamine (10.4 cc) in anhydrous pyridine (350 cc) is saturated by bubbling hydrogen sulphide in for 5 hours at 25° C. The clear solution obtained is kept stirred for 12 hours at 25° C., and the mixture is then outgassed by bubbling nitrogen through for 90 minutes. The reaction mixture is then diluted with ethyl acetate (1000 cc) and washed with distilled water (5×1000 cc). The organic phase is dried over magnesium sulphate and filtered, and the filtrate is concentrated to dryness under reduced pressure (30 mm Hg; 4 kPa). The residue is purified by chromatography on a column of 0.02-0.6 mm silica gel (height: 31 cm; diameter: 7.5 cm), eluting with an 80:20 (by volume) mixture (30 liters) of cyclohexane and ethyl acetate and collecting 1000 cc-fractions. Fractions 22 to 38 are combined and concentrated under reduced pressure (30 mm Hg; 4 kPa) to give an oil containing the expected product. The oil obtained is purified by chromatography on a column of 0.04-0.06 mm silica gel with a slight excess pressure of nitrogen (40 kPa) (height: 30 cm; diameter: 4.5 cm), eluting with pure ethyl acetate (1.5 liters) and collecting 100-cc fractions. Fractions 8 to 12 are combined and concentrated to dryness under reduced pressure (30 mm Hg; 4 kPa) to give 7-chloro-10-[(2RS)-1-diethylamino-2-propyl]-2-phenothiazinecarbothioamide (1.7 g). An autoclave is charged with (2RS)-2-(7-chloro-2-cyano-10-phenothiazinyl)propyl methanesulphonate (36 g) and ethylamine (200 cc). The mixture is brought to 100° C. for 17 hours. After cooling, the reaction mixture is poured into water (1 liter). The solution is extracted with ethyl acetate (500 cc) and the organic phase is washed with distilled water (2×500 cc). After settling has taken place, the organic phase is dried over magnesium sulphate, filtered and concentrated to dryness at 40° C. to give a brown gum, which is purified by chromatography on a column (height: 50 cm; diameter: 6 cm) of silica (0.06-0.3 mm), eluting with pure ethyl acetate (8 liters) and then with a mixture of ethyl acetate and methanol (97:3 by volume mixture of ethyl acetate and triethylamine) (2 liters) and finally with a mixture (10:90 by volume) (2 liters) of diethylamine and methanol and collecting 500-cc fractions. The fractions 32 to 37 are combined and concentrated to dryness at 40° C. under reduced pressure (30 mm Hg; 4 kPa) to give 7-chloro-10-[ (2RS)-1-ethylamino-2-propyl]-2-phenothiazinecarbonitrile (20 g) in the form of a brown product of meringue-like consistency.

A mixture of 7-chloro-10-[(2RS)-1-ethylamino-2-propyl]-2-phenothiazinecarbonitrile (5 g), iodethane (2.2 cc) and sodium carbonate (2 g) in dimethylformamide (50 cc) is charged, and the mixture is brought for 9 hours to 160° C. After cooling, the reaction mixture is poured into a mixture of distilled water (500 cc) and ethyl acetate (500 cc). The organic phase is separated after settling has taken place, washed with distilled water (4×300 cc), dried over magnesium sulphate, filtered and concentrated to dryness at 40° C. under reduced pressure (30 mm Hg; 4 kPa) to give 7-chloro-10-[(2RS)-1-diethylamino-2-propyl]-2-phenothiazinecarbonitrile (5 g).

EXAMPLE 9

A solution of 10-[(2RS)-1-(N-methyl-N-propylamino)-2-propyl]-2-phenothiazinecarbothioamide acid fumarate (1.6 g) and propylamine (4 cc) in ethanol (32 cc) is heated for 16 hours to a temperature in the region of 100° C. After cooling, the mixture is concentrated to dryness under reduced pressure (30 mm Hg; 4 kPa) at 50° C. The residue is taken up with ethyl ether (200 cc) and the solution obtained is washed with N aqueous sodium hydroxide solution (10 cc), then washed with saturated aqueous sodium chloride (50 cc) dried over magnesium sulphate, filtered and concentrated to dryness under reduced pressure (30 mm Hg; 4 kPa) at 40° C. The residual yellow oil (1.6 g) is purified by chromatography on a column (height: 30 cm; diameter: 3 cm) of silica gel (0.04-0.063 mm) with a slight excess pressure of nitrogen (40 kPa), eluting with a mixture (97:3 by volume) (1 liter) of methylene chloride and methanol and collecting 60-cc fractions. The combined fractions 4 to 9 are concentrated to dryness under reduced pressure (30 mm Hg; 4 kPa) at 40° C. The residual yellow oil (1 g) is dissolved in ethyl ether (100 cc), a 3N solution (1 cc) of hydrochloric acid in ethyl ether is added and the mixture is stirred for 1 hour at a temperature in the region of 20° C. The solid formed is drained, washed with ethyl ether (10 cc) and dried under reduced pressure (5 mm Hg; 0.68 kPa) at 40° C. 10-[(2RS)-1-(N-Methyl-N-propylamino)-2-propyl]-N'-propyl-2-phenothiazinecarbothioamide hydrochloride (0.64 g) is thereby obtained in the form of a yellow solid, m.p. 137°-139° C. (melts forming a paste).

Proton NMR(250 MHz, DMSO, δ in ppm, J in Hz):

In solution in DMSO, two forms are observed, due to salification of the nitrogen.

0.78 and 0.83 (2T, J=7.5, 3H, —N(CH$_2$)$_2$CH$_3$); 0.95 (T, J=7.5, 3H, —(CH$_2$)$_2$CH$_3$); 1.35 to 1.80 (Mt, 2H, —NCH$_2$CH$_2$CH$_3$); 1.75 (Mt, 2H, —CH$_2$CH$_2$CH$_3$); 1.84 (2D, J=7, 3H, —CH$_3$); 2.8 (2D, J=5, 3H, N—CH$_3$); 2.90 to 3.25 (Mt, 2H, >N—CH$_2$—CH$_2$—CH$_3$); 3.53 (broad D, 1H, 1H of >N—CH$_2$); 3.70 (Mt, 2H, —CSNH—CH$_2$—); 3.8 (Mt, 1H, other H of N—CH$_2$—); 4.88 (Mt, 1H, N—CH); 7 to 7.35 (Mt, 5H, aromatic); 7.44 (broad D, J=8, 1H, —H at 3-position); 7.58 (broad S, 1H, —H at 1-position); 10.3 and 10.4 (2Cx, 1H, —NH+); 10.5 (Mt, 1H —CSNH—).

Infrared spectrum (KBr), characteristic bands in cm$^{-1}$: 3190, 2960, 2940, 2880, 2580, 2490, 1590, 1535, 1465, 880, 820, 750.

A solution of 10-[(2RS)-1-(N-methyl-N-propylamino)-2-propyl]-2-phenothiazinecarbonitrile (4.3 g) and triethylamine (1.77 cc) in pyridine (86 cc) is treated with hydrogen sulphide and left stirred for 16 hours at a temperature in the region of 20° C. The green solution obtained is diluted with ethyl acetate (200 cc), washed with distilled water (5×40 cc), dried over magnesium sulphate, filtered and concentrated to dryness under reduced pressure (30 mm Hg; 4 kPa) at 40° C. The residual oil (5.4 g) is purified by chromatography on a column (height: 30 cm; diameter: 5.5 cm) of silica gel (0.04-0.063 mm) with a slight excess pressure of nitrogen (40 kPa), eluting with a mixture (97.5:2.5 by volume) (5 liters) of methylene chloride and methanol and collecting 100-cc fractions. The combined fractions 13 to 44 are concentrated to dryness under reduced pressure (30 mm Hg; 4 kPa) at 40° C. The residual yellow oil (4.37 g) is dissolved in ethanol (12 cc) under reflux and treated, with stirring, with a solution of fumaric acid (1.4 g) in ethanol (15 cc) under reflux. After 2 hours, stirring at a temperature in the region of 5° C., the solid formed is drained, washed with ethanol (5 cc) and dried under reduced pressure (5 mm Hg; 0.68 kPa) at 40° C. 10-[(2RS)-1-(N-Methyl-N-propylamino)-2-propyl]-2-phenothiazinecarbothioamide acid fumarate (4.35 g) is thereby obtained in the form of yellow crystals, m.p. 204° C.

10-[(2RS)-1-(N-Methyl-N-propylamino)-2-propyl]-2-phenothiazinecarbonitrile may be obtained in the following manner:

A suspension of 10-[(2RS)-1-methylamino-2-propyl]-2-phenothiazinecarbonitrile (4.7 g), 1-iodopropane (1.55 cc) and sodium hydrogen carbonate (2 g) in dimethylformamide (47 cc) is heated for 6 hours to a temperature of 140° C. After cooling, the reaction mixture is diluted with ethyl acetate (200 cc), washed with distilled water (4×30 cc), dried over magnesium sulphate, filtered and concentrated to dryness under reduced pressure (30 mm. Hg; 4 kPa) at 40° C. The residual oil (5.2 g) is purified by chromatography on a column (height: 25 cm; diameter: 4 cm) of silica gel (0.04–0.063 mm) with a slight excess pressure of nitrogen (40 kPa), eluting with a mixture (70:30 by volume) (1 liter) of cyclohexane and ethyl acetate and collecting 60-cc fractions. The combined fractions 6 to 14 are concentrated to dryness under reduced pressure (30 mm Hg; 4 kPa) at 40° C. 10-[(2RS)-1-(N-Methyl-N-propylamino)-2-propyl]-2-phenothiazinecarbonitrile (4.4 g) is thereby obtained in the form of a yellow oil.

10-[(2RS)-1-Methylamino-2-propyl]-2-phenothiazinecarbothioamide may be prepared in the following manner:

A solution of (2RS)-2-(2-cyano-10-phenothiazinyl)-1-propyl methanesulphonate (25 g) in toluene (375 cc) is cooled to a temperature in the region of −20° C. and methylamine (50 cc) (condensed to a temperature in the region of −60° C.) is added, and this mixture is then brought to a temperature in the region of 100° C. for 14 hours. After cooling, the mixture is concentrated to dryness under reduced pressure (30 mm Hg; 4 kPa) at 40° C. The residue is taken up with ethyl acetate (750 cc) and the mixture is extracted with N aqueous hydrochloric acid solution (2×500 cc). The combined aqueous phases are washed with ethyl acetate (200 cc), alkalinized with caustic soda (d=1.33) to pH 13 at a temperature in the region of 5° C. and extracted with ethyl acetate (2×500 cc). The combined organic phases are washed successively with distilled water (2×250 cc) and with saturated aqueous sodium chloride solution (250 cc), dried over magnesium sulphate, filtered and concentrated to dryness under reduced pressure (30 mm Hg; 4 kPa) at 40° C. 10-[(2RS)-1-Methylamino-2-propyl]-2-phenothiazinecarbothioamide (19.3 g) is thereby obtained in the form of a yellow oil.

EXAMPLE 10

A mixture of 10-{(2RS)-1-[N-methyl-N-(1-methylethyl)amino]-2-propyl}-2-phenothiazinecarbothioamide hydrochloride (1.6 g) and propylamine (4.8 cc) in absolute ethanol (32 cc) is heated for 16 hours at a temperature in the region of 100° C. After cooling, the mixture is concentrated to dryness under reduced pressure (30 mm Hg; 4 kPa) at 40° C. The residue is dissolved in ethyl ether (100 cc) and the solution obtained is washed with N aqueous sodium hydroxide solution (4 cc) and then with saturated aqueous sodium chloride solution (2×10 cc), dried over magnesium sulphate, filtered and concentrated to dryness under reduced pressure (30 mm Hg; 4 kPa) at 40° C. The residual red-brown gum is purified by chromatography on a column (height: 25 cm; diameter: 3 cm) of silica gel (0.04–0.063 mm) with a slight excess pressure of nitrogen (40 kPa), eluting with a mixture (97:3 by volume) (1 liter) of methylene chloride and methanol and collecting 60-cc fractions. Fractions 6 to 12 are combined and concentrated to dryness under reduced pressure (30 mm Hg; 4 kPa) at 40° C. The residual yellow oil (0.85 g) is dissolved in ethyl ether (50 cc) in the presence of charcoal 3S. The mixture is filtered and a 3N solution (1 cc of hydrochloric acid in ethyl ether is added to the yellow filtrate, and the mixture is stirred for 1 hour at a temperature in the region of 20° C. The solid formed is drained washed with ethyl ether (5 cc) and dried under reduced pressure (5 mm Hg; 0.68 kPa) at 40° C. 10-{(2RS)-1-[N-Methyl-N-(1-methylethyl)amino]-2-propyl}-N-propyl-2-phenothiazinecarbothioamide hydrochloride (0.58 g) is thereby obtained in the form of a yellow solid, m.p. about 140° C. (melts forming a a paste).

Proton NMR (250 MHz, DMSO, δ in ppm, J in Hz):

In solution in DMSO, two forms are observed, due to salification of the nitrogen; this phenomenon disappears on adding CD$_3$COOD.

0.96 and 1.24 (Mt, approximately 9H, —(CH$_2$)$_2$CH$_3$ and —CH(CH$_3$)$_2$); 1.75 (Mt, 2H, —CH$_2$CH$_2$CH$_3$); 1.85 (D, J=7, 3H, —CH$_3$); 2.72 and 2.77 (2D, J=5, 3H in toto, >NCH$_3$); 3.45 to 4 (Mt, 5H, N—CH$_2$—, —CH(CH$_3$)$_2$—, —CSNH—CH$_2$—); 4.92 (Mt, 1H, >N—CH<); 7.05 to 7.68 (Mt, 7H, aromatic); 9.85 −10.10, 10.5 and 10.6 (4Cx, 2H in toto, —NH$^+$ and —CSNH—).

Infrared spectrum (KBr), characteristic bands in cm$^{-1}$:

3200, 2960, 2930, 2870, 2640, 2480, 1590, 1530, 1460, 880, 820, 750.

10-{(2RS)-1-[N-Methyl-N-(1-methylethyl)amino]-2-propyl}-2-phenothiazinecarbothioamide hydrochloride may be prepared in the following manner:

A solution of 10-{(2RS)-1-[N-methyl-N-(1-methylethyl)amino]-2-propyl}-2-phenothiazinecarbonitrile (4.2 g) and triethylamine (1.75 cc) in pyridine (84 cc) is treated with hydrogen sulphide for 1 hour and then stirred for 16 hours at a temperature in the region of 20° C. The reaction mixture is diluted with ethyl acetate (500 cc), washed with distilled water (5×50 cc), dried over magnesium sulphate, filtered and concentrated to dryness under reduced pressure (30 mm Hg; 4 kPa) at 40° C. The residual brown oil (4.9 g) is purified by chromatography on a column (height: 25 cm; diameter: 6 cm) of silica gel (0.04–0.063 mm) with a slight excess pressure of nitrogen (40 kPa), eluting successively with a mixture (97.5:2.5 by volume) (1 liter) of methylene chloride and methanol and then with a mixture (95:5 by volume) (1.5 liters) of methylene chloride and methanol and a mixture (92.5:7.5 by volume) (1 liter) of methylene chloride and methanol and collecting 100-cc fractions. Fractions 18 to 32 are combined and concentrated to dryness under reduced pressure (30 mm Hg; 4 kPa) at 40° C. The residue is dissolved in ethyl acetate (100 cc) in the presence of charcoal 3S. The mixture is filtered and the yellow filtrate is concentrated to dryness under reduced pressure (30 mm Hg; 4 kPa) at 40° C. The oily yellow residue (2.6 g) is dissolved in ethyl ether (100 cc) and a 3N solution (2.35 cc) of hydrochloric acid in ethyl ether is added with stirring, and the stirring is then continued for 1 hour at a temperature in the region of 20° C. The precipitate formed is drained, washed with ethyl ether (2×10 cc) and dried under reduced pressure (5 mm Hg; 0.68 kPa) at 35° C. 10-{(2RS)-1-[N-Methyl-N-(1-methylethyl)amino]-2-propyl}-2-phenothiazinecarbothioamide hydrochloride (2.3 g) is thereby obtained in the form of a yellow solid, m.p. 168°–172° C.

10-{(2RS)-1-[N-Methyl-N-(1-methylethyl)amino]-2-propyl}-2-phenothiazinecarbonitrile may be obtained in the following manner:

A mixture of 10-[(2RS)-1-methylamino-2-propyl]-phenothiazinecarbonitrile (4.55 g), 2-iodopropane (2 cc) and sodium hydrogen carbonate (1.9 g) in dry dimethylformamide (45.5 cc) is heated for 6 hours to a temperature in the region of 140° C. After cooling, the reaction mixture is diluted with ethyl acetate (200 cc), washed with distilled water (4×30 cc), dried over magnesium sulphate, filtered and concentrated to dryness under reduced pressure (30 mm Hg; 4 kPa) at 40° C. The oily yellow residue is purified by chromatography on a column (height: 25 cm; diameter: 4 cm) of silica gel (0.04–0.063 mm) with a slight excess pressure of nitrogen (40 kPa) and with a mixture (97.5:2.5 by volume) (1 liter) of methylene chloride and methanol, and collecting 60-cc fractions. Fractions 4 to 12 are combined and concentrated to dryness under reduced pressure (30 mm Hg; kPa) at 40° C. The oily yellow residue (2.9 g) is purified again by chromatography on a column (height: 25 cm; diameter: 4 cm) of silica gel (0.2–0.063 mm), eluting with a mixture (80:20 by volume) (1 liter) of cyclohexane and ethyl acetate and collecting 60-cc fractions. Fractions 4 to 12 are combined and concentrated to dryness under reduced pressure (30 mm Hg; 4 kPa) at 40° C. 10-{(2RS)-1-[N-Methyl-N-(1-methylethyl) amino]-2-propyl}-2-phenothiazinecarbonitrile (2.2 g) is thereby obtained in the form of a yellow oil.

EXAMPLE 11

A solution of 10-((2RS)-1-[N-ethyl-N-(1-methylethyl)amino]-2-propyl}-2-phenothiazinecarbothioamide (2.1 g) and propylamine (6.7 cc) in absolute ethanol (27 cc) is saturated with hydrogen sulphide and heated for 16 hours to a temperature in the region of 100° C. After cooling, the mixture is concentrated to dryness under reduced pressure (30 mm Hg; 4 kPa) at 40° C. The residual orange oil is purified by chromatography on a column (height: 25 cm; diameter: 4 cm) of silica gel (0.04–0.063 mm) with a slight excess pressure of nitrogen (40 kPa), eluting with a mixture (50:50 by volume) (1 liter) of ethyl acetate and cyclohexane and collecting 60-cc fractions. The combined fractions 7 to 14 are concentrated to dryness under reduced pressure (30 mm Hg; 4 kPa) at 40° C. The residual orange oil (0.7 g) is dissolved in isopropyl ether (100 cc) and then treated, dropwise, with stirring and at a temperature in the region of 5° C., with a 0.156N solution (10.48 cc) of hydrochloric acid in isopropyl ether. After 1 hour's stirring at a temperature in the region of 5° C., the solid formed is drained, washed with isopropyl ether (3×10 cc) and dried under reduced pressure (5 mm Hg; 0.68 kPa) at 40° C. 10-((2RS)-1-[N-Ethyl-N-(1-methylethyl)amino]-2-propyl}-N-propyl-2-phenothiazine carbothioamide hydrochloride (0.7 g) is thereby obtained in the form of a yellow solid, m.p. 109° C.

Proton NMR (250 MHz, DMSO, δ in ppm, J in Hz):

In solution in DMSO, two forms are observed, due to salification of the nitrogen.

0.89 and 1.33 (2D, J=7.5, 3H, 1 CH$_3$ of isopropyl); 0.97 (T, J=7.5, 3H, —(CH$_2$)$_2$CH$_3$); 1.10 and 1.29 (2T, J=7.5, 3H, —NCH$_2$CH$_3$); 1.21 (Mt, 3H, 1 CH$_3$ of isopropyl); 1.73 (Mt, 2H, —CH$_2$CH$_2$CH$_3$); 1.89 (D, J=7, 3H, —CH$_3$); 3.05 to 3.35 (2Mt, 2H, >N—CH$_2$CH$_3$); 3.5 to 3.9 (Mt, 3H, >N—CH< and >N—CH$_2$—); 3.68 (Mt, 2H, —CSNH—CH$_2$—); 4.9 (Mt, 1H, >N—CH—); 7.05 to 7.35 (Mt, 5H, aromatic); 7.42 (broad D, J=8, 1H, —H at 3-position); 7.6 (broad S, 1H, —H at 1-position); 9.68 and 9.89 (2Cx, 1H, —NH+); 10.5 (Mt, 1H, —CSNH—).

10-{(2RS)-1-[N-Ethyl-N-(1-methylethyl)amino]-2-propyl}-2-phenothiazinecarbothioamide may be prepared in the following manner:

A solution of 10-{(2RS)-1-[N-ethyl-N-(1-methylethyl)amino]-2-propyl}-2-phenothiazinecarbonitrile (2.3 g) and triethylamine in anhydrous pyridine (46 cc) is treated with hydrogen sulphide and stirred for 16 hours at a temperature in the region of 20° C. The greenish solution obtained is purged with nitrogen, poured into distilled water (200 cc) and extracted with ethyl acetate (200 cc and then 100 cc). The combined organic phases are washed with distilled water (3×100 cc), dried over magnesium sulphate, filtered and concentrated to dryness under reduced pressure (30 mm Hg; 4 kPa) at 40° C. The residual yellow oil (4 g) is purified by chromatography on a column (height: 25 cm; diameter: 4 cm) of silica gel (0.04–0.063 mm) with a slight excess pressure of nitrogen (40 kPa), eluting with a mixture (75:25 by volume) (750 cc) of ethyl acetate and cyclohexane and collecting 60-cc fractions. The combined fractions 6 to 10 are concentrated to dryness under reduced pressure (30 mm Hg; 4 kPa) at 40° C. 10-((2RS)-1-[N-Ethyl-N-(1-methylethyl)-amino]-2-propyl}-2-phenothiazinecarbothioamide (2.5 g) is thereby obtained in the form of a yellow oil.

10-{(2RS)-1-[N-Ethyl-N-(1-methylethyl)amino]-2-propyl}-2-phenothiazinecarbonitrile may be prepared in the following manner:

A suspension of 10-[(2RS)-1-ethylamino-2-propyl]-2-phenothiazinecarbonitrile (4.5 g), 2-iodopropane (7.2 cc) and sodium carbonate (4.6 g) in dry dimethylformamide (60 cc) is heated for 34 hours at a temperature in the region of 150° C. After cooling, the mixture is concentrated to dryness under reduced pressure (5 mm Hg; 0.68 kPa) at 40° C. The residue is taken up with ethyl acetate (200 cc), washed with distilled water (3×100 cc), dried over magnesium sulphate, filtered and concentrated to dryness under reduced pressure (30 mm Hg; 4 kPa) at 40° C. The residual brown oil is purified by chromatography on a column (height: 25 cm; diameter: 4 cm) of silica gel (0.04–0.063 mm) under a slight excess pressure of nitrogen (40 kPa), eluting with a mixture (75:25 by volume) (500 cc) of ethyl acetate and cyclohexane and collecting 60-cc fractions. The combined fractions 3 to 7 are concentrated to dryness under reduced pressure (30 mm Hg; 4 kPa) at 40° C. 10-{(2RS)-1-[N-Ethyl-N-(1-methylethyl)amino]-2-propyl}-2-phenothiazinecarbonitrile (2.37 g) is thereby obtained in the form of an orange oil.

10-[(2RS)-1-ethylamino-2-propyl]-2-phenothiazinecarbonitrile may be prepared in the following manner:

A solution of (2RS)-2-(2-cyano-10-phenothiazinyl)-propyl methanesulphonate (50 g) and ethylamine (100 cc) in toluene (600 cc) is heated for 24 hours to a temperature in the region of 105° C. After cooling, the mixture is concentrated to dryness under reduced pressure (30 mm Hg; 4 kPa) at 40° C. The residue is taken up with distilled water (250 cc) and the mixture is extracted successively with ethyl acetate (500 cc and 250 cc). The combined organic phases are extracted with N aqueous hydrochloric acid solution (2×500 cc). The aqueous phases are alkalinized with caustic soda (d=1.33) to pH 13 and extracted successively with ethyl acetate (500 cc and 250 cc). The combined organic phases are washed with saturated aqueous sodium chloride solution (250 cc), dried over magnesium sulphate, filtered and concentrated to dryness under reduced pressure (30 mm Hg; 4 kPa) at 40° C. 10-[(2RS)-1-Ethylamino-2-propyl]-2-phenothiazinecarbonitrile (30.4 g) is thereby obtained in the form of an orange oil.

EXAMPLE 12

A solution of 10-{(2RS)-1-[N-methyl-N-(2-hydroxyethyl)amino]-2-propyl}-2-phenothiazinecarbothioamide (1.5 g) and propylamine (5 cc) in absolute ethanol (20 cc) is heated for 16 hours to a temperature in the region of 100° C. After cooling, the mixture is concentrated to dryness under reduced pressure (30 mm Hg; 4 kPa) at 40° C. The residual orange oil is purified by chromatography on a column (height: 35 cm; diameter: 2.8 cm) of silica gel (0.2–0.063 mm), eluting with a mixture (75:25 by volume) (1 liter) of ethyl acetate and cyclohexane and collecting 50-cc fractions. Fractions 9 to 16 are combined and concentrated to dryness under reduced pressure (30 mm Hg; 4 kPa) at 40° C. The residual yellow oil (1 g) is dissolved in isopropyl ether (100 cc) and a 3.3N solution (0.7 cc) of hydrochloric acid in isopropyl ether is added with stirring at a temperature in the region of 5° C. Stirring is continued for 1 hour at a temperature in the region of 5° C. The precipitate formed is drained, washed with isopropyl ether (3×10 cc) and dried under reduced pressure (5 mm Hg; 0.68 kPa) at 40° C. 10-{(2RS)-1-[N-methyl-N-(2-hydroxyethyl)amino]2-propyl}-N-propyl-2-phenothiazinecarbothioamide hydrochloride (0.7 g) is thereby obtained in the form of a yellow solid, m.p. 126° C. (melts forming a paste at about 90° C.).

Proton NMR (250 MHz, DMSO, δ in ppm, J in Hz):

In solution in DMSO, two forms are observed, due to salification of the nitrogen; this phenomenon disappears on adding CD₃COOD.

0.96 (T, J=7.5, 3H —(CH₂)₂(CH₃); 1.73 (Mt, 2H, —CH₂—CH₂CH₃); 1.81 (broad D, 3H —CH₃); 2.85 (broad S, 3H, >NCH₃); 3 to 4 (Mt, 8H,

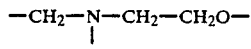

and —CSNH—CH₂—); 4.82 (Mt, 1H, N-CH); 5.36 (Cx, 1H, —OH); 7.05 to 7.4 (Mt, 5H, aromatic); 7.44 (broad D, J=8, 1H, —H at 3-position); 7.58 (broad S, 1H, —H at 1-position); 10.01 (Cx, 1H, —NH+); 10.50 (Mt, 1H, —CSNH—).

Infrared spectrum (KBr), characteristic bands in cm⁻¹: 3250, 2960, 2930, 2875, 2640, 1590, 1530, 1460, 880, 820, 750.

10-{(2RS)-1-[N-Methyl-N-(2-hydroxyethyl)amino]-2-propyl}-2-phenothiazinecarbothioamide may be obtained in the following manner:

A solution of 10-{(2RS)-1-[N-methyl-N-(2-hydroxyethyl)amino]-2-propyl}-2-phenothiazinecarbonitrile (3.1 g) and triethylamine (1.3 cc) in anhydrous pyridine (62 cc) is treated with hydrogen sulphide. The greenish solution obtained is then stirred for 16 hours at a temperature in the region of 20° C., purged with nitrogen, poured into distilled water (500 cc) and extracted with ethyl acetate (2×250 cc). The combined organic phases are washed successively with distilled water (2×100 cc) and with saturated aqueous sodium chloride solution (100 cc), dried over magnesium sulphate, filtered and concentrated to dryness under reduced pressure (30 mm Hg; 4 kPa) at 40° C. The residual orange oil (4.8 g) is purified by chromatography on a column (height: 30 cm, diameter: 2.8 cm) of silica gel (0.2–0.063 mm), eluting with a mixture (75:25 by volume) (3 liters) of ethyl acetate and cyclohexane and collecting 50-cc fractions. The combined fractions 19 to 50 are concentrated to dryness under reduced pressure (30 mm Hg; 4 kPa) at 40° C. 10-{(2RS)-1-[N-methyl-N-(2-hydroxyethyl)amino]-2-propyl}-2-phenothiazinecarbothioamide (2.2 g) is thereby obtained in the form of a yellow product of meringue-like consistency.

10-{(2RS)-1-[N-Methyl-N-(2-hydroxyethyl)amino]-2-propyl}-2-phenothiazinecarbonitrile may be obtained in the following manner:

A suspension of 10-[(2RS)-1-methylamino-2-propyl]-2-phenothiazinecarbonitrile (3.7 g), sodium hydrogen carbonate (1.6 g) and 2-bromoethanol (0.9 cc) in dimethylformamide (60 c ) is heated under reflux for 6 hours 15 minutes. After cooling, the mixture is concentrated to dryness under reduced pressure (5 mm Hg; 0.68 kPa) at 40° C. The residue is taken up with ethyl acetate (100 cc), washed successively with distilled water (2×50 cc) and with saturated aqueous sodium chloride solution (50 cc), dried over magnesium sulphate, filtered and concentrated to dryness under reduced pressure (30 mm Hg; 4 kPa) at 40° C. The residual orange oil (4.4 g) is purified by chromatography on a column (height: 35 cm; diameter: 2.6 cm) of silica gel (0.2–0.063 mm), eluting with a mixture (70:30 by volume) (1.25 liters) of ethyl acetate and cyclohexane and collecting 50-cc fractions. The combined fractions 9 to 22 are concentrated to dryness under reduced pressure (30 mm Hg; 4 kPa) at 40° C. 10-{(2RS)-1-[N-methyl-N-(2-hydroxyethyl)amino]-2-propyl}-2-phenothiazinecarbonitrile (3.1 g) is thereby obtained in the form of a yellow oil.

EXAMPLE 13

A solution of 10-[(2RS)-1-(1-pyrrolidinyl)-2propyl]-2-phenothiazinecarbothioamide (0.9 g) and propylamine (3 cc) in absolute ethanol (18 cc) is saturated with hydrogen sulphide, and the mixture is brought to a temperature in the region of 100° C. for 16 hours. After cooling, the mixture is concentrated to dryness under reduced pressure (30 mm Hg; 4 kPa) at 40° C. to obtain a yellow oil. This oil is purified by chromatography on a column (height: 25 cm; diameter 2.5 cm) of silica gel (0.04–0.063 mm) with a slight excess pressure of nitrogen (40 kPa), eluting successively with methylene chloride (100 cc) and then a mixture (95:5 by volume) (300 cc) of methylene chloride and methanol and collecting 50-cc fractions. Fractions 3 to 5 are combined and concentrated to dryness under reduced pressure (30 mm Hg; 4 kPa) at 40° C. The residual yellow oil (1 g) is dissolved in ethanol (9 cc) under reflux and treated with a boiling solution of fumaric acid (0.29 g) in ethanol (5 cc). The mixture is allowed to cool and is maintained for 4 hours at a temperature in the region of 5° C. The crystals formed are drained, washed with ice-cold ethanol (2 cc) and dried under reduced pressure (5 mm Hg; 0.7 kPa) at 35° C. N-propyl-10-[(2RS)-1-(1-pyrrolidinyl)-2-propyl]-2-phenothiazinecarbothioamide neutral fumarate (1.12 g) is thereby obtained in the form of yellow crystals, m.p. 150°–152° C.

Proton NMR (250 MHz, DMSO, δ in ppm, J in Hz):

0.92 (T, J 7.5, 3H, propyl —CH₃); 1.58 (D, J=7, 3H, —CH₃); 1.6 to 1.8 (Mt, 6H, pyrrolidine —CH₂— and propyl —CH$_2$CH$_3$); 2.5 to 2.7 (Mt, 4H, pyrrolidine >N—CH$_2$—); 2.99 (DD, J=13 and 7.5, 1H, 1H of >N—CH$_2$—); 3.11 (DD, J=13 and 6, 1H, 1H of >NCH$_2$—); 3.63 (Mt, 2H, —CSNH—CH$_2$—); 4.26 (Mt, J=7.5, 7 and 6, 1H, >N—CH<); 6.59 (S, 1H, hemifumarate —CH=CH—); 6.95 to 7.30 (Mt, 5H, aromatic); 7.31 (DD, J=8 and 1, 1H, —H at 3-position); 7.6 (D, J=1, 1H, —H at 1-position); 10.28 (T, J=5, 1H, —CSNH—).

Infrared spectrum (KBr), characteristic bands in cm$^{-1}$: 3210, 2960, 2930, 2880, 1700, 1590, 1535, 1460, 880, 820, 760, 670.

EXAMPLE 14

A mixture of 10-[1-(1-pyrrolidinyl)-2-propyl]-2-phenothiazinecarbothioamide, L series (10.3 g) and propylamine (32 cc) in ethanol (150 cc) is saturated with hydrogen sulphide and then heated for 16 hours to 105° C. in an autoclave. After cooling, the solution is concentrated to dryness under reduced pressure (30 mm Hg; 4 kPa) at 40° C. An orange oil (10.2 g) is obtained, which is purified by chromatography on column of silica (0.2-0.063 mm) (diameter: 4 cm, height: 25 cm), eluting with a 95:5 (by volume) mixture (2 liters) of methylene chloride and methanol and collecting 100-cc fractions. Fractions 13 to 17 are combined and concentrated under reduced pressure (30 mm Hg; 4 kPa) at 40° C. N-Propyl-10-[1-(1-pyrrolidinyl)-2-propyl]-2-phenothiazinecarbothioamide, L series (9.5 g) is obtained in the form of a yellow oil.

$[\alpha]_D^{20} = 30.4° \pm 0.6°$ (1%; methanol).

A solution of 10-[1-(1-pyrrolidinyl)-2-propyl]-N-propyl-2-phenothiazinecarbothioamide, L series (2.9 g) in ethanol (14 cc) at a temperature in the region of 70° C. is added to a solution of fumaric acid (0.82 g) in ethanol (14 cc) under reflux.

The mixture is allowed to cool and kept for 16 hours at a temperature in the region of 5° C. The precipitate formed is drained, washed with ethanol (2 cc) and dried under reduced pressure (5 mm Hg; 0.68 kPa) at 40° C. 10-[1-(1-Pyrrolidinyl)-2-propyl]-N-propyl-2-phenothiazinecarbothioamide neutral fumarate, L series (0.73 g) is thereby obtained in the form of a yellow solid, m.p. 118°-123° C. (melts forming a paste), the NMR characteristics of which are identical to those of the product of Example 13.

Infrared spectrum (KBr), characteristic bands in cm$^{-1}$: 3210, 2960, 2920, 2870, 2580, 2470, 1700, 1590, 1530, 1460, 980, 880, 815, 750, 670.

10-[1- 1-Pyrrolidinyl)-2-propyl]-2-phenothiazinecarbothioamide, L series may be prepared in the following manner:

A mixture of 10-[1-(1-pyrrolidinyl)-2-propyl]-2-phenothiazinecarbonitrile, L series (11.2 g) and triethylamine (4.7 cc) in anhydrous pyridine (225 cc) is saturated by bubbling hydrogen sulphide in for one hour at 25° C. The mixture is stirred for 20 hours at 25° C. The reaction mixture is outgassed by bubbling nitrogen through and then diluted with ethyl acetate (500 cc) and washed with distilled water (500 cc). The aqueous phase is extracted again with ethyl acetate (250 cc). The combined organic phases are washed with water (2×200 cc) and saturated aqueous sodium chloride solution (200 cc), dried over magnesium sulphate and concentrated under reduced pressure (30 mm Hg; 4 kPa) at 40° C. An orange oil (14.4 g) is obtained, which is purified by chromatography on a column of silica (0.2-0.063 mm) (diameter: 4 cm, height: 30 cm), eluting with a 95:5 (by volume) mixture (3 liters) of methylene chloride and methanol and collecting 120-cc fractions. Fractions 12 to 27 are combined and concentrated under reduced pressure (30 mm Hg; 4 Kpa) at 40° C. 10-[1-(1-Pyrrolidinyl)-2-propyl]-2-phenothiazinecarbothioamide, L series (10.3 g) is obtained in the form of an orange product of meringue-like consistency.

$[\alpha]_D^{20} = -43.5° \pm 0.6°$ (1.3%; chloroform).

10-[1-(1-Pyrrolidinyl)-2-propyl]-2-phenothiazinecarbonitrile, L series may be prepared in the following manner:

A mixture of 2-(2-cyano-10-phenothiazinyl)-1-propyl methanesulphonate, L series (25 g) and pyrrolidine (26.6 cc) in toluene (250 cc) is heated for 55 hours to a temperature in the region of 90° C. The reaction mixture is concentrated to dryness under reduced pressure (30 mm Hg; 4 kPa) at 40° C. The residue is taken up with ethyl ether (500 cc) and extracted with 2N aqueous methanesulphonic acid solution (2×100 cc). The aqueous phase is alkalinized with caustic soda at a temperature in the region of 5° C., and extracted with ethyl ether (2×250 cc). The combined organic phases are washed successively with ethyl ether (100 cc). The combined organic phases are washed successively with distilled water (100 cc) and with saturated aqueous sodium chloride solution (100 cc), dried over magnesium sulphate and filtered, and the yellow filtrate is concentrated to dryness under reduced pressure (30 mm Hg; 4 kPa) at 40° C. The orange oil (17.1 g) thereby obtained is chromatographed on a column (height: 45 cm; diameter: 4 cm) of silica gel (0.063-0.2 mm), eluting with a mixture (95:5 by volume) (1 liter) of methylene chloride and methanol and collecting 100-cc fractions. Fractions 3 to 7 are combined and concentrated to dryness under reduced pressure (30 mm Hg; 4 kPa) at 40° C. 10-[1-(1-Pyrrolidinyl)-2-propyl]-2-phenothiazinecarbonitrile, L series (11.2 g) is thereby obtained in the form of a yellow oil.

$[\alpha]_D^{20} = +9.7° \pm 0.3°$ (1.2%; chloroform).

2-(2-Cyano-10-phenothiazinyl)-1-propyl methanesulphonate, L series may be prepared in the following manner:

Triethylamine (10 cc) is added with stirring to a solution, cooled to a temperature in the region of 5° C., of 10-(1-hydroxy-2-propyl)-2-phenothiazinecarbonitrile, L series (12.6 g) in methylene chloride (126 cc), a solution of methanesulphonyl chloride (5.6 cc) in methylene chloride (56 cc) is then introduced dropwise during 25 minutes, and stirring is continued for 1 hour 15 minutes at a temperature in the region of 10°-15° C. The reaction mixture is washed successively with distilled water (2×100 cc) and with saturated aqueous sodium chloride solution (100 cc), dried over magnesium sulphate, filtered and concentrated to dryness under reduced pressure (30 mm Hg; 4 kPa) at 40° C. 2-(2-Cyano-10-phenothiazinyl)-1-propyl methanesulphonate, L series (16.2 g) is thereby obtained in the form of an orange oil, which is used without further purification for the next stage of the syntheses.

$[\alpha]_D^{20} = +29.9° \pm 0.3°$ (2.4%; chloroform).

10-(1-hydroxy-2-propyl)phenothiazinecarbonitrile, L series, may be prepared in the following manner:

A 1.97M alcoholic solution (84.9 cc) of potassium hydroxide is added to a solution of (+)-2-(2-cyano-10-phenothiazinyl)propyl(R)-1-phenylethylammoniumphthalate (42 g) in ethanol (420 cc) under reflux, and refluxing is continued with stirring for 15 minutes. The reaction mixture is then poured onto crushed ice (500 cc) and extracted with ethyl acetate (500 cc and then 2×250 cc). The organic phases are combined, washed successively with 0.5N aqueous hydrochloric acid solution (200 cc), with 0.1N aqueous hydrochloric acid solution (100 cc), with saturated aqueous sodium hydrogen carbonate solution (2×250 cc) and with saturated aqueous sodium chloride solution (100 cc), dried over magnesium sulphate, filtered and concentrated to dryness under reduced pressure (30 mm Hg; 4 kPa) at 40° C. The residual yellow solid is taken up with isopropyl ether (100 cc), ground, drained, washed with isopropyl ether (10 cc) and dried under reduced pressure (5 mm Hg; 0.7 kPa) at 40° C. 10-(1-Hydroxy-2-propyl)-2-phenothiazinecarbonitrile, L series (17.8 g) is thereby obtained in the form of yellow crystals, m.p. 136° C.

$[\alpha]_D^{20} = -13° \pm 0.4°$ (1.2%; chloroform).

(+)-2-(2-Cyano-10-phenothiazinyl)propyl (1R)-1-phenylethylammonium phthalate may be prepared in the following manner:

A suspension of 10-[(2RS)-1-hydroxy-2-propyl]-2-phenothiazinecarbonitrile (56.5 g) and phthalic anhydride (32.6 g in anhydrous pyridine (100 cc) is brought to reflux for 6 hours with stirring. After cooling, the reaction mixture is diluted with methylene chloride (500 cc), washed with distilled water (4×100 cc), dried over magnesium sulphate, filtered and concentrated to dryness under reduced pressure (30 mm Hg; 4 kPa) at 40° C. The residue is stirred with N aqueous hydrochloric acid solution (500 cc), and is then separated after settling has taken place and dissolved in ethyl acetate (500 cc). The solution is washed with N aqueous hydrochloric acid solution (2×100 cc) and then with aqueous sodium chloride solution (100 cc) The organic phase is dried over magnesium sulphate, filtered and concentrated to dryness under reduced pressure (30 mm Hg; 4 kPa) at 50° C. A thick oil (102 g) containing 2-{[2-(2-cyano-10-phenothiazinyl)- 1-propyl]oxycarbonyl}benzenecarboxylic acid is thereby obtained, and is subsequently used as it is.

The oil (102 g) obtained above and containing 2-{[(2RS)-2-(2-cyano-10-phenothiazinyl)-1-propyl]oxycarbonyl)benzenecarboxylic acid is dissolved in ethyl acetate (500 cc) and a solution of (1S)-(-)-1-phenylethylamine (24.2 g) in ethyl acetate (360 cc) is added with stirring and at a temperature in the region of 20° C. After 2 days stirring at a temperature in the region of 20° C., the solid formed is filtered off and kept.

The filtrate is concentrated to dryness under reduced pressure (30 mm Hg; 4 kPa) at 40° C. The residue is taken up with N aqueous hydrochloric acid solution (500 cc) and extracted with ethyl acetate (2×250 cc). The combined organic phases ar concentrated to dryness under reduced pressure (30 mm Hg; 4 kPa) at 40° C. The residue (50 g) is dissolved in ethyl acetate (500 cc) and (1R)-(+)-1-phenylethylamine (14 g) is added. After 16 hours, stirring at a temperature in the region of 20° C., the solid formed is drained and dissolved in ethyl acetate (450 cc) under reflux. After cooling, the solid formed is drained, washed with ethyl acetate (40 cc) and dried under reduced pressure (50 mm Hg; 4 kPa) at 40° C. (+)-2-(2-Cyano-10-phenothiazinyl)propyl (1R)-1-phenylethylammonium phthalate (44.3 g) is thereby obtained in the form of pale yellow crystals, m.p. 154°-155° C.

$[\alpha]_D^{20} = +20.8° \pm 0.5°$ (1.1%; chloroform).

10-[(2RS)-1-Hydroxy-2-propyl)-2-phenothiazinecarbonitrile may be prepared in the following manner:

Into a suspension of sodium borohydride (52 g) in tetrahydrofuran (1.4 liters), 1,2-ethanedithiol (113 cc) is introduced with stirring in the course of 15 minutes and at a temperature in the region of 20° C., followed, in the course of 15 minutes under the same conditions, by a solution of ethyl (2RS)-2-(2-cyano-10-phenothiazinyl)-propionate (296 g) in tetrahydrofuran (1.4 liters). When the addition is complete, the reaction mixture is heated for 20 hours to a temperature in the region of 60° C. After cooling to a temperature of 5° C., 4N aqueous sodium hydroxide solution (1 liter) is introduced during 1 hour: a brisk evolution of gas is observed. The reaction mixture is then poured into a mixture of 4N aqueous sodium hydroxide solution (1 liter) and methylene chloride (3 liters) with stirring. The organic phase is isolated and the aqueous phase re-extracted with methylene chloride (1 liter). The combined organic phases are washed with saturated aqueous sodium chloride solution (2×1 liter), dried over magnesium sulphate, filtered and concentrated t dryness under reduced pressure (30 mm Hg; 4 kPa) at 30° C. The viscous orange oil (290 g) is purified on a column (height: 50 cm; diameter: 8.5 cm) of silica gel (0.2–0.063 mm), eluting successively with methylene chloride (3 liters), then with a mixture (97.5:2.5 by volume) (4 liters) of methylene chloride and methanol and with a mixture (95:5 by volume) (10 liters) of methylene chloride and methanol and collecting 1-liter fractions. Fractions 3 to 15 are combined and concentrated to dryness under reduced pressure (30 mm Hg; 4 kPa) at 30° C. 10-[(2RS)-1-Hydroxy-2-propyl]-2-phenothiazinecarbonitrile (169.7 g) is thereby obtained in the form of a yellow solid, m.p. 123° C.

Ethyl (2RS)-2-(2-cyano-10-phenothiazinyl) propionate may be prepared in the following manner:

A solution of 2-phenothiazinecarbonitrile (224.5 g) in dimethylformamide (1 liter) is introduced, with stirring and in the course of 2 hours 30 minutes, into a suspension of sodium hydride (24 g) in dimethylformamide (1 liter) at a temperature in the region of 25° C., and the mixture is left stirred for a further 1 hour 15 minutes until the evolution of gas has ceased. The fine suspension obtained is introduced, with stirring and at a temperature in the region of 25° C., in the course of 4 hours 30 minutes, into a solution of ethyl 2-chloropropionate (255 cc) in dimethylformamide (1 liter), and stirring is continued for 16 hours. Ethanol (100 cc) is then poured into the reaction mixture, and thereafter the whole is poured into a mixture of ice (2 kg) in distilled water (4 liters): a gum precipitates and then crystallizes. The solid formed is drained, washed successively with distilled water (6×500 cc) and petroleum ether (2× 500 cc) and dried in the air. Ethyl (2RS)-2-(2-cyano-10-phenothiazinyl)propionate (296.5 g) is thereby obtained in the form of yellowish brown crystals, m.p. 117°-8° C., which are used as they are in the next stage.

EXAMPLE 15

A solution of 10-[1-(1-pyrrolidinyl)-2-propyl]-2-phenothiazinecarbothioamide, D series (2.5 g) and propylamine (8.3 cc) in absolute ethanol (50 cc) is saturated with hydrogen sulphide and heated for 16 hours to a temperature in the region of 100° C. After cooling, the orange solution obtained is concentrated to dryness under reduced pressure (30 mm Hg; 4 kPa) at 40° C. The residual brown oil is purified by chromatography on a column (height: 25 cm; diameter: 2 cm) of silica gel (0.04–0.063 mm) with a slight excess pressure of nitrogen (40 kPa), eluting with a mixture (80:20 by volume)

(1 liter) of ethyl acetate and cyclohexane and collecting 40-cc fractions. The combined fractions 8 to 18 are concentrated to dryness under reduced pressure (30 mm Hg; 4 kPa) at 40° C. N-Propyl-10-[1-(1-pyrrolidinyl)-2-propyl]-2-phenothiazinecarbothioamide, D series (2.4 g) is thereby obtained in the form of a yellow oil $\{[\alpha]_D^{20}=22\pm0.5°$ (0.06%; methanol)$\}$. This oil is dissolved in 2-propanol (7.5 cc) at a temperature in the region of 50° C., and this solution is poured with stirring into a solution of fumaric acid (0.68 g) in 2-propanol (7.5 cc) at a temperature in the region of 60° C. Stirring is continued for 2 hours at a temperature in the region of 5° C. The solid formed is drained, washed with 2-propanol (2×2 cc) and dried under reduced pressure (5 mm Hg; 0.68 kPa) at 40° C. N-Propyl-10-[1-(1-pyrrolidinyl)-2-propyl]-2-phenothiazinecarbothioamide acid fumarate, D series (2 g) is thereby obtained in the form of a yellow solid, m.p. 206° C., the NMR characteristics of which are identical to those described in Example 13.

$[\alpha]_D^{20}=+5.9°\pm0.5°$ (0.9%; dimethylformamide).

Infrared spectrum (KBr), characteristic bands in cm$^{-1}$: 3240, 2960, 2935, 2880, 2580, 2480, 1700, 1590, 1530, 1460, 980, 820, 755, 645.

EXAMPLE 16

A solution of 10-((2RS)-1-[(2RS,5RS)-2,5-dimethyl-1-pyrrolidinyl]-2-propyl)-2-phenothiazinecarbothioamide hydrochloride (0.9 g) and propylamine (2.9 cc) in absolute ethanol (20 cc) is saturated with hydrogen sulphide and heated for 12 hours to a temperature in the region of 120° C. After cooling, the solution obtained is purged with nitrogen and concentrated to dryness under reduced pressure (30 mm Hg; 4 kPa) at 40° C. The residue is dissolved in ethyl acetate (100 cc) and I the solution is washed with distilled water (2×20 cc), dried over magnesium sulphate, filtered and concentrated to dryness under reduced pressure (30 mm Hg; 4 kPa) at 40° C. The residual yellow oil (1.09 g) is purified by chromatography on a column (height: 30 cm; diameter: 1 cm) of silica gel (0.04–0.063 mm) with a slight excess pressure of nitrogen (40 kPa), eluting with methylene chloride (200 cc) and then with a mixture (95:5 by volume) (250 cc) of methylene chloride and methanol and collecting 50-cc fractions. The combined fractions 3 to 7 are concentrated to dryness under reduced pressure (30 mm Hg; 4 kPa) at 40° C. The residual yellow oil (0.75 g) is dissolved in ethyl acetate (20 cc) and treated with stirring, with a 3N solution (0.6 cc) of hydrochloric acid in ethyl ether. The gum formed is separated by decanting the solvent, taken up in solution in 2-propanol (2 cc) and treated with ethyl ether (10 cc). The solid formed is drained, washed with ethyl ether (2×5 cc) and dried under reduced pressure (5 mm Hg; 0.68 kPa) at 40° C. 10-{(2RS)-1-[(2RS,5RS)-2,5-Dimethyl-1-pyrrolidinyl]-2-propyl}-N-propyl-2-phenothiazinecarbothioamide hydrochloride (0.63 g) is thereby obtained in the form of a yellow solid, m.p. 138°-140° C. (melts forming a paste).

Proton NMR (200 MHz, DMSO, δ in ppm, J in Hz): 0.94 (T, J=7.5, 3H, (—CH$_2$)$_2$C$_3$); 1.17 and 1.27 (2D, J=6.5, 6H, 2,5-dimethylpyrrolidinyl —CH$_3$); 1.38-1.60 and 2.05 (3Mt, 1H-1H and 2H, respectively, pyrrolidinyl —CH$_2$—); 1.72 (Mt, 2H, —CH$_2$—CH$_2$CH$_3$); 1.88 (D, J=7, 3H, —CH$_2$—); 3.3 to 3.9 (Mt, 4H, >N——CH$_2$— and >N—CH— of 2,5-dimethylpyrrolidinyl); 3.65 (Mt, 2H, —CSNH—CH$_2$-); 4.83 (Mt, 1H, CH—N); 7 to 7.4 (Mt, 5H, aromatic); 7.43 (D, J=8, 1H, —H at 3-position); 7.61 (S, 1H, —H at 1-position); 10 (Cx, 1H, —NH+); 10.58 (T, J=5, 1H, —CSNH—).

Infrared spectrum (KBr), characteristic bands in cm$^{-1}$; 3180, 2960, 2930, 2880, 2590, 2500, 1600, 1535, 1560, 1415, 880, 820, 750.

10-{(2RS)-1-[(2RS,5RS)-2,5-dimethyl-1-pyrrolidinyl]-2-propyl}-2-phenothiazinecarbothioamide hydrochloride may be prepared in the following manner:

A solution of 10-{(2RS)-1-[(2RS,5RS)-2,5-dimethyl-1-pyrrolidinyl]-2-propyl}-2-phenothiazinecarbonitrile (0.85 g) and triethylamine (0.325 cc) in anhydrous pyridine (17 cc is treated with hydrogen sulphide, and the mixture is stirred for 16 hours at a temperature in the region of 20° C. The reaction mixture is diluted with ethyl acetate (50 cc), washed with distilled water (3×20 cc), dried over magnesium sulphate, filtered and concentrated to dryness under reduced pressure (30 mm Hg; 4 kPa) at 40° C. The residual yellow gum is purified by chromatography on a column (height: 20 cm; diameter: 1 cm) of silica gel (0.04–0.063 mm) with a slight excess pressure of nitrogen (40 kPa), eluting with a mixture (95:5 by volume) (500 cc) of methylene chloride and methanol and collecting 40-cc fractions. The combined fractions 5 to 9 are concentrated to dryness under reduced pressure (30 mm Hg; 4 kPa) at 40° C. The residual yellow gum (1 g) is dissolved in ethyl acetate (20 cc) and treated, with stirring, with a 3.4N solution (0.75 cc) of hydrochloric acid in ethyl ether. The crystallized solid formed is drained, washed with ethyl ether (5 cc and dried under reduced pressure (5 mm Hg; 0.68 kPa) at 40° C. The product 1 g is dissolved in ethanol (50 cc) under reflux in the presence of charcoal 3S, and the solution is filtered at a temperature in the region of 70° C. After cooling, the mixture is maintained for 4 hours at a temperature in the region of 5° C. and the crystals formed are drained, washed with ethanol (2×5 cc) and dried under reduced pressure (5 mm Hg; 0.68 kPa) at 40° C. 10-{(2RS)-1-[(2RS,5RS)-2,5-dimethyl-1-pyrrolidinyl]-2-propyl}-2-phenothiazinecarbothioamide hydrochloride (0.7 g) is thereby obtained in the form of bright yellow crystals, m.p. 210°-215° C. (decomposition).

Proton NMR (250 MHz, DMSO, δ in ppm, J in Hz):
In solution in DMSO, two forms are observed, due to salification of the nitrogen; this phenomenon disappears on adding CD$_3$COOD.

1.59 and 2.05 (2Mt, 2H each, pyrrolidinyl —CH$_2$—); 1.9 (D, J=7, 3H, —CH$_3$); 4.7 (Mt, 1H, >N—CH<); 7 to 7.35 (Mt, 5H, aromatic); 7.56 (DD, J=8 and 1, 1H, 1H of >N—CH$_2$—); 7.68 (D, J=1, 1H, 1H of >N—CH$_2$—); 9.7 and 9.95 (2Cx, 1H and 2H, respectively, —CSNH$_2$ and —NH+).

10-{(2RS)-1-[(2RS,5RS)-2,5-Dimethyl-1-pyrrolidinyl]-2-propyl}-2-phenothiazinecarbonitrile may be prepared in the following manner:

A solution of 2-(2-cyano-10-phenothiazinyl)-1-propyl methanesulphonate (5 g) and (2RS,5RS)-2,5-dimethylpyrrolidine (5 g) in toluene (50 cc) is heated for 4 days to a temperature in the region of 100° C. After cooling, the reaction mixture is diluted with ethyl acetate (200 cc) and extracted successively with N aqueous hydrochloric acid solution (50 cc and 2×25 cc). The combined aqueous phases are alkalinized with 10N aqueous sodium hydroxide solution to pH 13, and extracted successively with ethyl ether (200 cc and 50 cc). The combined organic phases are dried over magnesium sulphate, filtered and concentrated to dryness under reduced pressure (30 mm Hg; 4 kPa) at 30° C. The residual yellow gum (2.8 g) is purified by chromatography on a column (height: 30 cm; diameter: 2 cm) of silica gel (0.2–0.063 mm), eluting with a mixture (80:20 by volume) (500 cc) of cyclohexane and ethyl acetate and collecting 30-cc fractions. The combined fractions 5 to 11 are concentrated to dryness under reduced pressure (30 mm Hg; 4 kPa) at 40° C. The viscous yellow residue (2.4 g) is dissolved in isopropyl ether (15 cc) under reflux. The solution is cooled and then kept for 2 hours at a temperature in the region of 5° C. The crystals formed are drained, washed with isopropyl ether (2 cc) and dried under reduced pressure (5 mm Hg; 0.68 kPa) at 40° C. 10-((2RS)-1-[(2RS,5RS)-2,5-dimethyl-1-pyrrolidinyl]-2-propyl}-2-phenothiazine carbonitrile (1 g) is thereby obtained in the form of pale yellow crystals, m.p. 105° C.

EXAMPLE 17

A mixture of 10-{(2RS)-1-[(3RS)-3-methyl-1-piperidyl]-2-propyl}-2-phenothiazinecarbothioamide acid fumarate (1 g) and propylamine (2.5 cc) in absolute ethanol (20 cc) is saturated with hydrogen sulphide and heated for 16 hours to a temperature in the region of 100° C. After cooling, the mixture is concentrated to dryness under reduced pressure (30 mm Hg; 4 kPa) at 40° C. The residual orange oil (1.5 g) is purified by chromatography on a column (height: 25 cm; diameter: 2 cm) of silica gel (0.04–0.063 mm) with a slight excess pressure of nitrogen (40 kPa), eluting with a mixture (80:20 by volume) (250 cc) of ethyl acetate and cyclohexane and collecting 40-cc fractions. The combined fractions 3 and 4 are concentrated to dryness under reduced pressure (30 mm Hg; 4 kPa) at 40° C. The residual yellow oil (0.9 g) is dissolved in ethanol (3 cc) at 60° C., and this hot solution is poured, with stirring, into a solution of fumaric acid (0.23 g) in ethanol (3.5 cc) under reflux. After cooling, stirring is continued for 2 hours at a temperature in the region of 5° C. The solid formed is drained, washed with ethanol (2×1 cc) and dried under reduced pressure (5 mm Hg; 0.68 kPa) at 40° C. 10-{(2RS}-1-[(3RS)-3-Methyl-1-piperidyl]-2-propyl}-N-propyl-2-phenothiazinecarbothioamide neutral fumarate (0.53 g) is thereby obtained in the form of a yellow solid, m.p. 126° C.

Proton NMR (250 MHz, DMSO, δ in ppm, J in Hz):
0.76 (D, J=7, 3H, 3-methylpiperidyl —CH3); 0.93 (T, J=7.5, 3H, —(CH2)2CH3); 0.8, from 1.35 to 1.80, 1.98 and 2.80 (4Mt, integrating, respectively for 1H, 5H, 1H and 2H, —CH2—, >CH— and >N—CH2—); 1.56 (D, J=7, 3H, —CH3); 1.7 (Mt, 2H, —CH2CH2CH3); 2.68 (DD, J=13 and 6, 1H, 1H of >N—CH2—); 2.93 (DD, J=13 and 6.5, 1H, 1H of >N—CH2—); 3.64 (Mt, 2H, —CSNH—CH2—); 4.23 (Mt, J=7–6.5 and 6, 1H, >N—CH>); 6.6 (S, 1H, hemifumarate —CH=CH—); 6.9 to 7.2 (Mt, 5H, aromatic); 7.25 (DD, J=8 and 1, 1H, —H at 3-position); 7.61 (D, J=1, 1H, —H at 1-position); 10.25 (T, J=5, 1H, —CSNH—).

Infrared spectrum (KBr), characteristic bands in cm$^{-1}$; 3200, 2960, 2930, 2875, 1700, 1590, 1570, 1530, 1460, 980, 820, 755, 665.

10-{(2RS)-1-[(3RS)-3-Methyl-1-piperidyl]-2-propyl}-2-phenothiazinecarbothioamide acid fumarate may be prepared in the following manner:

A solution of 10-{(2RS)-1-[(3RS)-3-methyl-1-piperidyl]-2-propyl}-2-phenothiazinecarbonitrile (7.2 g) and triethylamine (2.8 cc) in anhydrous pyridine (148 cc) is treated with hydrogen sulphide and stirred for 16 hours at a temperature in the region of 20° C. The solution obtained is purged with nitrogen for 40 minutes, diluted with distilled water (1 liter) and extracted with ethyl acetate (2×500 cc). The combined organic phases are washed successively with distilled water (2×250 cc) and with saturated aqueous sodium chloride solution (250 cc), dried over magnesium sulphate, filtered and concentrated to dryness under reduced pressure (30 mm Hg; 4 kPa) at 40° C. The residual orange oil (9.8 g) is purified by chromatography o a column (height: 40 cm; diameter: 3 cm) of silica gel (0.2–0.063 mm), eluting with a mixture (60:40 by volume) (1.5 liters) of ethyl acetate and cyclohexane and collecting 100-cc fractions. The combined fractions 6 to 10 are concentrated to dryness under reduced pressure (30 mm Hg; 4 kPa) at 40° C. A yellow product (6.7 g) of meringue-like consistency is thereby obtained. 2.3 g of this product are dissolved in ethanol (10 cc) at 60° C., and the hot solution obtained is poured, with stirring, into a solution of fumaric acid (0.67 g) in ethanol (10 cc) at 60° C. After cooling, stirring is continued for 3 hours at a temperature in the region of 5° C. The solid formed is drained, washed with ethanol (3×5 cc) and dried under reduced pressure (5 mm Hg; 0.68 kPa) at 40° C. 10-{(2RS)-1-[(3RS)-3-Methyl-1-piperidyl]-2-propyl}-2-phenothiazinecarbothioamide acid fumarate (2.45 g) is thereby obtained in the form of a yellow solid, m.p. 236° C.

Proton NMR (250 MHz, DMSO, δ in ppm, J in Hz):
6.9 to 7.25 (Mt, 5H, aromatic); 7.42 (DD, J=8 and 1, 1H, —H at 3-position); 7.75 (broad S, 1H, —H at 1-position); 9.48 and 9.85 (2S, 1H each, —CSNH2).

10-{(2RS)-1-[(3RS)-3-Methyl-1-piperidyl]-2-propyl}-2-phenothiazinecarbonitrile may be prepared in the following manner:

A solution of (2RS)-2-(2-cyano-10-phenothiazinyl)-1-propyl methanesulphonate (14.4 g) and (3RS)-3-methylpiperidine (9.4 cc) in toluene (75 cc) is stirred under reflux for 20 hours. After cooling, the mixture is extracted with N aqueous hydrochloric acid solution (2×100 cc). The combined aqueous phases are alkalinized with caustic soda (d=1.33) to pH 13 and extracted with ethyl acetate (2×200 cc). The combined organic phases are washed successively with distilled water (2×50 cc) and with saturated aqueous sodium chloride solution (50 cc), dried over magnesium sulphate, filtered and concentrated to dryness under reduced pressure (30 mm Hg; 4 kPa) at 40° C. The residual yellow oil (14.4 g) is purified by chromatography on a column (height: 40 cm; diameter: 4 cm) of silica gel (0.2–0.063 mm), eluting with a mixture (80:20 by volume) (2.5 liters) of cyclohexane and ethyl acetate and collecting 100-cc fractions. The combined fractions 10 to 12 are concentrated to dryness under reduced pressure (30 mm Hg; 4 kPa) at 40° C. 10-((2RS)-1-[(3RS)-3-Methyl-1-piperidyl]-2-propyl}-2-phenothiazinecarbonitrile (7.2 g) is thereby obtained in the form of a yellow oil, which is subsequently used as it is.

EXAMPLE 18

A solution of 10-[(2RS)-1-(perhydro-1-azepinyl)-2-propyl]-2-phenothiazinecarbothioamide (5.1 g) and propylamine (3.78 g) in ethanol (100 cc) is heated for 16 hours to a temperature in the region of 150° C. After cooling, the reaction mixture is concentrated to dryness under reduced pressure (30 mm Hg; 4 kPa) at 40° C. The residue is dissolved in ethyl acetate (250 cc), washed successively with distilled water (3×100 cc)

and then with half-saturated aqueous sodium chloride solution (100 cc), dried over magnesium sulphate, filtered and concentrated to dryness under reduced pressure (30 mm Hg; 4 kPa) at 40° C. The residue (4.74 g) is purified by chromatography on a column (height: 30 cm; diameter: 4.6 cm) of silica gel (0.04–0.063 mm) under a slight excess pressure of nitrogen (40 kPa), eluting with a mixture (70:30 by volume) (1.5 liters) of cyclohexane and ethyl acetate and collecting 60-cc fractions. Fractions 11 to 20 are combined and concentrated to dryness under reduced pressure (30 mm Hg; 4 kPa) at 40° C. to give an oily residue (0.77 g). This residue is dissolved in ethanol (15 cc), and a 4N solution (0.45 cc) of hydrochloric acid in ethanol is added. The solution obtained is concentrated to dryness under reduced pressure (30 mm Hg; 4 kPa) at 40° C. The residue is solidified in diethyl ether (50 cc) with stirring for 16 hours, and the solid is filtered off, washed with diethyl ether (2×10 cc) and dried under reduced pressure (5 mm Hg; 0.67 kPa) at 45° C. 10-[(2RS)-1-(Perhydro-1-azepinyl)-2-propyl]-N-propyl-2-phenothiazinecarbothioamide hydrochloride (0.62 g) is thereby obtained in the form of a beige powder, m.p. 187°–188° C.

Proton NMR (250 MHz, DMSO-d6, δ in ppm, J in Hz):

0.95 (T, J=7, 3H, —(CH$_2$)$_2$CH$_3$); 1.4 to 1.9 (Mt, H, perhydroazepinyl —CH$_2$—); 1.73 (Mt, 2H, —CH$_2$CH$_2$CH$_3$); 1.81 (D, J=7, 3H, —CH$_3$); 3.15 to 3.45 (Mt, 4H, perhydroazepinyl >N—CH$_2$; 3.50 and 3.8 (2Mt, 1H each, N—CH$_2$—); 3.70 (Mt, J=7 and 5, 1H, —CONH—CH$_2$—); 4.85 (Mt, 1H, >N—CH<); 7.05 to 7.4 (Mt, 5H, aromatic); 7.41 (broad D, J=8, 1H, —H at 3-position); 7.59 (D, J=1, 1H, —H at 1-position); 10.15 (Cx, 1H, —NH$^+$Cl—); 10.44 (T, J=5, 1H, —CONH—).

Infrared spectrum (KBr), characteristic bands in cm$^{-1}$ 3175, 2960, 2930, 2870, 2620, 2530, 1590, 1465, 1530, 885, 825, 750.

10-[(2RS)-1-(Perhydro-1-azepinyl)-2-propyl]-2-phenothiazinecarbothioamide may be prepared in the following manner:

A mixture of 10-[(2RS)-1-(perhydro-1-azepinyl)-2-propyl]-2-phenothiazinecarbonitrile (5.11 g) and triethylamine (1.96 cc) in anhydrous pyridine (50 cc) is saturated by bubbling hydrogen sulphide in for 3 hours at 25° C. The clear solution obtained is kept stirred for 16 hours at 25° C., and the mixture is then outgassed by bubbling nitrogen through for 2 hours. The reaction mixture is diluted with ethyl acetate (300 cc) and washed with distilled water (10×100 cc). The organic phase is dried over magnesium sulphate and filtered and the filtrate is concentrated to dryness under reduced pressure (30 mm Hg; 4 kPa) at 40° C. The residue is purified by chromatography on a column of 0.06–0.2 mm silica gel (height: 38 cm; diameter: 3 cm), eluting with a mixture (proportions of 50:50 by volume) (1.5 l) of cyclohexane and ethyl acetate and collecting 125-cc fractions. Fractions 3 to 9 are combined and concentrated to dryness under reduced pressure (30 mm Hg; 4 kPa) to give 10-[(2RS)-1-(perhydro-1-azepinyl)-2-propyl]-2-phenothiazinecarbothioamide (5.15 g) in the form of an orange oil.

10-[(2RS)-1-(Perhydro-1-azepinyl)-2-propyl]-2-phenothiazinecarbonitrile may be prepared in the following manner:

A solution of 2-(2-cyano-10-phenothiazinyl)propyl mesylate (9.05 g) in hexamethylenimine (28.2 cc) is brought to 90° C. for 16 hours. After cooling, the mixture is diluted with ethyl acetate (200 cc) and washed with distilled water (4×150 cc). The organic phase is dried over magnesium sulphate, filtered and concentrated to dryness under reduced pressure (30 mm Hg; 4 kPa) at 40° C. The residue is purified by chromatography on a column of 0.06–0.2 mm silica gel (height: 44 cm; diameter: 3.8 cm), eluting with mixture of cyclohexane and ethyl acetate in proportions (by volume) of 80:20 (500 cc) and 70:30 (1500 cc) and collecting 125-cc fractions. Fractions 7 to 15 are combined and concentrated to dryness under reduced pressure (30 mm Hg; 4 kPa) at 40° C. to give 10-[(2RS)-1-(perhydro-1-azepinyl)-2-propyl]-2-phenothiazinecarbonitrile (5.27 g) in the form of a yellow product of honey-like consistency.

EXAMPLE 19

A solution of 10-[1-(2,5-dihydro-1-pyrrolyl)-2-propyl]-2-phenothiazinecarbothioamide, L series (5 g) and propylamine (4.02 g) in ethanol (35 cc) is saturated by bubbling hydrogen sulphide in for 25 minutes and then heated for 16 hours to a temperature in the region of 150° C. After cooling, the reaction mixture is concentrated to dryness under reduced pressure (30 mm Hg; 4 kPa) at 40° C. The residue is dissolved in ethyl acetate (50 cc), washed successively with distilled water (5×50 cc) and then with half-saturated aqueous sodium chloride solution (50 cc), dried over magnesium sulphate, filtered and concentrated to dryness under reduced pressure (30 mm Hg; 4 kPa) at 40° C. The residue (5.34 g) is purified by chromatography on a column (height: 23 cm; diameter: 4.4 cm) of silica gel (0.04–0.063 mm) under a slight excess pressure of nitrogen (40 kPa), eluting with a mixture (70:30 by volume) (2.5 liters) of cyclohexane and ethyl acetate and collecting 125-cc fractions. Fractions 5 to 16 are combined and concentrated to dryness under reduced pressure (30 mm Hg; 4 kPa) at 40° C. to give a yellowish product (3 g) of meringue-like consistency. 1 g of this residue is dissolved in 2-propanol (5 cc) under reflux and treated with a lukewarm solution of fumaric acid (0.28 g) in 2-propanol (5.6 cc). After cooling and crystallization, the solid formed is filtered washed successively with 2-propanol (2 cc) and with diethyl ether (10 cc) and then dried under reduced pressure (5 mm Hg; 0.67 kPa). N-Propyl-10-[1-(2,5-dihydro-1-pyrrolyl)-2-propyl]-2-phenothiazinecarbothioamide fumarate, L series (0.77 g) is thereby obtained in the form of a yellow powder, m.p. about 206° C.

$[\alpha]_D^{20}$ = +39.5°±0.8° (0.8%; methanol).

Proton NMR (250 MHz, DMSO-d6, δ in ppm, J in Hz):

0.95 (T, J=7.5, 3H, —(CH$_2$)$_2$Cl$_3$); 1.62 (D, J=7, 3H, —CH$_3$); 1.7 (Mt, 2H, —Ch$_2$CH$_2$CH$_3$); 3.12 (DD, J=12.5 and 6.5, 1H, 1H of >N—CH$_2$—); 3.32 (DD, J, =12.6 and 6, 1H, 1H of >N—CH$_2$—); 3.57 (AB, 6H, pyrroline >N—CH$_2$—); 3.65 (Mt, 2H, —CS—N-H—CH$_2$—); 4.22 (Mt, J=7, 6.5 and 6, 1H, >N—CH<); 5.79 (Cx, 2H, —CH=CH—); 6.63 (S, 2H, fumarate —CH=CH—); 6.90 to 7.30 (Mt, 5H, aromatic); 7.31 (DD, J=8 and 1, 1H, —H at 3-position); 7.59 (D, J=1, 1H, —H at 1-position); 10.26 (T, J—5.5, 1H, —C-S—NH—).

Infrared spectrum (KBr), characteristic bands in cm$^{-1}$: 2965, 2930, 2870, 2750, 2250, 1850, 1680, 1640, 1590, 1555, 1460, 1530, 980, 880, 810, 800, 755, 645.

10-[1-(2,5-dihydro-1-pyrrolyl)-2-propyl]2-phenothiazinecarbothioamide, L series may be prepared in the following manner:

A solution of 10-[1-(2,5-dihydro-1-pyrrolyl)-2-propyl]-2-phenothiazinecarbonitrile, L series (12.57 g) and triethylamine (5.5 cc) in pyridine (115 cc) is treated with hydrogen sulphide by bubbling in for 2 hours. After 16 hours' stirring at a temperature in the region of 25° C., the light brown solution obtained is purged with nitrogen for 2 hours, diluted with ethyl acetate (300 cc), washed with distilled water (10×100 cc), dried over magnesium sulphate, filtered and concentrated to dryness under reduced pressure (30 mm Hg; 4 kPa) at 40° C. The yellow product (13.3 g) of meringue-like consistency is purified by chromatography on a column (height: 47 cm; diameter: 3.8 cm) of silica gel (0.04–0.063 mm) under a slight excess pressure of nitrogen (40 kPa), eluting with ethyl acetate (2 liters) and collecting 125-cc fractions. Fractions 4 to 10 are combined and concentrated to dryness under reduced pressure (30 mm Hg; 4 kPa) at 40° C. to give 10-[1-(2,5-dihydro-1-pyrrolyl)-2-propyl]-2-phenothiazinecarbothioamide, L series (10.6 g) in the form of a yellow product of meringue-like consistency.

$[\alpha]_D^{20} = -41.9 \pm 0.7°$ (1%; chloroform).

10-[1-(2,5-dihydro-1-pyrrolyl)-2-propyl]-2-phenothiazinecarbonitrile, L series may be prepared in the following manner:

A solution of 2-(2-cyano-10-phenothiazinyl)-1-propyl methanesulphonate, L series (44 g) and 2,5-dihydropyrrol (42.2 g) in anhydrous toluene (250 cc) is heated to 90° C. with stirring for 18 hours. After cooling, the reaction mixture is extracted with distilled water (2×100 cc) and then with N aqueous hydrochloric acid solution (250 cc). The combined acidic aqueous phases are alkalinized with aqueous N sodium hydroxide solution and extracted with ethyl acetate (3×100 cc). The organic phases are combined, washed successively with distilled water (100 cc) and then with saturated aqueous sodium chloride solution (100 cc), dried over magnesium sulphate, filtered and concentrated to dryness under reduced pressure (30 mm Hg; 4 kPa) at 50° C. The yellowish oily residue (30.4 g) is purified by chromatography on a column (height: 38 cm; diameter 3.8 cm) of silica gel (0.04–0.063 mm) under a slight excess pressure of nitrogen (40 kPa), eluting with a mixture (75:25 by volume) (15 liters) of cyclohexane and ethyl acetate and collecting 1-liter fractions. Fractions 6 to 11 are combined and concentrated to dryness under reduced pressure (30 mm Hg; 4 kPa) at 40° C. to give 10-[1-(2,5-dihydro-1-pyrrolyl)-2-propyl]-2-phenothiazinecarbonitrile, L series (11.15 g) in the form of a yellow oil.

$[\alpha]_D^{20} = +32.6° \pm 0.6°$ (1%; methanol)

EXAMPLE 20 n-Butylamine (0.35 cc) is added to a solution of 10-[(2RS)-1-dimethylamino-2-propyl]-2-phenothiazinecarbothioamide in absolute ethanol (5 cc). The mixture is brought to 200° C. for 5 hours and then diluted with ethyl acetate (500 cc), washed with distilled water (3×500 cc), dried over magnesium sulphate and then concentrated to dryness under reduced pressure (30 mm Hg; 4 kPa). The residual solid is purified by chromatography on a column (height: 18 cm; diameter: 5 cm) of silica gel (0.6–0.02 mm), eluting with mixtures of ethyl acetate and cyclohexane in proportions (by volume) of 20:80 (1.5 liters) and 30:70 (11.5 liters) collecting 250-cc fractions. Fractions 28 to 45 are combined and concentrated under reduced pressure (30 mm Hg; 4 kPa) to give a brown oil (11.5 g), an aliquot portion (1.5 g) of which is dissolved in ethyl acetate (30 cc). Oxalic acid (1.01 g) dissolved in ethyl acetate (30 cc) is added to this solution. A solid forms, and the suspension obtained is filtered to give N-butyl-10-[(2RS)-1-dimethylamino-2-propyl]-2-phenothiazinecarbothioamide acid oxalate (0.42 g), m.p. 154° C.

NMR spectrum (250 MHz, DMSO, δ in ppm, J in Hz):

0.93 (T, J=7.5, 3H, butyl —CH$_3$); 1.36 (Mt, 2H, butyl —CH$_2$CH$_3$); 1.67 (Mt, 2H, butyl —CH$_2$CH$_2$CH$_3$); 1.72 (D, J=7.5, 3H, —CH$_3$); 2.7 (S, 6H, —N(CH$_3$)$_2$); 3.36 (DD, J=14 and 4.5, 1H, 1H of >NCH$_2$—); 3.56 (DD, J=14 and 7.5, 1H, 1H of >NCH$_2$—); 3.70 (Q, J=7, 2H, —CSNH—CH$_2$—); 4.63 (Mt, >NH—CH<); 7 to 7.35 (Mt, 5H, aromatic); 7.4 (DD, J=8.5 and 1, 1H, —H at 3-position); 7.53 (D, J=1, 1H, —H at 1-position).

Infrared spectrum (KBr), characteristic bands in cm$^{-1}$: 3230, 2960, 2930, 2270, 2690, 1720, 1640, 1590, 1530, 1460, 880, 830, 750.

EXAMPLE 21

A mixture of 10-[(2RS)-1-(N-ethyl-N-methylamino)-2-propyl]-2-phenothiazinecarbothioamide (2.1 g) and butylamine (8.5 cc) in absolute ethanol (30 cc) is saturated with hydrogen sulphide and heated for 16 hours to a temperature in the region of 100° C. After cooling, the orange solution obtained is concentrated to dryness under reduced pressure (30 mm Hg; 4 kPa) at 40° C. The residual brown oil is purified by chromatography on a column (height: 4 cm; diameter: 3 cm) of silica gel (0.2–0.063 mm), eluting successively with methylene chloride (2 liters) and with a mixture (90:10 by volume) (1 liter) of methylene chloride and methanol and collecting 60-cc fractions. Fractions 36 to 39 are combined and concentrated to dryness under reduced pressure (30 mm Hg; 4 kPa) at 40° C. The residual orange oil (1.8 g) is again purified by chromatography on a column (height: 25 cm; diameter: 4 cm) of silica gel (0.04–0.063 mm) under a slight excess pressure of nitrogen (40 kPa), eluting with mixture (75:25 by volume) (1 liter) of ethyl acetate and cyclohexane and collecting 60-cc fractions. Fractions 5 to 12 are combined and concentrated to dryness under reduced pressure (30 mm Hg; 4 kPa) at 40° C. N-Butyl-10-[(2RS)-1-(N-ethyl-N-methylamino)-2-propyl]-2-phenothiazinecarbothioamide (1.25 g) is thereby obtained in the form of a yellow oil. This product is dissolved in isopropyl ether (100 cc) and treated, dropwise and with stirring, with a 0.28N solution (10.9 cc) of hydrochloric acid in isopropyl ether. After 1 hour's stirring at a temperature in the region of 5° C, the precipitate formed is drained, washed with isopropyl ether (3×10 cc) and dried under reduced pressure (5 mm Hg; 0.68 kPa) at 40° C. N-Butyl-10-[(2RS)-1-(N-methyl-N-ethylamino)-2-propyl]-2-phenothiazinecarbothioamide hydrochloride (1.1 g) is thereby obtained in the form of a yellow solid, m.p. 102° C. (melts forming a paste).

Proton NMR (250 MHz, DMSO, δ in ppm, J in Hz).

In solution in DMSO, two forms are observed, due to salification of the nitrogen.

0.96 (T, J=7.5, 3H, —(CH$_2$)$_3$CH$_3$); 1.07 and 1.21 (2T, J=7.5, 3H, —NCH$_2$CH$_3$); 1.4 (Mt, 2H —(CH$_2$)$_2$CH$_2$CH$_3$); 1.72 (Mt, 2H, —CH$_2$—CH$_2$CH$_3$); 1.83 (Mt, 3H, —CH$_3$). 2.8 (Mt, 3H, >N—CH$_3$); 3 to 3.35 (Mt, 2H, >NCH$_2$CH$_3$); 3.5 to 3.90 (Mt, 2H, >N—CH₂—); 3.75 (Mt, 2H, —CSNH—CH₂—); 4.8 (Mt, 1H, >N—CH<); 7 to 7.4 (Mt, 5H, aromatic); 7.45 (D, J=8, 1H, —H at 3-position); 7.6 (S, 1H, —H at 1-position); 10.12 (Cx,1H, —NH⁺); 10.5 (Mt, 1H, —CSNH—).

Infrared spectrum (KBr), characteristic bands in cm⁻¹: 3200, 2960, 2930, 2870, 2660, 2600, 2480, 1590, 1530, 1460, 870, 820, 755.

10-[(2RS)-1-(N-Methyl-N-ethylamino)-2-propyl]-2-phenothiazinecarbothioamide may be prepared in the following manner:

A solution of 10-[(2RS)-1-(N-ethyl-N-methylamino)-2-propyl]-2-phenothiazinecarbonitrile (3 g) and triethylamine (1.3 cc) in anhydrous pyridine (60 cc) is treated with excess hydrogen sulphide, and stirring is then continued for 16 hours at a temperature in the region of 20° C. The solution obtained is purged with a stream of nitrogen for 1 hour, poured into ethyl acetate (100 cc), washed with distilled water (3×200 cc), dried over magnesium sulphate, filtered and concentrated to dryness under reduced pressure (30 mm Hg; 4 kPa) at 40° C. The residual brown oil is purified by chromatography on a column (height: 40 cm; diameter: 3 cm) of silica gel (0.2-0.06 mm), eluting successively with methylene chloride (1 liter), a mixture (95:5 by volume) (1 liter) of methylene chloride and methanol and a mixture (80:20 by volume) (3 liters) of methylene chloride and methanol and collecting 150-cc fractions. Fractions 26 to 30 are combined and concentrated to dryness under reduced pressure (30 mm Hg; 4 kPa) at 40° C. 10-[(2RS)-1-(N-Ethyl-N-methylamino)-2-propyl]-2-phenothiazinecarbothioamide (2.15 g) is thereby obtained in the form of an orange oil.

10-[(2RS)-1-(N-Ethyl-N-methylamino)-2-propyl]-2-phenothiazinecarbonitrile may be prepared in the following manner:

A mixture of 10-[(2RS)-1-ethylamino-2-propyl]-2-phenothiazinecarbonitrile (4.4 g), sodium carbonate (2.25 g) and iodomethane (0.9 cc) in dimethylformamide (60 cc) is heated for 6 hours to a temperature in the region of 150° C. The reaction mixture is then concentrated to dryness under reduced pressure (5 mm Hg; 0.7 kPa) at 40° C. and the residue is taken up with distilled water (100 cc) and extracted with ethyl acetate (2×100 cc). The combined organic phases are extracted with N-aqueous hydrochloric acid solution (2×50 cc). The combined aqueous phases are alkalinized with sodium hydroxide (d=1.33) to pH 13 and extracted with ethyl acetate (2×100 cc). The combined organic phases are washed successively with distilled water (50 cc) and with saturated aqueous sodium chloride solution (50 cc), dried over magnesium sulphate, filtered and concentrated to dryness under reduced pressure (30 mm Hg; 4 kPa) at 40° C. 10-[(2RS)-1-(N-Ethyl-N-methylamino)-2-propyl]-2-phenothiazinecarbonitrile (3 g) is thereby obtained in the form of an orange oil.

EXAMPLE 22

A solution of 10-[(2RS)-1-diethylamino-2-propyl]-2-phenothiazinecarbothioamide (2.1 g and butylamine (8.2 cc) in absolute ethanol (30 cc) is saturated with hydrogen sulphide and then heated for 16 hours to a temperature in the region of 100° C. After cooling, the yellow solution obtained is concentrated to dryness under reduced pressure (30 mm Hg; 4 kPa) at 40° C. The residue is taken up with distilled water (50 cc) and the mixture is extracted successively with ethyl acetate (100 cc and then 50 cc). The combined organic phases are washed with saturated aqueous sodium chloride solution (50 cc), dried over magnesium sulphate, filtered and concentrated to dryness under reduced pressure (30 mm Hg; 4 kPa) at 40° C. The oily orange residue (2.25 g) is purified by chromatography on a column (height: 25 cm; diameter: 3 cm) of silica gel (0.04-0.063 mm) with a slight excess pressure of nitrogen (40 kPa), eluting with a mixture (80:20 by volume) (500 cc) of ethyl acetate and cyclohexane and collecting 50-cc fractions. Fractions 6 to 8 are combined and concentrated to dryness under reduced pressure (30 mm Hg; 4 kPa) at 40° C. The residual yellow oil (1.8 g) is dissolved in isopropyl ether (100 cc) and treated with stirring with a 3.3N solution (1 cc) of hydrochloric acid in isopropyl ether. After 15 minutes' stirring at a temperature in the region of 20° C, the solid formed is drained, washed with isopropyl ether (3×20 cc) and dried under reduced pressure (5 mm Hg; 0.68 kPa) at 40° C. N-Butyl-10-[(2RS)-1-diethylamino-2-propyl]-2-phenothiazinecarbothioamide hydrochloride (1.5 g) is thereby obtained in the form of a yellow solid, m.p. 116° C. (melts forming a paste).

Proton NMR (250 MHz, DMSO, δ in ppm, J in Hz): 0.93 (T, J=7, 3H, —(CH₂)₃CH₃); 1 and 1.15 (2T, J=7, 6H, —N(CH₂CH₃)₂); 1.37 (Mt, 2H, —(CH₂-)₂—CH₂—CH₃); 1.69 (Mt, 2H, —CH₂—CH₂CH₂CH₃); 1.83 (D, J=7, 3H, —CH₃); 3.17 (Mt, 4H, —N(CH₂CH₃)₂); 3.41 (broad D, J=14, 1H, 1H of >N—CH₂—); 3.70 (Mt, 2H, —CSNH—CH₂—); 3.77 (DD, J=14 and 7.5, 1H, 1H of >N—CH₂—); 4.88 (Mt, 1H, >N—CH>); 7 to 7.35 (Mt, 5H, aromatic); 7.41 (D, J=8, 1H, —H at 3-position); 7.56 (S, 1H, —H at 1-position): 10.4 (Cx, 1H, —NH⁺); 10.5 (T, J=5, 1H, —CSNH—).

Infrared spectrum (KBr), characteristic bands in cm⁻¹: 3200, 2960, 2930, 2870, 2580, 2480, 1590, 1535, 1465, 870, 825, 750.

EXAMPLE 23

A solution of 10-{(2RS)-1-[N-methyl-N-(2-methylethyl)amino]-2-propyl}-2-phenothiazinecarbothioamide (1.91 g) and butylamine (3 cc) in absolute ethanol (20 cc) is treated with hydrogen sulphide for 10 minutes and then heated to a temperature in the region of 125° C. for 24 hours. After cooling, the mixture is concentrated to dryness under reduced pressure (30 mm Hg; 4 kPa) at 50° C. The residual yellow paste is taken up with ethyl ether (50 cc) and distilled water (25 cc). The organic phase is separated, washed with distilled water (25 cc), dried over potassium carbonate, filtered and concentrated to dryness under reduced pressure (30 mm Hg; 4 kPa) at 40° C. The residual yellow oil (1.9 g) is purified by chromatography on a column (height: 40 cm; diameter: 3.2 cm) of silica gel (0.04-0.063 mm) with a slight excess pressure of nitrogen (40 kPa), eluting with ethyl acetate (750 cc) and collecting 25-cc fractions. The combined fractions 11 to 20 are concentrated to dryness under reduced pressure (30 mm Hg; 4 kPa) at 50° C. The residual viscous yellow oil (1.6 g) is dissolved in isopropyl ether (50 cc) and treated, with stirring, with a 3N solution (2 cc) of hydrochloric acid in isopropyl ether. The yellow flocculent precipitate formed is drained, washed with isopropyl ether (3×15 cc) and dried under reduced pressure (5 mm Hg; 0.68 kPa) at 20° C. in the presence of sulphuric acid. N-Butyl-10-{(2RS)-1-[N-methyl-N-(2-methylethyl)amino]-2-propyl}-2-phenothiazinecarbothioamide hydrochloride (1.2 g) is thereby obtained in the form of a yellow powder, m.p. 130°-140° C. (melts forming a paste).

Proton NMR (250 MHz, CDCl$_3$, δ in ppm, J in Hz):

In solution in CDCl$_3$, two forms are observed, due to salification of the nitrogen.

0.98 (T, J=7.5, 3H, —(CH$_2$)$_3$CH$_3$); 1.02. 1.33 and 1.39 (3D, J=7, 6H, —CH(CH$_3$)$_2$); 1.47 (Mt, 2H, —(CH$_2$)$_2$—CH$_2$—CH$_3$); 1.84 (D, J=7, 3H, —CH$_3$); 1.85 (Mt, 2H, —CH$_2$—CH$_2$—CH$_2$—CH$_3$); 2.65 and 2.85 (2D, J=5, 3H, >N—CH$_3$); 3.08 and 3.16 (broad 2D, 1H, 1H of >N—CH$_2$—); 3.51 and 4.08 (2Mt, 1H, —CH(CH$_3$)$_2$); 3.55 to 4 (Mt, 4H, >NCH$_2$— and —CSNH—CH$_2$—); 5.65 and 5.90 (2Mt, 1H, N—CH); 6.90 to 7.55 (Mt, 7H, aromatic); 9.08 and 9.15 (2T, 1H—, —CSNH—); 11.7 (Cx, 1H, —NH+).

Infrared spectrum (KBr), characteristic bands in cm$^{-1}$: 3210, 2960, 2930, 2865, 2660, 2500, 1590, 1530, 1460, 1415, 820, 750.

EXAMPLE 24

Butylamine (9.6 cc) is added to a solution of 10-[1-(1-pyrrolidinyl)-2-propyl]-2-phenothiazinecarbothioamide, L series (3.7 g) in absolute ethanol (55 cc), and this solution is saturated with hydrogen sulphide. The mixture is then brought to a temperature in the region of 105° C. for 16 hours. After cooling, the solution is concentrated to dryness under reduced pressure (30 mm Hg; 4 kPa) at 40° C. An orange oil is obtained, which is purified by chromatography under a slight excess pressure of nitrogen (40 kPa) on a column (height: 25 cm; diameter: 4 cm) of silica gel (0.2-0.063 mm), eluting with a mixture (70:30 by volume) (one liter) of ethyl acetate and cyclohexane and collecting 60-cc fractions. Fractions 7 to 12 are combined and concentrated to dryness under reduced pressure (30 mm Hg; 4 kPa) at 40° C. An orange oil (3.4 g) is thereby obtained. This product is dissolved in isopropyl ether (150 cc), and a 3.3N solution (2.4 cc) of hydrochloric acid in isopropyl ether is added. The precipitate formed is drained, washed with isopropyl ether (3×10 cc) and dried at 40° C. under reduced pressure (5 mm Hg; 0.7 kPa). N-Butyl-10-[1-(1-pyrrolidinyl)-2-propyl]-2-phenothiazinecarbothioamide hydrochloride, L series (3.16 g) is obtained in the form of a yellow solid, m.p. 125°-130° C. (melts forming a paste).

$[\alpha]_D^{20}$ = +27.5°±0.6° (1%; dimethylformamide).

Proton NMR (250 MHz, CDCl$_3$, δ in ppm, J in Hz):

1 (T, J=7.5, 3H, butyl —CH$_3$); 1.49 (Mt, 2H, —CH$_2$CH$_3$); 1.85 (D, J=7, 3H, —CH$_3$); 1.86 (Mt, 2H, —CH$_2$—CH$_2$CH$_3$); 1.9 to 2.25 (Mt, 4H, pyrrolidine —CH$_2$—CH$_2$—); 2.82, 2.98, 3.85 and 4.08 (4Cx, 1H each, pyrrolidine

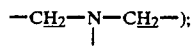

3.45 (broad D, J=13, 1H, 1H of >N—CH$_2$—); 3.65 to 3.95 (Mt, 3H, other H of >N—CH$_2$— and CSNH—CH$_2$); 5.6 (Mt 1H, CH—N); 6.9 to 7.25 (Mt, 5H, aromatic); 7.33 (D, J=1, 1H, —H at 1-position); 7.5 (DD, J=8 and 1, 1H, —H at 3-position); 8.93 (Cx, 1H, —CSNH—); 12.25 (Cx, 1H, —NH+).

EXAMPLE 25

A solution of 10-[1-(1-pyrrolidinyl)-2-propyl]-phenothiazinecarbothioamide, D series (3.7 g) and butylamine (9.6 cc) in absolute ethanol (55 cc) is saturated with hydrogen sulphide and heated for 16 hours to a temperature in the region of 105° C. After cooling, the mixture is concentrated to dryness under reduced pressure (30 mm Hg; 4 kPa) at 40° C. The residual orange oil is purified by chromatography on a column (height: 35 cm; diameter: 3 cm) of silica gel (0.2-0.063 mm), eluting with a mixture (97.5:2.5 by volume) (1 liter) of methylene chloride and methanol and collecting 40-cc fractions. The combined fractions 16 to 19 are concentrated to dryness under reduced pressure (30 mm Hg; 4 kPa) at 40° C. The residual orange oil (2.43 g) is dissolved in isopropyl ether (100 cc) and treated, with stirring, with a 0.84N solution (6.7 cc) of hydrochloric acid in isopropyl ether. After 30 minutes' stirring at a temperature in the region of 5° C., the precipitate formed is drained, washed with isopropyl ether (3×10 cc) and dried under reduced pressure (5 mm Hg; 0.68 kPa) at 40° C. N-Butyl-10-[1-(1-pyrrolidinyl)-2-propyl]-2-phenothiazinecarbothioamide hydrochloride, D series (2.1 g) is thereby obtained in the form of a yellow solid, m.p. 105°-110° C. (melts forming a paste), the NMR characteristics of which are identical to those of the product described in Example 24.

$[\alpha]_D^{20}$: =−25.6±0.8° (0.6%; dimethylformamide).

Infrared spectrum (KBr), characteristic bands in cm$^{-1}$: 3200, 2955, 2925, 2870, 2580, 2470, 1590, 1530, 1460, 1415, 870, 820, 750.

EXAMPLE 26

Isobutylamine (3.8 cc) is added to a solution of 10-[(2RS)-1-dimethylamino-2-propyl]-2-phenothiazinecarbothioamide (2.16 g) in absolute ethanol (4 cc). The mixture is brought to 200° C. for 5 hours and then diluted with ethyl acetate (75 cc), washed with distilled water (3×75 cc), dried over magnesium sulphate and then concentrated to dryness under reduced pressure (30 mm Hg; 4 kPa) at 40° C. The residual solid is purified by chromatography on a column (height: 25 cm; diameter: 4 cm) of silica gel (0.6-0.02 mm), eluting with a 50:50 (by volume) mixture (1 liter) of ethyl acetate and cyclohexane, collecting 30-cc fractions. Fractions 3 to 13 are combined and concentrated under reduced pressure (30 mm Hg; 4 kPa) at 50° C. to give a brown oil (1.79 g), an aliquot portion (1.5 g) of which is dissolved in acetonitrile (7 cc). Fumaric acid (0.52 g) dissolved in ethanol (5 cc) is added to this solution. The solution obtained is concentrated under reduced pressure (30 mm Hg; 4 kPa) to a residual volume of 2 cc and then treated with acetonitrile (8 cc). After scratching, crystallization develops and the suspension obtained is filtered to give N-(2-methylpropyl)-10-[(2RS)-1-dimethylamino-2-propyl]-2-phenothiazinecarbothioamide acid fumarate (1.7 g), m.p. 200° C.

NMR spectrum (200 MHz, DMSO, δ in ppm, J in Hz):

0.95 (D, J =7, 6H, 2-methylpropyl —CH$_3$); 1.65 (D, J=7, 3H, —CH$_3$); 2.18 (Mt, 1H, 2-methylpropyl —CH<); 2.35 (S, 6H, —N(CH$_3$)$_2$); 2.86 (DD, J=13 and 6, 1H, 1H of >N—CH$_2$—); 3.1 (DD, J=13 and 6.5, 1H, 1H of >N—CH$_2$); 3.57 (Mt, 2H, —CSNH—CH$_2$—); 4.35 (Mt, J=7, 6.5 and 6, 1H, N—CH); 6.63 (S, 2H, fumarate -CH=CH-); 6.95 to 7.3 (Mt, 5H, aromatic); 7.35 (broad D, J =8, 1H, -H at 3-position); 7.57 (broad S, 1H, —H at 1-position).

Infrared spectrum (KBr), characteristic bands in cm$^{-1}$: 3250, 2960, 2930, 2880, 2460, 1690, 1590, 1570, 1560, 1525, 1465, 980, 885, 815, 760, 645.

EXAMPLE 27

A solution of 10-[(2RS)-1-diethylamino-2-propyl]-2-phenothiazinecarbothioamide (2.3 g) and 2-methylpropylamine (9.4 cc) in absolute ethanol (30 cc) is saturated with hydrogen sulphide and heated for 16 hours to a temperature in the region of 100° C. The yellow solution obtained is concentrated to dryness under reduced pressure (30 mm Hg; 4 kPa) at 40° C. The residual orange oil is purified by chromatography on a column (height: 25 cm; diameter: 4 cm) of silica gel (0.04–0.063 mm) with a slight excess pressure of nitrogen (40 kPa), eluting with a mixture (75:25 by volume) (750 cc) of ethyl acetate and cyclohexane and collecting 60-cc fractions. The combined fractions 5 to 10 are concentrated to dryness under reduced pressure (30 mm Hg; 4 kPa) at 40° C. The residual orange oil (2.4 g) is dissolved in isopropyl ether (100 cc) and treated, dropwise and with stirring at a temperature in the region of 5° C. with a solution of methanesulphonic acid (0.29 cc) in a mixture (66:33 by volume) (30 cc) of isopropyl ether and ethyl acetate. Stirring is maintained for 30 minutes at a temperature in the region of 5° C. The solid formed is drained, washed with isopropyl ether (5×10 cc) and dried under reduced pressure (5 mm Hg; 0.68 kPa) at 40° C. 10-[(2RS)-1-Diethylamino-2-propyl]-N-(2-methylpropyl)-2-phenothiazinecarbothioamide methanesulphonate (2.1 g) is thereby obtained in the form of a yellow solid, m.p. 143° C.

Proton NMR (400 MHz, DMSO, $\delta$ in ppm, J in Hz):

In solution in DMSO, two forms are observed, due to salification of the nitrogen.

0.92 and 1.17 (2T, J=7, 3H each, —N(CH$_2$CH$_3$)$_2$); 0.95 (D, J=7, 6H, —CH(CH$_3$)$_2$); 1.83 (D, J=7, 3H, —CH$_3$); 2.17 (Mt, 1H, —CH(CH$_3$)$_2$); 2.33 (S, 3H, methanesulphonate —CH$_3$); 3.17 (Mt, 4H, —N(CH$_2$CH$_3$)$_2$); 3.41 (Mt, 1H, 1H of >NCH$_2$—); 3.55 (Mt, 2H, —CSNH—CH$_2$—); 3.77 (Mt, 1H, 1H of >N—CH$_2$—); 4.71 (Mt, 1H, N—CH); 7.05 to 7.35 (Mt, 5H, aromatic); 7.40 (broad D, J=8, 1H, —H at 3-position); 7.55 (broad S, 1H, —H at 1-position); 9.22 (Cx, 1H —NH$^+$); 10.37 (T, J=5.5, 1H, —CSNH—).

Infrared spectrum (KBr), characteristic bands in cm$^{-1}$: 3240, 2960, 2930, 2870, 2660, 1590, 1535, 1465, 1210, 1040, 885, 820, 755.

EXAMPLE 28

A mixture of 10-(1-diethylamino-2-propyl)-2-phenothiazinecarbothioamide, L series (3 g) and 2-methylpropylamine (3 cc) in ethanol (60 cc) is saturated with hydrogen sulphide and brought to a temperature in the region of 100° C. for 16 hours. After cooling, the reaction mixture is concentrated to dryness under reduced pressure (30 mm Hg; 4 kPa) at 40° C. to give an orange oil (3.5 g). This product is purified by chromatography on a column (height: 25 cm; diameter: 3 cm) of silica gel (0.063–0.2 mm), eluting with a mixture (97.5:2.5 by volume) (one liter) of methylene chloride and methanol and collecting 50-cc fractions. Fractions 12 to 18 are combined and concentrated to dryness under reduced pressure (30 mm Hg; 4 kPa) at 40° C. An orange oil (2.42 g) is thereby obtained, which is dissolved in a mixture (89:11 by volume) (260 cc) of isopropyl ether and ethyl acetate and then treated, dropwise and with stirring and at a temperature in the region of 5° C., with a 0.22N solution (28 cc) of hydrochloric acid in isopropyl ether. The precipitate formed is drained, washed with isopropyl ether (3×28 cc) and dried under reduced pressure (5 mm Hg; 0.68 kPa) at 40° C. 10-(1-Diethylamino-2-propyl)-N-(2-methylpropyl)-2-phenothiazinecarbothioamide hydrochloride, L series (1.9 g) is thereby obtained in the form of a yellow solid, m.p. 110°–115° C. (melts forming a paste), the NMR characteristics of which are identical to those of the product obtained in Example 27.

$[\alpha]_D^{20}$: = +29.8°±1.2° (0.4%; dimethylformamide).

Infrared spectrum (KBr), characteristic bands in cm$^{-1}$: 3210, 2960, 2930, 2870, 2640, 2480, 1590, 1570, 1530, 1460, 865, 820, 755.

EXAMPLE 29

A suspension of 10-[(2RS)-1-(1-pyrrolidinyl)-2-propyl]-2-phenothiazinecarbothioamide (2 g) and 2-methylpropylamine (3 cc) in absolute ethanol (20 cc) is saturated for 15 minutes with hydrogen sulphide and then heated for 23 hours to a temperature in the region of 115° C. After cooling, the mixture is concentrated to dryness under reduced pressure (30 mm Hg; 4 kPa) at 30° C. The residual paste is taken up with ethyl acetate (30 cc) and distilled water (20 cc). The organic phase is separated, washed with saturated aqueous sodium chloride solution (20 cc), dried over potassium carbonate, filtered and concentrated to dryness under reduced pressure (30 mm Hg; 4 kPa) at 50° C. The residual viscous yellow oil (2.5 g) is purified by chromatography on a column (height: 35 cm; diameter: 2.6 cm) of silica gel (0.2–0.063 mm), eluting with a mixture (92:8 by volume) (200 cc) of ethyl acetate and methanol and collecting 15-cc fractions. Fractions 5 to 11 are combined and concentrated to dryness under reduced pressure (30 mm Hg; 4 kPa) at 40° C. N-(2-Methylpropyl)-10-[(2RS)-1-(1-pyrrolidinyl-2-propyl]-2-phenothiazinecarbothioamide (2.04 g) is thereby obtained in the form of a viscous yellow oil. 0.51 g of this oil is dissolved in isopropyl ether (20 cc), and a 3.3N solution (0.5 cc) of hydrochloric acid in isopropyl ether is added. The precipitate formed is drained, washed with isopropyl ether (3×5 cc) and dried under reduced pressure (5 mm Hg; 0.68 kPa) at 40° C. N-(2-Methylpropyl)-10-[(2RS)-1-(1-pyrrolidinyl)-2-propyl]-2-phenothiazinecarbothioamide hydrochloride (0.5 g) is thereby obtained in the form of a yellow powder, m.p. 150°–155° C. (melts forming a paste).

Proton NMR (250 MHz, DMSO, $\delta$ in ppm, J in Hz):
0.95 (D, J=7, 6H, —CH(CH$_3$)$_2$); 1.77 (D, J=7, 3H, —CH$_3$); 1.75 to 2 (Mt, 4H, pyrrolidine —CH$_2$—); 2.20 (Mt, 1H, —CH(CH$_3$)$_2$); 2.83, 3.12 and 3.50 to 3.95 (2Cx of 1H each and Mt, pyrrolidine N—CH$_2$—); 3.56 (Mt, 2H, —CSNH— CH$_2$—); 3.5 to 3.95 (Mt, 2H, >N—CH$_2$—); 4.77 (Mt, 1H, >N—CH<); 7 to 7.35 (Mt, 5H, aromatic); 7.42 (DD, J=8 and 1, 1H, —H at 3-position); 7.55 (D, J=1, 1H, —H at 1-position); 10.5 (T, J=5 and Cx, 2H, —CSNH— and —NH$^+$).

Infrared spectrum (KBr), characteristic bands in cm$^{-1}$: 3190, 2950, 2920, 2860, 2580, 2470, 1590, 1530, 1460, 1410, 820, 750.

EXAMPLE 30

A suspension of 10-[(2RS)-1-(1-pyrrolidinyl)-2-propyl]-2-phenothiazinecarbothioamide (2 g) and pentylamine (3 cc) in absolute ethanol (30 cc) is saturated with hydrogen sulphide and then heated for 2 hours at a temperature in the region of 100° C. After cooling, the mixture is concentrated to dryness under reduced pressure (30 mm Hg; 4 kPa) at 40° C. The pasty residue is taken up with ethyl ether (50 cc) and distilled water (15 cc). The organic phase is separated, dried over potassium carbonate and concentrated to dryness under reduced pressure (30 mm Hg; 4 kPa) at 40° C. The residual viscous yellow oil is purified by chromatography on a column (height: 35 cm; diameter: 2.6 cm) of silica gel (0.2–0.063 mm), eluting with ethyl acetate (300 cc) and collecting 25-cc fractions. Fractions 3 to 9 are combined and concentrated to dryness under reduced pressure (30 mm Hg; 4 kPa) at 40° C. N-Pentyl-10-[(2RS)-1-(1-pyrrolidinyl)-2-propyl]-2-phenothiazinecarbothioamide (2.25 g) is thereby obtained in the form of a yellow oil. 0.55 g of this product is dissolved in isopropyl ether (20 cc), and a 3.3N solution (0.6 cc) of hydrochloric acid in isopropyl ether is introduced dropwise and with stirring. The precipitate formed is drained, washed with isopropyl ether (3×5 cc) and dried under reduced pressure (5 mm Hg; 0.68 kPa) at 40° C. N-Pentyl-10-[(2RS)-1-(1-pyrrolidinyl)-2-propyl]-2-phenothiazinecarbothioamide hydrochloride (0.56 g) is thereby obtained in the form of a pale yellow powder, m.p. 155°–160° C. (melts forming a paste).

Proton NMR (250 MHz, DMSO, $\delta$ in ppm, J in Hz): 0.92 (T, J=7, 3H, pentyl —CH$_3$); 1.35 (Mt, 4H, —CH$_2$—CH$_2$—CH$_3$); 1.7 (Mt, 2H, —CH$_2$—(CH$_2$)$_2$CH$_3$); 3.55 to 3.90 (Mt, 4H, >N—CH$_2$— and —CSNH—CH$_2$—); 7 to 7.35 (Mt, 5H, aromatic); 7.43 (DD, J=8 and 1, 1H, —H at 3-position); 7.57 (D, J=1, 1H, —H at 1-position).

Infrared spectrum (KBr), characteristic bands in cm$^{-1}$: 3200, 2960, 2930, 2860, 2580, 2470, 1590, 1530, 1460, 1410, 870, 820, 750.

EXAMPLE 31

A mixture of 10-[(2RS)-1-dimethylamino-2-propyl]-2-phenothiazinecarbothioamide (1 g) and 3-methylbutylamine (5.2 cc) in absolute ethanol (15 cc) is saturated with hydrogen sulphide and heated for 16 hours to a temperature in the region of 100° C. After cooling, the mixture is concentrated to dryness under reduced pressure (30 mm Hg; 4 kPa) at 40° C. The oily orange residue is purified by chromatography on a column (height: 25 cm; diameter: 4 cm) of silica gel (0.04–0.063 mm) with a slight excess pressure of nitrogen (40 kPa), eluting with ethyl acetate (one liter) and collecting 60-cc fractions. Fractions 6 to 11 are combined and concentrated to dryness under reduced pressure (30 mm Hg; 4 kPa) at 40° C. The residual yellow oil (1.2 g) is dissolved in isopropyl ether (100 cc) and treated, dropwise and with stirring at a temperature in the region of 5° C., with a 0.267N solution (10.85 cc) of hydrochloric acid in isopropyl ether. After 1 hour, the solid formed is drained, washed with isopropyl ether (5×10 cc) and dried under reduced pressure (5 mm Hg; 0.68 kPa) at 40° C. 10-[(2RS)-1-Dimethylamino-2-propyl]-N-(3-methylbutyl)-2-phenothiazinecarbothioamide hydrochloride (0.9 g) is thereby obtained in the form of a yellow solid, m.p. 112° C. (melts forming a paste).

Proton NMR (250 MHz, DMSO, $\delta$ in ppm, J in Hz): 0.96 (D, J=7, 6H, —CH(CH$_3$)$_2$); 1.62 (Mt, 2H, —CH$_2$—CH); 1.7 (Mt, 1H, —CH(CH$_3$)$_2$); 1.8 (D, J=7, 3H, —CH$_3$); 2.82 (S, 6H, —N(CH$_3$)$_2$); 3.53 (DD, J=14 and 4.5, 1H, of >NCH$_2$—); 3.74 (Mt, 3H, —CSNHCH$_2$— and 1H of NCH$_2$—); 4.76 (Mt, 1H, >N—C<); 7 to 7.4 (Mt, 5H, aromatic); 7.45 (DD, J=8 and 1, 1H, —H at 3-position); 7.55 (D, J=1, 1H, —H at 1-position); 10.4 (Cx, 1H, —NH$^+$); 10.5 (T, J=5.5, 1H, —CSNH—).

Infrared spectrum (KBr), characteristic bands in cm$^{-1}$: 3250, 2960, 2930, 2870, 2680, 2500, 2470, 1590, 1530, 1460, 870, 820, 750.

EXAMPLE 32

A solution of 10-[(2RS)-1-(N-ethyl-N-methylamino)-2-propyl]-2-phenothiazinecarbothioamide (1 g) and 3-methylbutylamine (4.9 cc) in absolute ethanol (15 cc) is saturate with hydrogen sulphide and heated for 16 hours to a temperature in the region of 100° C. After cooling, the orange solution obtained is concentrated to dryness under reduced pressure (30 mm Hg; 4 kPa) at 40° C. The residual orange oil is purified by chromatography on a column (height: 25 cm; diameter: 2 cm) of silica gel (0.04–0.063 mm) under a slight excess pressure of nitrogen (40 kPa), eluting with a mixture (80:20 by volume) (500 cc) of ethyl acetate and cyclohexane and collecting 30-cc fractions. Fractions 4 to 8 are combined and concentrated to dryness under reduced pressure (30 mm Hg; 4 kPa) at 40° C.

N-(3-Methylbutyl)-10-[(2RS)-1-(N-ethyl-N-methylamino)-2-propyl]-2-phenothiazinecarbothioamide (1.3 g) is thereby obtained in the form of an orange oil. 1 g of this product is dissolved in ethyl acetate (5 cc), isopropyl ether (40 cc) is added and a 0.41N solution (5.68 cc) of hydrochloric acid in isopropyl ether is introduced with stirring and at a temperature in the region of 5° C. After 30 minutes, stirring at a temperature in the region of 5° C., the precipitate formed is drained, washed with isopropyl ether (3×5 cc) and dried under reduced pressure (5 mm Hg; 0.68 kPa) at 40° C. N-(3-Methylbutyl)-10-[(2RS)-1-(N-ethyl-N-methylamino)-2-propyl]-2-phenothiazinecarbothioamide hydrochloride (0.9 g) is thereby obtained in the form of a yellow solid, m.p. 105°–110° C. (melts forming a paste).

Proton NMR (250 MHz, DMSO, $\delta$ in ppm, J in Hz):

In solution in DMSO, two forms are observed, due to salification of the nitrogen.

0.93 (D, J=7, 6H, —CH(CH$_3$)$_2$); 1.05 and 1.18 (2T, J=7, 3H, >NCH$_2$CH$_3$); 1.6 (Mt, 2H, —CH$_2$—CH<); 1.66 (Mt, 1H, 3-methylbutyl >CH—); 1.8 (Mt, 3H, —CH$_3$); 2.77 (Cx, 3H, >N—CH$_3$); 3 to 3.35 (Mt, 2H, >N—CH$_2$CH$_3$); 3.50 and 3.65 to 3.90 (2MT, 2H, >N—CH$_2$—); 3.73 (Mt, 2H, —CSNHCH$_2$—); 4.84 (Mt, 1H, N—CH); 7 to 7.35 (Mt, 5H, aromatic); 7.41 (broad D; J=8, 1H, —H at 3-position); 7.54 (broad S, 1H, —H at 1-position); 10.45 and 10.55 (Cx and Mt, 2H, —NH$^+$ and —CSNH—).

Infrared spectrum (KBr), characteristic bands in cm$^{-1}$: 3180, 2960, 2930, 2870, 2590, 2480, 1590, 1535, 1465, 870, 820, 750.

EXAMPLE 33

3-Methylbutylamine (2.9 cc) is added to a solution of 10-[(2RS)-1-diethylamino-2-propyl]-2-phenothiazinecarbothioamide (1.86 g) in absolute ethanol (25 cc). The mixture is brought to 150° C. for 16 hours. The reaction mixture is diluted with ethyl acetate (100 cc) and then washed with distilled water (3×50 cc). The organic phase is dried over magnesium sulphate, filtered and then concentrated to dryness under reduced pressure (30 mm Hg; 4 kPa) at 50° C. The residue is purified by chromatography on a column (height: 18.5 cm; diameter: 2.6 cm) of silica gel (0.04–0.06 mm) with a slight excess pressure of nitrogen (40 kPa), eluting with a 50:50 (by volume) mixture (1 liter) of cyclohexane and ethyl acetate and then with pure ethyl acetate (500 cc), collecting 60-cc fractions. Fractions 2 to 4 are combined and concentrated to dryness under reduced pressure (30 mm Hg; 4 kPa) at 50° C. to give an orange product (1.10 g) of meringue-like consistency. This product is taken up in isopropyl ether (50 cc) to give a suspension which is filtered, washed with ethyl ether (3×1 cc) and dried at 50° C. under reduced pressure (5 mm Hg; 0.7 kPa) to give 10-[(2RS)-1-diethylamino-2-propyl]-N-(3-methylbutyl)-2-phenothiazinecarbothioamide (0.95 g), m.p. 80° C.

NMR spectrum (250 MHz, DMSO, δ in ppm, J in Hz):

Two forms are observed, which disappear on addition of CD$_3$COOD.

0.93 (D, J=6.5, 6H, —CH(CH$_3$)$_2$); 1.02 (T, J=7, 6H, —CH(CH$_3$)$_2$); 1.5 to 1.75 (Mt, 3H, —CH$_2$—CH(CH$_3$)$_2$); 1.77 D, J=7, 3H, —CH$_3$); 3.03 (Mt, 4H, —N(CH$_2$CH$_3$)$_2$); 3.3 (Mt, 1H, 4 of >N—CH$_2$—); 3.45 to 3.8 (Mt, other H of >N-CH$_2$— and —CSN-H—CH$_2$—); 4.45 to 4.75 (Mt, 1H, >NCH<); 7 to 7.6 (Mt, 7H, aromatic); 10.34 (T, J=5, 1H, —CSNH—).

Infrared spectrum (KBr), characteristic bands in cm$^{-1}$: 3280, 2960, 2660, 1725, 1630, 1590, 1535, 1460, 865, 825.

EXAMPLE 34

3-Methylbutylamine (10.7 cc) is added to a solution of 10-(1-diethylamino-2-propyl)-2-phenothiazinecarbothioamide acid fumarate, L series (3 g) in absolute ethanol (45 cc) and this solution is saturated with hydrogen sulphide. The mixture is then brought to a temperature in the region of 105° C. for 16 hours and concentrated to dryness under reduced pressure (30 mm Hg; 4 kPa). The residual orange oil is purified by chromatography on a column (height: 35 cm; diameter: 3 cm) of silica gel (0.2–0.063 mm), eluting with a mixture (70:30 by volume) (400 cc) of ethyl acetate and cyclohexane, collecting 30-cc fractions. Fractions 7 to 11 are combined and concentrated to dryness under reduced pressure (30 mm Hg; 4 kPa) at 50° C. to give an orange oil (3.1 g). g of this product is dissolved in isopropyl ether (100 cc), and a 0.158M solution (10.7 cc) of hydrochloric acid in isopropyl ether is added a 5° C. with stirring. After 30 minutes, the precipitate formed is drained, washed with isopropyl ether (3×10 cc) and dried at 40° C. under reduced pressure (5 mm Hg; 0.68 kPa) to give 10-(1-diethylamino-2-propyl)-N-(3-methyl-1-butyl)-2-phenothiazinecarbothioamide hydrochloride, L series (0.85 g), a solid, m.p. 110°-116° C. (melts forming a paste), the NMR characteristics of which are identical to those of Example 33.

$[\alpha]_D^{20}$=+24.2° (0.7%; dimethylformamide).

Infrared spectrum (KBr), characteristic bands in cm$^{-1}$: 3180, 2950, 2920, 2860, 2580, 2480, 1590, 1530, 1460, 1415, 820, 750.

10-(1-Diethylamino-2-propyl)-2-phenothiazinecarbothioamide acid fumarate, L series may be prepared in the following manner:

A solution of 10-(1-diethylamino-2-propyl)-2-phenothiazinecarbonitrile, L series (5.2 g) and triethylamine (2.2 cc) in anhydrous pyridine (104 cc) is saturated with hydrogen sulphide at 20° C. for 1 hour with stirring, and then stirred at 20° C. for 17 hours. The reaction mixture is purged with nitrogen for 1 hour, poured into distilled water (500 cc) and extracted with ethyl acetate (2×250 cc). The combined organic phases are washed successively with distilled water (3×100 cc) and with saturated aqueous sodium chloride solution (100 cc), dried over magnesium sulphate and filtered. The yellow filtrate is concentrated to dryness under reduced pressure (30 mm Hg; 4 kPa) at 40° C. to give an orange oil (6.5 g). This product is purified by chromatography on a column (height: 44 cm; diameter: 3.4 cm) of silica gel (0.2–0.063 mm), eluting with a mixture (30:70 by volume) (3 liters) of cyclohexane and ethyl acetate and collecting 150-cc fractions. Fractions 8 to 17 are combined and concentrated to dryness under reduced pressure (30 mm Hg; 4 kPa) at 40° C. An orange oil (5.08 g) ($[\alpha]_D^{20}$=−33.7°±0.6°; 1.006%; chloroform) is obtained. This product is dissolved at a temperature in the region of 60° C. in ethanol (20 cc) and this solution is poured into a solution of fumaric acid (1.56 g) in ethanol (20 cc) at a temperature in the region of 60° C. and then left to stand for 16 hours at a temperature in the region of 5° C. The crystals formed are drained, washed with ethanol (2×2 cc) and dried at 40° C. under reduced pressure (5 mm Hg; 0.7 kPa). 10-(1-Diethylamino-2-propyl)-2-phenothiazinecarbothioamide acid fumarate, L series (5.5 g) is thereby obtained in the form of yellow crystals, m.p. 186° C.

$[\alpha]_D^{20}$=+29.1≧±0.6° (1%; dimethylformamide).

10-(1-Diethylamino-2-propyl)-2-phenothiazinecarbonitrile, L series may be prepared in the following manner:

Sodium carbonate (3.2 g) and iodoethane (2.3 cc) are added to a solution of 10-(1-ethylamino-2-propyl)-2-phenothiazinecarbonitrile, L series (7 g) in dimethylformamide (86 cc), and this mixture is then brought to a temperature in the region of 150° C. for 6 hours. After cooling, the reaction mixture is concentrated to dryness under reduced pressure (30 mm Hg; 4 kPa) at 40° C. and the residue is taken up with ethyl acetate (250 cc). The solution obtained is washed successively with distilled water (2×100 cc) and with saturated aqueous sodium chloride solution (100 cc), dried over magnesium sulphate in the presence of charcoal 3S and filtered. The yellow filtrate is concentrated to dryness under reduced pressure (30 mm Hg; 4 kPa) at 40° C. to give an orange oil (6.65 g) which crystallizes slowly. This residue is dissolved in the minimum amount of isopropyl ether under reflux. The small amount of insoluble matter is filtered off, hot, and the filtrate is kept for 3 days at a temperature in the region of 5° C. The crystals formed are drained, washed with isopropyl ether (2×2 cc) and dried at 40° C. under reduced pressure (5 mm Hg; 0.7 kPa). 10-(1-Diethylamino-2-propyl)-2-phenothiazinecarbonitrile, L series (2.9 g) is thereby obtained in the form of beige crystals, m.p. 83° C. ($[\alpha]_D^{20}$=+9≧±0.3°; 0.978% chloroform). form). The filtrate is then concentrated to dryness under reduced pressure (30 mm Hg; 4 kPa) at 40° C. to give a further 2.3 g of 10-(1-diethylamino-2-propyl)-2-phenothiazinecarbonitrile, L series, in the form of a beige solid, m.p. 81°-82° C.

$[\alpha]_D^{20}$=+8.7≧±0.3° (1.2; chloroform).

10-(1-Ethylamino-2-propyl)-2-phenothiazinecarbonitrile, L series, may be prepared in the following manner:

Ethylamine (30 cc) is added to a solution of 2-(2-cyano-10-phenothiazinyl)-1-propyl methanesulphonate, L series (16 g) in toluene (160 cc), and this mixture is brought to a temperature in the region of 105° C. for 24 hours. After cooling, the reaction mixture is concentrated to dryness under reduced pressure (30 mm Hg; 4 kPa) at 40° C. and the residue is taken up with ethyl ether (250 cc) and N aqueous sodium hydroxide solution (50 cc). After stirring, the organic phase is separated, washed successively with distilled water (50 cc) and with saturated aqueous sodium chloride solution (50 cc), dried over magnesium sulphate, filtered and concentrated to dryness under reduced pressure (30 mm Hg; 4 kPa) to give a yellow oil (13.8 g). This residue is dissolved at a temperature in the region of 60° C. in ethanol (46 cc), and this solution is poured into a solution at 60° C. of fumaric acid (5.2 g) in ethanol (46 cc) and then left for 16 hours at a temperature in the region of 5° C. The yellow precipitate formed is drained, washed with ethanol (2×5 cc) and dried at 40° C. under reduced pressure (5 mm Hg; 0.7 kPa). 10-(1-Ethylamino-2-propyl)-2-phenothiazinecarbonitrile fumarate, L series (9.7 g) ($[\alpha]_D^{20} = +6.2 \geqq \pm 0.4°$; 1.008%; dimethylformamide) is thereby obtained. This product is suspended in ethyl ether (200 cc) and N aqueous sodium hydroxide solution (100 cc) is added. After stirring, the organic phase is separated and the aqueous phase is extracted with ethyl ether (50 cc). The organic phases are combined, washed with saturated aqueous sodium chloride (100 cc), dried over magnesium sulphate, filtered and concentrated to dryness under reduced pressure (300 mm Hg; 40 kPa - then 30 mm Hg; 4 kPa) at 40° C. 10-(1-Ethylamino-2-propyl)-2-phenothiazinecarbonitrile, L series (7 g) is thereby obtained in the form of a yellow oil.

$[\alpha]_D^{20} = +12 \geqq \pm 0.3°$ (2%; chloroform).

EXAMPLE 35

3-Methylbutylamine (10.7 cc) is added to a solution of 10-(1-diethylamino-2-propyl)-2-phenothiazinecarbothioamide acid fumarate, D series (3 g) in absolute ethanol (45 cc), and this solution is saturated with hydrogen sulphide. The mixture is then brought to a temperature in the region of 105° C. for 16 hours and concentrated to dryness under reduced pressure (30 mm Hg; 4 kPa) at 50° C. The residual orange oil is purified by chromatography on a column (height: 35 cm; diameter: 3 cm) of silica gel (0.2-0.063 mm), eluting with a mixture (75:25 by volume) (400 cc) of ethyl acetate and cyclohexane and collecting 40-cc fractions. Fractions 4 to 6 are combined and concentrated to dryness under reduced pressure (30 mm Hg; 4 kPa) at 50° C. to give an orange oil (3.1 g). 1 g of this product is dissolved in isopropyl ether (100 cc) and treated at 5° C. and with stirring with a 0.158M solution (10.7 cc) of hydrochloric acid in isopropyl ether. After 30 minutes, the precipitate formed is drained, washed with isopropyl ether (3×10 cc) and dried at 40° C. under reduced pressure (5 mm Hg; 0.68 kPa) to give 10-(1-diethylamino-2-propyl)-N-(3-methyl-1-butyl)-2-phenothiazinecarbothioamide hydrochloride, D series (0.8 g) in the form of a yellow solid, m.p. 115°-120° C. (melts forming a paste), the NMR characteristics of which are identical to those of the product described in Example 33.

Infrared spectrum (KBr), characteristic bands in cm$^{-1}$: 3190, 2960, 2870, 2580, 2480, 1590, 1530, 1460, 1415, 865, 825, 750.

10-(1-Diethylamino-2-propyl)-2-phenothiazinecarbothioamide acid fumarate, D series may be obtained in the following manner:

Working as described in Example 34, but starting with 10-(1-diethylamino-2-propyl)-2-phenothiazinecarbonitrile, D series (3.4 g) and triethylamine (1.4 cc) in anhydrous pyridine (68 cc), an orange oil (4 g) is obtained. This product is dissolved at a temperature in the region of 60° C. in ethanol (13 cc), and this solution is poured into a solution of fumaric acid (1.16 g) in ethanol (13 cc) at a temperature in the region of 5° C. The crystals formed are drained, washed with ethanol (2×2 cc) and dried at 40° C. under reduced pressure (5 mm Hg; 0.7 kPa). 10-(1-Diethylamino-2-propyl)-2-phenothiazinecarbothioamide acid fumarate, D series (3.47 g) is thereby obtained in the form of a yellow solid, m.p. 180° C.

$[\alpha]_D^{20} = -32.8 \geqq \pm 0.6°$ (0.9%; dimethylformamide).

10-(1-Diethylamino-2-propyl)-2-phenothiazinecarbonitrile, D series may be obtained in the following manner:

A mixture of 10-(1-ethylamino-2-propyl)-2-phenothiazinecarbonitrile acid fumarate, D series (4 g), sodium carbonate (1.32 g) and iodoethane (1 cc) in dimethylformamide (50 cc) is heated to a temperature in the region of 150° C. for 6 hours. After cooling, the reaction mixture is concentrated to dryness (30 m Hg; 4 kPa) at 50° C. and the residue is taken up with ethyl acetate (100 cc) and washed successively with distilled water (50 cc) and with saturated aqueous sodium chloride solution (50 cc). The organic phase is dried over magnesium sulphate, filtered and concentrated to dryness under reduced pressure (30 mm Hg; 4 kPa) at 40° C. 10-(1-diethylamino-2-propyl)-2-phenothiazinecarbonitrile, D series (3.4 g) is thereby obtained in the form of a yellow oil.

$[\alpha]_D^{20} = -6.8 \geqq \pm 0.4°$ (1.3%; chloroform).

10-(1-Ethylamino-2-propyl)-2-phenothiazinecarbonitrile acid fumarate, D series may be obtained in the following manner:

Ethylamine (18.75 cc) is added to a solution of 2-(2-cyano-10-phenothiazinyl)-1-propyl methanesulphonate, D series (10 g) in toluene (100 cc), and this mixture is brought to a temperature in the region of 105° C. for 24 hours. After cooling, the reaction mixture is concentrated to dryness under reduced pressure (30 mm Hg; 4 kPa) at 40° C. The residue is taken up with ethyl ether (250 cc) and extracted successively with N-aqueous hydrochloric solution (2×100 cc). The combined aqueous phases are alkalinized with caustic soda (d = 1.33) to pH 13 and extracted with ethyl ether (2×200 cc). The combined organic phases are washed successively with distilled water (50 cc) and with saturated aqueous sodium chloride solution (50 cc), dried over magnesium sulphate, filtered and concentrated to dryness under reduced pressure (30 mm Hg; 4 kPa) at 40° C. 10-(1-Ethylamino-2-propyl)-2-phenothiazinecarbonitrile, D series (5 g) is thereby obtained in the form of an orange oil. This product is dissolved at a temperature in the region of 60° C. in ethanol (17 cc), and this solution is poured into a solution of fumaric acid (1.9 g) in ethanol (17 cc) at the same temperature, crystallization is then primed and the mixture is left for 16 hours at a temperature in the region of 20° C. The solid is drained, washed with ethanol (2×2 cc) and dried under reduced pressure (5 mm Hg; 0.7 kPa) at 40° C. 10-(1-Ethylamino-2-propyl)-2-phenothiazinecarbonitrile acid fumarate, D series (4 g) is thereby obtained in the form of a yellow solid, m.p. 208° C.

$[\alpha]_D^{20} = -5.2 \geqq \pm 0.5°$ (0.9% dimethylformamide).

EXAMPLE 36

A solution of 10-[(2RS)-1-(1-pyrrolidinyl)-2-propyl]-2-phenothiazinecarbothioamide (1.89 g) and 3-methylbutylamine (8.9 cc) in absolute ethanol (28 cc) is saturated with hydrogen sulphide, and this mixture is heated for 16 hours to a temperature in the region of 110° C. After cooling, the reaction mixture is concentrated to dryness under reduced pressure (30 mm Hg; 4 kPa) at 40° C., and the oily yellow residue (2.8 g) is purified by chromatography on a column (height: 30 cm; diameter: 2 cm) of silica gel (0.04–0.063 mm) under a slight excess pressure of nitrogen (40 kPa), eluting successively with methylene chloride (100 cc) and then a mixture (95:5 by volume) (300 cc) of methylene chloride and methanol and collecting 30-cc fractions. Fractions 4 to 8 are combined and concentrated to dryness under reduced pressure (30 mm Hg; 4 kPa) at 40° C. The oily yellow residue (2.1 g) is dissolved in ethyl acetate (15 cc), and a 3N solution (2 cc) of hydrochloric acid in ethyl ether is added. The mixture is kept stirred for 1 hour at a temperature in the region of 5° C. The precipitate formed is drained, washed with ethyl acetate (2 cc) and dried under reduced pressure (5 mm Hg; 0.7 kPa) at 35° C. N-(3-Methylbutyl)-10-[(2RS)-1-(1-pyrrolidinyl)-2-propyl]-2-phenothiazinecarbothioamide hydrochloride (2.1 g) is thereby obtained in the form of yellow crystals, m.p. 190° C., the NMR spectrum of which is identical to that of the carbothioamide described below in Example 37.

Infrared spectrum (KBr), characteristic bands in cm$^{-1}$: 3210, 2950, 2920, 2860, 2680, 2610, 2480, 1590, 1535, 1460, 1410, 820, 745.

EXAMPLE 37

3-Methylbutylamine (12.9 cc) is added to a solution of 10-[1- 1-pyrrolidinyl)-2-propyl]-2-phenothiazinecarbothioamide, D series (4.1 g) in ethanol (61.5 cc), and the mixture is then saturated with hydrogen sulphide and heated for 16 hours to a temperature in the region of 105° C. After cooling, the solution is concentrated to dryness under reduced pressure (30 mm Hg; 4 kPa) at 40° C. A yellow oil is obtained, which is purified by chromatography on a column (height: 30 cm; diameter: 4 cm) of silica gel (0.2–0.063 mm), eluting with a mixture (95:5 by volume) (1.5 liters) of methylene chloride and methanol and collecting 80-cc fractions. Fractions 14 to 17 are combined and concentrated to dryness under reduced pressure (30 mm Hg; 4 kPa) at 40° C. N-(3-Methylbutyl)-10-[1-(1-pyrrolidinyl)-2-propyl]-2-phenothiazinecarbothioamide, D series (4.7 g) is obtained in the form of an orange oil. ($[\alpha]_D^{20} = -3.2 \geq \pm 0.2°$; 1.92%; chloroform). 2.7 g of this product are dissolved in ethyl acetate (20 cc), and a 3.3N solution (1.85 cc) of hydrochloric acid in isopropyl ether is then added. The precipitate formed is drained, washed with isopropyl ether (3×5 cc) and dried under reduced pressure (5 mm Hg; 0.68 kPa). N-(3-Methylbutyl)-10-[1-(1-pyrrolidinyl)-2-propyl]-2-phenothiazinecarbothioamide hydrochloride, D series (1.7 g) is thereby obtained in the form of a yellow solid, m.p. 189° C.

$[\alpha]_D^{20} = -26.3 \geq \pm 0.5°$ (1.2%; dimethylformamide).

Proton NMR (250 MHz, DMSO, δ in ppm, J in Hz): 0.94 (D, J=7, 6H, —CH(CH$_3$)$_2$); 1.6 (Mt, 2H, —NHCH$_2$CH$_2$—); 1.64 (Mt, 1H, >CH—); 1.77 (D, J=7, 3H, —CH$_3$); 1.7 to 2 (Mt, 4H, pyrrolidine —CH$_2$—CH$_2$—); 2.85, 3.10 and 3.5 to 3.9 (2Cx of 1H each and Mt, pyrrolidine

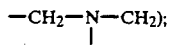

3.5 to 3.9 (Mt, 4H, >N—CH$_2$— and —CSNH—C$_2$—); 4.75 (Mt, 1H, >CH—N<); 7 to 7.4 (Mt, 5H, aromatic); 7.42 (DD, J=8 and 1, 1H, —H at 3-position); 7.55 (D, J=1, 1H, —H at 1-position); 10.48 T, J=5, 1H, —CSNH—); 10.68 (Cx, 1H, —NH+).

Infrared spectrum (KBr), characteristic bands in cm$^{-1}$: 3200, 2955, 2930, 2870, 2600, 2480, 1590, 1530, 1460, 1415, 870, 820, 750.

10-[1-(1-Pyrrolidinyl)-2-propyl]-2-phenothiazinecarbothioamide, D series may be prepared in the following manner:

A mixture of 10-[1-(1-pyrrolidinyl)-2-propyl]-2-phenothiazinecarbonitrile, D series (11.7 g) and triethylamine (4.9 cc) in anhydrous pyridine (234 cc) is saturated with hydrogen sulphide for 1 hour at 25° C. The reaction mixture is stirred for 20 hours at 25° C. and then outgassed by bubbling nitrogen through, diluted with ethyl acetate (100 cc), poured into distilled water (1 liter) and extracted with ethyl acetate (2×500 cc). The combined organic phases are washed successively with distilled water (2×250 cc) and saturated aqueous sodium chloride solution (250 cc), dried over magnesium sulphate and filtered, and the yellow filtrate is concentrated to dryness under reduced pressure (30 mm Hg; 4 kPa) at 40° C. A yellow oil (18 g) is obtained, which is purified by chromatography on a column (height: 45 cm; diameter: 4 cm) of silica gel (0.2–0.063 mm), eluting with methylene chloride (1 liter) and then with a mixture (95:5 by volume) (5 liters) of methylene chloride and methanol and collecting 100-cc fractions. Fractions 23 to 50 are combined and concentrated to dryness under reduced pressure (30 mm Hg; 4 kPa) at 40° C. 10-[1-(1-Pyrrolidinyl)-2-propyl]-2-phenothiazinecarbothioamide, D series (10.7 g) is thereby obtained in the form of a yellow product of meringue-like consistency.

$[\alpha]_D^{20} = +40.7 \geq \pm 0.6°$ (1.1%; chloroform).

10-[1-(1-Pyrrolidinyl)-2-propyl]-2-phenothiazinecarbonitrile, D series may be prepared in the following manner:

A mixture of 2-(2-cyano-10-phenothiazinyl)-1-propyl methanesulphonate D series (25.5 g) and pyrrolidine (29.6 cc) in toluene (260 cc) is heated for 52 hours to a temperature in the region of 90° C. The reaction mixture is concentrated to dryness under reduced pressure (30 mm Hg; 4 kPa) at 40° C. The residue is taken up with ethyl ether (500 cc) and extracted with 2N aqueous methanesulphonic acid solution (2×100 cc). The aqueous phase is alkalinized with caustic soda (d=1.33) to pH 13 at a temperature in the region of 5° C., and extracted successively with distilled water (100 cc) and saturated aqueous sodium chloride solution (100 cc), dried over magnesium sulphate in the presence of charcoal 3S and filtered, and the yellow filtrate is concentrated to dryness under reduced pressure (30 mm Hg; 4 kPa) at 40° C. The orange oil (18.2 g) thereby obtained is chromatographed on a column (height: 45 cm; diameter: 4 cm) of silica gel (0.063–0.2 mm), eluting with a mixture (97.5:2.5 by volume) (2.5 liters) of methylene chloride and methanol and collecting 150-cc fractions. Fractions 8 to 16 are combined and concentrated to dryness under reduced pressure (30 mm Hg; 4 kPa) at 40° C. 10-[1-(1-Pyrrolidinyl)- 2-propyl]-2-phenothiazinecarbonitrile, D series (11.7 g) is thereby obtained in the form of a yellow oil.

$[\alpha]_D^{20} = -9.8 \geq \pm 0.4°$ (1.1%; chloroform).

2-(2-Cyano-10-phenothiazinyl)-1-propyl methanesulphonate, D series may be prepared in the following manner:

Triethylamine (16.2 cc) is added with stirring to a solution, cooled to a temperature in the region of 5° C., of 10-(1-hydroxy-2-propyl)phenothiazinecarbonitrile, D series (20 g) in methylene chloride (200 cc), a solution of methanesulphonyl chloride (8.9 cc) in methylene chloride (89 cc) is then introduced dropwise during 25 minutes, and stirring is continued for 50 minutes at a temperature in the region of 10° C. The reaction mixture is washed successively with distilled water (2×100 cc) and with saturated aqueous sodium chloride solution (100 cc), dried over magnesium sulphate, filtered and concentrated to dryness under reduced pressure (30 mm Hg; 4 kPa) at 40° C. 2-(2-Cyano-10-phenothiazinyl)-1-propyl methanesulphonate, D series (25.8 g) is thereby obtained in the form of an orange gum, which is used without further purification for the next stage of the synthesis.

$[\alpha]_D^{20} = -23.1 \geq \pm 0.4°$ (1.4%; chloroform).

10-(1-Hydroxy-2-propyl)-2-phenothiazinecarbonitrile, D series may be prepared in the following manner:

(−)-2-(2-Cyano-10-phenothiazinyl)propyl (S)-1-phenylethylammonium phthalate (95.4 g) is added to a solution of potassium hydroxide (23.5 g) in ethanol (1150 cc) under reflux. The refluxing is continued with stirring for 10 minutes. The reaction mixture is then cast into ice-cold water (1 liter) and extracted with ethyl acetate (2 liters and then 500 cc). The combined organic phases are washed successively with 0.1N aqueous hydrochloric acid solution (2×500 cc), with saturated aqueous sodium hydrogen carbonate solution (2×500 cc) and with saturated aqueous sodium chloride solution (500 cc) and dried over magnesium sulphate, filtered and concentrated to dryness under reduced pressure (30 mm Hg; 4 kPa) at 40° C. The residual yellow solid (44 g) is taken up with isopropyl ether (200 cc) under reflux and the product crystallizes in the heated state. The mixture is allowed to return to a temperature in the region of 20° C. and the solid is drained, washed with isopropyl ether (20 cc) and dried under reduced pressure (5 mm Hg; 0.7 kPa) at 20° C. 10-(1-Hydroxy-2-propyl)-2-phenothiazinecarbonitrile, D series (36.5 g) is thereby obtained in the form of yellow crystals, m.p. 135° C.

$[\alpha]_D^{20} = +13.1 \geq \pm 0.5°$ (1.0%; chloroform).

(−)-2-(2-Cyano-10-phenothiazinyl)propyl (S)-1-phenylethylammonium phthalate may be prepared in the manner described in Example 14 for the production of its isomer. The solid previously kept from Example 14 is dissolved in ethyl acetate (600 cc) under reflux. After cooling, the solid formed is drained, washed with ethyl acetate (50 cc) and dried under reduced pressure (30 mm Hg; 4 kPa) at 40° C. (−)-2-(2-Cyano-10-phenothiazinyl)propyl (1s)-1-phenylethylammonium phthalate (44.2 g) is thereby obtained in the form of pale yellow crystals, m.p. 154° C.

$[\alpha]_D^{20} = -21.5° \pm 0.6°$ (1%; chloroform).

EXAMPLE 38

A solution of 10-[1-(1-pyrrolidinyl)-2-propyl]-2-phenothiazinecarbothioamide, L series (6 g) and 3-methylbutylamine (18.9 cc) in absolute ethanol (90 cc) is saturated with hydrogen sulphide and brought for 16 hour to a temperature in the region of 105° C. After cooling, the reaction mixture is concentrated to dryness under reduced pressure (30 mm Hg; 4 kPa) at 40° C. The oily brown residue is purified by chromatography on a column (height: 40 cm; diameter: 4 cm) of silica gel (0.02–0.063 mm), eluting with methylene chloride (1 liter) and then with a mixture (95:5 by volume) (1.5 liters) of methylene chloride and methanol and collecting 80-cc fractions. Fractions 23 to 36 are combined and concentrated to dryness under reduced pressure (30 mm Hg; 4 kPa) at 40° C. N-(3-Methylbutyl)-10-[1-(1-pyrrolidinyl)-2-propyl]-2-phenothiazinecarbothioamide, L series (6.76 g) is thereby obtained in the form of an orange oil. 1 g of this oil is dissolved in ethyl acetate (10 cc), and a 3.3N solution (0.7 cc) of hydrochloric acid in isopropyl ether is introduced with stirring. After 30 minutes' stirring at a temperature in the region of 5° C., the crystals formed are drained, washed with diethyl ether (3×10 cc) and dried under reduced pressure (5 mm Hg; 0.68 kPa) at 40° C. N-(3-Methylbutyl)-10-[1-(1-pyrrolidinyl)-2-propyl]-2-phenothiazinecarbothioamide hydrochloride, L series (0.75 g) is thereby obtained in the form of yellow crystals, m.p. 186° C., the NMR spectrum of which is identical to that of the product obtained in Example 35.

$[\alpha]_D^{20} = +22.2 \geq \pm 0.6°$ (0.8%; dimethylformamide).

Infrared spectrum (KBr), characteristic bands in cm$^{-1}$: 3200, 2955, 2870, 2600, 2480, 1590, 1530, 1460, 1415, 865, 820, 750.

EXAMPLE 39

3-Methylbutylamine (1.74 cc) is added to a solution of 10-{1-[(2S)-2-hydroxymethyl-1-pyrrolidinyl]-2-propyl}-2-phenothiazinecarbothioamide, L series (1.20 g) in absolute ethanol (20 cc). The mixture is brought to 150° C. for 16 hours. The reaction mixture is concentrated to dryness under reduced pressure (30 mm Hg; 4 kPa) at 40° C. The residue is diluted with ethyl acetate (100 cc), washed with distilled water (2×50 cc), dried over magnesium sulphate and then concentrated to dryness under reduced pressure (30 mm Hg; 4 kPa) before being purified by chromatography on a column (height: 14.5 cm; diameter: 2.8 cm) of silica gel (0.04–0.06 mm) with a slight excess pressure of nitrogen (40 kPa) eluting with mixtures of cyclohexane and ethyl acetate in proportions (by volume) of 65:35 (1.2 liters) and 35:65 (1.2 liters), collecting 60-cc fractions. Fractions 5 to 13 are combined and evaporated under reduced pressure (30 mm Hg; 4 kPa) at 40° C. to give 10-{1-[(2S)-2-hydroxymethyl-1-pyrrolidinyl]-2-propyl}-N-(3-methylbutyl)-2-phenothiazinecarbothioamide, L series (0.64 g) in the form of a yellow resin.

A 2.2N ethereal solution (0.41 cc) of hydrochloric acid is added to a solution of 10-{1-[(2S)-2-hydroxymethyl-1-pyrrolidinyl]-2-propyl}-N-(3-methylbutyl)-2-phenothiazinecarbothioamide, L series (0.42 g) in ethyl ether (40 cc). A gummy precipitate is deposited on the walls of the flask. The mixture is concentrated to dryness under reduced pressure (30 mm Hg; 4 kPa) at 40° C. The suspension is stirred for 12 hours at 25° C. in ethyl ether (50 cc). The precipitate is separated by filtration, washed with ethyl ether (2×10 cc) and dried at 40° C. under reduced pressure (5 mm Hg; 0.068 kPa) to give 10-{1-[(2S)-2-hydroxymethyl-1-pyrrolidinyl]-2-propyl}-N-(3-methylbutyl)-2-phenothiazinecarbothioamide hydrochloride, L series (0.39 g), m.p. 131° C.

Proton NMR (250 MHz, DMSO, δ in ppm, J in Hz):
0.95 (D, J=6.5, 6H, —CH(CH$_3$)$_2$); 1.62 (Mt, 2H, —NHCH$_2$CH$_2$—); 1.72 (D, J=7, 3H—CH$_3$); 1.6 to 2.2 (Mt, 5H, —CH(CH$_3$)$_2$ and —CH$_2$— of pyrrolidine); 3.25, 3.7 and 4.05 (3Mt, 9H, >N—CH$_2$—, —CSN-H—CH$_2$—, NCH$_2$— and NCH of pyrrolidine, —CH$_2$O—); 4.08 (Mt, 1H, >N—CH<); 5.55 (Cx, 1H, —OH); 7 to 7.4 (Mt, 5H, aromatic); 7.46 (DD, J=8 and 1, 1H, —H at 3-position); 7.56 (D, J=1, 1H, —H at 1-position); 9.96 (Cx, 1H, —NH+); 10.51 (T, J=5.5, 1H, —CSNH—).

Infrared spectrum (KBr), characteristic bands in cm$^{-1}$: 3260, 2960, 2870, 2800 to 2300, 1590, 1535, 1460, 1415, 1060, 825, 755.

10-{1[(2S)-2-hydroxymethyl-1-pyrrolidinyl]-2-propyl}-2-phenothiazinecarbothioamide, L series, may be prepared in the following manner:

A mixture of 10-{1-[(2S)-2-hydroxymethyl-1-pyrrolidinyl]-2-propyl}-2-phenothiazinecarbonitrile, L series (3.66 g) and triethylamine (1.4 cc) in anhydrous pyridine (30 cc) is saturated by bubbling hydrogen sulphide in for 4 hours at 25° C. The clear solution obtained is kept stirred for 12 hours at 25° C., and the mixture is then outgassed by bubbling nitrogen through for 2 hours and then diluted with ethyl acetate (500 cc) and washed with distilled water (6×100 cc). The organic phase is dried over magnesium sulphate, filtered and the filtrate is concentrated to dryness under reduced pressure (30 mm Hg; 4 kPa) at 50° C. The residue is purified by chromatography on a column (height: 48 cm; diameter: 2.5 cm) of silica gel (0.06-0.2 mm), eluting with a 50:50 by volume mixture (1 litre) of cyclohexane and ethyl acetate and then with pure ethyl acetate (2 liters) and collecting 50-cc fractions. Fractions 22 to 35 are combined and concentrated to dryness under reduced pressure (30 mm Hg; 4 kPa) at 50° C. to give 10-{(1-[(2S)-2-hydroxymethyl-1-pyrrolidinyl]-2-propyl}-2-phenothiazinecarbothioamide, L series (2.12 g).

10-{1-[(2S)-2-Hydroxymethyl-1-pyrrolidinyl]-2-propyl}-2-phenothiazinecarbonitrile, L series may be prepared in the following manner:

(S)-(+)-2-Pyrrolidinylmethanol (39.5 cc) is added to a suspension of (2RS)-2-(2-cyano-10-phenothiazinyl)-propyl methanesulphonate (72.1 g) in toluene (500 cc). The mixture is brought to 90° C. for 160 hours. After cooling, the mixture is washed with distilled water (4×200 cc). The organic phase is dried over magnesium sulphate, filtered and concentrated to dryness under reduced pressure (30 mm Hg; 4 kPa). The residue is purified by chromatography on a column of neutral alumina (height: 47 cm; diameter: 5 cm), eluting with mixtures of isopropyl ether and acetone in proportions (by volume) of 97:3 (22 liters), 95:5 (12 liters) and 93:7 (12 liters), collecting 500-cc fractions. Fractions 4 to 88 are combined and concentrated to dryness under reduced pressure (30 mm Hg; 4 kPa) at 50° C. to give a yellow material (56.9 g) of meringue-like consistency containing the expected product. This residue is again purified by chromatography on a column of neutral alumina (height: 42 cm; diameter: 6 cm), eluting with mixtures of isopropyl ether and acetone in proportions (by volume) of 98:2 (10 liters), 96:4 (10 liters) and 94:6 (60 liters), collecting 500-cc fractions. Fractions 51 to 70 are combined and concentrated t dryness under reduced pressure (30 mm Hg; 4 kPa) at 50° C. to give 10-{1-[(2S)-2-hydroxymethyl-1-pyrrolidinyl]-2-propyl}-2-phenothiazinecarbonitrile, L series (13.7 g).

EXAMPLE 40

3-Methylbutylamine (8.5 cc) is added to a solution of 10-{1-[(2R)-2-hydroxymethyl-1-pyrrolidinyl]-2-propyl}-2-phenothiazinecarbothioamide, L series (5.86 g) in absolute ethanol (135 cc). The mixture is saturated with hydrogen sulphide and then brought to 150° C. for 16 hours. The reaction mixture is concentrated to dryness under reduced pressure (30 mm Hg; 4 kPa) at 50° C. The residue is diluted with ethyl acetate (150 cc), washed with distilled water (3×100 cc) and with saturated sodium chloride solution (100 cc), dried over magnesium sulphate and concentrated to dryness under reduced pressure (30 mm Hg; 4 kPa) at 50° C. before being purified by chromatography on a column (height: 32 cm; diameter: 4 cm) of silica gel (0.06-0.2 mm), eluting with pure ethyl acetate (1000 cc), collecting 60-cc fractions. Fractions 6 to 12 are combined and concentrated to dryness under reduced pressure (30 mm Hg; 4 kPa) to give a residue which is dissolved in isopropyl ether (80 cc). Crystallization is primed by scratching, and the mixture is stirred for 12 hours at 25° C. The crystals are filtered off to give 10-{1-[(2R)-2-hydroxymethyl-1-pyrrolidinyl]-2-propyl}-N-(3-methylbutyl)-2-phenothiazinecarbothioamide, L series (4.3 g) in the form of yellow crystals, m.p. 140° C.

Proton NMR (250 MHz, DMSO, δ in ppm and J in Hz):

0.95 (D, J=7, 6H, —CH(CH$_3$)$_2$); 1.4 to 1.85 (Mt, 7H, >CH—CH$_2$— and —CH$_2$— of pyrrolidine); 1.6 (D, J=7, 3H, —CH$_3$); 2.22 (Mt, 1H, of the pyrrolidine >N—CH$_2$—); 2.55 (Mt, approximately 1H, pyrrolidine >N—CH<); 2.92 (DD, J=12.5 and 5.5, 1H, of >N—CH$_2$—); 3.2 (Mt, approximately 1H, 1H of the pyrrolidine NCH$_2$—); 3.25 to 3.55 (Mt, >N—CH$_2$— and —CH$_2$O—); 3.74 (Mt, 2H, —CSNH—CH$_2$—); 4.18 (Mt, 1H, >N—CH<); 4.42 (Cx, 1H, —OH); 6.9 to 7.25 (Mt, 5H, aromatic); 7.29 (broad D, J=8, 1H, —H at 3-position); 7.63 (broad S, 1H, —H at 1-position); 10.21 (T, J=5, 1H, —CSNH—).

Infrared spectrum (CHCl$_3$), characteristic bands in cm$^{-1}$: 3390, 3280, 2960, 2930, 2875, 2820, 1600, 1570, 1550, 1510, 1460, 1415, 810.

EXAMPLE 41

(2RS)-2-Methylbutylamine (2.9 cc) is added to a solution of 10-[(2RS)-1-diethylamino-2-propyl]-2-phenothiazinecarbothioamide (1.86 g) in absolute ethanol (25 cc). The mixture is brought to 150° C. for 16 hours. The reaction mixture is diluted with ethyl acetate (150 cc) and then washed with distilled water (3×70 cc). The organic phase is dried over magnesium sulphate, filtered and then concentrated to dryness under reduced pressure (30 mm Hg; 4 kPa) at 50° C. The residue is purified by chromatography on a column (height: 16.5 cm; diameter: 2.8 cm) of silica gel (0.04-0.06 mm) with a slight excess pressure of nitrogen (40 kPa), eluting with a 75:25 (by volume) mixture (0.5 litre) of cyclohexane and ethyl acetate, collecting 25-cc fractions. Fractions 5 to 15 are combined and concentrated to dryness under reduced pressure (30 mm Hg; 4 kPa) at 50° C. to give an orange product (1.12 g) of meringue-like consistency. This product is again chromatographed on a column (height: 14 cm; diameter: 3.0 cm) of silica gel (0.04-0.06 mm) with a slight excess pressure of nitrogen (40 kPa), eluting with a 75:25 (by volume) mixture (300 cc) of cyclohexane and ethyl acetate, collecting 20-cc fractions. Fractions 4 to 15 are combined and concentrated to dryness under reduced pressure (30 mm Hg; 4 kPa) at 50° C. to give a yellow product, which is chromatographed a final time on a column (height: 14 cm; diameter: 3.0 cm) of silica gel (0.04-0.06 mm) with a slight excess pressure of nitrogen (40 kPa), eluting with mixtures of cyclohexane and ethyl acetate in proportions (by volume) of 90:10 (300 cc) and 75:25 (350 cc), collecting 20-cc fractions. Fractions 19 to 32 are combined and concentrated to dryness under reduced pressure (30 mm Hg; 4 kPa) at 50° C. to give a yellow product (0.53 g) which is dissolved in boiling 2-propanol (5 cc), and fumaric acid (0.14 g) dissolved in 2-propanol (3 cc) is added to the solution obtained. Crystallization is primed by scratching. The mixture is left stirred for 24 hours at 5° C., and the crystals are then filtered off and dried at 50° C. under reduced pressure (5 mm Hg; 0.7 kPa) to give 10-[(2RS)-1-diethylamino-2-propyl]-N-[(2RS)-2-methylbutyl]-2-phenothiazinecarbothioamide fumarate (0.48 g), m.p. 168° C.

Infrared spectrum (KBr), characteristic bands in cm$^{-1}$: 3240, 2960, 2930, 2880, 2650, 2490, 1700, 1590, 1535, 1460, 1420, 980, 885, 820.

NMR spectrum (250 MHz, DMSO, δ in ppm, J in Hz):

0.9 (Mt, 12H, —CH$_2$CH(CH$_3$)—CH$_2$CH$_3$ and —N(CH$_2$CH$_3$)$_2$); 1.20 and 1.43 (2Mt, 1H each, —CH(CH$_3$)CH$_2$—CH$_3$); 1.64 (D, J=7.5, 3H, —CH$_3$); 1.95 (Mt, 1H, 2-methylbutyl —CH<); 2.57 (Mt, 4H, —N(CH$_2$CH$_3$)$_2$); 2.80 (DD, J=14 and 5.5, 1H, 1H of >N—CH$_2$—); 3.10 (DD, J=14 and 7, 1H, 1H of >N—CH$_2$—); 3.50 and 3.64 (2Mt, 1H each, —CSNH—CH$_2$—); 4.25 (Mt, J=7.5, 7 and 5.5, 1H, >N—CH<); 6.6 (S, 2H, fumarate —CH=CH—); 6.9 to 7.3 (Mt, 6H, aromatic); 7.56 (D, J=1, 1H, —H at 1-position); 10.25 (T, J=5, 1H, —CSNH—).

EXAMPLE 42

A solution of 10-[(2RS)-1-(N-ethyl-N-methylamino)-2-propyl]-2-phenothiazinecarbothioamide (1 g) and (2RS)-2-methylbutylamine (4.9 cc) in absolute ethanol (15 cc) is saturated with hydrogen sulphide and heated for 16 hours to a temperature in the region of 100° C. After cooling, the mixture is concentrated to dryness under reduced pressure (30 mm Hg; 4 kPa) at 40° C. The oily orange residue is purified by chromatography on a column (height: 25 cm; diameter: 2 cm) of silica gel (0.04-0.063 mm) under a slight excess pressure of nitrogen (40 kPa), eluting with a mixture 80:20 by volume (500 cc) of ethyl acetate and cyclohexane and collecting 40-cc fractions. Fractions 4 to 8 are combined and concentrated to dryness under reduced pressure (30 mm Hg; 4 kPa) at 40° C. A yellow oil (1.88 g) is obtained. 0.8 g of this oil is dissolved in ethyl acetate (5 cc), and isopropyl ether (50 cc) is added, followed, dropwise and with stirring and at a temperature in the region of 5° C., by a 0.335N solution (5.55 cc) of hydrochloric acid in isopropyl ether, and stirring is continued for 30 minutes at the same temperature. The precipitate formed is drained, washed with isopropyl ether (2 cc) and dried under reduced pressure (5 mm Hg; 0.68 kPa) at 40° C. 10-[(2RS)-1-(N-Methyl-N-ethylamino)-2-propyl]-N-[(2RS)-2-methylbutyl]-2-phenothiazinecarbothioamide hydrochloride (0.73 g) is thereby obtained in the form of yellow solid, m.p. 105°-110° C. (melts forming a paste).

Proton NMR (250 MHz, DMSO, δ in ppm, J in Hz): In solution in DMSO, two forms are observed, due to salification of the nitrogen.

0.91 (T, J=7.5, —CH$_2$—CH$_3$); 0.93 (D, J=7.5, 2-methylbutyl >CH—CH$_3$); 1.05 and 1.16 (2T, J=7.5, 3H, —NCH$_2$CH$_3$); 1.20 and 1.39 (2Mt, 2H, —CH$_2$CH$_3$); 1.78 (broad D, 3H, —CH$_3$); 1.99 (Mt, 1H, 2-methylbutyl >CH—); 2.77 (broad S, 3H, >N—CH$_3$); 3.12 (Cx, 2H, >N—CH$_2$—CH$_3$); 3.35 to 3.90 (Mt, 4H, >N—CH$_2$ and —CSNH—CH$_2$—); 4.82 (Mt, 1H, >N—CH<); 7 to 7.35 (Mt, 5H, aromatic); 7.41 (D, J=8, 1H, —H at 3-position); 7.55 (S, 1H, —H at 1-position); 10.30 (Cx, 1H, —NH$^+$); 10.50 (Mt, 1H, —CSNH—).

Infrared spectrum (KBr), characteristic bands in cm$^{-1}$: 3200, 2960, 2920, 2875, 2580, 2480, 1590, 1530, 1460, 880, 820, 750.

EXAMPLE 43

A stirred suspension of 10-[(2RS)-1-(1-pyrrolidinyl)-2-propyl]-2-phenothiazinecarbothioamide (2 g) and 2-methylbutylamine (3 cc) in anhydrous ethanol (15 cc) is saturated with hydrogen sulphur and heated for 1 hour to a temperature in the region of 115° C. After cooling, the mixture is concentrated to dryness under reduced pressure (30 mm Hg; 4 kPa) at 50° C. The residual yellow paste is taken up with ethyl acetate (30 cc) and distilled water (20 cc). The organic phase is separated, washed with saturated aqueous sodium chloride solution (20 cc), dried over magnesium sulphate, filtered and concentrated to dryness under reduced pressure (30 mm Hg; 4 kPa) at 40° C. The residual viscous yellow oil (2.2 g) is purified by chromatography on a column (height: 40 cm; diameter: 3.2 cm) of silica gel (0.04-0.063 mm), eluting with a mixture (92:8 by volume) (300 cc) of ethyl acetate and methanol and collecting 25-cc fractions. Fractions 6 to 11 are combined and concentrated to dryness under reduced pressure (30 mm Hg; 4 kPa) at 40° C. N-[(2RS)-2-Methylbutyl]-10-[(2RS)-1-(1-pyrrolidinyl)-2-propyl]-2-phenothiazinecarbothioamide (1.8 g) is thereby obtained in the form of a viscous yellow oil. 0.4 g of this oil is dissolved in isopropyl ether (15 cc), and a 3.3N solution (0.4 cc) of hydrochloric acid in isopropyl ether is added. The precipitate formed is drained, washed with isopropyl ether (3×5 cc) and dried under reduced pressure (5 mm Hg; 0.68 kPa) at 40° C. N-[(2RS)-2-Methylbutyl]-10-[(2RS)-1-(1-pyrrolidinyl)-2-propyl]-2-phenothiazinecarbothioamide hydrochloride (0.4 g is thereby obtained in the form of a yellow powder, m.p. 155°-160° C. (melts forming a paste).

Proton NMR (250 MHz, DMSO, δ in ppm, J in Hz): 0.93 (T, J=7.5, 3H, —CH$_2$CH$_3$); 0.95 (D, J=7.5, 3H, 2-methylbutyl >CH—CH$_3$); 1.20 AND 1.45 (2Mt, 1H each, —CH$_2$CH$_3$); 1.78 (D, J=7, 3H, —CH$_3$); 1.7 to 2 (Mt, 4H, pyrrolidine —CH$_2$CH$_2$—); 2 (Mt, 1H, 2-methylbutyl >CH—); 2.85, 3.13 and from 3.4 to 3.95 (2Cx of 1H each and Mt, pyrrolidine

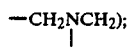

3.4 to 3.95 (Mt, 4H, N—CH$_2$— and —CSNH—CH$_2$—); 4.78 (Mt, 1H, >N—CH<); 7 to 7.35 (Mt, 5H, aromatic); 7.43 (broad D, J=8, 1H, —H at 3-position); 7.55 (broad S, 1H, —H at 1-position); 10.48 (T, J=5, 1H —CSNH—); 10.57 (Cx, 1H —NH$^+$).

Infrared spectrum (KBr), characteristic bands in cm$^{-1}$: 3210, 2960, 2920, 2870, 2580, 2470, 1590, 1530, 1460, 1415, 820, 750.

EXAMPLE 44

A mixture of 10-[1-(1-pyrrolidinyl)-2-propyl]-2-phenothiazinecarbothioamide, L series (2 g) and (2RS)-2-methylbutylamine (9.5 cc) in ethanol (30 cc) is saturated with hydrogen sulphide and then heated for 16 hours to 100° C. After cooling, the solution is concentrated to dryness under reduced pressure (30 mm Hg; 4 kPa) at 40° C. An orange oil (3.8 g) is obtained, which is purified by chromatography on a column (height: 40 cm; diameter: 3 cm) of silica gel (0.063-0.2 mm), eluting with a mixture (97.5:2.5 by volume) (1.5 liters) of methylene chloride and methanol and collecting 30-cc fractions. Fractions 35 to 46 are combined and concentrated &.o dryness under reduced pressure (30 mm Hg; 4 kPa) at 40° C. An orange oil (1.8 g) is obtained. This product is dissolved in a mixture (80:20 by volume) (60 cc) of isopropyl ether and ethyl acetate, and a 0.37N solution (11 cc) of hydrochloric acid in isopropyl ether is then added with stirring and at a temperature in the region of 5° C. The precipitate formed is drained, washed with isopropyl ether (3×10 cc) and dried under reduced pressure (5 mm Hg; 0.7 kPa) at 40° C. N-[(2RS)-2-methylbutyl]-10-[1-(1-pyrrolidinyl)-2-propyl]-2-phenothiazinecarbothioamide hydrochloride, L series (1.4 g) is thereby obtained in the form of a yellow solid, m.p. 120°-125° C. (melts forming a paste), the NMR spectrum of which is identical to that of the thioamide described in Example 43.

$[\alpha]_D^{20} = \pm 24.3° \pm 0.8°$ (0.7%; dimethylformamide).

Infrared spectrum (KBr), characteristic bands in cm$^{-1}$: 3210, 2960, 2930, 2880, 2580, 2480, 1590, 1530, 1460, 870, 820, 755.

EXAMPLE 45

A mixture of 10-[1-(1-pyrrolidinyl)-2-propyl]-2-phenothiazinecarbothiamide, L series (4 g) and (2S)-2-methylbutylamine (5 g) in ethanol (60 cc) is saturated with hydrogen sulphide and then heated for 16 hours to 100° C. After cooling, the solution is concentrated to dryness under reduced pressure (30 mm Hg; 4 kPa) at 40° C. An orange oil (5.3 g) is obtained, which is purified by chromatography on a column (height: 48 cm; diameter: 4 cm) of silica gel (0.063-0.2 mm), eluting with a mixture (97.5:2.5 by volume) (2 liters) of methylene chloride and methanol and collecting 60-cc fractions. Fractions 23 to 29 are combined and concentrated to dryness under reduced pressure (30 mm Hg, 4 kPa) at 40° C. An orange oil (4.1 g) is obtained. This product is dissolved in a mixture (75:25 by volume) (200 cc) of isopropyl ether and ethyl acetate, and a 0.72N solution (12.8 cc) of hydrochloric acid in isopropyl ether is then added with stirring and at a temperature in the region of 5° C. The precipitate formed is drained, washed with isopropyl ether (3×20 cc) and dried under reduced pressure (5 mm Hg; 0.7 kPa) at 40° C. N-[(2S)-2-Methylbutyl]-2-phenothiazinecarbothioamide hydrochloride, L series (3.2 g) is thereby obtained in the form of a yellow solid, m.p. 135°-140° C. (melts forming a paste), the NMR spectrum of which is identical to that of the thioamide described in Example 43.

$[\alpha]_D^{20} = +28.3° \pm 0.6°$ (1%; dimethylformamide).

Infrared spectrum (KBr), characteristic bands in cm$^{-1}$: 3220, 2950, 2925, 2870, 2680, 2600, 2475, 1590, 1530, 1460, 865, 820, 750.

EXAMPLE 46

A solution of 10-[(2RS)-1-(1-pyrrolidinyl)-2-propyl]-2-phenothiazinecarbothioamide (2 g) and 4-methylpentylamine hydrochloride (7.4 g) is absolute ethanol (30 cc) is saturated with hydrogen sulphide. The reaction mixture is then brought for 16 hours to a temperature in the region of 105° C. After cooling, the mixture is concentrated to dryness under reduced pressure (30 mm Hg; 4 kPa) at 40° C. The pasty residue (5 g) is purified by chromatography on a column (height: 35 cm; diameter: 3 cm) of silica gel (0.2-0.063 mm), eluting successively with methylene chloride (500 cc) and then with a mixture (95:5 by volume) (500 cc) of methylene chloride and methanol, collecting 30-cc fractions. Fractions 25 to 28 are combined and concentrated to dryness under reduced pressure (30 mm Hg; 4 kPa) at 40° C. The residual orange oil (2.16 g) is dissolved in ethyl acetate (10 cc), and a 3.3N solution (1.5 cc) of hydrochloric acid in isopropyl ether is added with stirring, followed by ethyl ether until a persistent cloudiness has formed. After 1 hour at a temperature in the region of 5° C., the solid formed is drained, washed with ethyl ether (3×10 cc) and dried under reduced pressure (5 mm Hg; 0.7 kPa) at 40° C. N-(4-Methylpentyl)-10-[(2RS)-1-(1-pyrrolidinyl)-2-propyl]-2-phenothiazinecarbothioamide hydrochloride (1.7 g) is thereby obtained in the form of a yellow solid, m.p. 186° C.

Proton NMR (250 MHz, DMSO, δ in ppm, J in Hz): 0.90 (D, J=7, 6H, —CH(CH$_3$)$_2$); 1.26 (Mt, 2H, —CH$_2$—CH(CH$_3$)$_2$); 1.58 (Mt, 1H, 4-methylpentyl >CH—); 1.7 (Mt, 2H, —NHCH$_2$—CH$_2$—); 3.72 (Mt, 2H, —CSNHCH$_2$—); 7 to 7.35 (Mt, 5H, aromatic); 7.45 (broad D, J=8, 1H, —H at 3-position); 7.55 (broad S, 1H, —H at 1-position): 10.52 (T, J=5, 1H, —CSNH—).

Infrared spectrum (KBr), characteristic bands in cm$^{-1}$: 3200, 2950, 2920, 2860, 2680, 2600, 2470, 1590, 1530, 1460, 1410, 815, 745.

EXAMPLE 47

A mixture of 10-[(2RS)-1-(1-pyrrolidinyl)-2-propyl]-2-phenothiazinecarbothioamide (3.7 g), (3RS)-3-methyl-1-pentylamine hydrochloride (3.3 g) and triethylamine (3.4 cc) in ethanol (55 cc) is saturated with hydrogen sulphide and then heated for 16 hours to 105° C. After cooling, the solution is concentrated to dryness under reduced pressure (30 mm Hg; 4 kPa) at 40° C. An orange oil (5.6 g) is obtained, which is purified by chromatography under an excess pressure of nitrogen (40 kPa) on a column (height: 25 cm; diameter 4 cm) of silica gel (0.063-0.2 mm), eluting with a mixture (95:5 by volume) (1 litre) of methylene chloride and methanol and collecting 60-cc fractions. Fractons 8 to 9 are combined and concentrated to dryness under reduced pressure (30 mm Hg; 4 kPa) at 40° C. An orange oil (2.3 g) is obtained. This product is dissolved in a mixture of ethyl acetate (10 cc) and isopropyl ether (100 cc) and a 3.3N solution (1.5 cc) of hydrochloric acid in isopropyl ether is then added. The precipitate formed is drained, washed with isopropyl ether (3×10 cc) and dried under reduced pressure (5 mm Hg; 0.7 kPa) at 40° C. N-[(3RS)-3-Methyl-1-pentyl]-10-[(2RS)-1-(1-pyrrolidinyl)-2-propyl]-2-phenothiazinecarbothioamide hydrochloride (1.7 g) is thereby obtained in the form of a yellow oil, m.p. 135°-140° C. (melts forming a paste).

Proton NMR (250 MHz, DMSO, δ in ppm, J in Hz): 0.88 (T, J=7, 3H, —CH$_2$—CH$_3$; 0.93 (D, J=7, 3H, 3-methylpentyl >CH—CH$_3$); 1.2 and 1.4 (2Mt, 1H each, —C$_2$CH$_3$); 1.49 (Mt, 2H, —NHCH$_2$CH$_2$—); 1.72 (Mt, 1H, 3-methylpentyl —CH—); 3.50 to 3.90 (Mt, 4H, N—CH$_2$ and —CSNHCH—); CH$_2$); 7 to 7.35 (Mt, 5H, aromatic); 7.41 (broad D, J=8, 1H, —H at 3-position); 7.56 (broad S, 1H, —H at 1-position); 10.4 (T, J=5, 1H, —CSNH—).

Infrared spectrum (KBr), characteristic bands in cm$^{-1}$: 3220, 2960, 2930, 2880, 2680, 2600, 2480, 1590, 1535, 1460, 1415, 870, 825, 755.

10-[(2RS)-1-(1-pyrrolidinyl)-2-propyl]-2-phenothiazinecarbothioamide may be obtained in the following manner:

A solution of 10-[(2RS)-1-(1-pyrrolidinyl)-2-propyl]-2-phenothiazinecarbonitrile (5.3 g) and triethylamine (2.2 cc) in anhydrous pyridine (106 cc) is saturated with hydrogen sulphide and left stirred for 16 hours at a temperature in the region of 20° C. The reaction mixture is poured into distilled water (500 cc) and extracted successively with ethyl acetate (500 cc and then 2×250 cc). The combined organic phases are washed with distilled water (3×200 cc), dried over magnesium sulphate, filtered and concentrated to dryness under reduced pressure (30 mm Hg; 4 kPa) at 40° C. The orange oil (6.5 g) obtained is chromatographed on a column (height: 30 cm; diameter 4 cm) of silica gel (0.2–0.063 mm) under an excess pressure of nitrogen (40 kPa), eluting with a mixture (95:5 by volume) (1 litre) of methylene chloride and methanol and then with a mixture (90:10 by volume) (1 litre) of methylene chloride and methanol and collecting 100-cc fractions. Fractions 8 to 16 are combined and concentrated to dryness under reduced pressure (30 mm Hg; 4 kPa) at 40° C. 10-[(2RS)-1-(1-pyrrolidinyl)-2-propyl]-2-phenothiazinecarbothioamide (5.1 g) is thereby obtained in the form of a yellow solid. 1.4 g of this product are dissolved at a temperature in the region of 60° C. in isopropanol (25 cc). After cooling, the crystals formed are drained, washed with cold isopropanol (5 cc) and dried under reduced pressure (5 mm Hg; 0.7 kPa) at 30° C. 10-[(2RS)-1-(1-pyrrolidinyl)-2-propyl]-2-phenothiazinecarbothioamide (1.1 g) is thereby obtained in the form of yellow crystals, m.p. 150° C.

10-[(2RS)-1-(1-Pyrrolidinyl)-2-propyl]-2-phenothiazinecarbonitrile may be prepared in the following manner:

A mixture of (2RS)-2-(2-cyano-10-phenothiazinyl)-1-propyl methanesulphonate (10 g) and pyrrolidine (11.6 cc) in toluene (50 cc) is brought to 90° C. with stirring for 24 hours. After cooling, the mixture is concentrated to dryness under reduced pressure (30 mm Hg; 4 kPa) at 40° C. and the residue is taken up with ethyl ether (200 cc) and 4N aqueous sodium hydroxide solution (15 cc). After stirring for 10 minutes, settling is allowed to take place and the organic phase is washed with saturated aqueous sodium chloride solution (3×25 cc), dried over magnesium sulphate, filtered and concentrated to dryness under reduced pressure (30 mm Hg; 4 kPa) at 20° C. The residual oil (11.3 g) is dissolved in 0.5N aqueous hydrochloric acid solution (60 cc). This solution is washed with ethyl ether (100 cc), then alkalinized with an excess of N aqueous sodium hydroxide solution and extracted with ethyl ether (100 cc). The organic phase is washed with saturated aqueous sodium chloride solution (50 cc), dried over magnesium sulphate, filtered and concentrated to dryness under reduced pressure (30 mm Hg; 4 kPa) at 20° C. The residual yellow oil (9.5 g) is purified on a column (height: 30 cm; diameter: 5.8 cm) on silica gel (0.04–0.063 mm) under a slight excess pressure of nitrogen (40 kPa), eluting with a mixture (95:5 by volume) (one litre) of methylene chloride and methanol and collecting 100-cc fractions. Fractions 3 to 10 are combined and concentrated to dryness under reduced pressure (30 mm Hg; 4 kPa) at 40° C. 10-[2RS]-1-(1-Pyrrolidinyl)-2-propyl]-2-phenothiazinecarbonitrile (5.45 g) is thereby obtained in the form of a yellow oil.

(2RS)-2-(2-Cyano-2-phenothiazinyl)-1-propyl methanesulphonate may be obtained in the following manner:

Into a solution, cooled to a temperature in the region of 5° C., of 10-[(2RS)-1-hydroxy-2-propyl]-2-phenothiazinecarbonitrile (120,5 g) in methylene chloride (1280 cc), there is introduced, with stirring, triethylamine (100 cc) followed, in the course of 30 minutes, by methanesulphonyl chloride (55.9 cc), and stirring is continued for 15 minutes while the temperature is maintained at about 10°–15° C. The reaction mixture is diluted with distilled water (500 cc) at 5° C. and the organic phase is separated, washed with saturated aqueous sodium chloride solution (500 cc), dried over sodium sulphate, filtered and concentrated to dryness under reduced pressure (30 mm Hg; 4 kPa) at 40° C. The residual oil (164 g) is purified by chromatography on a column (height: 54 cm; diameter: 8.5 cm) of silica gel (0.2–0.063 mm), eluting with methylene chloride (4.4 liters) and then with a mixture (99:1 by volume) (7 liters) of methylene chloride and methanol and collecting 1-litre fractions. Fractions 3 to 11 are combined and concentrated to dryness under reduced pressure (30 mm Hg; 4 kPa) at 40° C. A yellow oil (153.5 g) is thereby obtained, which is taken up with isopropyl ether (400 cc) under reflux. On cooling, a product crystallizes, and stirring is continued for 1 hour at a temperature in the region of 5° C. The solid formed is drained, washed with ice-cold isopropyl ether (2×50 cc) and dried at 30° C. under reduced pressure (34 mm Hg; 0.4 kPa). (2RS)-2-(2 Cyano-10-phenothiazinyl)-1-propyl methanesulphonate (131.6 g) is thereby obtained in the form of pale yellow crystals, m.p. 124° C.

EXAMPLE 48

A mixture of 10-[(2RS)-1-(1-pyrrolidinyl)-2-propyl]-2-phenothiazinecarbothioamide (3 g) and 3,3-dimethylbutylamine (5.7 g) in absolute ethanol (30 cc) is brought to a temperature in the region of 100° C. for 16 hours. After cooling, the mixture is concentrated to dryness under reduced pressure (30 mm Hg; 4 kPa) at 40° C. The residue is dissolved in ethyl acetate (100 cc) and this solution is washed with distilled water (3×20 cc), dried over magnesium sulphate in the presence of charcoal 3S and concentrated to dryness under reduced pressure (30 mm Hg; 4 kPa) at 40° C. The residue (5 g) is purified by chromatography on a column (height: 30 cm, diameter: 5 cm) of silica gel (0.04–0.063 mm), eluting with a mixture (97:3 by volume) (2.5 liters) of methylene chloride and methanol and collecting 100-cc fractions. Fractions 18 to 24 are combined and concentrated to dryness under reduced pressure (30 mm Hg; 4 kPa) at 40° C. The residue (3.68 g) is dissolved in ethyl acetate (35 cc). This solution is filtered and a 3N solution (3.5 cc) of hydrochloric acid in ethyl ether is added. The mixture is left to stand for 2 hours at a temperature in the region of 5° C., and the solid formed is drained, washed with ethyl ether (5 cc) and dried under reduced pressure (5 mm Hg; 0.7 kPa) at 35° C. N-(3,3-Dimethylbutyl)-10-[(2RS)-1-(1-pyrrolidinyl)-2-propyl]-2-phenothiazinecarbothioamide hydrochloride (3.2 g) is thereby obtained in the form of yellow crystals, m.p. 199°–200° C.

Proton NMR (250 MHz, DMSO, δ in ppm, J in Hz): 0.97 (S, 9H, —C(CH$_3$)$_3$); 1.61 (Mt, 2H, —CH$_2$—C(CH$_3$)$_3$); 1.78 (D, J=7, 3H, —CH$_3$); 3.5 to 3.9 (Mt, 4H, >N—CH$_2$ and —CSNHCH$_2$—); 7 to 7.35 (Mt, 5H, aromatic); 7.42 (D, J=8, 1H, —H at 3-position); 7.53 (S, 1H, —H in 1-position); 10.45 (T, J=5, 1H, —CSNH—).

Infrared spectrum (KBr), characteristic bands in cm$^{-1}$: 3190, 2950, 2860, 2680, 2600, 2470, 1590, 1530, 1460, 1410, 865, 820, 745.

EXAMPLE 49

A solution of 10-[1-(1-pyrrolidinyl)-2-propyl]-2-phenothiazinecarbothioamide, L series (7.4 g) in absolute ethanol (40 cc) is saturated by bubbling hydrogen sulphide in for 20 minutes, a solution of cyclobutylmethylamine (8.5 g) in ethanol (50 cc) is then added and the mixture is brought to a temperature of 130° C. for 20 hours. After cooling, the reaction mixture is concentrated to dryness under reduced pressure (30 mm Hg; 4 kPa) at 40° C. The residue is purified by chromatography on a column (height: 38 cm; diameter: 4.5 cm) of silica gel (0.04–0.06 mm) with a slight excess pressure of nitrogen (40.5 kPa), eluting with ethyl acetate (2 liters) and collecting 125-cc fractions. Fractions 1 to 6 are combined and concentrated to dryness under reduced pressure (30 mm Hg; 4 kPa) at 40° C. to give N-cyclobutylmethyl-10-[1-(1-pyrrolidinyl)-2-propyl]-2-phenothiazinecarbothioamide, L series (8.53 g).

$[\alpha]_D^{20} = +24.4 \geq \pm 0.5°$ (c = 1%; methanol)

A solution of fumaric acid (0.58 g) in 2-propanol (14 cc) under reflux is added to a solution of N-cyclobutylmethyl-10-[1-(1-pyrrolidinyl)-2-propyl]-2-phenothiazinecarbothioamide, L series (2.19 g) in 2-propanol (16 cc) under reflux. After cooling, the mixture is concentrated to dryness under reduced pressure (30 mm Hg; 4 kPa) at 40° C. and the residue is taken up with stirring for 16 hours with isopropyl ether (70 cc). The suspension obtained is filtered and the solid is dried under reduced pressure (5 mm Hg; 4 kPa) at 50° C. and dissolved in 2-propanol under reflux (50 cc). After cooling, the product crystallizes and stirring is continued for 16 hours at 20° C. The crystals are filtered off and dried under reduced pressure (5 mm Hg; 4 kPa) at 50° C. N-Cyclobutylmethyl-10-[1-(1-pyrrolidinyl)-2-propyl]-2-phenothiazinecarbothioamide fumarate, L series (1.52 g) is thereby obtained in the form of yellow crystals, m.p. 194° C.

$[\alpha]_D^{20} = +29.9 \geq \pm 0.6°$ (c = 1%; methanol)

Proton NMR (250 MHz, DMSO-d6, δ in ppm, J in Hz):

1.62 (D, J=7, 3H, —CH₃); 1.74 (Mt, 4H, pyrrolidine —CH₂—); 1.7 to 1.95 and 2.05 (2Mt, respectively 4H and 2H, cyclobutylmethyl —CH₂—); 2.6 to 2.9 (Mt, 5H, cyclobutylmethyl >CH— and pyrrolidine >N—CH₂—); 3.11 (DD, J=12.5 and 6, 1H, 1H of >N—CH₂—); 3.23 (DD, J=12.5 and 6.5, 1 H, 1H of >N—CH₂—); 3.77 (DD, J=7 and 5.5, 2H, —CSNHCH₂—); 4.37 (Mt, J=7, 6.5 and 6, 1H, >N—CH<); 6.59 (S, 2H, fumarate —CH=CH—); 6.95 to 7.35 (Mt, 6H, aromatic); 7.54 (broad S, 1H, —H at 1-position); 10.3 (T, J=5.5, 1H, —CSNH—).

Infrared spectrum (KBr), characteristic bands in cm⁻¹: 3220, 2970, 2860, 2800, 2060, 2000, 1800, 1700, 1590, 1540, 1485, 1460, 980, 870, 815, 755, 640.

EXAMPLE 50

A mixture of 10-[(2RS)-1-dimethylamino-2-propyl]-2-phenothiazinecarbothioamide (2 g) and cyclohexylmethylamine 11.4 cc) in absolute ethanol (30 cc) is saturated with hydrogen sulphide and heated for 16 hours to a temperature in the region of 125° C. After cooling, the orange solution obtained is concentrated to dryness under reduced pressure (30 mm Hg; 4 kPa) at 40° C. The residual orange oil is purified by chromatography on a column (height: 25 cm; diameter: 4 cm) of silica gel (0.06–0.04 mm) under a slight excess pressure of nitrogen (40 kPa) eluting with a 60:40 by volume mixture (1 litre) of ethyl acetate and cyclohexane and collecting 60-cc fractions. The combined fractions 6 to 13 are concentrated to dryness under reduced pressure (30 mm Hg; 4 kPa) at 40° C. The residual orange gum (2.5 g) is dissolved in isopropanol (8 cc) under reflux and treated, with stirring, with a solution at 50° C. of fumaric acid (0.6 g) in isopropanol (8 cc). The mixture is allowed to cool and stirring is continued for 1 hour at a temperature in the region of 5° C. The solid formed is drained, washed with isopropanol (2×1 cc) and dried under reduced pressure (5 mm Hg; 0.68 kPa) at 40° C. N-Cyclohexylmethyl-10-[(2RS)-1-dimethylamino-2-propyl]-2-phenothiazinecarbothioamide neutral fumarate (2.53 g) is thereby obtained in the form of a yellow solid, m.p. 167° C.

Proton NMR (250 MHz, DMSO, δ in ppm, J in Hz):
0.9 to 1.35 and 1.5 to 1.95 (Mt, 11H, —C₆H₁₁); 1.58 (D, J=7, 3H, —CH₃); 2.28 (S, 6H, —N(CH₃)₂); 2.75 (DD, J=13 and 6.5, 1H, 1H of >N—CH₂—); 2.99 (DD, J=13 and 6, 1H, 1H of >N—CH₂—); 3.55 (Mt, 2H, —CSNH—CH₂—); 4.24 (Mt, J=7, 6.5 and 6, 1H, >N—CH<); 6.58, (S, 1H, hemifumarate —CH=CH—); 6.9 to 7.25 (Mt, 5H, aromatic); 7.27 (DD, J=8 and 1, 1H, —H at 3-position); 7.50 (D, J=1, 1H, —H at 1-position); 10.23 (T, J=5.5, 1H, —CSNH—).

Infrared spectrum (KBr), characteristic bands in cm⁻¹: 3180, 2980, 2920, 2860, 1700, 1590, 1535, 1460, 760, 670.

EXAMPLE 51

A solution of 10-[1-(2,5-dihydro-1-pyrrolyl)-2-propyl]-2-phenothiazinecarbothioamide, L series (0.74 g) in allylamine (7 cc) is saturated by bubbling hydrogen sulphide in for 25 minutes, and then heated for 5 hours to a temperature in the region of 55° C. After cooling, the reaction mixture is concentrated to dryness under reduced pressure (30 mm Hg; 4 kPa) at 40° C. The residue is dissolved in ethyl acetate (30 cc), washed successively with distilled water (5×30 cc), dried over magnesium sulphate, filtered and concentrated to dryness under reduced pressure (30 mm Hg; 4 kPa) at 40° C. The residue (0.89 g) is purified by chromatography on a column (height: 18 cm; diameter: 2.4 cm) of silica gel (0.04–0.63 mm) under a slight excess pressure of nitrogen (40 kPa), eluting with a mixture (50:50 by volume) (0.5 liters) of cyclohexane and ethyl acetate and collecting 25-cc fractions. Fractions 4 to 8 are combined and concentrated to dryness under reduced pressure (30 mm Hg; 4 kPa) at 40° C. to give a yellowish oil (0.42 g). This residue is dissolved in 2-propanol (2 cc) under reflux and treated with a lukewarm solution of fumaric acid (0.11 g) in 2-propanol (2.3 cc). After cooling, the crystallized solid form is filtered off, washed with diethyl ether (10 cc) and dried under reduced pressure (5 mm Hg; 0.67 kPa). N-Allyl-10-[1-(2,5-dihydro-1-pyrrolyl)-2-propyl]-2-phenothiazinecarbothioamide fumarate, L series (0.30 g) is thereby obtained in the form of a yellow powder, m.p. about 197° C.

$[\alpha]_D^{20} = +36.4 \geq \pm 0.7°$ (1%; methanol)

Proton NMR (250 MHz, DMSO-d6, δ in ppm, J in Hz):

1.63 (D, J=7, 3H, —CH₃); 3.1 (DD, J=12.5 and 7.5, 1H, 1H of >N—CH₂—); 3.28 (DD, J=12.5 and 6.5, 1H, 1H of >N-CH₂—); 3.54 (AB, 4H, pyrroline >N-CH₂—); 4.20 (Mt, J=7.5, 7 and 6.5, 1H, >N-CH); 4.37 (DD, J=6.5 and 5, 2H, —CSNHCH₂—); 5.23 (Mt, 2H, —CH₂CH=CH₂); 5.80 (Cx, 2H, pyrroline —CH=CH—); 5.97 (Mt, 1H, —CH=CH₂); 6.64 (S, 2H, fumarate —CH=CH—); 6.9 to 7.3 (Mt, 5H, aromatic); 7.34 (DD, J=8 and 1, 1H, —H at 3-position); 7.62 (D, J=1, 1H, —H at 1-position); 10.45 (T, J=5, 1H, —CSNH—).

Infrared spectrum (KBr), characteristic bands in cm$^{-1}$: 3240, 2980, 2930, 2720, 2100, 1800, 1705, 1640, 1590, 1560, 1460, 1530, 985, 925, 885, 820, 755, 645.

EXAMPLE 52

A mixture of 10-{(2RS)-1-[N-ethyl-N-(2-hydroxyethyl)amino]-2-propyl}-2-phenothiazinecarbothioamide (2.5 g) and benzylamine (7 cc) in ethanol (50 cc) is saturated with hydrogen sulphide gas and then heated for 13 hours to 110° C. in an autoclave. After cooling, the solution is concentrated to dryness under reduced pressure (30 mm Hg; 4 kPa) at 40° C. The residue is diluted with ethyl acetate (100 cc) and the organic phase is washed with distilled water (4×50 cc), dried over magnesium sulphate and filtered. The filtrate is concentrated to dryness at 40° C. under reduced pressure (30 mm Hg; 4 kPa) to give an orange oil, which is purified by chromatography on a column (height: 30 cm; diameter: 3 cm) of silica (0.06–0.2 mm), eluting with a 50:50 (by volume) mixture (600 cc) of cyclohexane and ethyl acetate and collecting 50-cc fractions. Fractions 5 to 10 are combined and concentrated to dryness under reduced pressure (30 mm Hg; 4 kPa) at 40° C. A yellow oil (2.6 g) is thereby obtained.

Fumaric acid (0.6 g) dissolved in ethanol (10 cc) at 50° C. is added to a solution of N-benzyl-10-{(2RS)-1-[N-ethyl-N-(2-hydroxyethyl)amino]-2-propyl}-2-phenothiazinecarbothioamide (2.6 g) in ethanol (30 cc) at 50° C. Crystallization is primed by scratching, and the mixture is stirred for 1 hour at 20° C. The solid is separated by filtration, washed with ethanol (2×4 cc) and dried at 40° C. under reduced pressure (1 mm Hg; 0.13 kPa) to give N-benzyl-10-{(2RS)-1-[N-ethyl-N-(2-hydroxyethyl)amino}2-propyl}-2-phenothiazinecarbothioamide neutral fumarate (2.1 g) in the form of yellow crystals, m.p. 154° C.

Proton NMR (250 MHz, DMSO, δ in ppm, J in Hz): 0.85 (T, J=7, 3H>NCH$_2$CH$_3$); 1.63 (D, J=7, 3H, —CH$_3$); 2.50 (masked Mt, 4H,

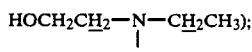

2.8 (DD, J=13 and 6, 1H, 1H of N—CH$_2$—); 3.10 (DD, J=13 and 6.5, 1H, 1H of >N—CH$_2$—); 3.37 (Mt partially masked, —CH$_2$OH); 4.20 (Mt, J=7, 6.5 and 6, 1H, N—CH); 5 (D, J=6, 2H, —CSNH-CH$_2$—); 6.64 (S, 1H, hemifumarate —CH=CH—); 6.90 to 7.45 (Mt, 11H, aromatic); 7.72 (D, J=1, 1H, —H at 1-position); 10.77 (T, J=6, 1H, —CSNH—).

Infrared spectrum (KBr), characteristic bands in cm$^{-1}$: 3200, 2970, 2930, 2870, 1590, 1530, 1495, 1485, 1460, 985, 750, 700, 660, 650.

10-{(2RS)-1-[N-Ethyl-N-(2-hydroxyethyl)amino]-2-propyl}-2-phenothiazinecarbothioamide may be prepared in the following manner:

Triethylamine (1.2 cc) is added to a mixture of 10-{(2RS)-1-[N-ethyl-N-(2-hydroxyethyl)amino]-2-propyl}-2-phenothiazinecarbonitrile (3.1 g) in pyridine (62 cc), and the mixture is then saturated with hydrogen sulphide by bubbling in for 1 hour. The clear solution obtained is kept stirred for 12 hours at 25° C., and then outgassed by bubbling nitrogen through for 1 hour. The reaction mixture is then diluted with ethyl acetate (150 cc) and washed with distilled water (6×100 cc) and with saturated sodium chloride solution (3×120 cc). The organic phase is dried over magnesium sulphate and filtered and the filtrate is concentrated to dryness at 40° C. under reduced pressure (30 mm Hg; 4 kPa). The residue is purified by chromatography on a column (height: 29 cm; diameter: 2.5 cm) of silica gel (0.06–0.2 mm), eluting with a 30:70 (by volume) mixture (1 liter) of cyclohexane and ethyl acetate and collecting 50-cc fractions. Fractions 5 to 15 are combined and concentrated to dryness at 50° C. under reduced pressure (30 mm Hg; 4 kPa) to give 10-{(2RS)-1-[N-ethyl-N-(2-hydroxyethyl)amino]-2-propyl}-2-phenothiazinecarbothioamide (2.5 g) in the form of an orange product of meringue-like consistency.

10-{(2RS)-1-[N-Ethyl-N-(2-hydroxyethyl)amino]-2-propyl}-2-phenothiazinecarbonitrile may be prepared in the following manner:

2-Bromoethanol (1.2 g) and potassium hydrogen carbonate (2.4 g) are added to a solution of 10-[(2RS)-1-ethylamino-2-propyl]-2-phenothiazinecarbonitrile (5 g) in dimethylformamide (50 cc). The mixture is heated to 130° C. for 6 hours. After cooling, the solution is concentrated to dryness at 80° C. under reduced pressure (10 mm Hg; 1.33 kPa). The residue is taken up with ethyl acetate (100 cc) and then washed with distilled water (6×100 cc) and with brine (100 cc). The organic phase is dried over magnesium sulphate and filtered, and the filtrate is concentrated to dryness at 40° C. under reduced pressure (30 mm Hg; 4 kPa) to give a pale yellow oil (5.0 g) which is purified by chromatography on a column (height: 35 cm; diameter: 3 cm) on silica gel (0.06–0.2 mm), diluting with a 30:70 by volume mixture (600 cc) of cyclohexane and ethyl acetate and collecting 60-cc fractions. Fractions 5 to 7 are combined and concentrated to dryness at 50° C. under reduced pressure (30 mm Hg; 4 kPa) to give 10-{(2RS)-1-[N-ethyl-N-(2-hydroxyethyl)-amino]-2-propyl}-2-phenothiazinecarbonitrile (3.2 g) in the form of a yellow oil.

EXAMPLE 53

Working in a manner similar to that described below in Example 80, but starting with N-(3-chlorobenzyl)-10-[1-(1-pyrrolidinyl)-2-propyl]-2-phenothiazinecarbothioamide, L series (2 g) in acetic acid (60 cc) and with mercuric acetate (1.3 g), N-(3-chlorobenzyl)-10-[1-(1-pyrrolidinyl)-2-propyl]-2-phenothiazinecarboxamide, L series (1.2 g) is obtained in the form of a yellow product of meringue-like consistency. This product is dissolved in acetonitrile (20 cc), and a 2.4 N solution (0.8 cc) of hydrochloric acid in ethyl ether is then added. The crystals are separated by filtration and dried under reduced pressure (5 mm Hg; 0.67 kPa) at 40° C. N-(3-Chlorobenzyl)-10-[1-(1-pyrrolidinyl)-2-propyl]-2-phenothiazinecarboxamide hydrochloride, L series (1.0 g) is obtained in the form of white crystals, m.p. 208° C. [α]$_D^{20}$ = +15.7 (c=1%; methanol).

Proton NMR (250 MHz, DMSO-d6, δ in ppm, J in Hz):

1.77 (D, J=7, 3H, —CH$_3$); 1.7 to 2 (Mt, 4H, pyrrolidine —CH$_2$—); 2.80, 3.08 and 3.45 to 3.9 (3Mt, respectively 1H, 1H and 2H, pyrrolidine >N—CH$_2$—); 3.75 (Mt, 2H, >N—CH$_2$—); 4.48 (D, J=6, 2H, —CONHCH$_2$—); 4.7 (Mt, 1H, >N—CH<); 7 to 7.45 (Mt, 9H, aromatic); 7.57 (S, 1H, —H at 1-position); 7.59 (D, J=8, 1H, —H at 3-position); 9.28 (T, J=6, 1H, —CONH—); 10.35 (Cx, 1H, —NH$^+$Cl$^-$).

Infrared spectrum (KBr), characteristic bands in cm⁻¹: 3280, 2970, 2940, 2680, 2630, 2480, 1660, 1590, 1570, 1530, 1460, 865, 855, 830, 790, 755, 710.

EXAMPLE 54

3-Fluorobenzylamine (2.3 cc) is added to a solution of 10-[(2RS)-1-(1-pyrrolidinyl)-2-propyl]-2-phenothiazinecarbothioamide (3.70 g) in absolute ethanol (50 cc). The mixture is saturated with hydrogen sulphide and brought to 110° C. for 20 hours. After cooling to 20° C., the mixture is concentrated to dryness under reduced pressure (30 mm Hg; 4 kPa) at 40° C. and the residue is purified by chromatography on a column (height: 22 cm; diameter: 4.2 cm) of silica gel (0.04–0.06 mm) with a slight excess pressure of nitrogen (40 kPa), eluting with pure ethyl acetate (400 cc) and then with a 90:10 (by volume) mixture (400 cc) of ethyl acetate and methanol and collecting 80-cc fractions. Fractions 3 to 5 are combined and concentrated to dryness under reduced pressure (30 mm Hg; 4 kPa) at 40° C. to give N-(3-fluorobenzyl)-10-[(2RS)-1-(1-pyrrolidinyl)-2-propyl]-2-phenothiazinecarbothioamide (2.3 g) in the form of a yellow product of meringue-like consistency.

Fumaric acid (0.6 g) dissolved in ethanol (5 cc) is added to a solution of N-(3-fluorobenzyl)-10-[(2RS)-1-(1-pyrrolidinyl)-2-propyl]-2-phenothiazinecarbothioamide (2.3 g) in boiling ethanol (30 cc). After 4 hours of cooling to 4° C., the crystallized solid is separated by filtration, washed with cold ethanol (2×5 cc) and then dried at 50° C. under reduced pressure (5 mm Hg; 0.7 kPa) to give N-(3-fluorobenzyl)-10-[(2RS)-1-(1-pyrrolidinyl)-2-propyl]-2-phenothiazinecarbothioamide neutral fumarate (2.2 g), m.p. 205° C.

Proton NMR (250 MHz, DMSO, δ in ppm, J in Hz).
1.61 (D, J=7, 3H, —CH₃); 1.7 (Mt, 4H, pyrrolidine —CH₂—CH2—); 2.65 (Mt, 4H, pyrrolidine

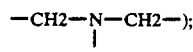

3 (DD, J12.5 and 6.5, 1H, 1H of >N—CH2—); 3.14 (DD, J=12.5 and 7, 1H, 1H of >N—CH2—); 4.28 (Mt, J=7 and 6.5, 1H, >N—CH<); 5.02 (D, J=5, 2H, —CSNH—CH₂—); 6.6 (S, 1H, hemifumarate —CH=CH); 6.95 to 7.45 (Mt, 9H, aromatic); 7.4 (DD, J=8 and 1, 1H, —H at 3-position); 7.67 (D, J=1, 1H, —H at 1-position); 10.8 (T, J=5, 1H, —CSNH—).

Infrared spectrum (KBr), characteristic bands in cm⁻¹: 3200, 1610, 1590, 1530, 1485, 1460, 965, 755, 670.

EXAMPLE 55

2-Methylbenzylamine (6.0 cc) is added to a solution of 10-[(2RS)-1-(1-pyrrolidinyl)-2-propyl]-2-phenothiazinecarbothioamide (3.70 g) in absolute ethanol (50 cc). The mixture is saturated with hydrogen sulphide and brought to 110° C. for 20 hours. After cooling to 20° C., the mixture is concentrated to dryness under reduced pressure (30 mm Hg, 4 kPa) at 40° C. and the residue is purified by chromatography on a column (height: 22 cm; diameter: 4.2 cm) of silica gel (0.04–0.06 mm) with a slight excess pressure of nitrogen (40 kPa), eluting with pure ethyl acetate (400 cc) and then with a 90:10 (by volume) mixture (400 cc) of ethyl acetate and methanol and collecting 80-cc fractions. Fractions 3 to 5 are combined and concentrated to dryness under reduced pressure (30 mm Hg; 4 kPa) to give N-(2-methylbenzyl)-10-[(2RS)-1-(1-pyrrolidinyl)-2-propyl]-2-phenothiazinecarbothioamide (2.6 g) in the form of a yellow product of meringue-like consistency.

Fumaric acid (1.0 g) dissolved in ethanol (20 cc) is added to a solution of N-(2-methylbenzyl)-10-[(2RS)-1-(1-pyrrolidinyl)-2-propyl]-2-phenothiazinecarbothioamide (2.6 g) in boiling ethanol (30 cc). The mixture is concentrated to dryness under reduced pressure (30 mm Hg; 4 kPa) at 40° C. and the residue is taken up in isopropyl ether (60 cc). The suspension is stirred for 2 hours. The solid is separated by filtration, washed with isopropyl ether (2×5 cc) and then dried at 35° C. under reduced pressure (5 mm Hg; 0.7 kPa) to give N-(2-methylbenzyl)-10-[(2RS)-1-(1-pyrrolidinyl)-2-propyl]-2-phenothiazinecarbothioamide acid fumarate (3.1 g), m.p. 110° C.

Proton NMR (250 MHz, DMSO, δ in ppm, J in Hz):
1.67 (D, J=7.5, 3H, —CH₃); 1.77 (Mt, 4H, pyrrolidine —CH₂—CH₂—); 2.35 (S, 3H, 2-methybenzyl —CH₃); 2.75 to 3 (Mt, 4H, pyrrolidine

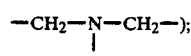

3.26 (DD, J = 13.5 and 5.5, 1H, 1H of >N—CH₂—); 3.4 (DD, J=13.5 and 7, 1H, 1H of >N—CH₂—); 4.48 (Mt, J=7.5, 7 and 5.5, 1H, >N—CH<); 4.93 (limiting AB, 2H, —CSNH—CH₂—); 6.63 (S, 2H, fumarate —CH=CH—); 7 to 7.3 (Mt, 9H, aromatic); 7.43 (DD, J=8 and 1, 1; H, —H at 3-position); 7.62 (D, J=1, 1H, —H at 1-position); 10.75 (T, J=5.5, 1H, —CSNH—).

Infrared spectrum (KBr), characteristic bands in cm⁻¹; 3220, 3100 to 2100, 1685, 1630, 1590, 1530, 1460, 970, 870, 820, 750, 645.

EXAMPLE 56

A solution of mercuric acetate (1.46 g) in acetic acid (30 cc) is added dropwise and with stirring at a temperature in the region of 45° C. to a solution of N-propyl-10-[1-(2,5-dihydro-1-pyrrolyl)-2-propyl]-2-phenothiazinecarbothioamide, L series (1.8 g) in acetic acid (30 cc). After 1 hour, the black suspension obtained is filtered and the filtrate is concentrated to dryness under reduced pressure (30 mm Hg; 4 kPa) at 60° C. The residue is taken up with ethyl acetate (60 cc), washed successively with 2N aqueous sodium hydroxide solution (2 x 20 cc) and then with distilled water (3×20 cc), dried over magnesium sulphate, filtered and concentrated to dryness under reduced pressure (30 mm Hg; 4 kPa) at 40° C. The oily yellow residue is purified by chromatography on a column (height: 18 cm; diameter: 2.8 cm) of silica gel (0.04–0.063 mm) under a slight excess pressure of nitrogen (40 kPa), eluting with ethyl acetate (1 liter) and collecting 25-cc fractions. Fractions 7 to 25 are combined and concentrated to dryness under reduced pressure (30 mm Hg; 4 kPa) at 40° C. to give a yellow resin (11.09 g). This product is dissolved in 2-propanol (5.25 cc) at a temperature in the region of 50° C., and treated, with stirring, with a solution of fumaric acid (0.31 g) in 2-propanol (6.2 cc) under reflux. After cooling, the yellow solution is concentrated to dryness under reduced pressure (30 mm Hg; 4 kPa) at 40° C. and the residue is taken up with acetonitrile (10 cc). After 16 hours at a temperature in the region of 5° C., the crystals formed are filtered off, washed with acetonitrile (2 cc) and then with diethyl ether (3 cc) and dried under reduced pressure (5 mm Hg; 0.67 kPa) at 40° C. N-Propyl-10-[(2,5-dihydro-1-pyrrolyl)-2-propyl]-2-phenothiazinecarboxamide fumarate, L series (0.95 g) is thereby obtained in the form of a white solid, m.p. 160° C.

$[\alpha]_D^{20} = +21.1 \pm 0.5°$ (1%; methanol).

Proton NMR (250 MHz, DMSO-d6, δ in ppm and J in Hz):

0.9 (T, J=7.5, 3H, —(CH$_2$)$_2$CH$_3$); 1.54 (Mt, 2H, —CH$_2$CH$_2$CH$_3$); 1.63 (D, J=7, 3H, —CH$_3$); 3.11 (DD, J=12.5 and 7.5, 1H, 1H of >N—CH$_2$—); 3.23 (Mt, 2H, —CONHCH$_2$—); 3.29 (DD, J=12.5 and 6.5, 1H, 1H of >N—CH$_2$—); 3.56 (AB, 4H, pyrroline N—CH$_2$—); 4.21 (Mt, J=7.5, 7 and 6.5, 1H, >N—CH<); 5.79 (Cx, 2H, fumarate —CH=CH—); 6.9 to 7.3 (Mt, 5H, aromatic); 7.43 (broad D, J=8, 1H, —H at 3-position); 7.54 (broad S, 1H, —H at 1-position); 8.45 (T, J=5.5, 1H, —CONH—).

Infrared spectrum (KBr), characteristic bands in cm$^{-1}$: 2960, 2930, 2870, 2700, 2100, 1800, 1700, 1635, 1590, 1460, 1550, 980, 890, 830, 755, 645.

EXAMPLE 57

3-Methylbutylamine (1.74 cc) is added to a solution of 10-{1-[(2S)-2-hydroxymethyl-1-pyrrolidinyl]-2-propyl}-2-phenothiazinecarbothioamide, L series (1.20 g) in absolute ethanol (20 cc). The mixture is brought to 150° C. for 16 hours and then concentrated to dryness under reduced pressure (30 mm Hg; 4 kPa) at 50° C. The residue is diluted with ethyl acetate (100 cc), washed with distilled water (2×50 cc), dried over magnesium sulphate and then concentrated to dryness under reduced pressure (30 mm Hg; 4 kPa) at 50° C., before being purified by chromatography on a column (height: 14.5 cm; diameter: 2.8 cm) of silica gel (0.04–0.06 mm) with a slight excess pressure of nitrogen (40 kPa), eluting with mixtures of cyclohexane and ethyl acetate in proportions (by volume) of 65:35 (1200 cc) and 35:65 (1.2 liters), collecting 60-cc fractions. Fractions 16 to 33 are combined and concentrated to dryness under reduced pressure (30 mm Hg; 4 kPa) at 50° C. to give 10-{1-[(2S)-2-hydroxymethyl-1-pyrrolidinyl]-2-propyl}-N-(3-methylbutyl)-2-phenothiazinecarboxamide, L series (0.34 g) in the form of a yellow resin.

A 2.2 N ethereal solution (0.25 cc) of hydrochloric acid is added to a solution of 10-{1-[(2S-2-hydroxymethyl-1-pyrrolidinyl]-2-propyl}-N-(3-methylbutyl)-2-phenothiazinecarboxamide, L series (0.25 g) in ethyl ether (25 cc). A gummy precipitate deposits on the walls of the flask. The mixture is concentrated to dryness under reduced pressure (30 mm Hg; 4 kPa) at 50° C. The suspension is stirred for 12 hours at 25° C. in ethyl ether (50 cc). The precipitate is filtered off on sintered glass, washed with ethyl ether (2×10 cc) and dried at 40° C. under reduced pressure (5 mm Hg; 0.068 kPa) to give 10-{1-[(2S)-2-hydroxymethyl-2-pyrrolidinyl]-2-propyl}-N-(3-methylbutyl)-2-phenothiazinecarboxamide hydrochloride, L series (0.39 g), m.p. 145°–147° C.

Proton NMR (250 MHz, DMSO, δ in ppm, J in Hz):
0.92 (D, J=6.5, 6H, —CH(CH$_3$)$_2$); 1.45 (Mt, 2H, —CH$_2$—CH(CH$_3$)$_2$); 1.65 (Mt, 1H, —CH(CH$_3$)$_2$); 1.72 (D, J=7, 3H, —CH$_3$); 1.7 to 2.2 (Mt, 4H, pyrrolidine —CH$_2$—CH$_2$—); 3.3, 3.7 and 4.05 (3Mt, 3H, 5H and 1H respectively, —CONH—CH$_2$—, >N—CH$_2$—, >NCH$_2$— and >N—CH—< of pyrrolidine, —CH$_2$O—); 4.75 (Mt, 1H, N—CH); 5.55 (extended Cx, 1H, —OH); 7 to 7.4 (Mt, 5H, aromatic); 7.52 (D, J=8, 1H, —H at 3-position); 7.55 (S, 1H, —H at 1-position); 8.67 (T, J=5.5, 1H, —CONH—); 10.02 (Cx, 1H, —NH[30]).

Infrared spectrum (KBr), characteristic bands in cm$^{-1}$: 3300, 2960, 2870, 2800 to 2200, 1640, 1595, 1540, 1465, 1415, 1060, 830, 755.

EXAMPLE 58

A suspension of cyclopropylmethylamine hydrochloride (5.4 g) dispersed in ethanol (25 cc) containing 10-[(2RS)-1-dimethylamino-2-propyl]-2-phenothiazinecarbothioamide (3.43 g) is added to a 0.05 M solution of sodium ethylate in ethanol (10 cc). The mixture is brought to 200° C. for 5 hours and then diluted with ethyl acetate (150 cc), washed with distilled water (2×100 cc), dried over magnesium sulphate and then concentrated to dryness under reduced pressure (30 mm Hg; 4 kPa) at 50° C. The residual solid is purified by chromatography on a column (height: 18 cm; diameter: 2.5 cm) of silica gel (0.6-0.02 mm), eluting with mixtures of ethyl acetate and cyclohexane in proportions (by volume) of 30:70 (2.5 liters) and 50:50 (1.1 liters), collecting 60-cc fractions. Fractions 50 to 59 are combined and concentrated to dryness under reduced pressure (30 mm Hg; 4 kPa) at 50° C. to give N-cyclopropylmethyl-10-[(2RS)-1-dimethylamino-2-propyl]-2-phenothiazinecarboxamide (0.42 g), m.p. 90° C.

NMR spectrum (250 MHz, DMSO, δ in ppm, J in Hz):
0.22 and 0.44 (2Mt, 2H each, cyclopropyl —CH$_2$—CH$_2$—); 1.03 (Mt, 1H, cyclopropyl —CH<); 1.58 (D, J=7.5, 3H, —CH$_3$); 2.22 (S, 6H, —N(CH$_3$)$_2$); 2.63 (DD, J=13 and 7, 1H, 1H of N—CH$_2$—); 2.85 (DD, J=13 and 5.5, 1H, 1H of >N—CH$_2$—); 3.14 (T, J=6.5, 2H, —CONH—CH$_2$—); 4.14 (Mt, J=7.5, 7 and 5.5, 1H, >N—CH<); 6.90 to 7.3 (Mt, 5H, aromatic); 7.42 (D, J=8.5, 1H, —H at 3-position); 7.52 (S, 1H, —H at 1-position); 8.51 (T, J=6.5, 1H, —CONH—).

Infrared spectrum (KBr), characteristic bands in cm$^{-1}$: 3230, 2970, 2940, 2860, 2820, 2765, 1630, 1590, 1535, 1460, 1420, 885, 830, 750.

10-[(2RS)-1-dimethylamino-2-propyl]-2-phenothiazinecarbothioamide may be obtained in the following manner:

A mixture of 10-[(2RS)-1-dimethylamino-2-propyl]-2-phenothiazinecarbonitrile (30.9 g) and triethylamine (1.42 cc) in anhydrous pyridine (310 cc) is saturated by bubbling hydrogen sulphide in for 5 hours at 25° C. The clear solution obtained is kept stirred for 12 hours at 25° C. and the mixture is then outgassed by bubbling nitrogen through for 90 minutes. The reaction mixture is then diluted with ethyl acetate (500 cc) and washed with distilled water (8×200 cc). The organic phase is dried over magnesium sulphate and filtered, and the filtrate is concentrated to dryness at 50° C. under reduced pressure (30 mm Hg; 4 kPa). The residue is purified by chromatography on a column (height 31 cm; diameter: 4.5 cm) of silica gel (0.02–0.6 mm), eluting with a 40:60 (by volume) mixture (7 liters) of cyclohexane and ethyl acetate and collecting 500-cc fractions. Fractions 8 to 10 are combined and concentrated to dryness at 50° C. under reduced pressure (30 mm Hg; 4 kPa) to give 10-[(2RS)-1-dimethylamino-2-propyl]-2-phenothiazinecarbothioamide (25.4 g).

10-[(2RS)-1-Dimethylamino-2-propyl]-2-phenothiazinecarbonitrile may be obtained in the following manner:

An Erlenmeyer is charged with a solution of (2RS)-2-chloro-1-dimethylaminopropan hydrochloride (342 g) in distilled water (700 cc). 10N sodium hydroxide solution (270 cc) is added and the mixture is extracted with toluene (1.3 liters). The organic phase is dried over magnesium sulphate, filtered and concentrated at 50° C. under reduced pressure (30 mm Hg; 4 kPa) until a residual volume of 800 cc is obtained.

Powdered potassium hydroxide (96.7 g) is added to a suspension of 2-cyanophenothiazine (242 g) in methyl ethyl ketone (2.2 liters). The temperature of the mixture rises spontaneously to 24° C. and the mixture is brought to 60° C. for half an hour while stirring. The toluene solution of 2-chloro-1-dimethylaminopropane prepared above is added in the course of 30 minutes. The mixture is heated under reflux for 12 hours. After cooling, the mixture is transferred to a separating funnel and washed with distilled water (2×2 liters). The organic phase is dried over magnesium sulphate, filtered and then concentrated to dryness under reduced pressure (30 mm Hg; 4 kPa) at 50° C. to give an oil, which is diluted in ethyl ether (2 liters). The solution obtained is cooled and primed by scratching. The crystallized yellow precipitate is removed by filtration. The mother liquors are concentrated to dryness under reduced pressure (100 mm Hg; 13.3 kPa) at 30° C. to give a brown oil which is purified by chromatography on a column (height: 80 cm; diameter: 8.5 cm) of silica (0.2–0.06 mm), eluting with an 80:20 (by volume) mixture of cyclohexane and ethyl acetate and collecting 1-liter fractions. Fractions 7 to 16 are combined and concentrated to dryness at 50° C. under reduced pressure (30 mm Hg; 4 kPa) to give 10-[(2RS)-1-dimethylamino-2-propyl]-2-phenothiazinecarbonitrile (54.8 g) in the form of a brown oil.

EXAMPLE 59

The procedure is as described in Example 56, but starting with N-allyl-10-[1-(2,5-dihydro-1-pyrrolyl)-2-propyl]-2-phenothiazinecarbothioamide, L series (1.49 g) in acetic acid (25 cc) and with a solution of mercuric acetate (1.16 g) in acetic acid (25 cc). The yellow residue (1.27 g) of meringue-like consistency is purified by chromatography on a column (height: 23 cm; diameter: 2.6 cm) of silica gel (0.04–0.063 mm) under a slight excess pressure of nitrogen (40 kPa), eluting with ethyl acetate (1.5 liters) and collecting 25-cc fractions. Fractions 10 to 58 are combined and concentrated to dryness under reduced pressure (30 mm Hg; 4 kPa) at 40° C. to give a yellow resin (0.45 g). 0.3 g of this product is dissolved in 2-propanol (1.5 cc) at a temperature in the region of 50° C., and a solution of fumaric acid (0.09 g) in 2-propanol (1.8 cc) under reflux is added with stirring. After cooling, the crystals formed are filtered off, washed with diethyl ether (10 cc) and dried under reduced pressure (5 mm Hg; 0.67 kPa) at 40° C. N-Allyl-10-[1-(2,5-dihydro-1-pyrrolyl)-2-propyl]-2-phenothiazinecarboxamide fumarate, L series (0.24 g) is thereby obtained in the form of a white solid, m.p. 164° C.

$[\alpha]_D^{20} = +20.4 \pm 0.5°$ (1%; methanol).

Proton NMR (250 MHz, DMSO-d6, δ in ppm, J in Hz):

1.62 (D, J=7, 3H, —CH3); 3.08 (DD, J=12.5 and 7.5, 1H, 1H of >N—CH2—); 3.26 (DD, J=12.5 and 6.5, 1H, 1H of >N—CH2—); 3.54 (AB, 4H, pyrroline >N—CH2); 3.91 (DD, J=6.5 and 5.5, 2H, —CONHCH2—); 4.19 (Mt, J=7.5, 7 and 6.5, 1H, >N—CH<); 5.14 (Mt, 2H, —CH=CH2); 5.8 (Cx, 2H, pyrroline —CH=CH—); 5.90 (Mt, 1H, —CH=CH2); 6.64 (S, 2H, fumarate —CH=CH—); 6.90 to 7.3 (Mt, 5H, aromatic); 7.47 (DD, J=8 and 1, 1H, —H at 3-position); 7.57 (D, J=1, 1H, —H at 1-position); 8.67 (T, J=5.5, 1H, —CONH—).

Infrared spectrum (KBr), characteristic bands in cm$^{-1}$: 2980, 2930, 2720, 2100, 1800, 1705, 1640, 1590, 1560, 1460, 1535, 985, 915, 830, 760, 645.

EXAMPLE 60

Benzylamine (5 cc) is added to a solution of 10-[(2RS)-1-dimethylamino-2-propyl]-2-phenothiazinecarbothioamide (3.43 g) in absolute ethanol (35 cc). The mixture is brought to 200° C. for 5 hours, and then to 150° C. for 48 hours. It is then diluted with ethyl acetate (100 cc) and thereafter washed with distilled water (3×100 cc). The organic phase is dried over magnesium sulphate, filtered and then concentrated to dryness under reduced pressure (30 mm Hg; 4 kPa) at 50° C. The residue is purified by chromatography on a column (height: 50 cm; diameter: 2.4 cm) of silica gel (0.06–0.2 mm), eluting with a 50:50 (by volume) mixture (1.8 liters) of ethyl acetate and cyclohexane and collecting 60-cc fractions. Fractions 21 to 28 are combined and concentrated to dryness under reduced pressure (30 mm Hg; 4 kPa) at 50° C. to give an orange product (1.5 g) of meringue-like consistency. An aliquot portion of this product (1.4 g) is dissolved in ethyl acetate (30 cc) and then treated with a solution of oxalic acid (0.29 g) in ethyl acetate (10 cc). The suspension obtained is stirred for 1 hour and filtered, and the solid is dried at 50° C. under reduced pressure (5 mm Hg; 0.7 kPa) to give N-benzyl-10[(2RS)-1-dimethylamino-2-propyl]-2-phenothiazinecarboxamide oxalate (1.79 g), m.p. 105° C.

NMR spectrum (250 MHz, DMSO, δ in ppm, J in Hz):

1.74 (D, J=7.5, 3H, —CH3); 2.66 (S, 6H, —N(CH3)2); 3.34 (DD, J=14 and 5, 1H, 1H of >N—CH2—); 3.53 (DD, J=14 and 7, 1H, 1H of >NCH2—); 4.50 (D, J=6, 2H, —CONH—CH2—); 4.58 (Mt, J=7.5, 7 and 5,5, 1H, >N—CH<); 7.00 to 7.6 (Mt, 12H, aromatic); 9.17 (T, J=6, 1H, —CONH—).

Infrared spectrum (KBr), characteristic bands in cm$^{-1}$; 3300, 2980, 2920, 2660, 1730, 1640, 1595, 1540, 1460, 1415, 870, 830, 750, 700.

EXAMPLE 61

2-Fluorobenzylamine (5.0 cc) is added to a solution of 10-[(2RS)-1-dimethylamino-2-propyl]-2-phenothiazinecarbothioamide (3.0 g) in ethanol (30 cc) and distilled water (3 cc). The mixture is brought to 200° C. for 10 hours. After cooling, the reaction mixture is diluted with ethyl acetate (150 cc) and then washed with distilled water (3×100 cc). The organic phase is dried over magnesium sulphate, filtered and then concentrated to dryness under reduced pressure (30 mm Hg; 4 kPa) at 50° C. The residue is purified by chromatography on a column (height: 25.0 cm; diameter: 3.5 cm) of silica gel (0.04–0.06 mm) with a slight excess pressure of nitrogen (40 kPa), eluting with mixtures of cyclohexane and ethyl acetate in proportions (by volume) of 80:20 (2.0 liters) and then 50:50 (3 liters) and then with pure ethyl acetate (2.5 liters), collecting 100-cc fractions. Fractions 62 to 71 are combined and concentrated to dryness under reduced pressure (30 mm Hg; 4 kPa) at 50° C. to give an orange product (0.7 g) of meringue-like consistency. This product is dissolved in boiling isopropyl ether (20 cc) and the suspension is brought to reflux for 2 hours. The solid is filtered off hot, washed with isopropyl ether (2×10 cc) and then dried in the air to give N-(2-fluorobenzyl)-10-[(2RS)-1-dimethylamino2-propyl]-2-phenothiazinecarboxamide (0.5 g), m.p. 130° C.

1 NMR spectrum (250 MHz, DMSO, δ in ppm, J in Hz).

1.59 (D, J7.5, 3H, —CH$_3$); 2.2 (S, 6H, —N(CH$_3$)$_2$); 2.65 (DD, J=13 and 7, 1H, 1H of >NCH$_2$—); 2.88 (DD, J=13 and 6, 1H, >N—CH$_2$—); 4.17 (Mt, J=7.5, 7 and 6, 1H, >N—CH<); 4.53 (D, J=5.5, 2H, —CONH—CH$_2$—); 6.90 to 7.45 (Mt, 9H, aromatic); 7.50 (broad D, J=8, 1H, —H at 3-position); 7.58 (broad S, 1H, —H at 1-position); 9 (T, J=5.5, 1H, —CONH—).

Infrared spectrum (KBr), characteristic bands in cm$^{31}$ $^1$: 3320, 2970, 2940, 2860, 2820, 2765, 1640, 1535, 1590, 1560, 1485, 1460, 1410, 835, 750.

EXAMPLE 62

2-Fluorobenzylamine (9.2 cc) is added to a solution of 10-[(2RS)-1-(1-pyrrolidinyl)-2-propyl]-2-phenothiazinecarbothioamide (6.00 g) in absolute ethanol (60 cc). The mixture is brought to 160° C. for 30 hours. After cooling, the mixture is concentrated to dryness under reduced pressure (30 mm Hg; 4 kPa) at 50° C. and the residue obtained is then diluted with ethyl acetate (200 cc) and thereafter washed with distilled water (2×200 cc). The organic phase is dried over magnesium sulphate, filtered and then concentrated to dryness under reduced pressure (30 mm Hg; 4 kPa) at 50° C. The residue is purified by chromatography on a column (height: 22 cm; diameter: 4.2 cm) of silica gel (0.04–0.06 mm) with a slight excess pressure of nitrogen (40 kPa), eluting with a 70:30 (by volume) mixture (6 liters) of cyclohexane and ethyl acetate and collecting 100-cc fractions. Fractions 40 to 53 are combined and concentrated to dryness at 50° C. under reduced pressure (30 mm Hg; 4 kPa) to give an orange product of meringue-like consistency. This product is dissolved in ethyl acetate (10 cc) and the solution is poured into petroleum ether (100 cc) which is kept stirred briskly. The solid is filtered off on sintered glass, washed with petroleum ether (2×25 cc) and then dried at 50° C. under reduced pressure (5 mm Hg; 0.7 kPa) at 50° C. to give N-(2-fluorobenzyl)-10-[(2RS)-1-(1-pyrrolidinyl)-2-propyl]-2-phenothiazinecarboxamide(0.80g), m.p. 60° C.

Proton NMR (250 MHz, DMSO, δ in ppm, J in Hz): 1.6 (D, J=7, 3H, —CH:); 1.67 (Mt, 4H, pyrrolidine —CH$_2$—CH$_2$—); approximately 2.52 (masked Mt, pyrrolidine

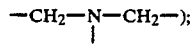

2.9 (DD, J=13 and 6.5, 1H, 1H of >N—CH$_2$—); 3.03 (DD, J=13 and 6, 1H, 1H of >N—CH$_2$—); 4.2 (Mt, J=7, 6.5 and 6, 1H, N—CH); 4.54 (D, J=5.5, 2H, —CONH—CH$_2$—); 6.90 to 7.45 (Mt, 9H, aromatic); 7.5 (D, J=8, 1H, —H at 3-position); 7.61 (S, 1H, —H at 1-position); 9 (T, J=5.5, 1H, —CONH—).

Infrared spectrum (KBr), characteristic bands in cm$^{-1}$: 3460, 2975, 2800, 1660, 1595, 1560, 1520, 1490, 1460, 1415, 870, 835.

EXAMPLE 63

4-Fluorobenzylamine (5 cc) is added to a solution of 10-[(2RS)-1-dimethylamino-2-propyl]-2-phenothiazinecarbothioamide (3.00 g) in absolute ethanol (30 cc). The mixture is brought to 170° C. for 10 hours. After cooling, the mixture is concentrated to dryness under reduced pressure (30 mm Hg; 4 kPa) at 50° C. and the residue obtained is then diluted with ethyl acetate (100 cc) and thereafter washed with distilled water (6×100 cc). The organic phase is dried over magnesium sulphate, filtered and then concentrated to dryness under reduced pressure (30 mm Hg; 4 kPa) at 50° C. The residue is purified by passage through a column (height: 22 cm; diameter: 4.2 cm) of silica gel (0.04–0.06 mm) with a slight excess pressure of nitrogen (40 kPa), eluting with mixtures of cyclohexane and ethyl acetate in proportions of 60:40 (3 liters) and 20:80 (2 liters), then with pure ethyl acetate (3 liters) and finally with a 95:5 (by volume) mixture (2 liters) of ethyl acetate and methanol and collecting 60-cc fractions. Fractions 55 to 80 are combined and concentrated to dryness under reduced pressure (30 mm Hg; 4 kPa) to give a yellow resin (1.61 g). This product is dissolved in ethyl ether (70 cc) and treated with a 2.2 N ethereal solution of hydrochloric acid. The suspension obtained is stirred at 25° C. for 2 hours. The solid is filtered off on sintered glass, washed with ethyl ether (2×4 cc) and then dried at 50° C. under reduced pressure (5 mm Hg; 0.7 kPa) to give N-(4-fluorobenzyl)-10-[(2RS)-1-dimethylamino-2-propyl]-2-phenothiazinecarboxamide hydrochloride (0.75 g), m.p. 140° C.

Proton NMR spectrum (250 MHz, DMSO, δ in ppm, J in Hz):

1.77 (D, J=7, 3H, —CH$_3$); 2.8 (S, 6H, —N(CH$_3$)$_2$); 3.53 and 3.75 (2Mt, 1H each, N—CH$_2$—); 4.45 (D, J=6, 2H, —CONH—CH$_2$—); 4.72 (Mt, 1H, >N—CH<); 7 to 7.45 (Mt, 9H, aromatic); 7.6 (Mt, 2H, —H at 1-position and —H at 3-position); 9.3 (T, J=6, —CONH—); 10.44 (Cx, 1H, NH$^{30}$).

Infrared spectrum (KBr), characteristic bands in cm$^{-1}$: 3280, 2960, 2930, 2600, 2500, 2460, 1645, 1590, 1530, 1510, 1460, 1415, 875, 835, 755.

EXAMPLE 64

Furfurylamine (3.85 cc) is added to a solution of 10-[(2RS)-1-dimethylamino-2-propyl]-2-phenothiazinecarbothioamide (3.00 g) in ethanol (30 cc) containing distilled water (3 cc). The mixture is brought to 160° C. for 30 hours. After cooling, the mixture is concentrated to dryness under reduced pressure (30 mm Hg; 4 kPa) at 50° C. and the residue obtained is then diluted with ethyl acetate (100 cc) and thereafter washed with distilled water (2×200 cc). The organic phase is dried over magnesium sulphate, filtered and then concentrated to dryness under reduced pressure (30 mm Hg; 4 kPa) at 50° C. The residue is purified by chromatography on a column (height: 22 cm; diameter: 4.2 cm) of silica gel (0.04 to 0.06 mm) with a slight excess pressure of nitrogen (40 kPa), eluting with a 50:50 mixture (2 liters) of cyclohexane and ethyl acetate, then with pure ethyl acetate (2.5 liters) and finally with mixtures of ethyl acetate and methanol in proportions (by volume) of 98:2 (3.5 liters), 95:5 (1 liter) and 90:10 (1 liter) and collecting 60-cc fractions. After the first five liters have been discarded, fractions 56 to 85 are combined and concentrated to dryness at 50° C. under reduced pressure (30 mm Hg; 4 kPa) to give a yellow resin (0.7 g). This product is dissolved in ethyl ether (60 cc) and treated with a 2.2 N ethereal solution of hydrochloric acid. The suspension obtained is stirred at 25° C. for 2 hours. The solid is filtered off on sintered glass, washed with ethyl ether (2×20 cc) and then dried at 50° C. under reduced pressure (5 mm Hg; 0.7 kPa) to give N-furfuryl-10-[(2RS)-1-dimethylamino-2-propyl]-2-phenothiazinecarboxamide hydrochloride (0.52 g), m.p. 134° C.

NMR spectrum (250 MHz, DMSO, δ in ppm, J in Hz):

1.8 (D, J=7, 3H, —CH$_3$); 2.77 (S, 6H, —N(CH$_3$)$_2$); 3.51 (broad DD, J=14 and 4, 1H, 1H of >NCH$_2$—); 3.72 (broad DD, J=14 and 7.5, 1H, 1H of >NCH$_2$—); 4.47 (D, J =6, 2H, —CONH—CH$_2$—); 4.74 (Mt, J=7.5, 7 and 4, 1H, >N—CH<); 6.29 (D, J=3, 1H, =CH—); 6.4 (DD, J=2.0 and 3, 1H, furyl —O—C=CH—); 7 to 7.35 (Mt, 5H, aromatic); 7.58 (Mt, 3H, —H at 1-position, —H at 3-position and —O—CH=); 9.18 (T, J=6, —CONH—); 10.75 (extended Cx, 1H, —NH+).

Infrared spectrum (KBr), characteristic bands in cm$^{-1}$: 3270, 2970, 2600, 2500, 2460, 1650, 1590, 1535, 1460, 1415, 870, 830, 755.

EXAMPLE 65

2-Thienylmethylamine (4.5 cc) is added to a solution of 10-[(2RS)-1-dimethylamino-2-propyl]-2-phenothiazinecarbothioamide (3.0 g) in ethanol (30 cc) and distilled water (3 cc). The mixture is brought to 200° C. for 5.5 hours. The reaction mixture is diluted with ethyl acetate (100 cc) and then washed with distilled water (3×100 cc). The organic phase is dried over magnesium sulphate, filtered and then concentrated to dryness under reduced pressure (30 mm Hg; 4 kPa) at 50° C. The residue is purified by chromatography on a column (height: 25.0 cm; diameter: 3.5 cm) of silica gel (0.04-0.06 mm) with a slight excess pressure of nitrogen (40 kPa), eluting with mixtures of cyclohexane and ethyl acetate in proportions (by volume) of 50:50 (2.5 liters) and 30:70 (0.5 liter) and then with pure ethyl acetate (1.5 liters), collecting 60-cc fractions. Fractions 59 to 79 are combined and concentrated to dryness at 50° C. under reduced pressure (30 mm Hg; 4 kPa) to give an orange product (2.0 g) of meringue-like consistency. This product is dissolved in boiling isopropyl ether (40 cc) and the suspension is brought to reflux for 2 hours. The solid is filtered off hot, washed with isopropyl ether (2×10 cc) and then dried in the air. It is then taken up in boiling toluene (30 cc), which is filtered hot. Crystallization is primed by scratching. The mixture is left stirred for 24 hours at 5° C. and the crystals are then filtered off and dried at 50° C. under reduced pressure (5 mm Hg; 0.7 kPa) to give 10-[(2RS)-1-dimethylamino-2-propyl]-N-(2-thienylmethyl)-2-phenothiazinecarboxamide (0.56 g), m.p. 135° C.

NMR spectrum (250 MHz, DMSO, δ in ppm, J in Hz).

1.6 (D, J=7, 3H, —CH$_3$); 2.20 (S, 6H, —N(CH$_3$)$_2$); 2.65 (DD, J=13 and 6.5, 1H, 1H of >N—CH$_2$—); 2.9 (DD, J=13 and 6, 1H, 1H of >N—CH$_2$—); 4.18 (Mt, J=7, 6.5 and 6, 1H, >CH—N<; 4.65 (D, J=5.5, 2H, —CONHCH$_2$); 6.95 to 7.25 (Mt, 7H, aromatic); 7.4 (DD, J=5 and 0.5, 1H, thiophene =CH—S—); 7.45 (DD, J=8 and 1, 1H, —H at 3-position); 7.57 (D, J=1, 1H, —H at 1-position); 9.14 (T, J=5.5, 1H, —CONH—).

Infrared spectrum (KBr), characteristic bands in cm$^{-1}$: 3310, 2970, 2930, 2860, 2820, 2760, 1625, 1590, 1545, 1460, 1420, 840, 820, 750, 705.

EXAMPLES 66 TO 77

By working as described in Example 62, starting with the corresponding thioamide of general formula (II) [X=S], the amide of general formula (I) [X=O], the characteristics of which are given below, is obtained:

| Example | Product (I) | Melting point |
|---|---|---|
| 66 | | 246-8° C. (hydrochloride) |
| 67 | | 90° C. (hydrochloride) |
| 68 | | 196° C. (hydrochloride) |

| Example | Product (I) | Melting point |
|---|---|---|
| 69 | Phenothiazine with 10-N-CH(CH₃)CH₂-pyrrolidine substituent and 2-CONHCH₂C₆H₅; serie L | 218° C. (hydrochloride) $[\alpha]_D^{20} = +15,8$ (methanol; c = 1,034%) |
| 70 | Phenothiazine with 10-N-CH(CH₃)CH₂-piperidine substituent and 2-CONHCH₂C₆H₅ | 220° C. (hydrochloride) |
| 71 | Phenothiazine with 10-N-CH(CH₃)CH₂-N(CH₃)₂ substituent and 2-CONHCH₂-(2-Cl-C₆H₄) | 158° C. (hydrochloride) |
| 72 | Phenothiazine with 10-N-CH(CH₃)CH₂-pyrrolidine substituent and 2-CONHCH₂-(2-Cl-C₆H₄); L series | 225° C. (hydrochloride) $[\alpha]_D^{20} = +11,6$ (base) (chloroform; c = 1,002%) |
| 73 | Phenothiazine with 10-N-CH(CH₃)CH₂-pyrrolidine substituent and 2-CONHCH₂-(2-F-C₆H₄); L series | 203° C. (hydrochloride) $[\alpha]_D^{20} = +9,4$ (base) (chloroform; c = 1,001%) |
| 74 | Phenothiazine with 10-N-CH(CH₃)CH₂-pyrrolidine substituent and 2-CONHCH₂-(3-F-C₆H₄); L series | approximately 70° C. |

| Example | Product (I) | Melting point |
|---|---|---|
| 75 | [phenothiazine with -CONHCH2-(2-methylphenyl) substituent; N-substituent: -CH(CH3)CH2-pyrrolidinyl; L series] | approximately 125° C. (hydrochloride) $[\alpha]_D^{20} = +4.8$ (DMF; c = 1.017%) |
| 76 | [phenothiazine with -CONHCH2-(3-methylphenyl) substituent; N-substituent: -CH(CH3)CH2-pyrrolidinyl] | approximately 120° C. (neutral fumarate) |
| 77 | [phenothiazine with -CONHCH2-(3-pyridyl) substituent; N-substituent: -CH(CH3)CH2-N(CH3)2] | 50° C. |

EXAMPLE 78

Mercuric acetate (2.91 g) dissolved in glacial acetic acid (60 cc) is added in the course of 20 minutes to a solution of 10-{1-[(2R)-2-hydroxymethyl-1-pyrrolidinyl]-2-propyl}-N-(3-methylbutyl)-2-phenothiazinecarbothioamide, L series (4.29 g) in acetic acid (60 cc), and the mixture is stirred for 45 minutes at a temperature in the region of 20° C. The black suspension obtained is filtered on sintered glass plugged with celite and the yellow filtrate is concentrated under reduced pressure (30 mm Hg; 4 kPa) at 40° C. The residue is taken up with ethyl acetate (250 cc) and distilled water (50 cc). The organic phase is washed successively with normal sodium hydroxide (2×100 cc) and distilled water (3×100 cc) and with saturated aqueous sodium chloride (100 cc) and dried over magnesium sulphate. After filtration, the yellow filtrate is concentrated under reduced pressure (30 mm Hg; 4 kPa) at 40° C. and a crude yellow oil (4.6 g) is thereby obtained. This residue is purified by chromatography on a column (height: 25 cm; diameter: 3.0 cm) of silica gel (0.04–0.06 mm), eluting with pure ethyl acetate (3.6 liters) with a slight excess pressure of nitrogen (40 kPa) and collecting 150-cc fractions. Fractions 12 to 24 are combined and concentrated to dryness under reduced pressure (30 mm Hg; 4 kPa) at 40° C. to give 10-{1-[(2R)-2-hydroxymethyl-1-pyrrolidinyl]-2-propyl}-N-(3-methylbutyl)-2-phenothiazinecarboxamide, L series (0.89 g) in the form of an off-white solid, m.p. 140° C.

Proton NMR (250 MHz, DMSO, δ in ppm, J in Hz): 0.93 (D, J=6.5, 6H, —CH(CH3)2); 1.45 (Mt, 2H, —CH2CH(CH3)2); 1.6 (D, J=7, 3H, —CH3); 1.5 to 1.85 (Mt, 5H, —CH2—CH2— of pyrrolidine and —CH(CH3)2); 2.22 (Mt, 1H, 1H of the pyrrolidine >NCH2—); 2.55 (Mt, 1H, pyrrolidine >N—CH<); 2.92 (DD, J=13 and 5.5, 1H, 1H of >NCH2—); 3.12 (Mt, 1H, 1H of the pyrrolidine >NCH2—); 3.20 to 3.5 (Mt, 5H, 1H of >NCH2—, —CH2O— and —CONH—CH2—); 4.18 (Mt, 1H, >N—CH<); 4.46 (Mt, 1H, —OH); 6.9 to 7.3 (Mt, 5H, aromatic); 7.43 (D, J=8, 1H, —H at 3-position); 7.6 (S, 1H, —H at 1-position); 8.4 (T, J=6, 1H, —CONH—).

Infrared spectrum (CHCl3), characteristic bands in cm$^{-1}$: 3460, 2960, 2880, 2820, 1650, 1595, 1560, 1520, 1460, 1415, 1040.

EXAMPLE 79

The procedure is as in Example 78, but collecting chromatographic fractions 25 to 48. These fractions are combined and concentrated to dryness under reduced pressure (30 mm Hg; 4 kPa) at 40° C. to give 10-{1-[(2R)-2-acetoxymethyl-1-pyrrolidinyl]-2-propyl}-N-(3-methylbutyl)-2-phenothiazinecarboxamide, L series (3.17 g) in the form of an orange oil.

A 2.2N ethereal solution (2.02 cc) of hydrochloric acid is added to a solution of 10-{1-[(2R)-2-acetoxymethyl-1-pyrrolidinyl]-2-propyl}-N-(3-methylbutyl)-2-phenothiazinecarboxamide, L series (2.40 g) in acetonitrile (14 cc). The solution obtained is introduced dropwise into ethyl ether (400 cc), briskly stirred; a precipitate develops and the suspension is stirred for 12 hours at 25° C. The precipitate is filtered off on sintered glass, washed with ethyl ether (3×20 cc) and dried at 40° C. under reduced pressure (5 mm Hg; 0.068 kPa) to give 10-{1-[(2R)-2-acetoxymethyl-1-pyrrolidinyl]-2-propyl}-N-(3-methylbutyl)-2-phenothiazinecarboxamide hydrochloride, L series (2.17 g), m.p. 140° C.

Proton NMR (250 MHz, DMSO, δ in ppm, J in Hz): 0.91 (D, J=7, 6H, —CH(CH₃)₂); 1.43 (Mt, 2H, CH₂—CH(CH₃)₂); 1.6 (Mt, 1H, —CH(CH₃)₂); 1.85 (D, J=7, 3H, —CH₃); 1.6 to 2.10 (Mt, 4H, pyrrolidine —CH₂—CH₂—); 2.06 (S, 3H, —OCOCH₃); 3.03 (Mt, 1H, 1H of the pyrrolidine >N—CH₂—); 3.27 (Mt, 2H, —CONH—C₂—); 3.65 to 4 (Mt, 4H, 1H of the pyrrolidine >N—CH₂), of the pyrrolidine >N—CH< and >N—CH₂—); 4.4 (limiting AB, 2H, —CH₂OCO—); 4.94 (Mt, 1H, >N—CH—); 7 to 7.35 (Mt, 5H, aromatic); 7.54 (S, 1H, —H at 1-position); 7.57 (D, J=8, 1H, —H at 3-position); 8.7 (broad T, J=6, —CONH—).

Infrared spectrum (KBr), characteristic bands in cm⁻¹: 3300, 2960, 2870, 2580, 2500, 1750, 1645, 1595, 1535, 1460, 1230, 1045, 835, 755.

EXAMPLE 80

A lukewarm solution of mercuric acetate (3.19 g) in acetic acid (40 cc) is added to a solution of N-cyclobutylmethyl-10-[1-(1-pyrrolidinyl)-2-propyl]-2-phenothiazinecarbothioamide, L series (4.36 g) in acetic acid (20 cc). After being stirred at a temperature in the region of 25° C. for 2 hours, the reaction mixture is filtered and the filtrate is concentrated to dryness under reduced pressure (30 mm Hg; 4 kPa) at 40° C. The residue is taken up with ethyl acetate (100 cc) and washed successively with 4N aqueous sodium hydroxide solution (2×50 cc) and then with distilled water (3×50 cc). The organic phase is dried over magnesium sulphate, filtered and concentrated to dryness under reduced pressure (30 mm Hg; 4 kPa) at 40° C. to give a pale yellow product (2.65 g) of honey-like consistency, which is purified by chromatography on a column (height: 38 cm; diameter: 2 cm) of silica gel (0.06-0.2 mm), eluting with ethyl acetate (900 cc) and collecting 60-cc fractions. Fractions 3 to 12 are combined and concentrated to dryness under reduced pressure (30 mm Hg; 4 kPa) to give N-cyclobutylmethyl-10-[1-(1-pyrrolidinyl)-2-propyl]-2-phenothiazinecarboxamide, L series (1.89 g).

$[\alpha]_D^{20} = +22° \pm 0.6°$ (c=1%; methanol).

A boiling solution of N-cyclobutylmethyl-10-[1-(1-pyrrolidinyl)-2-propyl]-2-phenothiazinecarboxamide, L series (1.7 g) in 2-propanol (17 cc) containing fumaric acid (0.47 g) is allowed to cool. The mixture is concentrated under reduced pressure (30 mm Hg; 4 kPa) at 40° C. to give a residue which is taken up in isopropyl ether (100 cc). The mixture is stirred for 1 hour at 20° C. The suspension obtained is filtered and the solid is washed with isopropyl ether (2×5 cc) and dried under reduced pressure (5 mm Hg; 0.67 kPa) at 50° C. to give a cream-coloured powder, which is dissolved in acetone (25 cc) under reflux. Crystallization develops. The mixture is stirred for 16 hours at 20° C. and the crystals are drained and dried under reduced pressure (5 mm Hg; 0.67 kPa) at 50° C. N-Cyclobutylmethyl-10-[1-(1-pyrrolidinyl)-2-propyl]-2-phenothiazinecarboxamide fumarate, L series (0.64 g) is thereby obtained in the form of cream-coloured crystals, m.p., 126°-128° C.

$[\alpha]_D^{20} = +12.4$ (C=0.8%; methanol).

Proton NMR (200 MHz, DMSO-d6, δ in ppm, J in Hz):

1.68 (D, J=7, 3H, —CH₃); 1.77 (Mt, 4H, pyrrolidine —CH₂—); 1.6 to 2.05 (Mt, 6H, cyclobutylmethyl —CH₂—); 2.5 (Mt, partially masked, cyclobutylmethyl >CH—); 2.85 and 3 (2Mt, respectively 2H each, pyrrolidine >N—CH₂—); 3.20 to 3.25 (Mt, 4H, >N—CH₂— and —CONHCH₂—); 4.46 (Mt, 1H, >N—CH<); 6.62 (S, 2H, fumarate —CH=CH—); 6.95 to 7.3 (Mt, 5H, aromatic); 7.47 (D, J=8, 1H, —H at 3-position); 7.51 (S, 1H, —H at 1-position); 8.5 (T, J=5.5, 1H, —CONH—).

Infrared spectrum (KBr), characteristic bands in cm⁻¹: 3320, 2975, 2930, 2860, 2750, 2000, 1800, 1710, 1640, 1595, 1465, 1560, 980, 835, 750, 640.

EXAMPLE 81

Mercuric acetate (0.9 g) is added in the course of 20 minutes to a solution of N-benzyl-10-{(2RS)-1-[N-ethyl-N-(2-hydroxyethyl)amino]-2-propyl}-2-phenothiazinecarbothioamide neutral fumarate (1.5 g) in acetic acid (25 cc) and the mixture obtained is stirred for 12 hours at a temperature in the region of 20° C. The black suspension obtained is filtered on sintered glass plugged with celite and the yellow filtrate is concentrated under reduced pressure (30 mm Hg; 4 kPa) at 40° C. The residue is taken up with ethyl acetate (100 cc) and the organic phase is washed successively with N sodium hydroxide (2×20 cc) and distilled water (2×20 cc) and with saturated aqueous sodium chloride solution (20 cc) and dried over magnesium sulphate. After filtration, the yellow filtrate is concentrated to dryness under reduced pressure (30 mm Hg; 4 kPa) at 40° C. and a yellow oil (1.0 g) is thereby obtained, which is purified by chromatography on a column (height: 30 cm; diameter: 1.5 cm) of silica (0.06-0.2 mm), eluting with pure ethyl acetate (500 cc) and collecting 40-cc fractions. Fractions 5 to 8 are combined and concentrated to dryness under reduced pressure (30 mm Hg; 4 kPa) at 40° C. A yellow oil (0.8 g) is obtained, which is dissolved in boiling ethanol (3 cc); fumaric acid (0.2 g) is added and the solution is concentrated to dryness under reduced pressure (30 mm Hg; 4 kPa) at 40° C. to give 2-[(2RS)-2-(2-benzylcarbamoyl-10-benothiazinyl)-N-ethyl-propylamino]ethylacetatefumarate 1.0 g) in the form of a yellow powder, m.p. approximately 70° C.

Proton NMR (250 MHz, DMSO, δ in ppm, J in Hz): 0.85 (T, J=7, 3H, —NCH₂CH₂); 1.65 (D, J=7, 3H, —CH₃); 1.90 (S, 3H, —OCOCH₃); 2.52 (Mt, >N—CH₂CH₃); 2.66 (T, J=6, 2H, >N—CH₂—CH₂OCOCH₃); 2.78 (DD, J=13 and 6, 1H, 1H of >N—CH₂—); 3.09 (DD, J=13 and 7.5, 1H, 1H of N—CH₂—); 3.93 (T, J=6, 2H, —CH₂OCO—); 4.15 (Mt, J=7.5, 7 and 6, 1H, N—CH ); 4.50 (D, J=6, 2H, —CSNH—CH₂—); 6.64 (S, 2H, fumarate —CH=CH—); 6.9 to 7.4 (Mt, 10H, aromatic); 7.48 (broad D, J=8, 1H, —H at 3-position); 7.58 (broad S, 1H, —H at 1-position); 9.05 (T, J=6, 1H, —CSNH—).

Infrared spectrum (KBr), characteristic bands in cm⁻¹: 2980, 2700 to 2100, 1740, 1710, 1640, 1590, 1460, 1235, 980, 825, 750, 700, 635.

EXAMPLE 82

Mercuric acetate (0.80 g) is added to a solution of N-(3-fluorobenzyl)-10-[(2RS)-1-(1-pyrrolidinyl)-2-propyl]-2-phenothiazinecarbothioamide neutral fumarate (1.30 g) in acetic acid (20 cc), and the mixture obtained is stirred for 20 hours at a temperature in the region of 20° C. The black suspension obtained is filtered on sintered glass plugged with celite and the yellow filtrate is concentrated under reduced pressure (30 mm Hg; 4 kPa) at 40° C. The residue is taken up with ethyl acetate (100 cc) and the organic phase is washed successively with normal sodium hydroxide (2×20 cc) and distilled water (2×20 cc) and with aqueous sodium chloride solution (20 cc) and dried over magnesium sulphate. After filtration, the yellow filtrate is concentrated under reduced pressure (30 mm Hg; 4 kPa) at 40° C. and a crude yellow oil (0.90 g) is thereby obtained. This residue is dissolved in hot ethanol (3 cc) and treated with fumaric acid (0.25 g) dissolved in ethanol (2 cc). After 4 hours' cooling to 4° C., the crystallized solid is separated by filtration, washed with cold ethanol (2×5 cc) and then dried at 50° C. under reduced pressure (5 mm Hg; 0.7 kPa) to give N-(3-fluorobenzyl)-10-[(2RS)-1-(1-pyrrolidinyl)-2-propyl]-2-phenothiazinecarboxamide neutral fumarate (0.7 g), m.p. 165° C.

Proton NMR (250 MHz, DMSO, δ in ppm, J in Hz): 1.62 (D, J=7.5, 3H, —CH₃); 1.7 (Mt, 4H, pyrrolidine —CH₂—CH₂—); 2.62 (Mt, 4H, pyrrolidine

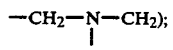

3.01 (DD, J=13.5 and 7, 1H, 1H of >N—CH₂—); 3.12 (DD, J=13.5 and 6, 1H, 1H of >N—CH₂—); 4.27 (Mt, J=7.5, 7 and 6, 1H, >N—C<); 4.51 (D, J=5.5, 2H, —CONH—CH₂—); 6.57 (S, 1H, hemifumarate —CH═CH—); 6.90 to 7.45 (Mt, 9H, aromatic); 7.5 (broad D, J=8, 1H, —H at 3-position); 7.6 (broad S, 1H, —H at 1-position); 8.09 (T, J=5.5, 1H, —CONH—).

Infrared spectrum (KBr), characteristic bands to cm⁻¹: 3240, 2970, 2915, 2500 to 2000, 1655, 1610, 1590, 1540, 1485, 1460, 820, 785, 760, 750, 670.

EXAMPLE 83

Mercuric acetate (1.1 g) is added to a solution of N-(2-methylbenzyl)-10-[(2RS)-1-(1-pyrrolidinyl)-2-propyl]-2-phenothiazinecarbothioamide acid fumarate (2.0 g) in acetic acid (28 cc), and the mixture obtained is stirred for 20 hours at a temperature in the region of 20° C. The white suspension obtained is filtered on sintered glass plugged with celite and the yellow filtrate is concentrated under reduced pressure (30 mm Hg; 4 kPa) at 40° C. The residue is taken up with ethyl acetate (100 cc) and the organic phase is washed successively with normal sodium hydroxide (2×20 cc) and distilled water (2×20 cc) and with aqueous sodium chloride solution (20 cc) and dried over magnesium sulphate. After filtration, the yellow filtrate is concentrated under reduced pressure (30 mm Hg; 4 kPa) at 40° C. and a yellow oil (1.0 g) is thereby obtained. This product is purified by chromatography on a column (height: 22 cm; diameter: 4.2 cm) of silica gel (0.04–0.06 mm) with a slight excess pressure of nitrogen (40 kPa), eluting with a 20:80 mixture (1,000 cc) of cyclohexane and ethyl acetate and collecting 50-cc fractions. Fractions 8 to 20 are combined and concentrated under reduced pressure (30 mm Hg; 4 kPa) at 40° C. to give N-(2-methylbenzyl)-10-[(2RS)-1-(1-pyrrolidinyl)-2-propyl]-2-phenothiazinecarboxamide (0.6 g) in the form of a yellow oil. This product is dissolved in methylene chloride (20 cc), and a 3.4N solution (1 cc) of hydrochloric acid in isopropyl ether is added. The mixture is concentrated to dryness under reduced pressure (30 mm Hg; 4 kPa) at 40° C. and the residue is taken up with ethyl ether (20 cc). The suspension is stirred for 2 hours at 25° C. and the solid is separated by filtration, washed with ether (2×5 cc) and then dried at 30° C. under reduced pressure (5 mm Hg; 0.7 kPa) to give N-(2-methylbenzyl-10-[(2RS)-1-(1-pyrrolidinyl)-2-propyl]-2-phenothiazinecarboxamide hydrochloride (0.5 g), m.p. 90° C.

Proton NMR (250 MHz, DMSO, δ in ppm, J in Hz): 1.8 (D, J=7, 3H, —CH₃); 1.7 to 2 (Mt, 4H, pyrrolidine —CH₂—CH₂—); 2.35 (S, 3H, 2-methylbenzyl —CH₃); 2.85, 3.12, 3.60 and 3.80 (4Cx, 1H each, pyrrolidine

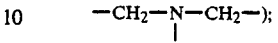

3.7 (broad DD, J=13 and 5, 1H, 1H of >NCH₂—); 3.85 (broad DD, J=13 and 7.5, 1H, 1H of —N—CH₂—); 4.48 (limiting AB, 2H, —CONH—CH₂—); 4.75 (Mt, J=7.5, 7 and 5, 1H, >N—CH<); 7 to 7.3 (Mt, 8H, aromatic); 7.35 (D, J=8, 1H, —H at 4-position); 7.58 (broad S, 1H, —H at 1-position); 7.63 (broad D, J=8, 1H, —H at 3-position); 9.15 (T, J=5.5, 1H, —CONH—); 10.6 (Cx, 1H, —NH⁺).

Infrared spectrum (KBr), characteristic bands in cm⁻¹: 3270, 2975, 2580, 2480, 1650, 1595, 1535, 1460, 1415, 870, 830, 750.

EXAMPLE 84

1,2-Diaminocyclohexane (9.3 g) is added to an ethanolic solution (35 cc) of 10-[(2RS)-1-dimethylamino-2-propyl]-2-phenothiazinecarbothioamide (2.8 g). The mixture is heated in an autoclave to 160° C. for 4.5 hours. The reaction mixture is diluted with ethyl acetate (100 cc) and washed with distilled water (3×100 cc). The organic phase is separated after settling has taken place, dried over magnesium sulphate, filtered and evaporated to dryness under reduced pressure (30 mm Hg; 4 kPa) at 40° C. The residue is purified by chromatography on a column (height: 22 cm; diameter: 4 cm) of silica gel (0.04–0.06 mm) with a slight excess pressure of nitrogen (40 kPa), eluting with 1,2-dichloroethane (1 liter) and mixtures of 1,2-dichloroethane and methanol in proportions (by volume) of 90:10 (3 liters), 80:20 (2 liters), 70:30 (2 liters) and 50:50 (1 liter) and with pure methanol (1 liter) and collecting 125-cc fractions. Fractions 63 to 80 containing the pure product are combined and concentrated to dryness under reduced pressure (30 mm Hg; 4 kPa) at 40° C. to give 10-[(2RS)-1-dimethylamino-2-propyl]-2-(3a,4,5,6,7,7a-hexahydro-1H-benzimidazol-2-yl)phenothiazine (1.2 g) in the form of a yellow product of meringue-like consistency.

The product obtained is taken up in boiling ethyl ether (80 cc) and treated dropwise with a 1.4N ethereal solution of hydrochloric acid with vigorous stirring until precipitation is complete. The suspension obtained is stirred for 1 hour. The precipitate is filtered off and the cake is washed with ethyl ether (2×20 cc) and then dried at 40° C. under reduced pressure (10 mm Hg; 1.3 kPa). 10-[(2RS)-1-Dimethylamino-2-propyl]-2-(3a,4,5,6,7,7a-hexahydro-1H-benzimidazol-2-yl)phenothiazine dihydrochloride (1.05 g), m.p. 175° C., is thereby obtained.

Proton NMR (250 MHz, DMSO, δ in ppm, J in Hz): 1.45 and 1.85 (2Mt, 8H, hexahydrobenzimidazole —CH₂—); 1.82 (D, J=7, 3H, —CH₃); 2.89 (2D, 6H, —N(CH₃)₂); 3.85 (broad limiting AB, 2H, >N—CH₂—); 4.32 (limiting AB, 2H, hexahydrobenzimidazole —CH); 4.78 (Mt, 1H, >N—CH<); 7.10 to 7.45 (Mt, 4H, aromatic); 7.54 (D, J=8, 1H, —H at 4- position); 7.77 (Mt, 2H, —H at 1-position and —H at 3-position); 10.70 (Mt, 1H, —NH+).

Infrared spectrum (KBr), characteristic bands in cm$^{-1}$: 3060, 2940, 2670, 1605, 1575, 1465, 870, 830, 755.

EXAMPLE 85

1,2-Diaminocyclohexane (9.12 g) is added to an ethanolic solution (32 cc) of 10-[(2RS)-1-(pyrrolidinyl)-2-propyl]-2-phenothiazinecarbothioamide (2.96 g). The mixture is heated in an autoclave to 150° C. for 10 hours. The reaction mixture is diluted with ethyl acetate (150 cc) and washed with distilled water (4×100 cc). The organic phase is separated after settling has taken place, dried over magnesium sulphate, filtered and concentrated to dryness under reduced pressure (30 mm Hg; 4 kPa) at 40° C. The residue is purified by chromatography on a column (height: 23 cm; diameter: 2.5 cm) of FLUKA type 507 C neutral alumina, eluting with 50:50 (by volume) mixtures (1 liter) of cyclohexane and ethyl acetate and collecting 50-cc fractions. Fractions 2 to 15 containing the pure product are combined and concentrated to dryness under reduced pressure (30 mm Hg; 4 kPa) at 40° C. to give 2-(3a,4,5,6,7,7a-hexahydro-1H-benzimidazol-2-yl)-10-[(2RS)-1-(pyrrolidinyl)-2-propyl]phenothiazine (1.07 g) in the form of a brown product of meringue-like consistency.

The product is dissolved in hexane (50 cc under reflux; crystallization is primed by scratching. The mixture is stirred at 0°-5° C. for 12 hours and the crystals are then filtered off and dried under reduced pressure (10 mm Hg; 1.4 kPa) at 40° C. for 4 hours. 2-(3a,4,5,6,7,7a-hexahydro-1H-benzimidazol-2-yl)-10-[(2RS)-1-(pyrrolidinyl)-2-propyl]phenothiazine (0.62 g) is thereby obtained in the state of cream-coloured crystals, m.p. 109° C.

NMR spectrum (250 MHz, DMSO, δ in ppm, J in Hz):

1.2 to 1.8 (Mt, 12H, hexahydrobenzimidazole —CH$_2$— and pyrrolidine —CH$_2$—CH$_2$—); 1.59 (D, J=7, 3H, —CH$_3$); 2.50 (masked Mt, 4H, pyrrolidine >N—CH$_2$—); 2.87 (DD, J=13 and 6.5, 1H, 1H of >NCH$_2$—); 2.98 (DD, J=13 and 6, 1H, 1H of <NCH$_2$—); 3.7 (Cx, 2H, hexahydrobenzimidazole— —CH<); 4.15 (Mt, J=7, 6.5 and 6, 1H, >CH—N<); 6.9 to 7.25 (Mt, 5H, aromatic); 7.35 (DD, J=8 and 1, 1H, —H at 3-position); 7.6 (D, J=1, 1H, —H at 1-position).

Infrared spectrum (CHCl$_3$), characteristic bands in cm$^{-1}$: 3400, 2940, 2860, 2810, 1615, 1590, 1560, 1470, 1445, 830.

EXAMPLE 86

1,2-Diaminocyclohexane (9.12 g) is added to an ethanolic solution (32 cc) of 10-[1-(1-pyrrolidinyl)-2-propyl]-2-phenothiazinethiocarboxamide, D series (2.96 g). The mixture is heated in an autoclave to 140° C. for 18 hours, then diluted with ethyl acetate (150 cc) and washed with distilled water (4×70 cc). The organic phase is separated after settling has taken place, dried over magnesium sulphate, filtered and concentrated to dryness under reduced pressure (30 mm Hg; 4 kPa) at 40° C. The residue is purified by chromatography on a column (height: 23.5 cm; diameter: 2.5 cm) of neutral alumina, eluting with mixtures of cyclohexane and ethyl acetate in proportions (by volume) of 75:25 (250 cc) and 50:50 (1250 cc) and collecting 50-cc fractions. Fractions 4 to 20 containing the pure product are combined and concentrated to dryness under reduced pressure (30 mm Hg; 4 kPa) at 40° C. to give a product (0.90 g) containing the expected product. The batch obtained is dissolved in boiling isopropyl ether (25 cc); the solution is filtered and hexane (25 cc) is added to the hot solution. Crystallization is primed by scratching, and the crystals are filtered off on sintered glass to give 2-(3a,4,5,6,7,7a-hexahydro-1H-benzimidazol-2-yl)-10-[1-(1-pyrrolidinyl)-2-propyl]phenothiazine, D series (0.48 g) in the form of white crystals, m.p. 108°-110° C., the NMR spectrum of which is identical to that of the product obtained in Example 85.

[α]$_D^{20}$ = +7.5 (chloroform; c=0.868%).

Infrared spectrum (KBr), characteristic bands in cm$^{-1}$: 3170, 2925, 2850, 2795, 1600, 1575, 1550, 1450, 875, 825, 750.

EXAMPLE 87

1,2-Diaminocyclohexane (7.98 g) is added to an ethanolic solution (32 cc) of 10-[1-(1-pyrrolidinyl)-2-propyl]-2-phenothiazinecarbothioamide, L series (2.96 g). The mixture is heated in an autoclave to 140° C. for 18 hours, then diluted with ethyl acetate (150 cc) and washed with distilled water (3×50 cc). The organic phase is separated after settling has taken place, dried over magnesium sulphate, filtered and concentrated to dryness under reduced pressure (30 mm Hg; 4 kPa) at 40° C. The residue is purified by chromatography on a column (height: 24 cm; diameter: 2.5 cm) of neutral alumina, eluting with mixtures of cyclohexane and ethyl acetate in proportions (by volume) of 75:25 (500 cc), 50:50 (750 cc) and 25:75 (750 cc) and collecting 50-cc fractions. Fractions 10 to 29 containing the pure product are combined and concentrated to dryness under reduced pressure (30 mm Hg; 4 kPa) at 40° C. to give 2-(3a, 4, 5, 6, 7, 7a-hexahydro-1H-benzimidazol-2-yl)-10-[1-(1-pyrrolidinyl)-2-propyl]phenothiazine, L series (0.38 g) in the form of a brown product of meringue-like consistency.

1.4N ethereal hydrochloric acid (1.13 cc) is added dropwise and with vigorous stirring to a solution of 2-(3a, 4, 5, 6, 7, 7a-hexahydro-1H-benzimidazol-2-yl)-10-[1-(1-pyrrolidinyl)-2-propyl]phenothiazine, L series (0.34 g) in boiling ethyl ether (34 cc). The suspension obtained is stirred for one hour. The precipitate is filtered off and the cake is washed with ethyl ether (2×10 cc) and then dried at 40° C. under reduced pressure (10 mm Hg; 1.3 kPa). 2-(3a, 4, 5, 6, 7, 7a-Hexahydro-1H-benzimidazol-2-yl)-10-[1-(1-pyrrolidinyl)-2-propyl]-phenothiazine dihydrochloride, L series (0.18 g), m.p. 198°-199° C., is thereby obtained, the NMR characteristics of which are identical to those of the product obtained in Example 85.

Infrared spectrum (KBr), characteristic bands in cm$^{-1}$: 2940, 2680, 1605, 1575, 1540, 1465, 865, 825, 755.

EXAMPLE 88

1,2-Diaminocyclohexane (15.78 cc) is added to an ethanolic solution (70 cc) of 7-chloro-10-[(2RS)-1-(1-pyrrolidinyl)-2-propyl]-2-phenothiazinecarbothioamide (5.20 g). The mixture is heated in an autoclave to 150° C. for 17 hours. After cooling, the reaction mixture is diluted with ethyl acetate (250 cc) and washed with j distilled water (5×250 cc). The organic phase is extracted with normal hydrochloric acid solution (300 cc). After separation of the organic phase when settling has taken place, the acidic aqueous phase is alkalinized with concentrated caustic soda and extracted with ethyl acetate (200 cc). The organic phase is separated after settling has taken place, dried over magnesium sulpate, filtered and evaporated under reduced pressure (30 mm Hg; 4 kPa) at 40° C. The residue is chromatographed on a column (height: 52 cm; diameter: 2.5 cm) of silica gel (0.2–0.06 mm), eluting with pure ethyl acetate (2 liters) and collecting 120-cc fractions. The first liter is discarded, and fractions 4 to 7 containing the pure product are combined and concentrated to dryness under reduced pressure (30 mm Hg; 4 kPa) at 40° C. to give 7-chloro-2-(3a, 4, 5, 6, 7, 7a-hexahydro-1H-benzimidazol-2-yl)-10-[(2RS)-1-(1-pyrrolidinyl)-2-propyl]-phenothiazine (0.72 g) in the form of a yellow solid, m.p. 120° C.

Proton NMR (250 MHz, DMSO, δ in ppm, J in Hz):
1.25 to 1.9 (Mt, 12H, —CH$_2$— of hexahydrobenzimidazole and of pyrrolidine); 1.62 (D, J=7.5, 3H, —CH$_3$); 2.82 (DD, J=13 and 6, 1H, 1H of >N—CH$_2$—); 3 (DD, J=13 and 7, 1H, 1H of N—CH$_2$—); 4 (Mt, 2H, hexahydrobenzimidazole >CH—CH<); 4.19 (Mt, J=7.5, 7 and 6, 1H, >N—CH—); 7.10 to 7.35 (Mt, 4H, aromatic); 7.45 (DD, J=8 and 1, 1H, —H at 3-position); 7.55 (D, J=1, 1H, —H at 1position).

Infrared spectrum (KBr), characteristic bands in cm$^{-1}$: 2920, 2860, 2790, 1605, 1535, 1460, 865, 805.

7-Chloro-10-[(2RS)-1-(1-pyrrolidinyl)-2-propyl]-2-phenothiazinecarbothioamide may be obtained in the following manner:

A mixture of 7-chloro-10-[(2RS)-1-(1-pyrrolidinyl)-2-propyl]-2-phenothiazinecarbonitrile (31.07 g) and triethylamine (11.8 cc) in anhydrous pyridine (300 cc) is saturated with hydrogen sulphide for 4 hours at 25° C. The clear solution obtained is kept stirred for 12 hours at 25° C. The mixture is outgassed by bubbling nitrogen through for 2 hours, then diluted with ethyl acetate (250 cc) and washed with distilled water (5×200 cc). The organic phase is dried over magnesium sulphate and filtered, and the filtrate is concentrated to dryness under reduced pressure (30 mm Hg; 4 kPa). The residue is purified by chromatography on a column (height: 38 cm; diameter: 6.5 cm) of silica gel (0.06–0.2 mm), eluting with a mixture of cyclohexane and ethyl acetate in proportions (by volume) of 70:30 (6 liters), 50:50 (4 liters) and 30:70 (4 liters), then with pure ethyl acetate (2 liters) and finally with a 90:10 mixture (6 liters) of ethyl acetate and methanol, collecting 50-cc fractions. The first 13.3 liters are discarded and fractions 6 to 94 are combined and concentrated to dryness under reduced pressure (30 mm Hg; 4 kPa) at 50° C. to give 7-chloro-10-[(2RS)-1-(1-pyrrolidinyl)-2-propyl]-2-phenothiazine-thiocarboxamide (21.43 g).

7-Chloro-10-[(2RS)-1-(1-pyrrolidinyl)-2-propyl]-2-phenothiazinecarbonitrile may be obtained in the following manner:

Pyrrolidine (21.1 cc) is added to a suspension of (2RS)-2-(7-chloro-2-cyano-10-phenothiazinyl)propyl methanesulphonate (72.1 g) in toluene (166 cc). The mixture is brought to 120° C. for 21 hours, and then to 150° C. for 12 hours. After cooling, the mixture is washed with distilled water (5×250 cc). The organic phase is dried over magnesium sulphate, filtered and concentrated to dryness under reduced pressure (30 mm Hg; 4 kPa) to give 7-chloro-10-[(2RS)-1-(1-pyrrolidinyl)-2-propyl]-2-phenothiazinecarbonitrile (19.2 g).

(2RS)-2-(7-Chloro-2-cyano-10-phenothiazinyl)propyl methanesulphonate may be obtained in the following manner:

Triethylamine (30 cc) is added to a solution of 7-chloro-10-[(2RS)-1-hydroxy-2-propyl]-2-phenothiazinecarbonitrile (40 g) in methylene chloride (400 cc). The mixture is cooled to 0° C. and then treated dropwise in the course of 1 hour with methanesulphonyl chloride (16.6 cc). Distilled water (1 liter) is then added, after which the constituents of the mixture are allowed to settle and the organic phase is separated and washed with distilled water (500 cc). The organic phase is then dried over magnesium sulphate, filtered and concentrated under reduced pressure (30 mm Hg; 4 kPa) to a residual volume of 100 cc. Isopropyl ether (150 cc) is then introduced slowly and the mixture is left stirred for 30 minutes. Isopropyl ether (300 cc) is then added slowly and the suspension is stirred for 48 hours. The precipitate is filtered off, washed with isopropyl ether (2×50 cc) and dried at 40° C. under reduced pressure (5 mm Hg; 0.67 kPa) to give (2RS)-2-(7-chloro-2-cyano-10-phenothiazinyl)propyl methanesulphonate (34.53 g), m.p. 132° C.

7-Chloro-10-[(2RS)-1-hydroxy-2-propyl]-2-phenothiazinecarbonitrile may be obtained in the following manner:

A solution of ethyl (2RS)-2-(7-chloro-2-cyano-10-phenothiazinyl)propionate (157.6 g) in dry tetrahydrofuran (720 cc) is added to a suspension of sodium borohydride 25.8 g) in anhydrous tetrahydrofuran (700 cc) containing ethanedithiol (57 cc). The mixture is brought to reflux for 20 hours and then cooled to 5° C., and 4N sodium hydroxide solution (1 liter) is added slowly. The reaction mixture is diluted with methylene chloride (2 liters) and stirred for 15 minutes. The constituents of the mixture are allowed to settle and the organic phase is separated and washed with distilled water (4×1.5 liters), dried over magnesium sulphate, filtered and concentrated to dryness under reduced pressure (30 mm Hg; 4 kPa) at 50° C. The residue is purified by chromatography on a column (height: 80 cm; diameter: 8 cm) of silica (0.02–0.6 mm), eluting with mixtures of ethyl acetate and cyclohexane in proportions of 15:85 (15 liters) and 36:65 (10 liters), collecting 600-cc fractions. The first 8 liters are discarded, and fractions 21 to 28 are combined and concentrated to dryness under reduced pressure (30 mm Hg; 4 kPa) at 50° C. to give 7-chloro-10-[(2RS)-1-hydroxy-2-propyl]-2-phenothiazinecarbonitrile (80 g).

Ethyl (2RS)-2-(7-chloro-2-cyano-10-phenothiazinyl)propionate may be obtained in the following manner:

Sodium hydride (1.85 g; in 50% strength dispersion in vaseline) is added slowly in the course of 10 minutes to a solution of 7-chloro-2-phenothiazinecarbonitrile (10 g) in N,N-dimethylformamide (250 cc). The mixture is then brought to 120° C. and treated in the course of 30 minutes with a solution of ethyl (2RS)-2-chloropropionate (18.5 cc) in N,N-dimethylformamide (100 cc). Heating is continued for 2 hours. After cooling, the mixture is diluted in ethyl acetate (1 liter) and washed with distilled water (1.5 liters). The organic phase is dried over magnesium sulphate, treated with charcoal 3S, filtered and concentrated to dryness under reduced pressure (30 mm Hg; 4 kPa) at 50° C. to give a residue which is purified by chromatography on a column (height: 25 cm; diameter: 4.0 cm) of silica (0.2-0.06 mm), eluting with a 90:10 (by volume) mixture (1.5 liters) of cyclohexane and ethyl acetate and collecting 100-cc fractions. Fractions 6 to 11 are combined and concentrated to dryness under reduced pressure (30 mm Hg; 4 kPa) to give ethyl (2RS)-2-(7-chloro-2-cyano-10- phenothiazinyl)propionate (5.3 g) in the form of a pale yellow product of meringue-like consistency.

7-Chloro-2-phenothiazinecarbonitrile may be prepared in the following manner.

Aluminium chloride (0.5 g) and sulphuryl chloride (39.7 cc) are added in the course of 4 hours to a solution, heated to 50° C., of 2-phenothiazinecarbonitrile (100 g) in 1,2-dichloroethane (3000 cc). The reaction mixture is brought to reflux for 2 hours, and then stirred for 48 hours at 25° C. The precipitate formed is filtered off, washed with 1,2-dichloroethane (2×200 cc) and then with ethyl ether (200 cc) and dried at 40° C. under reduced pressure (30 mm Hg; 4 kPa) to give 7-chloro-2-phenothiazinecarbonitrile (69.3 g) in the form of a yellow-green solid, m.p. 235° C.

EXAMPLE 89

1,2-Diaminocyclohexane (10.57 g) is added to an ethanolic solution (40 cc), saturated with hydrogen sulphide, of 10-{1-[(2R)-2-hydroxymethyl-1-pyrrolidinyl]-2-propyl}-2-phenothiazinecarbothioamide, D series (3.65 g). The mixture is heated in an autoclave to 150° C. for 11 hours, then diluted with ethyl acetate (250 cc) and washed with distilled water (4×200 cc). The organic phase is separated after settling has taken place, dried over magnesium sulphate, filtered and concentrated to dryness under reduced pressure (30 mm Hg; 4 kPa) at 40° C. The residue is diluted in boiling absolute ethanol (200 cc) and a small amount of insoluble matter is filtered off. The filtrate is stirred at 25° C. for 2 hours and then cooled to 5° C. for 12 hours. The precipitate formed is filtered off, washed with cold ethanol (3×10 cc) and dried under reduced pressure (5 mm Hg; 0.67 kPa) at 40° C. to give 2-(3a,4,5,6,7,7a-hexahydro-1H-benzimidazol-2-yl)-10-{1-[(2R)-2-(hydroxymethyl)pyrrolidinyl]-2-propyl}phenothiazine, D series (1.1 g) in the form of a cream-coloured solid.

$[\alpha]_D^{20} = 0.7$ (chloroform; c=1.144%).

Proton NMR (250 MHz, DMSO, δ in ppm, J in Hz):

1.2 to 1.9 (Mt, 12H, —CH$_2$— of hexahydrobenzimidazole and of pyrrolidine); 1.6 (D, J=7, 3H, —CH$_3$); 2.20 (Mt, 1H, 1H of the pyrrolidine NCH$_2$—); 2.48 (Mt, 1H, pyrrolidine NCH—); 2.65 (DD, J=13 and 5, 1H, 1H of N—CH$_2$—); 3.12 (D, J=5, 2H, —CH$_2$O—); 3.15 (Mt, 1H, 1H of the pyrrolidine NCH$_2$—); 3.5 (DD, J=13 and 6.5, 1H, 1H of N—CH$_2$—); 3.75 (Mt, 2H, hexahydrobenzimidazole CH—CH); 4.15 (Mt, J=7, 6.5 and 5, 1H, N—CH); 6.90 to 7.25 (Cx, 5H, aromatic); 7.35 (DD, J=8 and 1, 1H, —H at 3-position); 7.8 (D, J=1, 1H, —H at 1-position).

Infrared spectrum (CHCl$_3$), characteristic bands in cm$^{-1}$: 3400, 2940, 2860, 2800, 1610, 1580, 1550, 1445, 1040.

10-{1-[(2R)-2-(Hydroxymethyl)pyrrolidinyl]-2-propyl}-2-phenothiazinecarbothioamide, D series may be prepared in the following manner:

Triethylamine (1.01 cc) is added to a solution of 10-{1-[(2R)-2-hydroxymethyl-1-pyrrolidinyl]-2-propyl}-2-phenothiazinecarbonitrile, D series (3.65 g) in anhydrous pyridine (40 cc). The mixture is then saturated with hydrogen sulphide by bubbling the latter in for 6 hours, and is then stirred at 25° C. for 12 hours. The reaction mixture is then diluted with ethyl acetate (600 cc) and washed with distilled water (3×200 cc). The organic phase is separated after settling has taken place, dried over magnesium sulphate, filtered and concentrated to dryness under reduced pressure (30 mm Hg; 4 kPa) to give a residue which is chromatographed on a column (height: 46 cm; diameter: 5 cm) of silica gel (0.2–0.06 mm), eluting with ethyl acetate (3 liters) and collecting 250-cc fractions. Fractions 1 to 15 containing the pure product are combined and concentrated to dryness under reduced pressure (30 mm Hg; 4 kPa) at 40° C. to give 10-{1-[(2R)-2-(hydroxymethyl)pyrrolidinyl]-2-propyl}-2-phenothiazinecarbothioamide, D series (3.7 g) in the form of an orange product of meringue-like consistency.

10-{1-[(2R)-2-Hydroxymethyl-1-pyrrolidinyl]-2-propyl}-2-phenothiazinecarbonitrile, D series may be prepared in the following manner:

(R)-2-(—)-Pyrrolidinylmethanol (50 g) is added to a suspension of (2RS)-2-(2-cyano-10-phenothiazinyl)propyl methanesulphonate (89.1 g) in absolute ethanol (2000 cc). The mixture is brought to reflux for 23 hours. After cooling, the mixture is concentrated to dryness under reduced pressure (30 mm Hg; 4 kPa) at 50° C. The residue is diluted with ethyl acetate (350 cc) and filtered, and the filtrate is washed with distilled water (150 cc) and saturated sodium chloride solution (2×100 cc). After settling has taken place, the organic phase is extracted with hydrochloric acid (350 cc) in 3N solution. The acidic aqueous liquors are extracted with ethyl acetate (200 cc) and then alkalinized with concentrated sodium hydroxide and re-extracted with ethyl acetate (3×200 cc). The organic phase is washed with distilled water (2×200 cc), dried over magnesium sulphate, filtered and concentrated to dryness under reduced pressure (30 mm Hg; 4 kPa) at 50° C. to give a residue which is purified by chromatography on a column (height: 46 cm; diameter: 8.5 cm) of silica gel (0.06–0.2 mm), eluting with mixtures of cyclohexane and ethyl acetate in proportions (by volume) of 40:10 (12 liters) and 70:30 (30 liters), collecting 250-cc fractions. Fractions 1 to 44 are combined and evaporated under reduced pressure (30 mm Hg; 4 kPa) at 50° C. to give a yellow product (15.7 g) of meringue-like consistency containing the expected product. This residue is dissolved in isopropyl ether (15 cc) and crystallization is primed by scratching. The suspension is stirred for 12 hours at 25° C. and the crystals are filtered off on sintered glass to give 10-{1-[(2R)-2-hydroxymethyl-1-pyrrolidinyl]-2-propyl}-2-phenothiazinecarbonitrile, D series (14.4 g).

$[\alpha]_D^{20} = -4.6°$ (c=1.166%; chloroform).

EXAMPLE 90

1,2-Diaminocyclohexane (7.98 g) is added to an ethanolic solution (30 cc), saturated with hydrogen sulphide, of 10-{1-[(2R)-2-hydroxymethyl-1-pyrrolidinyl]-2-propyl}-2-phenothiazinecarbothioamide, L series (2.79 g). The mixture is heated in an autoclave at 150° C. for 17 hours, then diluted with ethyl acetate (250 cc) and washed with distilled water (4×200 cc). The organic phase is separated after settling has taken place, dried over magnesium sulphate, filtered and concentrated to dryness under reduced pressure (30 mm Hg; 4 kPa) at 40° C. The residue is stirred with boiling acetonitrile (6×30 cc), and the oil obtained is solidified by stirring with isopropyl ether (100 cc). The residue is chromatographed on a column (height: 52 cm; diameter: 2.5 cm) of silica gel (0.2–0.06 mm), eluting with a 60:40 (by volume) mixture (2 liters) of 1,2-dichloroethane and methanol and collecting 120-cc fractions. The first liter is discarded, and fractions 4 to 7 containing the pure product are combined and concentrated to dryness under reduced pressure (30 mm Hg; 4 kPa) at 40° C. to give 2-(3a,4,5,6,7,7a-hexahydro-1H-benzimidazol-2-yl)-10-{1-[(2R)-2-hydroxymethyl-1-pyrrolidinyl]-2-propyl}phenothiazine, L series (1.8 g) in the form of a yellow solid.

2.4N ethereal hydrochloric acid (2.9 cc) is added to a solution of 2-(3a,4,5,6,7,7a-hexahydro-1H-benzimidazol-2-yl)-10-{1-[(2R)-2-hydroxymethyl-1-pyrrolidinyl]-2-propyl}phenothiazine, L series (1.8 g) in absolute ethanol (14 cc). The solution thereby obtained is added dropwise to ethyl ether (500 cc) with brisk stirring. When the addition is complete, the suspension is stirred for 15 minutes at 25° C. and the mixture is filtered and washed with ethyl ether (3×25 cc) and the cake is then dried at 40° C. under reduced pressure (10 mm Hg; 1.3 kPa). 2-(3a,4,5,6,7,7a-Hexahydro-1H-benzimidazol-2-yl)-10-{1-[(2R)-2-hydroxymethyl-1-pyrrolidinyl]-2-propyl}phenothiazine dihydrochloride, L series (1.48 g) is thereby obtained in the form of an amorphous pale yellow solid, m.p. 240° C.

Proton NMR (250 MHz, DMSO, δ in ppm, J in Hz): 1.3 to 2.10 (Mt, 12H, —CH$_2$— of hexahydrobenzimidazole and of pyrrolidine); 1.87 (D, J=7, 3H, —CH$_3$); 3.04 (Mt, 1H, 1H of the pyrrolidine N—CH$_2$—; 3.50 to 4.05 (Mt, 6H, 1H of the pyrrolidine N—CH$_2$—, the pyrrolidine N—CH, —CH$_2$O— and N—CH$_2$—); 4.32 (Cx, 2H, hexahydrobenzimidazole CH—CH); 4.9 (Mt, 1H, N—CH); 7 to 7.55 (Mt, 5H, aromatic); 7.6 (broad S, 1H, —H at 1-position); 7.78 (broad D, J=8, 1H, —H at 3-position); 10.18 and 11.35 (2Cx, 3H in toto), —NH$^{30}$ and NH$_2$+).

Infrared spectrum (KBr), characteristic bands in cm$^{-1}$: 3060, 2940, 2870, 2740, 2660, 1605, 1575, 1460, 1420, 1060, 1040, 870, 820, 755.

10-{1-[(2R)-2-Hydroxymethyl-1-pyrrolidinyl]-2-propyl}-2-phenothiazinecarbothioamide, L series may be prepared in the following manner:

A mixture of 10-{1-[(2R)-2-hydroxymethyl-1-pyrrolidinyl]-2-propyl}-2-phenothiazinecarbonitrile, L series (1.3 g) and triethylamine (0.5 cc) in anhydrous pyridine (20 cc) is saturated by bubbling hydrogen sulphide in for 6 hours at 25° C. The clear solution obtained is kept stirred for 12 hours at 25° C. The mixture is outgassed by bubbling nitrogen through for 2 hours, then diluted with ethyl acetate (150 cc) and washed with distilled water (6×100 cc) and with saturated sodium chloride solution (3×120 cc). The organic phase is dried over magnesium sulphate and filtered and the filtrate is concentrated to dryness under reduced pressure (30 mm Hg; 4 kPa) at 40° C. The residue is purified by chromatography on a column (height: 25 cm; diameter: 4 cm) of silica gel (0.06–0.2 mm), eluting with ethyl acetate (2 liters) and collecting 100-cc fractions. Fractions 1 to 20 are combined and concentrated to dryness under reduced pressure (30 mm Hg; 4 kPa) at 40° C. to give 10-{1-[(2R)-2-hydroxymethyl-1-pyrrolidinyl]-2-propyl}-2-phenothiazinecarbothioamide, L series (0.96 g) in the form of an orange product of meringue-like consistency.

10-{1-[(2R)-2-Hydroxymethyl-1-pyrrolidinyl]-2-propyl}-2-phenothiazinecarbonitrile, L series may be prepared in the following manner:

(R)-(−)-2-Pyrrolidinylmethanol (50 g) is added to a suspension of (2RS)-2-(2-cyano-10-phenothiazinyl)propyl methanesulphonate (89.1 g) in absolute ethanol (2000 cc). The mixture is brought to reflux for 23 hours. After cooling, the mixture is concentrated to dryness under reduced pressure (30 mm Hg; 4 kPa). The residue is diluted with ethyl acetate (350 cc) and filtered, and the filtrate is washed with distilled water (150 cc) and saturated sodium chloride solution (2×100 cc). After settling has taken place, the organic phase is extracted with hydrochloric acid (350 cc) in 3N solution. The acidic aqueous extracts are extracted with ethyl acetate (200 cc) and then alkalinized with concentrated sodium hydroxide and re-extracted with ethyl acetate (3×200 cc). The organic phase is washed with distilled water (2×200 cc) and then dried over magnesium sulphate, filtered and concentrated to dryness under reduced pressure (30 mm Hg; 4 kPa) at 50° C. to give a residue which is purified by chromatography on a column (height: 46 cm; diameter: 8.5 cm) of silica gel (0.2–0.06 mm), eluting with mixtures of cyclohexane and ethyl acetate in proportions (by volume) of 80:20 (12 liters) and 70:30 (30 liters), collecting 250-cc fractions. The first 12 liters are discarded and fractions 61 to 118 are combined and evaporated under reduced pressure (30 mm Hg; 4 kPa) at 40° C. to give 10-{1-[(2R)-2-hydroxymethyl-1-pyrrolidinyl]-2-propyl}-2-phenothiazinecarbonitrile, L series (11.0 g) in the form of a yellow product of meringue-like consistency.

EXAMPLE 91

A solution of N$^2$-cyano-10-[(2RS)-1-(1-pyrrolidinyl)-2-propyl]-2-phenothiazinecarboxamidine hydrochloride (0.93 g) and propylamine (1.86 cc) in ethanol (25 cc) is brought to 100° C. for 16 hours. The reaction mixture is concentrated to dryness at 50° C. under reduced pressure (30 mm Hg; 4 kPa) to give a residue which is purified by chromatography on a column (height: 13.6 cm; diameter: 2.4 cm) of silica (0.04–0.06 mm) with a slight excess pressure of nitrogen (40 kPa), eluting with a 20:80 (by volume) mixture (750 cc) of cyclohexane and ethyl acetate, then with pure ethyl acetate (750 cc) and finally with a 90:10 (by volume) mixture (750 cc) of ethyl acetate and methanol, while collecting 50-cc fractions. The first 1000 cc are discarded and fractions 5 to 10 are combined and concentrated to dryness at 50° C. under reduced pressure (30 mm Hg; 4 kPa) to give a solid which is dissolved hot in toluene (4 cc). Crystallization is primed and, after cooling, the crystals are separated by filtration on sintered glass and dried under reduced pressure (1 mm Hg; 0.13 kPa) at 40° C. to give N$^2$-cyano-N$^1$-propyl-10-[(2RS)-1-(1-pyrrolidinyl)-2-propyl]-2-phenothiazinecarboxamidine (0.15 g) in the form of yellow crystals, m.p. 154° C.

Proton NMR (250 MHz, DMSO, δ in ppm, J in Hz): 0.93 (T, J=7.5, 3H, —(CH$_2$)$_2$CH$_3$); 1.6 (D, J=7, 3H, —CH$_3$); 1.63 (Mt, 2H, —CH$_2$CH$_2$CH$_2$); 1.69 (Mt, 4H, pyrrolidine —CH$_2$—CH$_2$—); 2.54 (Mt partially masked, 4H, pyrrolidine

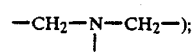

2.92 (DD, J=13 and 6.5, 1H, 1H of >NCH$_2$—); 3.06 (DD, J=13 and 6, 1H, 1H of >NCH$_2$—); 3.30 (Mt partially masked, 2H, —NHCH$_2$—CH$_2$CH$_3$); 4.23 (Mt, J=7–6.5 and 6, 1H, >N—CH<); 6.95 to 7.35 (Mt, 6H, aromatic); 7.42 (D, J=1, 1H, —H at 1-position); 9.10 (T, J=5.5, 1H, —NH—).

Infrared spectrum (KBr), characteristic bands in cm$^{-1}$: 3250, 2970, 2930, 2875, 2780, 2175, 1570, 1545, 1465, 880, 815, 750.

N²-Cyano-10-[(2RS)-1-(1-pyrrolidinyl)-2-propyl]-2-phenothiazinecarboxamidine may be obtained in the following manner:

Triethylamine (21.1 cc) is added to a solution of ethyl 10-[(2RS)-1-(1-pyrrolidinyl)-2-propyl]-2-phenothiazinecarboximidate dihydrochloride (38.7 g) in dry dioxane (1500 cc). The mixture is stirred for 10 minutes and then filtered on sintered glass. Cyanamide (3.15 g) is added to the filtrate. The mixture is then brought to reflux for 16 hours. The mixture is concentrated to dryness at 50° C. under reduced pressure (30 mm Hg; 4 kPa) to give a yellow product of meringue-like consistency, which is purified by chromatography on a column (height: 31 cm; diameter: 6 cm) of silica (0.04–0.06 mm) with a slight excess pressure of nitrogen (40 kPa), eluting with pure ethyl acetate (4 liters) and then with a 95:5 (by volume) mixture (9 liters) of ethyl acetate and methanol and collecting 125-cc fractions. The first 4.5 liters are discarded and fractions 47 to 68 are combined and concentrated to dryness at 50° C. under reduced pressure (30 mm Hg; 4 kPa) to give N²-cyano-10-[(2RS)-1-(1-pyrrolidinyl)-2-propyl-2-phenothiazinecarboxamidine(3.05g) in the form of a yellow product of meringue-like consistency.

N²-Cyano-10-[(2RS)-1-(1-pyrrolidinyl)-2-propyl]-2-phenothiazinecarboxamidine (2.6 g) is dissolved in boiling ethanol (85 cc). After filtration, 5N ethanolic hydrochloride acid (1.5 cc) is added. Crystallization is primed and the mixture is kept stirred for 12 hours. The crystals are filtered off on sintered glass, washed with ethyl ether (3×15 cc) and then dried at 40° C. under reduced pressure (1 mm Hg; 0.13 kPa) to give N²-cyano-10-[(2RS)-1-(1-pyrrolidinyl)-2-propyl]-2-phenothiazinecarboxamidine hydrochloride (1.61 g) in the form of yellow crystals, m.p. 184° C.

Ethyl 10-[(2RS)-1-(1-pyrrolidinyl)-2-propyl]-2-phenothiazinecarboximidate dihydrochloride may be prepared in the following manner:

Gaseous hydrochloric acid is bubbled for 5 hours into a solution of 10-[(2RS)-1-(1-pyrrolidinyl)-2-propyl]-2-phenothiazinecarbonitrile (25 16 g) in ethanol (150 cc) at 40° C. The solution is concentrated to dryness at 50° C. under reduced pressure (30 mm Hg; 4 kPa) to give ethyl 10-[(2RS)-1-(1-pyrrolidinyl)-2-propyl]-2-phenothiazinecarboximidate (38.7 g) in the form of a brown product of meringue-like consistency.

EXAMPLE 92

Thionyl chloride (2 cc) is added to a suspension, cooled to 5° C., of 10-[(2RS)-1-(1-pyrrolidinyl)-2-propyl]-2-phenothiazinecarboxylic acid hydrochloride (1.6 g) in methylene chloride (50 cc). The suspension is stirred for 3 hours at 15° C. and then concentrated to dryness at 30° C. under reduced pressure (30 mm Hg; 4 kPa) to give a yellow residue which is taken up in methylene chloride (50 cc) at 5° C. Cyclopentylmethylamine (1.1 g) is added and the mixture is stirred for 12 hours at 25° C., and saturated sodium bicarbonate solution (150 cc) is then added. The mixture is extracted with ethyl acetate (2×100 cc). The organic phase is washed successively with distilled water (100 cc) and with brine (100 cc), dried over magnesium sulphate, filtered and concentrated to dryness at 40° C. under reduced pressure (30 mm Hg; 4 kPa). The yellow solid obtained (1.6 g) is dissolved in boiling acetonitrile (30 cc) and the solution is filtered. The filtrate is primed by scratching and then cooled with stirring for 1 hour. The solid is separated off by filtration, washed with acetonitrile (2×2 cc) and dried at 40° C. under reduced pressure (1 mm Hg; 0.13 kPa). N-Cyclopentylmethyl 10-[(2RS)-1-(1-pyrrolidinyl)-2-propyl]-2-phenothiazinecarboxamide (1.3 g) is obtained in the form of white crystals, m.p. 124° C. 1 Proton NMR (250 MHz, CDCl₃, δ in ppm, J in Hz)

1.28, 1.64 and 1.83 (3 Mt, 2H–4H and 2H respectively, cyclopentyl —CH₂—); 1.7 (D, J=7, 3H, —CH₃); 1.84 (Mt, 4H, pyrrolidine —CH₂—CH₂—); 2.18 (Mt, 1H, cyclopentyl —CH—); 2.74 (Mt, 4H, pyrrolidine

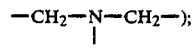

3.02 (DD, J=13.5 and 6, 1H, 1H of >N—CH₂—); 3.23 (DD, J=13.5 and 6.5, 1H, 1H of >N—CH₂—); 3.4 (DD, J=7 and 5.5, 2H, —CONH—CH₂—); 4.4 (Mt, J=7, 6.5 and 6, 1H, >N—CH<); 6.3 (T, J=5.5, 1H, —CONH—); 6.9 to 7.20 (Mt, 5H, aromatic); 7.29 (DD, J=8 and 1, 1H, —H at 3-position); 7.65 (D, J=1, 1H, —H at 1-position).

Infrared spectrum (KBr), characteristic bands in cm⁻¹: 3310, 2950, 2860, 2790, 1630, 1595, 1545, 1460, 870, 825.

EXAMPLE 93

By working in a manner similar to that described below in Example 103, but starting with 10-[(2RS)-1-(1-pyrrolidinyl)-2-propyl]-2-phenothiazinecarbonyl chloride hydrochloride (3.5 g) in dichloromethane (100 cc) and with cyclopropylmethylamine (3.8 g), N-(cyclopropylmethyl)-10-[(2RS)-1-(1-pyrrolidinyl)-2-propyl]-2-phenothiazinecarboxamide (3 g) is obtained in the form of a cream-coloured product of meringue-like consistency, which is dissolved in acetonitrile (20 cc). A 2.4N solution (8 cc) of hydrochloric acid in ethyl ether is then added. The crystals are drained and dried under reduced pressure (5 mm Hg; 0.67 kPa) at 40° C. N-(Cyclopropylmethyl)-10-[(2RS)-1-(1-pyrrolidinyl)-2-propyl]-2-phenothiazinecarboxamide hydrochloride (2.6 g) is obtained in the form of white crystals, m.p. 220° C.

Proton NMR (250 MHz, DMSO-d6, δ in ppm, J in Hz):

0.23 and 0.42 (2 Mt, 2H each, cyclopropyl —CH₂—); 1.04 (Mt, 1H, cyclopropyl >CH—); 1.77 (D, J=7, 3H, —CH₃); 1.7 to 2 (Mt, 4H, pyrrolidine —CH₂—); 2.83, 3.08, 3.55 and 3.73 (4 Cx, 1H each respectively, pyrrolidine >N—CH₂—); 3.14 (DD, J=7.5 and 5.5, 2H, —CONHCH₂—); 3.73 (limiting AB, 2H, N—CH₂—); 4.75 (Mt, 1H , >N—CH<); 7 to 7.35 (Mt, 5H, aromatic); 7.53 (broad S, 1H, —H at 1-position); 7.54 (broad D, J=8, 1H, —H at 3-position); 8.75 (T, J=5.5, 1H, —CONH—).

Infrared spectrum (KBr), characteristic bands in cm⁻¹: 3270, 2780 to 2000, 1655, 1595, 1575, 1560, 1465, 1535, 850, 820, 750.

EXAMPLE 94

By working in a manner similar to that described below in Example 103, but starting with 10-[(2RS)-1-(1-pyrrolidinyl)-2-propyl]-2-phenothiazinecarbonyl chloride hydrochloride (3.4 g) in dichloromethane (100 cc) and with cyclobutylmethylamine (4.5 g), N-(cyclobutylmethyl)-10-[(2RS)-1-(1-pyrrolidinyl)-2-propyl]-2-phenothiazinecarboxamide (1.7 g) is obtained, after recrystallization in isopropyl ether, in the form of white crystals, m.p. 133° C.

Proton NMR (250 MHz, CDCl$_3$, δ in ppm, J in Hz):
1.68 (D, J=7, 3H, —CH$_3$—); 1.82 (Mt, 4H, pyrrolidine —CH$_2$—); 1.7 to 2.2 (Mt, 6H, cyclobutylmethyl —CH$_2$—); 2.59 (Mt, 1H, cyclobutylmethyl >CH—); 2.65 (Mt, 4H, pyrrolidine N—CH$_2$); 2.96 (DD, J=12.5 and 6.5, 1H, 1H of >N—CH$_2$—); 3.17 (DD, J=12.5 and 6, 1H, 1H of >N—CH$_2$—); 3.49 (DD, J=7.5 and 5.5, 2H, —CONHCH$_2$—); 4.28 (Mt, J=7, 6.5 and 6, 1H, >N—CH<); 6.15 (T, J=5.5, 1H, —CONH—); 6.90 to 7.25 (Mt, 5H, aromatic); 7.27 (DD, J=8 and 1, 1H, —H at 3-position); 7.67 (D, J=1, 1H, —H at 1-position).

Infrared spectrum (KBr), characteristic bands in cm$^{-1}$: 3270, 2970, 2935, 2865, 2790, 1630, 1595, 1560, 1465, 1540, 870, 830, 745.

EXAMPLE 95

10-[(2RS)-1-(1-Pyrrolidinyl)-2-propyl]-2-phenothiazinecarboxylic acid hydrochloride (3.12 g) in methylene chloride (100 cc) is cooled to a temperature in the region of 5° C. and treated, with stirring, with thionyl chloride (4 cc). After 10 minutes, the temperature is brought to 20° C. and stirring is continued for 1 hour. The orange solution obtained is concentrated to dryness under reduced pressure (30 mm Hg; 4 kPa) at 30° C. The residual yellow product of meringue-like consistency is dissolved in methylene chloride (100 cc) and treated, dropwise and with stirring and at a temperature in the region of 5° C., with allylamine (1.5 cc), and stirring is then continued for 2 hours. The reaction mixture is then diluted with ethyl acetate (200 cc), washed successively with saturated aqueous sodium hydrogen carbonate solution (200 cc) and with saturated aqueous sodium chloride solution (200 cc), dried over magnesium sulphate, filtered and concentrated to dryness under reduced pressure (30 mm Hg; 4 kPa) at 40° C. to give a yellow oil (3.2 g). This product is dissolved in ethyl acetate (35 cc) and treated, with stirring, with a 3.3N solution (2.7 cc) of hydrochloric acid in isopropyl ether, at a temperature in the region of 5° C. The precipitate formed is drained, washed with isopropyl ether (10 cc) and dried under reduced pressure (5 mm Hg; 0.68 kPa) at 40° C. N-Allyl-10-[(2RS)-1-(1-pyrrolidinyl)-2-propyl]-2-phenothiazinecarboxamide hydrochloride (2.6 g) is thereby obtained in the form of a beige solid, m.p. 208° C.

Proton NMR (250 MHz, DMSO, δ in ppm, J in Hz):
In solution in DMSO, two forms are observed due to salification of the nitrogen.

1.8 (D, J=7, 3H, —CH$_3$); 1.9 (Mt, 4H, pyrrolidine —CH$_2$—); 2.84, 3.10, 3.58 and 3.74 (4 Cx, 1H each, pyrrolidine

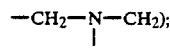

3.77 (Mt, 2H, >N—CH$_2$—); 3.92 (Mt, 2H, —CONH—CH$_2$—); 4.78 (Mt, 1H, >N—CH<); 5.10 and 5.19 (2DD, 1H each, =CH$_2$); 5.92 (Mt, 1H, —CH=); 7 to 7.35 (Mt, 5H, aromatic); 7.55 (broad S, 1H, —H at 1-position); 7.58 (broad D, J=8, 1H, —H at 3-position); 8.90 (T, J=5.5, 1H, —CONH—); 10.88 (Cx, 1H, —NH+).

Infrared spectrum (KBr), characteristic bands in cm$^{-1}$: 3260, 2975, 2680, 2610, 2480, 1655, 1590, 1555, 1530, 1460, 995, 910, 825, 750.

EXAMPLE 96

Thionyl chloride (7.7 cc) is introduced in the course of 5 minutes, with stirring into a suspension of 10-[1-(1-pyrrolidinyl)-2-propyl]-2-phenothiazinecarboxylic acid hydrochloride, L series (6 g) in methylene chloride (190 cc) while the temperature is maintained in the vicinity of 5° C. Stirring is continued for 4 hours while heating to a temperature in the region of 20° C., and the yellow solution obtained is concentrated in dryness under reduced pressure (30 mm Hg; 4 kPa) at 40° C. the residue is dissolved in methylene chloride (110 cc) and treated with a solution of allylamine (2.9 cc) in methylene chloride (30 cc) with stirring while the temperature is maintained at 5° C., and stirring is then continued for 16 hours at 20° C. The reaction mixture is diluted with ethyl acetate (250 cc), filtered, washed successively with saturated aqueous sodium hydrogen carbonate solution (50 cc) and with saturated aqueous sodium chloride solution (50 cc), dried over magnesium sulphate, filtered and concentrated to dryness under reduced pressure (30 mm Hg; 4 kPa) at 49° C. The oily yellow residue (4.7 g) is purified by chromatography on a column (height: 35 cm; diameter: 4 cm) of silica gel (0.04–0.06 mm) with a slight excess pressure of nitrogen (40.5 kPa), eluting with a mixture (90:10 by volume) (2 liters) of ethyl acetate and ethanol and collecting 60-cc fractions. Fractions 6 to 28 are combined and concentrated to dryness under reduced pressure (30 mm Hg; 4 kPa) at 40° C. to give a yellow oil (3.98 g). This oil is dissolved in diethyl ether (50 cc), and a 0.3N solution (3.4 cc) of hydrochloric acid in isopropyl ether is added with stirring at 6° C. After one hour's stirring at 6° C., the solid formed is filtered off, washed with diethyl ether (5 cc) and dried under reduced pressure (5 mm Hg; 0.67 kPa) at 40° C. to give N-allyl-10-[1-(1-pyrrolidinyl)-2propyl]-2-phenothiazinecarboxamide hydrochloride, L form (3.8 g) in the form of a yellow solid, m.p. about 170° C.

[α]$_D^{20}$ = +17.7°±0.5° (c=1%; methanol).

Proton NMR (250 MHz, DMSO-d6, δ in ppm, J in Hz):
1.8 (D, J=7, 3H, —CH$_3$); 1.7 to 2 (Mt, 4H, pyrrolidine —CH$_2$—); 2.83, 3.09, 3.59 and 3.77 (4 Cx, respectively 1H each, pyrrolidine >NCH$_2$—); 3.77 (Mt, 2H, >N—CH$_2$—); 3.92 (DD, J=7.5 and 5.5, 2H, —CONHCH$_2$—); 4.76 (Mt, 1H, >N—CH<); 5.15 (Mt, 2H, —CH=CH$_2$); 5.92 (Mt, 1H, —CH=CH$_2$); 7 to 7.4 (Mt, 5H, aromatic); 7.55 (broad S, 1H, —H at 1-position); 7.57 (broad D, J=8, 1H, —H at 3-position); 8.85 (T, J=5.5, 1H, —CONH—).

Infrared spectrum (KBr), characteristic bands in cm$^{-1}$: 3260, 2975, 2680, 2580, 2480, 1650, 1640, 1590, 1555, 1460, 1530, 870, 830, 755.

10-[1-(1-Pyrrolidinyl)-2-propyl]-2-phenothiazinecarboxylic acid hydrochloride, L series may be obtained in the following manner:

10-[1-(1-Pyrrolidinyl)-2-propyl]-2-phenothiazinecarboxylic hydrochloride, L series (5 g) is added to a solution of potassium hydroxide (1.75 g) in glycol (30 cc), and the mixture is stirred for 4 hours under reflux. After cooling, the yellow solution obtained is diluted with acetone (75 cc) and a 3N solution (5 cc) of hydrochloric acid in ethyl ether, filtered and diluted again with acetone (75 cc) and a 3N solution (5 cc) of hydrochloric acid in ethyl ether. After priming, the mixture is left to crystallize for 15 hours at a temperature in the region of 5° C. The solid obtained is drained, washed with ethyl ether (10 cc) and dried under reduced pressure (5 mm Hg; 0.7 kPa) at 40° C. 10-[1-(1-Pyrrolidinyl)-2-propyl]-2-phenothiazinecarboxylic acid hydrochloride, L series (2.9 g) is thereby obtained in the form of a pale yellow solid, m.p. 200°–210° C. (melts forming a paste).

EXAMPLE 97

Thionyl chloride (0.5 cc) is introduced during 5 minutes and with stirring into a suspension of 10-[(2RS)-1-(1-pyrrolidinyl)-2-propyl]-2-phenothiazinecarboxylic acid hydrochloride (1 g) in methylene chloride (30 cc) while the temperature is maintained in the vicinity of 5° C. Stirring is continued for 40 minutes while heating to a temperature in the region of 30° C., and the yellow solution obtained is concentrated to dryness under reduced pressure (30 mm Hg; 4kPa) at 40° C. The residue is dissolved in methylene chloride (30 cc) and 3-methyl-2butenylamine (0.73 g) and triethylamine (0.84 cc) are added. Stirring is maintained for 30 minutes at 20° C. The reaction mixture is diluted with ethyl acetate (100 cc), washed successively with N aqueous sodium hydroxide solution (50 cc) and then with saturated aqueous sodium chloride solution (2×50 cc), dried over magnesium sulphate, filtered and concentrated to dryness under reduced pressure (30 mm Hg; 4 kPa) at 40° C. The oily orange residue (0.9 g) is dissolved in a mixture (30:70 by volume) (35 cc) of ethyl acetate and isopropyl ether, and a 0.3N solution (5.5 cc) of hydrochloric acid in isopropyl ether is added with stirring at 6° C. After one hour's stirring at 6° C., the solid formed is filtered off, washed with isopropyl ether (5 cc) and dried under reduced pressure (5 mm Hg; 0.67 kPa) at 40° C. to give N-(3-methyl-2-butenyl)-10-[(2RS)-1-(1-pyrrolidinyl)-2-propyl]-2-phenothiazinecarboxamide hydrochloride (0.52 g) in the form of a cream-coloured solid, m.p. about 150° C.

Proton NMR (250 MHz, DMSO-d6+a few drops of CD₃COOD, δ in ppm, J in Hz):

1.69 (S, 6H, —CH=C(CH₃)₂); 1.79 (D, J=7, 3H, —CH₃); 1.87 (Mt, 4H, pyrrolidine —CH₂—); 3.19 and 3.43 (2 Mt, 2H each, pyrrolidine >N—CH₂—); 3.66 (DD, J=12.5 and 4.5, 1H, 1H of >N—CH₂—); 3.8 (DD, J=12.5 and 8, 1H, 1H of >N—CH₂—); 3.88 (T, J=5.5, 2H, —CONHCH₂—); 4.68 (Mt, J=8, 7 and 4.5, 1H, >N—CH<); 5.23 (broad T, J=5.5, 1H, =CH—); 7 to 7.35 (Mt, 5H, aromatic); 7.53 (S, 1H, —H at 1-position); 7.54 (D, J=8, 1H, —H at 3-position).

Infrared spectrum (KBr), characteristic bands in cm⁻¹: 3270, 2965, 2925, 2680, 2610, 2480, 1655, 1595, 1465, 1535, 855, 825, 755.

EXAMPLE 98

10-[(2RS)-1-(1-Pyrrolidinyl)-2-propyl]-2-phenothiazinecarboxylic acid hydrochloride (0.78 g) is added portionwise, with stirring and at a temperature in the region of 5° C., to a solution of thionyl chloride (1 cc) in methylene chloride (25 cc), and stirring is then continued for 3 hours at a temperature in the region of 20° C. The reaction mixture is then concentrated to dryness under reduced pressure (30 mm Hg; 4 kPa) at 40° C. and the residue is taken up with methylene chloride (25 cc). Propargylamine (0.75 cc) is added dropwise to the solution obtained while the latter is stirred and cooled to a temperature in the region of 5° C. After 1 hour, the reaction mixture is diluted with ethyl acetate (100 cc) and washed with saturated aqueous sodium hydrogen carbonate solution (2×50 cc) and then with saturated aqueous sodium chloride solution (50 cc). The separated organic phase is dried over magnesium sulphate, filtered and concentrated to dryness under reduced pressure (30 mm Hg; 4 kPa) at 40° C. A gummy yellow residue (0.94 g) is obtained. This product is purified by chromatography on a column (height: 40 cm; diameter: 3 cm) of silica gel (0.063–0.04 mm) under a slight excess pressure of nitrogen (40 kPa), eluting with a mixture (97.5:2.5 by volume) (1.5 liters) of methylene chloride and methanol and collecting 50-cc fractions. Fractions 10 to 25 are combined and concentrated to dryness under reduced pressure (30 mm Hg; 4 kPa) at 40° C. The gummy yellow residue obtained (0.59 g) is dissolved in ethyl ether (30 cc) and treated with a 0.23N solution (7 cc) of hydrochloric acid in ethyl ether. The precipitate formed is drained, washed with ethyl ether (2×10 cc) and dried under reduced pressure (5 mm Hg; 0.68 kPa) at 40° C. N-Propargyl-10-[(2RS)-1-(1-pyrrolidinyl)-2-propyl]-2-phenothiazinecarboxamide hydrochloride (0.6 g) is thereby obtained in the form of a pale yellow solid, m.p. 170°–180° C. (melts forming a paste).

Proton NMR (250 MHz, DMSO, δ in ppm, J in Hz):

In solution in DMSO, two forms are observed, due to salification of the nitrogen.

1.82 (D, J=7, 3H, —CH₃); 1.88 (Mt, 4H, pyrrolidine —CH₂—CH₂—); 2.82, 3.10, 3.58 and 3.78 (4Cx, 1H each, pyrrolidine

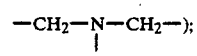

3.15 (T, J=2, 1H, ≡CH); 3.6 to 3.9 (Mt, 2H, >N—CH₂—); 4.07 (Mt, 2H, —CONH—CH₂—); 4.72 (Mt, 1H, >N—CH<); 7 to 7.4 (Mt, 5H, aromatic); 7.53 (broad S, 1H, —H at 1-position); 7.56 (broad D, J=8, 1H, —H at 3-position); 9.11 (T, J=5.5, 1H, —CONH—); 10.5 (Cx, 1H, —NH+).

Infrared spectrum (KBr), characteristic bands in cm⁻¹: 3240, 2680, 2610, 2480, 2120, 1655, 1595, 1560, 1530, 1460, 875, 825, 750.

10-[(2RS)-1-(1-Pyrrolidinyl)-2-propyl]-2-phenothiazinecarboxylic acid hydrochloride may be prepared in the following manner:

10-[(2RS)-1-(1-Pyrrolidinyl)-2-propyl]-2-phenothiazinecarbonitrile hydrochloride (3.72 g) is added to a solution of potassium hydroxide (1.7 g) in glycol (20 cc), and the mixture is stirred for 5 hours under reflux. After cooling, the yellow solution obtained is traeted with a 3N ethereal solution (10 cc) of hydrochloric acid, and diluted with acetone (100 cc) and ethyl ether (100 cc) and then filtered. The yellow filtrate, after priming, gives rise to the crystallization of a product, which is drained, washed with ethyl ether (2×10 cc) and dried under reduced pressure (5 mm Hg; 0.68 kPa) at 40° C. 10-[(2RS)-1-(1-Pyrrolidinyl)-2-propyl]-2-phenothiazinecarboxylic acid hydrochloride (3.5 g) is thereby obtained in the form of pale yellow crystals, m.p. 215°–217° C.

EXAMPLE 99

Thionyl chloride (7.7 cc) is introduced in the course of 5 minutes, with stirring, into a suspension of 10-[1-(1-pyrrolidinyl)-2-propyl]-2-phenothiazinecarboxylic acid hydrochloride, L series (6 g) in methylene chloride (190 cc) while the temperature is maintained in the vicinity of 5° C. Stirring is continued for 16 hours at a temperature in the region of 20° C., and the yellow solution obtained is concentrated to dryness under reduced pressure (30 mm Hg; 4 kPa) at 40° C. The residue is dissolved in methylene chloride (130 cc) and treated with a solution of propargylamine (2.45 cc) in methylene chloride (25 cc) with stirring and wile the temperature is maintained at 5° C., and stirring is then continued for 4 hours at 20° C. The reaction mixture is diluted with ethyl acetate (200 cc), filtered, washed successively with saturated aqueous sodium hydrogen carbonate solution (50 cc) and with saturated aqueous sodium chloride solution (50 cc), dried over magnesium sulphate, filtered and concentrated to dryness under reduced pressure (30 mm Hg; 4 kPa) at 49° C. The oily brown residue (5.32 g) is dissolved in diethyl ether (70 cc) under reflux. After cool ling, the solid formed is filtered off, washed with diethyl ether (10 cc) and taken up with ethyl acetate (40 cc). The solution obtained is washed successively with distilled water (50 cc) and then with saturated aqueous sodium chloride solution (50 cc), dried over magnesium sulphate, filtered and concentrated to dryness under reduced pressure (30 mm Hg; 4 kPa) at 40° C. to give a brown product (2.8 g) of meringue-like consistency. This product is taken up with diethyl ether (50 cc) and the suspension obtained is stirred for 2 hours at 20° C. The solid is filtered off, washed with diethyl ether (2×5 cc) and dried under reduced pressure (5 mm Hg; 0.67 kPa) at 40° C. to give N-proparyl-10-[1-(1-pyrrolidinyl)-2propyl]-2-phenothiazinecarboxamide, L series (1.42 g) in the form of an ochre-coloured solid, m.p. 130° C.

$[\alpha]_D^{20} = +24.8 \geqq \pm 0.6°$ (c=1%; methanol).

Proton NMR (250 MHz, DMSO-d6, δ on ppm, J in Hz):

1.62 (D, J=7, 3H, —CH$_3$); 1.7 (Mt, 4H, pyrrolidine —CH$_2$—); 3.90 (DD, J=12.5 and 6.5, 1H, 1H of >N—CH$_2$—); 3.02 (DD, J=12.5 and 6, 1H, 1H of >N—CH$_2$—); 3.11 (T, J=2, 1H, —C≡CH); 4.08 (DD, J=5.5 and 2, 2H, —CONHCH$_2$—); 4.2 (Mt, J=7, 6.5 and 6, 1H, >N—CH<); 6.90 to 7.3 (mt, 5H, aromatic); 7.44 (DD, J=8 and 1, 1H,—H at 3-position); 7.58 (D, J=1, 1H, —H at 3-position); 8.85 (T, J=5.5, 1H, —CONH—).

Infrared spectrum (KBr), characteristic bands in cm$^{-1}$: 3360, 3300, 3240, 2965, 2880, 2790, 2120, 1635, 1590, 1560, 1460, 1530, 880, 830, 745.

EXAMPLE 100

Thionyl chloride (3.6 cc) is added to a suspension, cooled to 5° C., of 10-[(2RS)-1-(1-pyrrolidinyl)-2-propyl]-2-phenothiazinecarboxylic acid hydrochloride (2.7 g) in methylene chloride (70 cc). The suspension is stirred for 3 hours at 25° C. and then concentrated to dryness at 30° C. under reduced pressure (30 mm Hg; 4 kPa) to give a yellow residue which is taken up with methylene chloride (50 cc) at 5° C. 3-Chlorobenzylamine (6.9 g) is added and the mixture is stirred for 12 hours at 25° C., and saturated sodium bicarbonate solution (150 cc) is then added. The mixture is extracted with ethyl acetate (2×100 cc). The organic phase is washed successively with distilled water (100 cc) and with brine (100 cc), dried over magnesium sulphate, filtered and concentrated to dryness at 40° C. under reduced pressure (30 mm Hg; 4 kPa) to give a brown oil which is purified by chromatography on a column (height: 30 cm; diameter: 2.5 cm) of silica (0.06–0.2 mm), eluting with methylene chloride (1 liter) and collecting 40-cc fractions. Fractions 12 to 24 are combined and concentrated to dryness under reduced pressure (30 mm Hg; 4 kPa) at 40° C. to give a cream-coloured solid which is taken up in isopropyl ether (20 cc). The solid is separated by filtration, washed with isopropyl ether (2×5 cc) and dried at 40° C. under reduced pressure (1 mm Hg; 0.13 kPa). N-(3-Chlorobenzyl)-10-[(2RS)-1-(1-pyrrolidinyl)-2-propyl]-2-phenothiazinecarboxamide (2 g) is obtained in the form of a yellow solid, m.p. approximately 80° C.

Proton NMR (250 MHz, CDCl$_3$, δ in ppm, J in Hz):

1.68 (D, J=7, 3H, —CH$_3$); 1.75 (Cx, 4H, pyrrolidine —CH$_2$—CH$_2$—); 2.62 (Mt, 4H, pyrrolidine

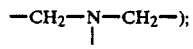

2.95 (DD, J=12.5 and 6.5, 1H, 1H of >N-CH$_2$—); 3.17 (DD, J=12.5 and 6, 1H, 1H of >N—CH$_2$—); 4.26 (Mt, J=7, 6.5 and 6, 1H, >N—CH<); 4.75 (D, J=5.5, 2H, —COHN—CH$_2$—); 6.68 (T, J=5.5, 1H, —COHN—); 6.9 to 7.5 (Mt, 10H, aromatic); 7.71 (D, J=1, 1H, —H at 1-position).

Infrared spectrum (KBr), characteristic bands in cm$^{-1}$: 3320, 2960, 2930, 2870, 2780, 1640, 1590, 1570, 1530, 1460, 1440, 875, 820, 750.

EXAMPLE 101

Thionyl chloride (4.44 cc) is introduced with stirring during 5 minutes into a suspension of 10-[(2RS)-1-(1-pyrrolidinyl)-2-propyl]-2-phenothiazinecarboxylic acid (3.42 g) in methylene chloride (100 cc) while the temperature is maintained in the vicinity of 5° C. Stirring is continued for 3 hours while heating to a temperature in the region of 20° C., and the yellow solution obtained is concentrated to dryness under reduced pressure (30 mm Hg; 4 kPa) at 30° C. The residue is dissolved in methylene chloride (80 cc), and a solution of 2,3-dichlorobenzylamine (2 g) in methylene chloride (20 cc) is added. Stirring is continued for 60 minutes at 20° C. The reaction mixture is concentrated to dryness under reduced pressure (30 mm Hg; 4 kPa) at 30° C. The residue is diluted with ethyl acetate (150 cc), washed successively with N aqueous sodium hydroxide solution (150 cc) and then with saturated aqueous sodium chloride solution (2×150 cc), dried over magnesium sulphate, filtered and concentrated to dryness under reduced pressure (30 mm Hg; 4 kPa) at 40° C. The oily orange residue is purified by chromatography on a column (height: 25 cm; diameter: 2.5 cm) of silica gel (0.04–0.06 mm) under a slight excess pressure of nitrogen (40.5 kPa), eluting with methylene chloride (1 liter) and collecting 100-cc fractions. Fractions 5 to 8 are combined and concentrated to dryness under reduced pressure (30 mm Hg; 4 kPa) at 30° C. The residue (4.18 g) is taken up in ethanol (10 cc) and filtered, and the mother liquors are treated with a 3.3N solution (5 cc) of hydrochloric acid in diisopropyl ether. After 30 minutes at 5° C., the solid formed is filtered off, washed with isopropyl ether (2×3 cc), drained and dried under reduced pressure (5 mm Hg; 0.67 kPa) at 40° C. to give N-(2,3-dichlorobenzyl)-10-[(2RS)-1-(1-pyrrolidinyl)-2-propyl]-2-phenothiazinecarboxamide hydrochloride (0.6 g) in the form of a cream-coloured solid, m.p. above 260° C.

Proton NMR (250 MHz, DMSO-d6+a few drops of CD$_3$COOD at a temperature of 413° C., δ in ppm, J in Hz):

1.75 (D, J=7, 3H, —CH$_3$); 1.9 (Cx, 4H, pyrrolidine —CH$_2$—); 3.24 and 3.38 (2 Mt, respectively 2H each, pyrrolidine >N—CH$_2$—); 3.54 (DD, J=13 and 6, 1H, 1H of >N—CH₂—; 3.76 (DD, J=13 and 8, 1H, 1H of >N—CH₂—); 4.63 (S, 2H —CONHCH₂—); 4.63 (Mt, J=8, 7 and 6, 1H, >N—CH<); 7 to 7.55 (Mt, 8H aromatic); 7.57 (D, J=8, 1H, —H at 3-position); 7.59 (S, 1H, —H at 1-position).

Infrared spectrum (KBr), characteristic bands in cm⁻¹: 3280, 2970, 2930, 2565, 2475, 1655, 1590, 1560, 1465, 1535, 820, 750.

EXAMPLE 102

Thionyl chloride (2.6 cc) is added to a suspension, cooled to 5° C., of 10-[(2RS)-1-(1-pyrrolidinyl)-2-propyl]-2-phenothiazinecarboxylic acid hydrochloride (2.0 g) in 1,2-dichloroethane (60 cc). The suspension is stirred for 3 hours at 25° C. and then concentrated to dryness at 30° C. under reduced pressure (30 mm Hg; 4 kPa) to give a yellow residue which is taken up in 1,2-dichloroethane (50 cc) at 5° C. 2,6-Dichlorobenzylamine (4.4 g) is added and the mixture is stirred for 12 hours at 25° C., and saturated sodium bicarbonate solution (150 cc) is then added. The mixture is extracted with ethyl acetate (2×100 cc). The organic phase is washed successively with distilled water (100 cc) and with brine (100 cc), dried over magnesium sulphate, filtered and concentrated to dryness at 40° C. under reduced pressure (30 mm Hg; 4 kPa) to give a yellow oil (5.8 g) which is purified by chromatography on a column (height: 35 cm; diameter: 4 cm) of silica (0.06–0.2 mm), eluting with a 95:5 (by volume) mixture (1.2 liters) of methylene chloride and methanol and collecting 40-cc fractions. Fractions 13 to 25 are combined and concentrated to dryness under reduced pressure (30 mm Hg; 4 kPa) at 40° C. to give a yellow oil which is dissolved in boiling acetonitrile (12 cc). Crystallization is primed by scratching. After cooling, the solid is separated by filtration, washed with acetonitrile (2×3 cc) and dried at 40° C. under reduced pressure (1 mm Hg; 0.13 kPa). N-(2,6-Dichlorobenzyl)-10-[(2RS)-1-(1-pyrrolidinyl)-2-propyl]-2-phenothiazinecarboxamide (1.6 g) is obtained in the form of cream-coloured crystals, m.p. 138° C.

Proton NMR (250 MHz, DMSO, δ in ppm, J in Hz): 1.57 (D, J=7, 3H, —CH₃); 1.67 (Cx, 4H, pyrrolidine —CH₂—CH₂—); 2.52 (masked Mt, 4H, pyrrolidine

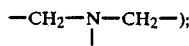

2.87 (DD, J=12.5 and 6.5, 1H, 1H of >N—CH₂); 3 (DD, J=12.5 and 6, 1H, 1H of >N—CH₂—); 4.18 (Mt, J=7, 6.5 and 6, 1H, >N—CH<); 4.68 (D, J=4.5, 2H, —CH₂—NHCO—); 6.9 to 7.6 (Mt, 10H, aromatic) 8.68 (D, J=4.5, 1H, —CONH—).

Infrared spectrum (KBr), characteristic bands in cm⁻¹: 3440, 3280, 2960, 2870, 2790, 1630, 1590, 1580, 1560, 1530, 1460, 1435, 865, 830, 780, 765, 750.

EXAMPLE 103

Thionyl chloride (12.7 cc) is added in the course of 5 minutes, with stirring at a temperature of 4° C., to a suspension of 10-[(2RS)-1-(1-pyrrolidinyl)-2-propyl]-2-phenothiazinecarboxylic acid hydrochloride (9.77 g) in methylene chloride (250 cc), and stirring is continued for 90 minutes at a temperature of 20° C. The clear yellow solution obtained is concentrated to dryness under reduced pressure (30 mm Hg; 4 kPa) at 40° C. and dried to constant weight under reduced pressure (5 mm Hg; 0.67 kPa) at 50° C. to give 10-[(2RS)-1-(1-pyrrolidinyl)-2-propyl]-2-phenothiazinecarbonyl chloride hydrochloride (10.2 g) in the form of a yellow paste.

2-Methoxybenzylamine (26.1 cc) is added dropwise at a temperature of 10° C. and with stirring to a solution of 10-[(2RS)-1-(1-pyrrolidinyl)-2-propyl]-2-phenothiazinecarbonyl chloride hydrochloride (13.2 g in methylene chloride (125 cc). Stirring is continued for 15 minutes at 10° C. and 16 hours at 20° C. The reaction mixture is washed with distilled water (3×100 cc) and the organic phase is dried over magnesium sulphate, filtered and concentrated to dryness under reduced pressure (30 mm Hg; 4 kPa) at 40° C. The residue is purified by chromatography on a column (height: 64 cm; diameter: 3 cm) of silica gel (0.06–0.2 mm), eluting with ethyl acetate (2 liters) and collecting 200-cc fractions. Fractions 3 to 10 are combined and concentrated to dryness under reduced pressure (30 mm Hg; 4 kPa) at 40° C. to give N-(2-methoxybenzyl)-10-[(2RS)-1-(1-pyrrolidinyl)-2-propyl]-2-phenothiazinecarboxamide (9.3 g) in the form of a white crystalline solid, m.p. 127° C.

N-(2-Methoxybenzyl)-10-[(2RS)-1-(1-pyrrolidinyl)-2-propyl]-2-phenothiazinecarboxamide (2 g) is dissolved in a mixture (50:50 by volume) (80 cc) of ethyl acetate and isopropyl ether under reflux. A small amount of insoluble matter is removed by filtration hot and, after cooling, crystallization develops. After 16 hours at 20° C., the solid formed is filtered off, washed with isopropyl ether (10 cc) and dried under reduced pressure (30 mm Hg; 4 kPa) at 50° C. to give N-(2-methoxybenzyl)-10-[(2RS)-1-(1-pyrrolidinyl)-2-propyl]-2-phenothiazinecarboxamide (1.49 g) in the form of white crystals with yellow glints, m.p. 131° C.

Proton NMR (250 MHz, CDCl₃, δ in ppm, J in Hz): 1.68 (D, J=7, 3H, —CH₃); 1.75 (Mt, 4H, pyrrolidine —CH₂—); 2.61 (Mt, 4H, pyrrolidine >N—CH₂—); 2.96 (DD, J=12.5 and 6.5, 1H, 1H of >N—CH₂—); 3.14 (DD, J=12.5 and 6, 1H, 1H of >N—CH₂—); 3.9 (S, 3H, —OCH₃); 4.26 (Mt, J=7, 6.5 and 6, 1H, >N—CH<); 4.65 (D, J=5.5, 2H, —CONHCH₂—); 6.7 (T, J=5.5, 1H, —CONH—); 6.85 to 7.4 (Mt, 9H, aromatic); 7.26 (DD, J=8 and 1, 1H, —H at 3-position); 7.69 (D, J=1, 1H, —H at 1-position).

Infrared spectrum (CHCl₃), characteristic bands in cm⁻¹: 3460, 2970, 2880, 2840, 2810, 1655, 1600, 1560, 1460, 1520, 1495, 1245, 1035, 820.

EXAMPLE 104

A solution of boron tribromide (5.01 g) in methylene chloride (100 cc) is added dropwise and with stirring during 15 minutes to a solution, cooled to −50° C., of N-(2-methoxybenzyl)-10-[(2RS)-1-(1-pyrrolidinyl)-2-propyl]-2-phenothiazinecarboxamide (4.74 g) in methylene chloride (100 cc). Stirring is maintained at −50° C. for 45 minutes and then at 20° C. for 48 hours. Saturated aqueous sodium hydrogen carbonate solution (120 cc) is then added cautiously. After stirring until the evolution of carbon dioxide has ceased, the organic phase is separated, washed with distilled water (3×100 cc), dried over magnesium sulphate, filtered and concentrated to dryness under reduced pressure (30 mm Hg; 4 kPa). The yellow meringue-like residue is purified by chromatography on a column (height: 48 cm; diameter: 2.4 cm) of silica gel (0.06–0.2 mm), eluting with ethyl acetate (2 liters) and collecting 100-cc fractions. Fractions 4 to 15 are combined and concentrated to dryness under reduced pressure (30 mm Hg; 4 kPa) at 40° C. The yellow meringue-like residue (2.84 g) is purified by chromatography on a column (height: 33 cm; diameter: 2.4 cm) of silica gel (0.06-0.2 mm), eluting successively with a mixture (50:50 by volume) (250 cc) of cyclohexane and ethyl acetate, then with a mixture (25:75 by volume) (500 cc) of cyclohexane and ethyl acetate and then with ethyl acetate (500 cc) and collecting 60-cc fractions. Fractions 7 to 18 are combined and concentrated to dryness under reduced pressure (30 mm Hg; 4 kPa) at 40° C. to give N-(2-hydroxybenzyl)-10-[(2RS)-1-(1-pyrrolidinyl)-2-propyl]-2-phenothiazinecarboxamide (1.9 g) in the form of a yellow product of meringue-like consistency.

N-(2-Hydroxybenzyl)-10-[(2RS)-1-(1-pyrrolidinyl)-2-propyl]-2-phenothiazinecarboxamide (1.86 g) is dissolved in boiling 2-propanol (22 cc). A solution of fumaric acid (0.47 g) in 2-propanol (18 cc) under reflux is added to this solution. After cooling, the crystals formed are washed with ethyl ether (2×10 cc), filtered and dried under reduced pressure (5 mm Hg; 0.67 kPa) at 50° C. N-(2-Hydroxybenzyl)-10-[(2RS)-1-(1-pyrrolidinyl)-2-propyl]-2-phenothiazinecarboxamide fumarate (1.09 g) is thereby obtained in the form of yellow crystals, m.p. about 80° C.

Proton NMR (250 MHz, DMSO-d6, δ in ppm, J in Hz):

1.64 (D, J=7, 3H, —CH3); 1.71 (Cx, 4H, pyrrolidine —CH2—); 2.6 to 2.85 (Mt, 4H, pyrrolidine >N—CH2—); 3.09 (DD, J=12 and 7.5, 1H, 1H of >N—CH2—); 3.18 (DD, J=12 and 6, 1H, 1H of >N—CH2—); 4.32 (Mt, J=7.5, 7 and 6, 1H, >N—CH<); 4.43 (D, J=5.5, 2H, —CONHCH2—); 6.59 (S, 2H, fumarate —CH=CH—); 6.75 (T, J=7.5, 1H, —H at 5-position of 2-hydroxybenzyl); 6.82 (D, J=7.5, 1H, —H at 3-position of 2-hydroxybenzyl); 6.95 to 7.30 benzyl); 7.52 (D, J=8, 1H, —H at 3-position); 7.60 (S, 1H, —H at 1-position); 9 (T, J=5.5, 1H —CONH—).

Infrared spectrum (KBr), characteristic bands in cm−1: 3260, 2965, 2880, 3200, 2800, 2800, 2000, 1700, 1630, 1590, 1555, 1485, 1460, 980, 870, 815, 755.

EXAMPLE 105

By working in a manner similar to that described in Example 103, but starting with 10-[(2RS)-1-(1-pyrrolidinyl)-2-propyl]-2-phenothiazinecarbonyl chloride hydrochloride (1.8 g) in dichloromethane (50 cc) and with 2-trifluoromethylbenzylamine (1.8 g), N-(3-trifluorobenzyl)-10-[(2RS)-1-(1-pyrrolidinyl)-2-propyl]-2-phenothiazinecarboxamide (1.2 g) is obtained, after recrystallization in isopropyl ether, in the form of white crystals, m.p. 112° C.

Proton NMR (250 MHz, CDCl3, δ in ppm, J in Hz):
1.68 (D, J=7, 3H, —CH3); 1.75 (Mt, 4H, pyrrrolidine —CH2—); 2.63 (Mt, 4H, pyrrolidine >N—CH2—); 2.95 (DD, J=12.5 and 6, 1H, 1H of >N—CH2—); 3.18 (DD, J=12.5 and 5.5, 1H, 1H ); 4.28 (Mt, J=7, 6 and 5.5, 1H, >N—CH<); 4.83 (D, J=6, 2H, —CONHCH2—); 6.61 (T, J=6, 1H, —CONH—); 6.90 to 7.80 (Mt, 9H, aromatic); 7.30 (DD, J=8 and 1, 1H, —H at 3-position); 7.72 (D, J=1, 1H, —H at 1-position).

Infrared spectrum (KBr), characteristic bands in cm−1: 3310, 2970, 2875, 2795, 1640, 1610, 1595, 1465, 1540, 1315, 1165, 1120, 875, 830, 765, 750.

EXAMPLE 106

By working in a manner similar to that described in Example 103, but starting with 10-[(2RS)-1-(1-pyrrolidinyl)-2-propyl]-2-phenothiazinecarbonyl chloride hydrochloride (2.5 g) in dichloromethane (50 cc) and with 2-nitrobenzylamine (2.1 g), N-(2-nitrobenzyl)-10-[(2RS)-1-(1-pyrrolidinyl)-2-propyl]-2-phenothiazinecarboxamide (1.1 g) is obtained, after recrystallization in isopropyl ether, in the form of yellow crystals, m.p. 95° C.

Proton NMR (250 MHz, DMSO-d6, δ in ppm, J in Hz):

1.60 (D, J=7, 3H, —CH3); 1.67 (Mt, 4H, pyrrolidine —CH2); 2.52 (Mt, partially masked, pyrrolidine >NCH2—); 2.90 (DD, J=12.5 and 6.5, 1H, 1H of >NCH2—); 3.02 (DD, J=12.5 and 6, 1H, 1H of >NCH2); 4.21 (Mt, J=7, 6.5 and 6, 1H >N—CH<); 4.76 (D, J=6, 2H, —CONHCH2—); 6.9 to 7.3 (Mt, 5H, aromatic); 7.45 to 7.65 (Mt, 4H, —H at 1-position and —H at 3-position of phenothiazine, and 2H of 2-nitrobenzyl); 8.07 (broad D, J=8, 1H, 2-nitrobenzyl); 9.10 (T, J=6, 1H, —CONH—).

Infrared spectrum (KBr), characteristic bands in cm−1: 3310, 2960, 2875, 2790, 1640, 1610, 1590, 1580, 1460, 1520, 1340, 875, 820, 855, 790, 750.

EXAMPLE 107

Thionyl chloride (5.2 cc) is added to a suspension, cooled to 5° C., of 10-[(2RS)-1-(1-pyrrolidinyl)-2-propyl]-2-phenothiazinecarboxylic acid hydrochloride (3.9 g) in methylene chloride (120 cc). The suspension is stirred for 3 hours at 25° C. and then concentrated to dryness at 30° C. under reduced pressure (30 mm Hg; 4 kPa) to give a yellow residue which is taken up in methylene chloride (50 cc) at 5° C. Cyclopentylamine (5 cc) is added and the mixture is stirred for 12 hours at 25° C., and saturated sodium bicarbonate solution (150 cc) is then added. The mixture is extracted with ethyl acetate (2×100 cc). The organic phase is washed successively with distilled water (100 cc) and with brine (100 cc), dried over magnesium sulphate, filtered and concentrated to dryness at 40° C. under reduced pressure (30 mm Hg; 4 kPa) to give a yellow oil which is dissolved in boiling acetonitrile (70 cc). Crystallization is primed by scratching. After cooling, the solid is separated by filtration, washed with acetonitrile (2×3 cc) and dried at 40° C. under reduced pressure (1 mm Hg; 0.13 kPa). N-Cyclopentyl-10-[(2RS)-1-(1-pyrrolidinyl)-2-propyl]-2-phenothiazinecarboxamide (2.1 g) is obtained in the form of cream-coloured crystals, m.p. 132° C.

Proton NMR (250 MHz, CDCl3, δ in ppm, J in Hz):
1.51, 1.72 and 2.10 (3Mt, 2H each, cyclopentyl —CH2—); 1.67 (D, J=7, 3H, —CH3); 1.82 (Mt, 4H, pyrrolidine —CH2—CH2—); 2.68 (Mt, 4H, pyrrolidine

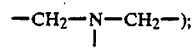
—CH2—N—CH2—);

2.98 (DD, J=12.5 and 6.5, 1H, 1H of >N—CH2—); 3.19 (DD, J=12.5 and 6, 1H, 1H of >N—CH2—); 4.34 (Mt, J=7, 6.5 and 6, 1H, 1H of >N—CH2—); 4.40 (Mt, 1H, —CONH—CH<); 6.14 (D, J=7, 1H, —CONH—); 6.9 to 7.25 (Mt, 5H, aromatic); 7.26 (DD, J=8 and 1, 1H, —H at 3-position); 7.62 (D, J=1, 1H, —H at 1-position).

Infrared spectrum (KBr), characteristic bands in cm−1: 3300, 2960, 2870, 2790, 1625, 1590, 1540, 1460, 880, 830, 750.

EXAMPLE 108

Thionyl chloride (2 cc) is added to a suspension, cooled to 5° C., of 10-[(2RS)-1-(1-pyrrolidinyl)-2-propyl]-2-phenothiazinecarboxylic acid hydrochloride (1.6 g) in methylene chloride (50 cc). The suspension is stirred for 3 hours at 25° C. and then concentrated to dryness at 30° C. under reduced pressure (30 mm Hg; 4 kPa) to give a yellow residue which is taken up in methylene chloride (50 cc) at 5° C. Cyclohexylmethylamine (1.1 g) is added and the mixture is stirred for 12 hours at 25° C., and saturated sodium bicarbonate solution (150 cc) is then added. The mixture is extracted with ethyl acetate (2×100 cc). The organic phase is washed successively with distilled water (100 cc) and with brine (100 cc), dried over magnesium sulphate, filtered and concentrated to dryness at 40° C. under reduced pressure (30 mm Hg; 4 kPa) to give a yellow solid (1.7 g) containing the expected product. The solid obtained is dissolved in boiling isopropyl ether (80 cc) and then filtered. The solution is primed by scratching and then cooled with stirring for 1 hour. The solid is separated by filtration, washed with isopropyl ether (2×4 cc) and dried at 40° C. under reduced pressure (1 mmHg; 0.13 kPa). N-(Cyclohexylmethyl)-10-[(2RS)-1-(1-pyrrolidinyl)-2-propyl]-2-phenothiazinecarboxamide (1.1 g) is obtained in the form of white crystals, m.p. 120° C.

Proton NMR (250 MHz, CDCl$_3$, δ in ppm, J in Hz): 1, 1.22 and from 1.5 to 1.8 (3Mt, 2H-3H and 6H respectively, —C$_6$H$_{11}$); 1.7 (D, J=7, 3H, —CH$_3$); 1.85 (Mt, 4H, pyrrolidine —CH$_2$—CH$_2$—); 2.75 (Mt, 4H, pyrrolidine —CH$_2$—N—CH$_2$—); 3.03 (DD, J=13 and 6.5, 1H, 1H of >N—CH$_2$—); 3.25 (DD, J=13 and 6, 1H, 1H of >N—CH$_2$—); 3.30 (T, J=6, 2H, —CONH—CH$_2$—); 4.42 (Mt, J=7, 6.5 and 6, 1H, >N—CH<); 6.38 (T, J=6, 1H, —CONH—); 6.9 to 7.25 (Mt, 5H, aromatic); 7.3 (DD, J=8 and 1, 1H, —H at 3-position); 7.67 (D, J=1, 1H, —H at 1-position).

Infrared spectrum (KBr), characteristic bands in cm$^{-1}$: 3300, 2920, 2850, 2790, 1630, 1595, 1545, 1460, 865, 820, 750.

EXAMPLE 109

Thionyl chloride (2.6 cc) is added to a suspension, cooled to 5° C., of 10-[(2RS)-1-(1-pyrrolidinyl)-2-propyl]-2-phenothiazinecarboxylic acid hydrochloride (2 g) in methylene chloride (60 cc). The suspension is stirred for 3 hours at 25° C. and then concentrated to dryness at 30° C. under reduced pressure (30 mm Hg; 4 kPa) to give a yellow residue which is taken up in methylene chloride (50 cc) at 5° C. Aniline (5 cc) is added and the mixture is stirred for 12 hours at 25° C., and saturated sodium bicarbonate solution (150 cc) is then added. The mixture is extracted with ethyl acetate (2×100 cc). The organic phase is washed successively with distilled water (100 cc) and with brine (100 cc), dried over magnesium sulphate, filtered and concentrated to dryness at 40° C. under reduced pressure (30 mm Hg; 4 kPa) to give a brown oil which is purified by chromatography on a column (height: 30 cm; diameter: 2.5 cm) of silica (0.06–0.2 mm), eluting with methylene chloride (1.8 liters) and collecting 40-cc fractions. Fractions 12 to 36 are combined and concentrated t dryness under reduced pressure (30 mm Hg; 4 kPa) at 40° C. to give a cream-coloured solid (1.1 g) which is dissolved in boiling acetonitrile (10 cc). The solution is primed by scratching and then cooled with stirring for 1 hour. The solid is separated by filtration, washed with acetonitrile (2×1 cc) and dried at 40° C. under reduced pressure (1 mm Hg; 0.13 kPa). N-Phenyl-10-[(2RS)-1-(1-pyrrolidinyl)-2-propyl]-2-phenothiazinecarboxamide (0.75 g) is obtained in the form of yellow crystals, m.p. 163° C.

Proton NMR (250 MHz, DMSO, δ in ppm, J in Hz): 1.61 (D, J=7, 3H, —CH$_3$); 1.68 (Cx, 4H, pyrrolidine —CH$_2$—CH$_2$—); 2.54 (masked Mt, pyrrolidine —CH$_2$—N—CH$_2$—); 2.91 (DD, J=13 and 6.5, 1H, 1H of >N—CH$_2$—); 3.06 (DD, J=13 and 6, 1H, 1H of >N—CH$_2$—); 4.25 (Mt, 1H, >N—CH<); 6.95 to 7.45 (Mt, 8H, aromatic); 7.55 (broad D, J=8, 1H, —H at 3-position); 7.68 (broad S, 1H, —H at 1-position); 7.77 (broad D, J=8.5, 2H, aromatic of phenyl ortho to the —CONH—); 10.22 (S, 1H, —CONH—).

Infrared spectrum (KBr), characteristic bands in cm$^{-1}$: 3370, 2970, 2880, 2790, 1650, 1600, 1570, 1560, 1535, 1500, 1470, 825, 750, 690.

EXAMPLE 110

Distilled water (0.75 cc) is added in the course of 2 minutes, with stirring and at a temperature of 20° C., to a suspension of potassium tert-butylate (4.7 g) in tert-butanol (45 cc).

A solution of 10-{1-[N-(cyclopropylmethyl)methylamino]-2-propyl}-2-phenothiazinecarbonitrile, L series (2.59 g) in tert-butanol (15 cc) is added with stirring and at a temperature of 20° C. to the solution obtained. The yellow suspension obtained is then brought to reflux for 30 minutes. After cooling to a temperature of 30° C., 1-iodopropane (4.1 cc) is added with stirring and the mixture is brought to reflux for 1 hour. After cooling, the mixture is concentrated to dryness under reduced pressure (30 mm Hg; 4 kPa) at 40° C. The residue is taken up with ethyl acetate (100 cc) and the organic phase is washed with distilled water (3×100 cc), dried over magnesium sulphate, filtered and concentrated to dryness under reduced pressure (30 mm Hg; 4 kPa) at 40° C. The oily yellow residue (3 g) is purified by chromatography on a column (height: 30 cm; diameter: 3.6 cm) of silica gel (0.04–0.063 mm) under a slight excess pressure of nitrogen (40 kPa), eluting successively with a mixture (80:20 by volume) (2.5 liters) of cyclohexane and ethyl acetate, then with a mixture (60:40 by volume) (2 liters) of cyclohexane and ethyl acetate and finally ethyl acetate (5 liters) and collecting 125-cc fractions. Fractions 37 to 72 are combined and concentrated to dryness under reduced pressure (30 mm Hg; 4 kPa) at 40° C. to give an oily yellow residue (2.52 g). 1.62 g of this residue are dissolved in ethyl ether (125 cc) and treated with a 3.6N solution (1.3 cc) of hydrochloric acid in ethyl ether. After 16 hours' stirring at 20° C., the precipitate formed is filtered off, washed with isopropanol ether (2×50 cc) and dried under reduced pressure (5 mm Hg; 0.67 kPa) at 40° C. to give 10-{1-[N-(cyclopropylmethyl)methylamino]-2-propyl}-N-propyl-2-phenothiazinecarboxamide hydrochloride, L series (1.2 g) in the form of a yellow solid, m.p. about 160° C. [α]$_D^{20}$= +19.4≧ ±0.9° (0.5%; methanol).

Proton NMR (250 MHz, DMSO-d6+a few drops of CD$_3$COOD, δ in ppm, J Hz):

0.27 and 0.53 (2 Mt, respectively 2H each, cyclopropylmethyl —CH$_2$—); 0.9 (T, J=7, 3H, —(CH$_2$)$_2$CH$_3$); 0.9 to 1.15 (Cx, 1H, cyclopropylmethyl >CH—); 1.06 (T, J=6.5, 3H, ethylamino —CH$_3$); 1.55 (Mt, 2H, —CH$_2$CH$_2$CH$_3$); 1.85 (D, J=7, 3H, —CH$_3$); 3.03 (D, J=7.5, 2H, cyclopropylmethyl >NCH$_2$—); 3.25 (Mt, 4H, >N—CH₂— of ethylamino and —CONHCH₂—); 3.45 (broad D, J=14, 1H, 1H of >NCH₂—); 3.83 (DD, J=14 and 7.5, 1H, 1H of >N—CH₂—); 4.78 (Mt, 1H, >N—CH<); 7 to 7.35 (Mt, 5H, aromatic); 7.54 (D, J=8, 1H, —H at 3-position); 7.54 (S, 1H, —H at 1-position).

Infrared spectrum (KBr), characteristic bands in cm⁻¹: 3270, 2960, 2930, 2870, 2580, 2500, 1645, 1590, 1555, 1460, 1535, 875, 830, 755.

10-{1-[N-(Cyclopropylmethyl)methylamino]-2-propyl}-2-phenothiazinecarbonitrile, L series may be prepared in the following manner:

A mixture of 10-(1-ethylamino-2-propyl)-2-phenothiazinecarbonitrile, L series (3.1 g), sodium carbonate (1.19 g) and bromomethylcyclopropane (2.7 g) in dimethylformamide (32 cc) is heated to 150° C. for 9 hours. After cooling, the reaction mixture is poured into distilled water (300 cc) and extracted with ethyl acetate (3×150 cc). The combined organic phases are washed with distilled water (4×100 cc), dried over magnesium sulphate, filtered and concentrated to dryness under reduced pressure (30 mm Hg; 4 kPa) at 50° C. The brown oily residue (3.38 g) is purified by chromatography on a column (height: 30 cm; diameter: 2.5 cm) of silica gel (0.06–0.20 mm), eluting with a mixture (80:20 by volume) (2 liters) of methylene chloride and ethyl acetate and collecting 60-cc fractions. Fractions 4 to 12 are combined and concentrated to dryness under reduced pressure (30 mm Hg; 4 kPa) at 40° C. 10-{1-[N-(Cyclopropylmethyl)-methylamino]-2-propyl}-2-phenothiazinecarbonitrile, L series (1.83 g) is thereby obtained in the form of a yellow oil.

$[\alpha]_D^{20} = -1.5 \cong \pm 0.3°$ (1%; chloroform).

EXAMPLE 111

A solution of propylamine (1.95 cc) in methanol (5 cc) is added dropwise in the course of 5 minutes to a solution, cooled to 0°–5° C., of methyl 10-[(2RS)-1-diethylamino-2-propyl]-2-phenothiazinecarboximidate dihydrochloride (3.49 g) in methanol (21 cc). The mixture is stirred for 2 hours at 5° C. and then concentrated to dryness under reduced pressure (30 mm Hg; 4 kPa) at 50° C. to give a residue which is taken up with distilled water (50 cc). The solution is washed with distilled water (50 cc) alkalinized to pH 9 with N sodium hydroxide. The two phases are allowed to settle and the organic phase is separated and washed with half-saturated (sodium chloride) solution (50 cc), dried over magnesium sulphate, filtered and then concentrated to dryness under reduced pressure (30 mm Hg; 4 kPa) at 50° C. The residue is purified by chromatography on neutral alumina (height: 20 cm; diameter: 2.1 cm), eluting with pure ethyl acetate (375 cc) and finally with mixtures of ethyl acetate and methanol in proportions (by volume) of 99:1 (375 cc), 98:2 (500 cc), 95:5 (500 cc), 90:10 (500 cc) and 80:20 (500 cc) and collecting 25-cc fractions. Fractions 40 to 70 are combined and concentrated to dryness under reduced pressure (30 mm Hg; 4 kPa) at 50° C. to give 10-[(2RS)-1-diethylamino-2-propyl]-N-propyl-2-phenothiazinecarboxamidine (1.49 g) in the form of a yellow product of meringue-like consistency.

A 3.5N acetone solution (1.42 cc) of hydrocholric acid is added dropwise to an acetone solution (7 cc) of 10-[(2RS)-1-diethylamino-2-propyl]-2-phenothiazinecarboxamidine (0.74 g). The mixture is stirred for 3 hours at 25° C. and then concentrated to dryness under reduced pressure (30 mm Hg; 4 kPa) at 50° C. The residue is taken up in ethyl ether (50 cc) and the suspension is kept stirred for 3 hours at 25° C. The solid is filtered off on sintered glass, washed with ethyl ether (2×5 cc) and dried for 12 hours under reduced pressure (5 mm Hg; 0.7 kPa) to give 10-[(2RS)-1-diethylamino-2-propyl]-N-propyl-2-phenothiazinecarboxamidine dihydrochloride (1.44 g), m.p. 216°–218° C.

Proton NMR (250 MHz, DMSO, δ in ppm, J in Hz): 0.96 (T, J=7.5, 3h, —(CH₂)₂CH₃); 1.05 to 1.25 (Mt, 6H, —N(CH₂CH₃)₂); 1.68 (Mt, 2H, —CH₂—CH₂CH₃); 1.87 (D, J=7.5, 3H, —CH₃); 3.21 (Mt, 4H, —N(CH₂—CH₃)₂); 3.40 (Mt, 2H, —NH—CH₂—); 3.45 (Mt, 1H, 1H of >NCH₂—); 3.8 (Mt, 1H, other H of >NCH₂—); 5.10 (Mt, 1H, >N—CH<); 7 to 7.5 (Mt, 7H, aromatic); 9.2 and 9.8 (2S, 1H each, C=NH₂⁺); 10.23 (T, J=5.5, 1H, —NH—); 10.67 (Cx, 1H, —NH⁺).

Infrared spectrum (KBr), characteristic bands in cm⁻¹: 3300 to 2700, 2650, 2480, 1670, 1620, 1590, 1560, 1460, 1420, 870, 810, 755.

EXAMPLE 112

A solution of (2RS)-2-methylbutylamine (3.18 cc) in methanol (5 cc) is added dropwise in the course of 5 minutes to a solution, cooled to 0°–5° C., of methyl 10-[(2RS)-1-diethylamino-2-propyl]-2-phenothiazinecarboximidate hydrochloride (3.49 g) in methanol (21 cc). The mixture is stirred for 2 hours at 5° C. and then concentrated to dryness under reduced pressure (30 mm Hg; 4 kPa) at 50° C. to give a residue which is taken up with ethyl acetate (50 cc). The solution is washed with distilled water (50 cc) alkalinized to pH 9 with N sodium hydroxide. The two phases are allowed to settle and the organic phase is separated and washed with half-saturated sodium chloride solution (50 cc), dried over magnesium sulphate, filtered and then concentrated to dryness under reduced pressure (30 mm Hg; 4 kPa) at 50° C. The residue is purified by chromatography on a column of neutral alumina (height: 23 cm; diameter: 2.1 cm), eluting with mixtures of ethyl acetate and cyclohexane in proportions (by volume) of 20:80 (850 cc) and 10:90 (500 cc), then with pure ethyl acetate (500 cc) and finally with mixtures of ethyl acetate and methanol in proportions (by volume) of 95:5 (500 cc), 90:10 (500 cc) and 80:20 (500 cc and collecting 50-cc fractions. The first litre is discarded and fractions 40 to 56 are then combined, concentrated to dryness under reduced pressure (30 mm Hg; 4 kPa) at 50° C. to give 10-[(2RS)-1-diethylamino-2-propyl]-N-[(2RS)-2-methylbutyl]-2-phenothiazinecarboxamidine (1.33 g) in the form of a yellow product of meringue-like consistency.

A 3.5N acetone solution (2.24 cc) of hydrochloric acid is added dropwise to an acetone solution (11 cc) of 10-[(2RS)-1-diethylamino-2-propyl]-N-[(2RS)-2-methylbutyl]-2-phenothiazinecarboxamidine (1.11 g). The mixture is stirred for 3 hours at 25° C. and then concentrated to dryness under reduced pressure (30 mm Hg; 4 kPa) at 50° C. The residue is taken up in ethyl ether (50 cc) and the suspension is kept stirred for 3 hours at 25° C. The solid is filtered off on sintered glass, washed with ethyl ether (2×5 cc) and dried for 12 hours under reduced pressure (5 mm Hg; 0.7 kPa) to give 10-[(2RS)-1-diethylamino-2-propyl]-N-[(2RS)-2-methylbutyl]-2-phenothiazinecarboxamidine dihydrochloride (1.07 g), m.p. 212°–214° C.

Proton NMR (250 MHz, DMSO, δ in ppm, J in Hz): 0.92 (Mt, 6H, —CH(CH₃)CH₂CH₃); 1.08 and 1.18 (2T, 6H, —N(CH₂CH₃)₂; approximately 1.20 and 1.5

(2Mt, 1H each, —CH(CH₃)CH₂CH₃); 1.85 (D, J=7.5, 3H, —CH₃); 1.9 (Mt, 1H, —CH₂—CH(CH₃)—); 3.25 (Mt, 6H, —N(CH₂CH₃)₂ and —NH—CH₂—); 3.45 and 3.80 (2Mt, 2H, >NCH₂—); 5.12 (Cx, 1H, >N—CH<); 7 to 7.5 (Mt, 7H, aromatic); 9.25 and 9.85 (2S, 1H each, C=NH₂+); 10.23 (T, J=5, 1H, —NH—); 10.75 (Cx, 1H, —NH+).

Infrared spectrum (KBr), characteristic bands in cm⁻¹: 3300 to 2700, 2660, 2490, 1670, 1620, 1595, 1560, 1460, 1420, 870, 810, 755.

EXAMPLE 113

A solution of benzylamine (3.18 cc) in methanol (5 cc) is added dropwise in the course of 5 minutes to a solution, cooled to 0°–5° C., of methyl 10-[(2RS)-1-diethylamino-2-propyl]-2-phenothiazinecarboximidate dihydrochloride (3.49 g) in methanol (21 cc). The mixture is stirred for 2 hours at 5° C. and is then concentrated to dryness at 50° C. under reduced pressure (30 mm Hg; 4 kPa) to give a residue which is taken up with distilled water (50 cc). The solution is washed with distilled water (50 cc) alkalinized to a pH in the region of 9 with N sodium hydroxide. The two phases are allowed to settle and the organic phase is separated and washed with half-saturated sodium chloride solution (50 cc), dried over magnesium sulphate, filtered and then concentrated to dryness under reduced pressure (30 mm Hg; 4 kPa) at 50° C. The residue is purified by chromatography on a column of neutral alumina (height: 24 cm; diameter: 2.1 cm), eluting successively with mixtures of cyclohexane and ethyl acetate in proportions of 50:50 (500 cc) and 25:75 (500 cc), then with pure ethyl acetate (500 cc) and finally with mixtures of ethyl acetate and methanol in proportions of 95:5 (500 cc) and 90:10 (500 cc) and collecting 50-cc fractions. Fractions 35 to 53 are combined and concentrated to dryness under reduced pressure (30 mm Hg; 4 kPa) at 50° C. to give N-benzyl-10-[(2RS)-1-diethylamino-2-propyl]-2-phenothiazinecarboxamidine (0.96 g) in the form of a yellow product of meringue-like consistency.

A 3.5N acetone solution (1.42 cc) of hydrocloric acid is added dropwise to an acetone solution (11 cc) of N-benzyl-10-[(2RS)-1-diethylamino-2-propyl]-2-phenothiazinecarboxamidine (0.74 g). The mixture is stirred for 3 hours at 25° C. and then concentrated to dryness under reduced pressure (30 mm Hg; 4 kPa) at 50° C. The residue is taken up in ethyl ether (50 cc) and the suspension is kept stirred for 3 hours at 25° C. The solid is filtered off on sintered glass, washed with ethyl ether (2×5 cc) and dried for 12 hours under reduced pressure (5 mm Hg; 0.7 kPa) to give N-benzyl-10-[(2RS)-1-diethylamino-2-propyl]-2-phenothiazinecarboxamidine dihydrochloride (0.76 g), m.p. 206°–207° C.

Proton NMR (250 MHz, DMSO, δ in ppm, J in Hz):
1.07 and 1.18 (2T, 6H, —N(CH₂CH₃)₂); 1.9 (D, J=7, 3H, —CH₃); 3.22 (Mt, 4H, —N(CH₂CH₃)₂); 3.5 and 3.85 (2Mt, 2H, >N—CH₂—); 4.75 (D, J=6, 2H, —NH—CH₂—); 5.06 (Mt, 1H, >N—CH<); 7.05 to 7.55 (Mt, 12H, aromatic); 9.4 and 9.95 (2S, 1H each, >C=NH₂+); 10.43 (Cx, 1H, —NH+); 10.75 (T, J=6, 1H —NH—).

Methyl 10[(2RS)-1-diethylamino-2-propyl]-2-phenothiazinecarboximidate dihydrochloride may be obtained in the following manner:

Hydrochloric acid is bubbled for 4 hours into a methanolic solution (80 cc), cooled to 0°–5° C. and kept stirred, of 10-[(2RS)-1-diethylamino-2-propyl]-2-phenothiazinecarbonitrile (8.0 g) and the mixture is left stirred for 12 hours at 25° C. The methanol is distilled off under reduced pressure (30 mm Hg; 4 kPa) at 30° C. and the residue is taken up in anhydrous methanol (50 cc). The solvent is again evaporated off under reduced pressure (30 mm Hg; 4 kPa) and the residue is diluted again with anhydrous methanol (50 cc). This operation is repeated once more to give finally a methanolic solution (50 cc) of methyl 10-[(2RS)-1-diethylamino-2-propyl]-2-phenothiazinecarboximidate dihydrochloride.

EXAMPLE 114

Chloroacetone (0.44 cc) and 4 A molecular sieve (1 g) are added to a solution of 10-[(2RS)-1-(1-pyrrolidinyl)-2-propyl]-2-phenothiazinecarboxamidine hydrochloride (1.76 g) in dry ethanol (17 cc). The suspension is maintained under reflux for 20 hours. After cooling, the suspension is filtered and concentrated to dryness at 40° C. under reduced pressure (30 mm Hg; 4 kPa) to give a residue which is diluted in 1,2-dichloroethane (200 cc). The organic phase is washed with distilled water (3×100 cc) and then with saturated sodium chloride solution (100 cc), dried over magnesium sulphate, filtered and concentrated to dryness at 40° C. under reduced pressure (30 mm Hg; 4 kPa) to give a residue which is purified by chromatography on a column (height: 15 cm; diameter: 2.4 cm) of silica (0.04–0.06 mm), eluting with a 90:10 (by volume) mixture (800 cc) of 1,2-dichloroethane and methanol and collecting 50-cc fractions. The first 300 cc of eluate are discarded and fractions 4 to 10 are concentrated to dryness at 40° C. under reduced pressure (30 mm Hg; 4 kPa) to give 2-(4-methyl-2-imidazolyl)-10-[(2RS)-1-(1-pyrrolidinyl)-2-propyl]phenothiazine(0.33g) in the form of a golden yellow solid.

1.2 N ethereal hydrochloric acid (0.64 cc) is added to a solution of 2-(4-methyl-2-imidazolyl)-10[(2RS)-1-(1-pyrrolidinyl)-2-propyl]phenothiazine (0.30 g) in anhydrous ethanol (3 cc). The mixture is stirred for 5 minutes and then concentrated to dryness at 40° C. under reduced pressure (30 mm Hg; 4 kPa) to give a residue which is taken up in ethyl ether (70 cc). The solid obtained is filtered off on sintered glass to give 2-(4-methyl-2-imidazolyl)-10-[(2RS)-1-(1-pyrrolidinyl)-2-propyl]phenothiazine hydrochloride (0.35 g), m.p. 210° C., in the form of a brown powder.

Proton NMR (250 MHz, DMSO, δin ppm, J in Hz):
In solution in DMSO, two forms are observed, due to salification of the nitrogen.

1.88 (D, J=7, 3H, —CH₃); 1.75 to 2.1 (Mt, 4H, —CH₂—CH₂—); 2.4 (S, 3H, 4-methyl-2-imidazolyl —CH₃); 2.98, 3.16, 3.64 and 3.78 (4Cx, 1H each, pyrrolidine

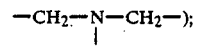

3.95 (Cx, 2H,>N—CH₂—); 4.77 (Mt, 1H, ×N—CH<); 7.05 to 7.55 (Mt, 5H, aromatic); 7.51 (S, 1H, 4-methyl-2-imidazolyl —CH=); 7.73 (broad S, 1H, —H at 1-position); 7.78 (broad D, J=8, 1H, —H at 3-position); 10.58 (Cx, 1H, 4-methyl-2-imidazolyl —NH—); 15.1 and 15.3 (2Cx, 1H in total, —NH+).

Infrared spectrum (KBr), characteristic bands in cm⁻¹: 2720, 2630, 1640, 1595, 1575, 1460, 860, 820, 755.

10-[(2RS)-1-(1-Pyrrolidinyl)-2-propyl]-2-phenothiazinecarboxamide hydrochloride may be prepared in the following manner:

Triethylamine (8.4 cc) is added to a solution of ethyl 10-[(2RS)-1-(1-pyrrolidinyl)-2-propyl]-2-phenothiazinecarboximidate dihydrochloride (13.63 g) in absolute ethanol (150 cc), and the reaction mixture is diluted with dry ethanol (100 cc). Gaseous ammonia is bubbled for 4 hours into the reaction mixture, which is then stirred for 12 hours at 25° C. The suspension obtained is filtered on sintered glass and the filtrate is concentrated to dryness at 25° C. under reduced pressure (30 mm Hg; 4 kPa) to give a yellow product of meringue-like consistency, which is purified by chromatography on a column of alumina (height: 23 cm; diameter: 4 cm), eluting with mixtures of methylene chloride and methanol in proportions of 95:5 (750 cc) and 50:50 (1,500 cc) and collecting 125-cc fractions. The first 900 cc of eluate are discarded and fractions 8 to 11 are combined and concentrated to dryness at 25° C. under reduced pressure (30 mm Hg; 4 kPa) to give 10-[(2RS)-1-(1-pyrrolidinyl)-2-propyl]-2-phenothiazinecarboxamidine hydrochloride (4.5 g) in the form of a yellow product of meringue-like consistency.

10-[(2RS)-1-(1-Pyrrolidinyl)-2-propyl]-2-phenothiazinecarboxamidine hydrochloride (4.3 g) is dissolved in acetone (150 cc) under reflux. Crystallization is primed by scratching. The suspension is kept stirred during cooling. After filtration on sintered glass, 10-[(2RS)-1-(1-pyrrolidinyl)-2-propyl]-2-phenothiazinecarboxamidine hydrochloride (3.35 g) is obtained in the form of yellow crystals, m.p. 228–30° C.

EXAMPLE 115

Sodium hydrogen carbonate (1.68 g) and then 3 Å molecular sieve (2 g) are added to a solution of 10-[(2RS)-1-(1-pyrrolidinyl)-2-propyl]-2-phenothiazinecarboxamidine hydrochloride (3.89 g) in ethanol (30 cc), and the mixture is brought to reflux for 1 hour. A solution of 1-bromo-2-butanone (1.84 g) in ethanol (25 cc) is then added dropwise with stirring and at a temperature in the region of 70° C. during 6 hours, and stirring is continued under reflux for 1 hour. After cooling, the suspension obtained is filtered and the insoluble matter is washed with ethanol (2×10 cc). The ethanolic solutions are combined and concentrated t dryness under reduced pressure (30 mm Hg; 4 kPa) at 40° C. The oily residue is taken up with methylene chloride (100 cc) and the insoluble matter is removed by filtration. The methylene chloride solution is concentrated to dryness under reduced pressure (30 mm Hg; 4 kPa) at 20° C. The residue is taken up with isopropyl ether (125 cc) and the suspension obtained is stirred for 1 hour. The solid formed is separated by filtration, washed with isopropyl ether (3×15 cc), drained and dried under reduced pressure (1 mm Hg; 0.13 kPa) to give a yellow solid (3 g) which is purified by chromatography on a column (height: 47 cm; diameter: 4 cm) of silica gel (0.04–0.063 mm) under a slight excess pressure of nitrogen (40 kPa), eluting with a mixture (80:20 by volume) (1 liter) of methylene chloride and methanol and collecting 100-cc fractions. Fractions 3 to 7 are combined and concentrated to dryness under reduced pressure (30 mm Hg; 4 kPa) at 40° C. to give a yellow product (1 g) of meringue-like consistency. This product is dissolved in distilled water (50 cc) treated with N/10 aqueous hydrochloric acid solution (20 cc), and the solution is washed with ethyl acetate (3×20 cc). The aqueous phase is alkalinized with caustic soda and extracted with ethyl acetate (3×50 cc). The organic phases are combined, washed successively with distilled water (50 cc) and with half-saturated aqueous sodium chloride solution (50 cc), dried over magnesium sulphate, filtered and concentrated to a volume of 10 cc under reduced pressure (30 mm Hg; 4 kPa) at 40° C. After the mixture has been standing for 16 hours at a temperature in the region of 20° C., the solid formed is drained, washed with ethyl acetate (2 cc) and dried under reduced pressure (5 mm Hg; 0.67 kPa) at 40° C. 10-[(2RS)-1-(1-Pyrrolidinyl)-2-propyl]-2-(4-ethyl-2-imidazolyl)phenothiazine (0.6 g) is thereby obtained in the form of a white solid, m.p. 197° C.

Proton NMR (250 MHz, DMSO-d6, $\delta$ in ppm, J in Hz): 1.24 (T, J=7, 3H, —CH$_2$CH$_3$); 1.66 (D, J=7, 3H, —CH$_3$); 1.7 (Mt, 4H, pyrrolidine —CH$_2$—; 2.55 (Mt, partially masked, >N—CH$_2$— of pyrrolidine and —CH$_2$CH$_3$); 2.98 (limiting AB, 2H, >NCH$_2$—); 4.20 (Mt, 1H, >NCH<); 6.73 (S, 1H, imidazole —CH=); 6.90 to 7.25 (Mt, 5H, aromatic); 7.46 (broad D, J=8, 1H, —H at 3-position); 7.66 (broad S, 1H, —H at 1-position); 12.2 (Cx, 1H, —NH—).

Infrared spectrum (KBr), characteristic bands in cm$^{-1}$: 3175, 2150, 2965, 2935, 2875, 2790, 1580, 1570, 1460, 875, 815, 750.

The present invention also relates to the pharmaceutical compositions consisting of a product of general formula (I), in free form or in the form of an addition salt with a pharmaceutically acceptable acid, in the pure state or in the form of a combination with any other pharmaceutically compatible product which can be inert or physiologically active. The medicinal products according to the invention may be used parenterally, orally, rectally or topically.

The sterile compositions for parenteral administration, which can be, in particular, used in the form of perfusions, are preferably solutions, aqueous or nonaqueous, suspensions or emulsions. As a solvent or vehicle, water, propylene glycol, a polyethylene glycol, vegetable oils, especially olive oil, injectable organic esters, e.g. ethyl oleate, or other suitable organic solvents may be used. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They can also be prepared in the form of sterile solid compositions which can be dissolved at the time of use in a sterile injectable medium.

The compositions for rectal administration are suppositories or rectal capsules which contain, apart from the active product, excipients such as cocoa butter, semi-synthetic glycerides or polyethylene glycols.

As solid compositions for oral administration, tablets, pills, powders or granules may be used. In these compositions, the active product according to the invention (optionally in combination with another pharmaceutically compatible product) is mixed with one or more inert diluents or adjuvants such as sucrose, lactose or starch. These compositions can also comprise substances other than diluents, e.g. a lubricant such as magnesium stearate.

As liquid compositions for oral administration, emulsions of a pharmaceutically acceptable nature, solutions, suspensions, syrups and elixirs containing inert diluents such as water or liquid paraffin may be used. These compositions can also comprise substances other than diluents, e.g. wetting, sweetening or flavouring products.

The compositions for topical administration can be e.g. creams, ointments or lotions.

In human therapy, the products according to the invention are especially useful in the treatment of pain of traumatic origin, postoperative, homotopic and menstrual pain, headaches, etc., as well as in diuretic treatments. The dosages depend on the effect sought and the treatment period. For an adult, they are generally between 0.25 and 1,500 mg per day, taken in several doses at intervals.

Generally speaking, the doctor will determine the dosage which he considers most suitable in accordance with the age, weight and all other factors specific to the subject to be treated.

The examples which follow, given without implied limitation, illustrate compositions according to the invention.

| | |
|---|---|
| N-(2-chlorobenzyl)-10-[1-(1-pyrrolidinyl)-2-propyl]-2-phenothiazinecarboxamide hydrochloride, L series | 16.9 mg |
| starch | 83 mg |
| silica | 30 mg |
| magnesium stearate | 3 mg |

| | | |
|---|---|---|
| N-(2-chlorobenzyl)-10-[1-(1-pyrrolidinyl)-2-propyl]-2-phenothiazinecarboxamide hydrochloride, L series | | 2.69 g |
| ascorbic acid | | 0.100 g |
| neutral sodium sulphite | | 0.050 g |
| sodium hydroxide, 1N (q.s. pH 4) | approximately | 0.08 cc |
| NaCl (q.s. isotonicity) | approximately | 0.650 g |
| water for injections | q.s. | 100 cc |

We claim:

1. A phonothiazine of the formula:

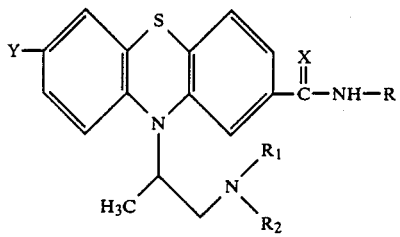

in which Y denotes hydrogen or halogen and $R_1$ and $R_2$, which may be identical or different, each denote alkyl, cycloalkylalkyl, hydroxyalkyl or acetyloxyalkyl or form, together with the nitrogen atom to which they are attached, a pyrrolidinyl, piperidinyl, perhydroazepinyl or dihydropyrrolyl which may be substituted by 1 or 2 alkyl hydroxyalkyl or acetyloxyalkyl radicals, and -either X denotes oxygen, sulphur or :N-$R_4$, in which $R_4$ is hydrogen or cyano, and R denotes 4- to 6-membered cycloalkyl or phenyl, or —$CH_2R_3$, in which $R_3$ is hydrogen, alkyl of 1 to 5 carbon atoms, alkenyl or alkynyl or 2 to 4 carbon atoms, 3- to 6-membered cycloakyl, or phenyl which is unsubstituted or substituted (by 1 or 2 halogen atoms or by a hydroxy, alkyl, alkyloxy, trifluoromethyl or nitro), or furyl, thienyl or pyridyl, provided that when R3 is hydrogen or alkyl, $R_1$ and $R_2$ are both alkyl or together form an unsubstituted nitrogen-containing heterocyclic ring and Y is a hydrogen, X is not oxygen; - or X is :N-$R_4$ and R forms, with $R_4$ and the atoms to which they are attached, imidazolinyl or imidazolyl unsubstituted or substituted by 1 or 2 alkyl radicals, or hexahydrobenzimidazolyl; the aforesaid alkyl radicals being (except where otherwise stated) linear or branched and having 1 to 4 carbon atoms each, in its optical isomers of asymmetric carbon, and its acid addition salts.

2. A phenothiazine according to claim 1, in which: Y is hydrogen or halogen, and $R_1$ and $R_2$, which may be identical or different, each denote alkyl of 1 to 3 carbon atoms in a straight or branched chain, or alkyl of 1 or 2 carbon atoms substituted by cycloalkyl, hydroxy or acetyloxy, or form, together with the nitrogen atom to which they are attached, a saturated or partially unsaturated 4- to 7-membered heterocyclic ring which is unsubstituted or substituted by 1 or 2 methyl radicals or by alkyl of 1 or 2 carbon atoms substituted by hydroxy or acetyloxy; and -either X denotes oxygen, sulphur or :N-$R_4$, in which $R_4$ is hydrogen or cyano and R denotes 4- to 6-membered cycloalkyl or phenyl, or —$CH_2R_3$, in which $R_3$ is hydrogen, linear or branched alkyl of 1 to 5 carbon atoms, alkenyl or alkynyl of 2 to 4 carbon atoms, 3- to 6-membered cycloalkyl, or phenyl which is unsubstituted or substituted(by 1 or 2 halogen atoms or by hydroxy, methyl, methoxy, trifluoromethyl or nitro), or furyl, thienyl or pyridyl, provided that when $R_3$ is hydrogen or alkyl, $R_1$ and $R_2$ are both alkyl or together form an unsubstituted nitrogen-containing heterocyclic ring and Y is hydrogen, X is not oxygen; - or X is ;N-$R_4$ and R forms, with $R_4$ and the atoms to which they are attached, imidazolyl unsubstituted or substituted by 1 or 2 alkyl radicals of 1 or 2 carbon atoms, or hexahydrobenzimidazolyl, in its isomeric forms and their mixtures, and its acid addition salts.

3. A phenothiazine according to claim 1, in which: Y is hydrogen or halogen, and $R_1$ and $R_2$, which may be identical or different, each denote alkyl of 1 or 2 carbon atoms but are not both methyl, or acetyloxyalkyl in which the alkyl contains 1 or 2 carbon atoms, or form, together with the nitrogen atom to which they are attached, a saturated or partially unsaturated 4- to 7-membered heterocyclic ring which is unsubstituted or substituted by 1 or 2 methyl, hydroxymethyl or acetyloxymethyl radicals; and - either X denotes oxygen, sulphur or :N-$R_4$, in which $R_4$ is hydrogen or cyano, and R denotes 4- to 6-membered cycloalkyl or -$CH_2R_3$, in which $R_3$ is a linear or branched alkyl of 1 to 5 carbon atoms, alkenyl or alkynyl of 2 to 4 carbon atoms, 3- to 6-membered cycloalkyl, or phenyl which is unsubstituted or substituted(by 1 or 2 halogen atoms or by hydroxy, methyl, methoxy, trifluoromethyl or nitro),or furyl, thienyl or pyridyl, provided that when $R_3$ is hydrogen or alkyl, $R_1$ and $R_2$ are both alkyl or together form an unsubstituted nitrogen-containing heterocyclic ring and Y is hydrogen, X is not oxygen; - or X is :N-$R_4$ and R forms, with $R_4$ and the atoms to which they are attached, imidazolyl which is unsubstituted or substituted by alkyl of 1 or 2 carbon atoms or hexahydrobenzimidazolyl, in the L form or in the form of a mixture of isomers, and its acid addition salts.

4. A phenothiazine according to claim 1 which is N-cyclobutylmethyl-10-[1-(1-pyrrolidinyl) -2- propyl]-2-phenothiazinecarboxamide in the L form, or in the form of a mixture of isomers, and its acid addition salts.

5. A phenothiazine according to claim 1 which is N-(3-chlorobenzyl)-10-[(1-(1-pyrrolidinyl)-2-propyl]-2-phenothiazinecarboxamide in the L form, or in the form of a mixture of isomers, and its acid addition salts.

6. A phenothiazine according to claim 1 which is N-(2-chlorobenzyl)-10-[1-(1-pyrrolidinyl)-2-propyl]-2-phenothiazinecarboxamide in the L form, or in the form of a mixture of isomers, and its acid addition salts.

7. A phenothiazine according to claim 1 which is N-(2-fluorobenzyl)-10-[1-(1-pyrrolidinyl)-2-propyl]-2-phenothiazinecarboxamide in the L form, or in the form of a mixture of isomers, and its acid addition salts.

8. A phenothiazine according to claim 1 which is N-benzyl-10-[1-(1-pyrrolidinyl)-2-propyl]-2-phenothiazinecarboxamide in the L form, or in the form of a mixture of isomers, and its acid addition salts.

9. A pharmaceutical composition, which comprises a phenothiazine as claimed in claim 1, in combination with one or more compatible and pharmaceutically acceptable adjuvants or diluents.

* * * * *